United States Patent
Grammenos et al.

(10) Patent No.: US 10,071,971 B2
(45) Date of Patent: Sep. 11, 2018

(54) SUBSTITUTED [1,2,4]TRIAZOLE COMPOUNDS AND THEIR USE AS FUNGICIDES

(71) Applicant: BASF SE, Ludwigshafen (DE)

(72) Inventors: Wassilios Grammenos, Ludwigshafen (DE); Ian Robert Craig, Ludwigshafen (DE); Nadege Boudet, Hirschberg (DE); Bernd Mueller, Frankenthal (DE); Jochen Dietz, Karlsruhe (DE); Erica May Cambeis, Wachenheim (DE); Jan Klaas Lohmann, Lambsheim (DE); Thomas Grote, Wachenheim (DE); Egon Haden, Speyer (DE); Ana Escribano Cuesta, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/652,924

(22) PCT Filed: Dec. 12, 2013

(86) PCT No.: PCT/EP2013/076315
§ 371 (c)(1),
(2) Date: Jun. 17, 2015

(87) PCT Pub. No.: WO2014/095548
PCT Pub. Date: Jun. 26, 2014

(65) Prior Publication Data
US 2015/0336905 A1    Nov. 26, 2015

(30) Foreign Application Priority Data

Dec. 19, 2012 (EP) .................... 12198149

(51) Int. Cl.
| | | |
|---|---|---|
| *A01N 43/82* | (2006.01) | |
| *A01N 43/78* | (2006.01) | |
| *A01N 43/653* | (2006.01) | |
| *C07D 249/08* | (2006.01) | |
| *C07D 401/04* | (2006.01) | |
| *C07D 401/06* | (2006.01) | |
| *C07D 401/10* | (2006.01) | |
| *C07D 401/12* | (2006.01) | |
| *C07D 403/04* | (2006.01) | |
| *C07D 403/06* | (2006.01) | |
| *C07D 403/12* | (2006.01) | |
| *C07D 409/10* | (2006.01) | |
| *C07D 417/04* | (2006.01) | |
| *C07D 417/06* | (2006.01) | |
| *C07D 417/10* | (2006.01) | |
| *C07D 417/12* | (2006.01) | |

(52) U.S. Cl.
CPC ......... *C07D 249/08* (2013.01); *A01N 43/653* (2013.01); *A01N 43/78* (2013.01); *A01N 43/82* (2013.01); *C07D 401/04* (2013.01); *C07D 401/06* (2013.01); *C07D 401/10* (2013.01); *C07D 401/12* (2013.01); *C07D 403/04* (2013.01); *C07D 403/06* (2013.01); *C07D 403/12* (2013.01); *C07D 409/10* (2013.01); *C07D 417/04* (2013.01); *C07D 417/06* (2013.01); *C07D 417/10* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 4,578,396 A | 5/1986 | Jaeger et al. | |
| 4,609,668 A | 9/1986 | Schaub et al. | |
| 4,935,436 A | 6/1990 | Markley et al. | |
| 4,945,100 A | 7/1990 | Nyfeler et al. | |
| 4,945,101 A | 7/1990 | Jaeger et al. | |
| 5,059,615 A * | 10/1991 | Fugmann | C07C 255/45 514/383 |
| 5,143,932 A | 9/1992 | Jautelat et al. | |
| 5,262,434 A | 11/1993 | Jautelat et al. | |

FOREIGN PATENT DOCUMENTS

| | | |
|---|---|---|
| DE | 3522440 | 1/1987 |
| EP | 0 029 542 | 6/1981 |
| EP | 0 094 167 | 11/1983 |

(Continued)

OTHER PUBLICATIONS

International Search Report dated Feb. 19, 2014, prepared in International Application No. PCT/EP2013/076315.
European Search Report dated Feb. 27, 2013, prepared in European Application No. 12 19 8148.
International Preliminary Report on Patentability dated Mar. 16, 2014, prepared in International Application No. PCT/EP2013/076315.
Extended European Search Report dated Apr. 7, 2017, prepared in European Application No. 16203214.

(Continued)

*Primary Examiner* — Alicia L Otton
(74) *Attorney, Agent, or Firm* — Brinks Gilson & Lione

(57) ABSTRACT

The present invention relates to compounds of the formula I

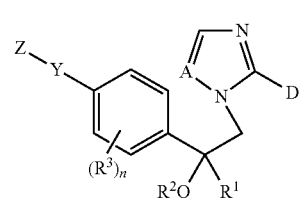

wherein the variables are defined in the description and claims, their preparation and uses thereof.

15 Claims, No Drawings

(56) References Cited

FOREIGN PATENT DOCUMENTS

| EP | 0 104 734 | 4/1984 |
|---|---|---|
| EP | 0 126 430 | 11/1984 |
| EP | 0 150 036 | 7/1985 |
| EP | 0 192 055 | 8/1986 |
| EP | 0 440 950 | 8/1991 |
| EP | 0 470 466 | 2/1992 |
| GB | 2 064 520 | 6/1981 |
| GB | 2 145 717 | 4/1985 |
| GB | 2 063 260 | 6/1991 |
| WO | WO 91/17162 | 11/1991 |
| WO | WO 2010/142779 | 12/2010 |
| WO | WO 2012/025506 | 3/2012 |

OTHER PUBLICATIONS

Extended European Search Report dated Mar. 20, 2017, prepared in European Application No. 17151133.

Ito, et al., "Tebuconazole derivatives are potent inhibitors of strigolactone biosynthesis", Journal of Pesticide Science, vol. 38, 2013, Issue 3, pp. 147-151.

Yamamoto, et al: "Preparation of 1,2,4-triazole derivatives as fungicides", XP002768493, retrieved from STN Database accession No. 1995:812842, Database CA [Online] 1-6 CHEMI.

Cano, et al., "Arylation of aryl chlorides, a convenient method for the synthesis of new potential triazolic fungicides", Tetrahedron, vol. 70, Issue 2, 2014, pp. 280-285.

* cited by examiner

SUBSTITUTED [1,2,4]TRIAZOLE COMPOUNDS AND THEIR USE AS FUNGICIDES

This application is a National Stage application of International Application No. PCT/EP2013/076315, filed Dec. 12, 2013. This application also claims priority under 35 U.S.C. § 119 to European Patent Application No. 12198149.2, filed Dec. 19, 2012.

The present invention relates to substituted [1,2,4]triazol and imidazole compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

EP 0 029 542 relates to hydroxybutyl-imidazol derivatives, processes for their preparation and their use as fungicides. FR 2 469 404 and FR 2 469 408 relate to imidazole derivatives, their preparation and use as fungicides. WO 2010/142779 relates inter alia to biphenyl- and phenoxyphenyl-substituted triazole compounds carrying a sulfur substituent.

EP 0 470 466 relates to halogen-alkyl azolyl derivatives. EP 0 150 036 relates to azolyl arly derivatives, but only biphenyl compounds, that are unsubstituted at the outer phenyl. EP 0 192 055 relates to hydroxyalkynyl azolyl derivatives and their use as fungicides, wherein the compounds that contain a biphenyl unit do not contain a substituent in the biphenyl group. GB 2 064 520 relates to alpha-amyl-1H-1,2,4-triazole-1-ethanols and their use as fungicides. GB 2 145 717 relates to alpha-(ethynyl-substituted phenyl)-alpha-hydrocarbyl-1H-azole-ethanols and their use as fungicides. EP 0 440 950 relates to halogen-allyl-azoolyl derivatives and their use as fungicides.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive substituted [1,2,4]triazol and imidazole compounds of formula I having favorable fungicidal activity against phytopathogenic fungi.

Accordingly, the present invention relates, to the compounds of the formula I

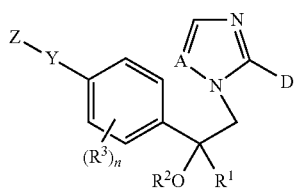

I

Wherein
A is CH or N;
D is H, halogen or $SR^D$, wherein
$R^D$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl or CN;
$R^1$ is $C_1$-$C_6$-alkyl, 1-($C_2$-$C_6$)-alkenyl, 1-($C_2$-$C_6$)-alkynyl, $C_3$-$C_8$-cycloalkyl, $C_3$-$C_8$-cycloalkyl-$C_1$-$C_6$-alkyl, phenyl-$C_2$-$C_4$-alkenyl or phenyl-$C_2$-$C_4$-alkynyl wherein the aliphatic moieties of $R^1$ are not further substituted or carry one, two, three or up to the maximum possible number of identical or different groups $R^{1a}$ which independently of one another are selected from:
$R^{1a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;
wherein the cycloalkyl and/or phenyl moieties of $R^1$ are not further substituted or carry one, two, three, four, five or up to the maximum number of identical or different groups $R^{1b}$ which independently of one another are selected from:
$R^{1b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy;
$R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;
wherein the aliphatic moieties of $R^2$ are not further substituted or carry one, two, three or up to the maximum possible number of identical or different groups $R^{2a}$ which independently of one another are selected from:
$R^{2a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;
wherein the cycloalkyl and/or phenyl moieties of $R^2$ are not further substituted or carry one, two, three, four, five or up to the maximum number of identical or different groups $R^{2b}$ which independently of one another are selected from:
$R^{2b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy;
n is 0, 1, 2, 3 or 4;
$R^3$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)-(N(C_3$-$C_6$-cycloalkyl)$_2$); wherein each of $R^{32}$ is unsubstituted or further substituted by one, two, three or four $R^{3a}$; wherein
$R^{3a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy;
Y is a direct bond or a divalent group selected from the group consisting of
—S—, SO—, —$SO_2$—, —NH—, —N($C_1$-$C_4$-alkyl)-, $CR^7R^8$—, —$CR^9R^{10}$—$CR^{11}R^{12}$—, —$CR^{13}$=$CR^{14}$— and —C≡C—; wherein
$R^7$, $R^8$, $R^9$, $R^{10}$, $R^{11}$, $R^{12}$, $R^{13}$, $R^{14}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy;
Z is five or six-membered heteroaryl, wherein the heteroaryl contains 1, 2, 3 or 4 heteroatoms selected from the group consisting of O, N and S, wherein the heteroaryl is unsubstituted (m1=0) or substituted by $(R^{41})_{m1}$; or is phenyl, that is substituted by $(R^{42})_{m2}$; wherein m1 is 0, 1, 2, 3 or 4;

m2 is 1, 2, 3, 4 or 5; and $R^{41}$, $R^{42}$ is in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, NH($C_1$-$C_4$-alkyl), N($C_1$-$C_4$-alkyl)$_2$, NH($C_3$-$C_6$-cycloalkyl), N($C_3$-$C_6$-cycloalkyl)$_2$, S(O)$_p$($C_1$-$C_4$-alkyl), C(=O)($C_1$-$C_4$-alkyl), C(=O)(OH), C(=O)(O—$C_1$-$C_4$-alkyl), C(=O)(NH($C_1$-$C_4$-alkyl)), C(=O)(N($C_1$-$C_4$-alkyl)$_2$), C(=O)(NH ($C_3$-$C_6$-cycloalkyl)) and C(=O)—(N($C_3$-$C_6$-cycloalkyl)$_2$); wherein each of $R^{41}$ or $R^{42}$ is unsubstituted or further substituted by one, two, three or four $R^{41a}$ or $R^{42a}$ wherein $R^{41a}$, $R^{42a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy;

p is 0, 1 or 2;

or Z—Y stands for group $Z^1$—Y, wherein Y is a triple bond and $Z^1$ is $C_3$-$C_6$-cycloalkyl; with the proviso, that if A is CH, Y is a direct bond, Z is phenyl, $R^1$ is tert-butyl, n=0 and m2=1, $R^{42}$ is not 2-Cl, 4-Cl, 4-$CH_3$, 4-$OCH_3$ or 4-C($CH_3$)$_3$ and if m2=2, ($R^{42}$)$_{m2}$ is not 2,4-$Cl_2$; and if A is N, Y is a direct bond and Z is phenyl, n is 0 or 1 and m is 1, $R^1$ is not ($C_3$-$C_8$)-cycloalkyl($C_1$-$C_3$)-alkyl, ($C_3$-$C_8$)-(chloro)cycloalkyl-($C_1$-$C_3$)-alkyl or ($C_3$-$C_8$)-(methyl)cycloalkyl-($C_1$-$C_3$)-alkyl; and if Y is C≡C, Z is phenyl, $R^2$ is H and $R^1$ is iso-$C_3H_7$, ($R^{42}$)$_{m2}$ is not 4-Cl, 4-F or 4-$OCH_3$; and, if Y is C≡C, Z is phenyl, $R^2$ is H and $R^1$ is tert-$C_4H_9$, ($R^{42}$)$_{m2}$ is not 4-Cl, 4-F, 4-$NO_2$, or 4-$OCH_3$;

and the N-oxides and the agriculturally acceptable salts thereof.

Compounds I can be synthesized using the below illustrated scheme. A commercially available or known acetophenone II carrying halogen X can be transformed to compound III using transition metal catalysis. The X (I,Br) in II can be transformed to compounds III with Y being —NH— (Synlett, (8), 1137-1142; 2011, European Journal of Organic Chemistry, (17), 3219-3223, S3219/1-S3219/38; 2010; Advanced Synthesis & Catalysis, 350(3), 395-398; 2008), —S— (Organic & Biomolecular Chemistry (2012), 10(13), 2562-2568; Organic Letters (2011), 13(15), 4100-4103), (Organic Letters, 14(1), 170-173; 2012; Journal of Organic Chemistry, 74(18), 7187-7190; 2009; Synlett (2011), (2), 268-272), —C(H)=C(H)— (Tetrahedron, 68(36), 7309-7316; 2012; Journal of Organometallic Chemistry, 344(2), 253-9; 1988; WO 2004046068 A2; Tetrahedron, 61(1), 259-266; 2004), C≡C— (EP 648723 A1; WO 2010099527; Organic Letters (2002), 4(24), 4305-4307). Halogenation of the ketone leads to halo ketones IV that can be subsequently transformed into compounds V using an azole compound and a base.

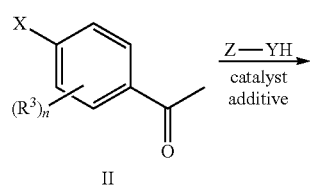

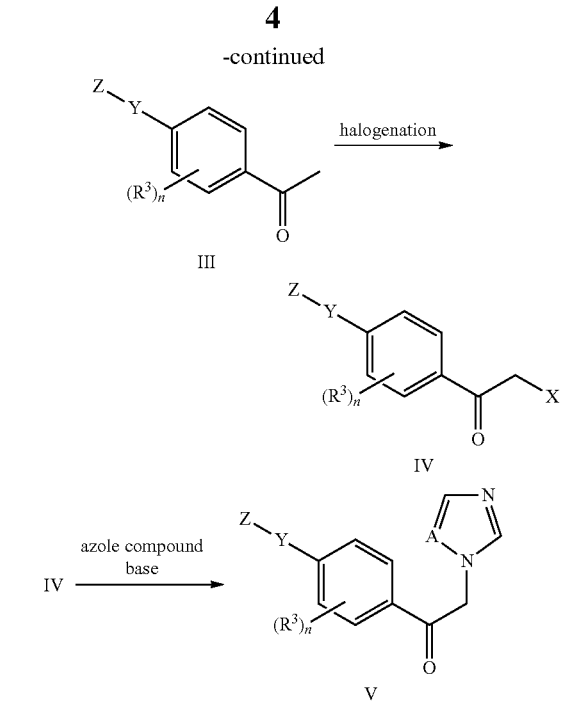

These azole compounds V can be reacted with a Grignard reagent such as $R^1$MgBr or an organolithium reagent $R^1$Li preferably under anhydrous conditions to obtain compounds I wherein $R^2$ is hydrogen. Optionally, a Lewis acid such as $LaCl_3$×2 LiCl or $MgBr_2$×$OEt_2$ can be used. If appropriate, these compounds can subsequently be alkylated e.g. with $R^2$-LG, wherein LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base, such as for example, NaH in a suitable solvent such as THF, to form further compounds. These compounds can be transformed into compounds wherein D is other than H using a strong base (eg BuLi, LDA, LHMDS, KHMDS, BuLi, LTMP, Zn-TMP) an electrophile E+($S_8$, $I_2$, ICl, $C_2F_4Br_2$) to obtain substituted azole compounds I (WO 2012025506 A1, Synthesis, (1), 100-106; 1999).

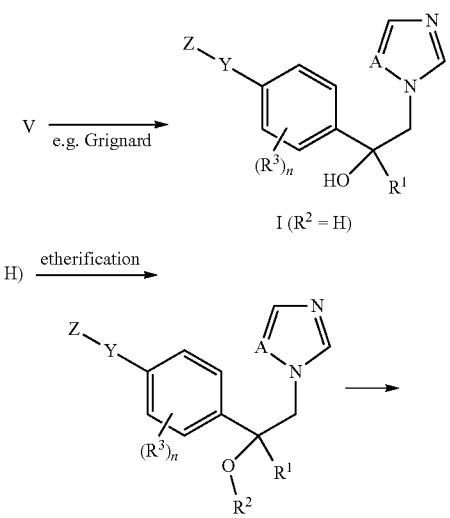

-continued

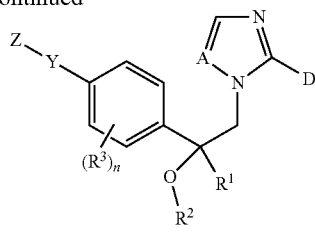

generated and transformed to a ketone (in analogy to the compounds in for example WO 2013/07767). Epoxidation followed by reaction with triazole leads to bromide VI.

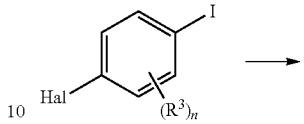

Alternatively, the inventive compounds I can be synthesized using the following scheme:

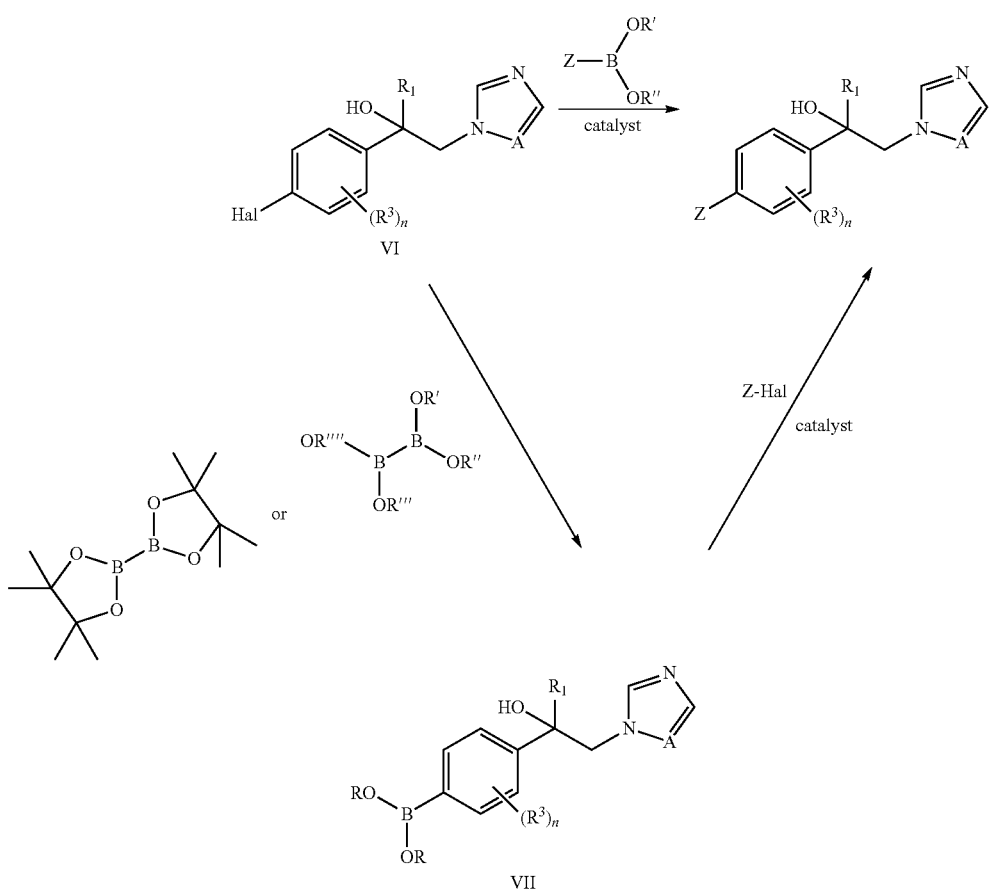

Hal = e.g. Br
A = in particular N

A 4-halo, in particular 4-bromo, phenyl compound VI can be transformed to a biaryl component using crosscoupling methodology known to the expert using e.g a boronic acid. Alternatively, the halide can be transformed into a boronic acid ester first and then coupled with a aryl halide. (see, e.g. WO 2007071434 A1, Journal of Organic Chemistry, 68(9), 3729-3732; 2003). R' and R" are independently hydrogen or $(C_1-C_4)$-alkyl. A catalyst such as $PdCl_2$, $PdCl_2(dppf)$, or $Pd(PPh_3)_4$ can be used. For the reaction of compounds VII with Z-Hal a catalyst such as $PdCl_2$, $PdCl_2(dppf)$, or $Pd(PPh_3)_4$ can be used.

Halo compounds VI can be prepared starting from known molecules. For example a substituted phenyl Grignard is -continued

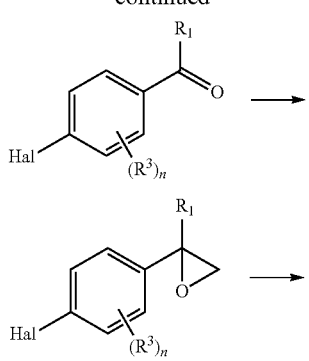

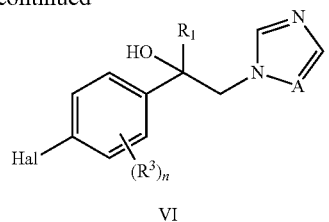

Hal = e.g. Br

Alternatively, bromo compounds VI can be prepared using the following scheme

A Grignard is generated and the so obtained acyl compounds is chlorinated using a chlorination agent (eg $SO_2Cl_2$, NCS, $Cl_2$). Addition of a metal organic species (e.g. a Grignard compound) leads to a chloro alcohol, that can be subsequently transformed into bromo compound VI.

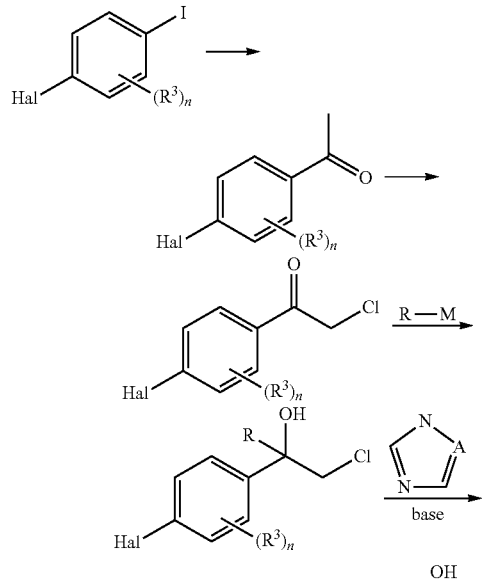

Hal = e.g. Br

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Compounds of formula V are at least partially new. Consequently, a further embodiment of the present invention are compounds of formula V (see above), wherein the variables are as defined and preferably defined for formula I herein.

Compounds of formula VI are at least partially new. Consequently, a further embodiment of the present invention are compounds of formula VI

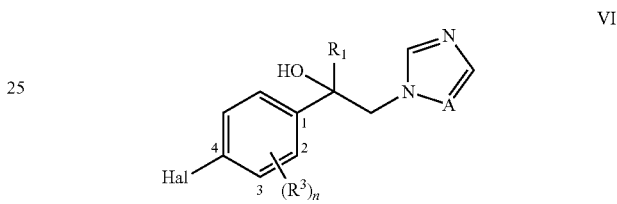

wherein the variables are as defined and preferably defined for formula I herein, and Hal stands for halogen, namely Br, Cl or F, wherein the substituents are specific embodiments independently of each other or in any combination. Compounds VI are also suitable as fungicides as described later.

In particular, Hal stands for Br.

In particular, A stands for N.

Preferred $R^1$ and $R^2$ can be found in the description for formula I.

Particularly preferred $(R^3)_n$ are the meanings as given in Table R3:

TABLE R3

| No. | No. $(R^3)_n$ |
|---|---|
| R3-1 | —* |
| R3-2 | 2-Cl |
| R3-3 | 3-Cl |
| R3-4 | 2-F |
| R3-5 | 3-F |
| R3-6 | 2,3-$Cl_2$ |
| R3-7 | 2,5-$Cl_2$ |
| R3-8 | 3,5-$Cl_2$ |
| R3-9 | 2,6-$Cl_2$ |
| R3-10 | 2,3-$F_2$ |
| R3-11 | 2,5-$F_2$ |
| R3-12 | 3,5-$F_2$ |
| R3-13 | 2,6-$F_2$ |
| R3-14 | 2-F-3-Cl |
| R3-15 | 2-F-6-Cl |
| R3-16 | 2-Cl-3-F |
| R3-17 | 2-$CF_3$ |
| R3-18 | 3-$CF_3$ |
| R3-19 | 2,3-$(CF_3)_2$ |
| R3-20 | 2,5-$(CF_3)_2$ |
| R3-21 | 2,6-$(CF_3)_2$ |
| R3-22 | 2-Br |
| R3-23 | 3-Br |
| R3-24 | 2,3-$Br_2$ |
| R3-25 | 2,5-$Br_2$ |

TABLE R3-continued

| No. | No. (R³)ₙ |
|---|---|
| R3-26 | 3,5-Br₂ |
| R3-27 | 2,6-Br₂ |

*"—" stands for n = 0

It may be preferred, if $(R^3)_n$ is selected from R3-2, R3-3, R3-6, R3-7, R3-8 and R3-9.

In particular with a view to their use, according to one embodiment, preference is given to the compounds of the formula VI that are compiled in the following Tables 1c to 26c. Each of the groups mentioned for a substituent in the tables is furthermore per se, independently of the combination in which it is mentioned, a particularly preferred aspect of the substituent in question.

Table 1c Compounds of the formula VI in which A is N, Hal is Br and $(R^3)_n$ corresponds to line R3-1 of Table R3 and the meaning for the combination of $R^1$ and $R^2$ for each individual compound corresponds in each case to one line of Table B (compounds VI.R3-1.B1 to VI.R3-1.B352).

Table 2c Compounds of the formula VI in which A is N, Hal is Br and $(R^3)_n$ corresponds to line R3-2 of Table R3 and the meaning for the combination of $R^1$ and $R^2$ for each individual compound corresponds in each case to one line of Table B (compounds VI.R3-2.B1 to VI.R3-2.B352).

Table 3c Compounds of the formula VI in which A is N, Hal is Br and $(R^3)_n$ corresponds to line R3-3 of Table R3 and the meaning for the combination of $R^1$ and $R^2$ for each individual compound corresponds in each case to one line of Table B (compounds VI.R3-3.B1 to VI.R3-3.B352).

Table 4c Compounds of the formula VI in which A is N, Hal is Br and $(R^3)_n$ corresponds to line R3-4 of Table R3 and the meaning for the combination of $R^1$ and $R^2$ for each individual compound corresponds in each case to one line of Table B (compounds VI.R3-4.B1 to VI.R3-4.B352).

Table 5c Compounds of the formula VI in which A is N, Hal is Br and $(R^3)_n$ corresponds to line R3-5 of Table R3 and the meaning for the combination of $R^1$ and $R^2$ for each individual compound corresponds in each case to one line of Table B (compounds VI.R3-5.B1 to VI.R3-5.B352).

Table 6c Compounds of the formula VI in which A is N, Hal is Br and $(R^3)_n$ corresponds to line R3-6 of Table R3 and the meaning for the combination of $R^1$ and $R^2$ for each individual compound corresponds in each case to one line of Table B (compounds VI.R3-6.B1 to VI.R3-6.B352).

Table 7c Compounds of the formula VI in which A is N, Hal is Br and $(R^3)_n$ corresponds to line R3-7 of Table R3 and the meaning for the combination of $R^1$ and $R^2$ for each individual compound corresponds in each case to one line of Table B (compounds VI.R3-7.B1 to VI.R3-7.B352).

Table 8c Compounds of the formula VI in which A is N, Hal is Br and $(R^3)_n$ corresponds to line R3-8 of Table R3 and the meaning for the combination of $R^1$ and $R^2$ for each individual compound corresponds in each case to one line of Table B (compounds VI.R3-8.B1 to VI.R3-8.B352).

Table 9c Compounds of the formula VI in which A is N, Hal is Br and $(R^3)_n$ corresponds to line R3-9 of Table R3 and the meaning for the combination of $R^1$ and $R^2$ for each individual compound corresponds in each case to one line of Table B (compounds VI.R3-9.B1 to VI.R3-9.B352).

Table 10c Compounds of the formula VI in which A is N, Hal is Br and $(R^3)_n$ corresponds to line R3-10 of Table R3 and the meaning for the combination of $R^1$ and $R^2$ for each individual compound corresponds in each case to one line of Table B (compounds VI.R3-10.B1 to VI.R3-10.B352).

Table 11c Compounds of the formula VI in which A is N, Hal is Br and $(R^3)_n$ corresponds to line R3-11 of Table R3 and the meaning for the combination of $R^1$ and $R^2$ for each individual compound corresponds in each case to one line of Table B (compounds VI.R3-11.B1 to VI.R3-11.B352).

Table 12c Compounds of the formula VI in which A is N, Hal is Br and $(R^3)_n$ corresponds to line R3-12 of Table R3 and the meaning for the combination of $R^1$ and $R^2$ for each individual compound corresponds in each case to one line of Table B (compounds VI.R3-12.B1 to VI.R3-12.B352).

Table 13c Compounds of the formula VI in which A is N, Hal is Br and $(R^3)_n$ corresponds to line R3-13 of Table R3 and the meaning for the combination of $R^1$ and $R^2$ for each individual compound corresponds in each case to one line of Table B (compounds VI.R3-13.B1 to VI.R3-13.B352).

Table 14c Compounds of the formula VI in which A is N, Hal is Br and $(R^3)_n$ corresponds to line R3-14 of Table R3 and the meaning for the combination of $R^1$ and $R^2$ for each individual compound corresponds in each case to one line of Table B (compounds VI.R3-14.B1 to VI.R3-14.B352).

Table 15c Compounds of the formula VI in which A is N, Hal is Br and $(R^3)_n$ corresponds to line R3-15 of Table R3 and the meaning for the combination of $R^1$ and $R^2$ for each individual compound corresponds in each case to one line of Table B (compounds VI.R3-15.B1 to VI.R3-15.B352).

Table 16c Compounds of the formula VI in which A is N, Hal is Br and $(R^3)_n$ corresponds to line R3-16 of Table R3 and the meaning for the combination of $R^1$ and $R^2$ for each individual compound corresponds in each case to one line of Table B (compounds VI.R3-16.B1 to VI.R3-16.B352).

Table 17c Compounds of the formula VI in which A is N, Hal is Br and $(R^3)_n$ corresponds to line R3-17 of Table R3 and the meaning for the combination of $R^1$ and $R^2$ for each individual compound corresponds in each case to one line of Table B (compounds VI.R3-17.B1 to VI.R3-17.B352).

Table 18c Compounds of the formula VI in which A is N, Hal is Br and $(R^3)_n$ corresponds to line R3-18 of Table R3 and the meaning for the combination of $R^1$ and $R^2$ for each individual compound corresponds in each case to one line of Table B (compounds VI.R3-18.B1 to VI.R3-18.B352).

Table 19c Compounds of the formula VI in which A is N, Hal is Br and $(R^3)_n$ corresponds to line R3-19 of Table R3 and the meaning for the combination of $R^1$ and $R^2$ for each individual compound corresponds in each case to one line of Table B (compounds VI.R3-19.B1 to VI.R3-19.B352).

Table 20c Compounds of the formula VI in which A is N, Hal is Br and $(R^3)_n$ corresponds to line R3-20 of Table R3 and the meaning for the combination of $R^1$ and $R^2$ for each individual compound corresponds in each case to one line of Table B (compounds VI.R3-20.B1 to VI.R3-20.B352).

Table 21c Compounds of the formula VI in which A is N, Hal is Br and $(R^3)_n$ corresponds to line R3-21 of Table R3 and the meaning for the combination of $R^1$ and $R^2$ for each individual compound corresponds in each case to one line of Table B (compounds VI.R3-21.B1 to VI.R3-21.B352).

Table 22c Compounds of the formula VI in which A is N, Hal is Br and $(R^3)_n$ corresponds to line R3-22 of Table R3 and the meaning for the combination of $R^1$ and $R^2$ for each individual compound corresponds in each case to one line of Table B (compounds VI.R3-22.B1 to VI.R3-22.B352).

Table 23c Compounds of the formula VI in which A is N, Hal is Br and $(R^3)_n$ corresponds to line R3-23 of Table R3 and the meaning for the combination of $R^1$ and $R^2$ for each individual compound corresponds in each case to one line of Table B (compounds VI.R3-23.B1 to VI.R3-23.B352).

Table 24c Compounds of the formula VI in which A is N, Hal is Br and $(R^3)_n$ corresponds to line R3-24 of Table R3 and the meaning for the combination of $R^1$ and $R^2$ for each individual compound corresponds in each case to one line of Table B (compounds VI.R3-24.B1 to VI.R3-24.B352).

Table 25c Compounds of the formula VI in which A is N, Hal is Br and $(R^3)_n$ corresponds to line R3-25 of Table R3 and the meaning for the combination of $R^1$ and $R^2$ for each individual compound corresponds in each case to one line of Table B (compounds VI.R3-25.B1 to VI.R3-25.B352).

Table 26c Compounds of the formula VI in which A is N, Hal is Br and $(R^3)_n$ corresponds to line R3-26 of Table R3 and the meaning for the combination of $R^1$ and $R^2$ for each individual compound corresponds in each case to one line of Table B (compounds VI.R3-26.B1 to VI.R3-26.B352).

Table 27c Compounds of the formula VI in which A is N, Hal is Br and $(R^3)_n$ corresponds to line R3-27 of Table R3 and the meaning for the combination of $R^1$ and $R^2$ for each individual compound corresponds in each case to one line of Table B (compounds VI.R3-27.B1 to VI.R3-27.B352).

Table B can be found below.

One further aspect of the invention are compounds of formula A and B:

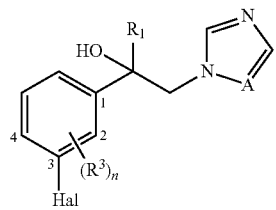

A

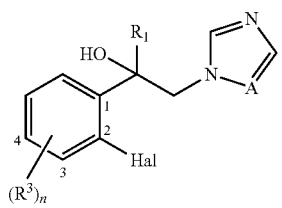

B wherein the variables are as defined and preferably defined for formula I herein, and Hal stands for halogen, namely Br, Cl or F, wherein the substituents are specific embodiments independently of each other or in any combination. Compounds A and B are also suitable as fungicides as described later.

In particular, Hal stands for Br.

In particular, A stands for N.

Preferred $R^1$ and $R^2$ can be found in the description for formula I.

Particularly preferred $(R^3)_n$ for formula A are the meanings as given in Table R3a:

TABLE R3a

| No. | $(R^3)_n$ |
|---|---|
| R3a-1 | —* |
| R3a-2 | 2-Cl |
| R3a-3 | 4-Cl |
| R3a-4 | 5-Cl |
| R3a-5 | 6-Cl |
| R3a-6 | 2-F |
| R3a-7 | 4-F |
| R3a-8 | 5-F |
| R3a-9 | 6-F |
| R3a-10 | 2,4-$Cl_2$ |

TABLE R3a-continued

| No. | $(R^3)_n$ |
|---|---|
| R3a-11 | 2,5-$Cl_2$ |
| R3a-12 | 2,6-$Cl_2$ |
| R3a-13 | 4,5-$Cl_2$ |
| R3a-14 | 4,6-$Cl_2$ |
| R3a-15 | 5,6-$Cl_2$ |
| R3a-16 | 2,4-$F_2$ |
| R3a-17 | 2,5-$F_2$ |
| R3a-18 | 2,6-$F_2$ |
| R3a-19 | 4,5-$F_2$ |
| R3a-20 | 4,6-$F_2$ |
| R3a-21 | 5,6-$F_2$ |
| R3a-22 | 2-F-4-Cl |
| R3a-23 | 2-F-6-Cl |
| R3a-24 | 2-Cl-3-F |
| R3a-25 | 2-$CF_3$ |
| R3a-26 | 4-$CF_3$ |
| R3a-27 | 5-$CF_3$ |
| R3a-28 | 6-$CF_3$ |
| R3a-29 | 2,4-$(CF_3)_2$ |
| R3a-30 | 2,5-$(CF_3)_2$ |
| R3a-31 | 2,6-$(CF_3)_2$ |
| R3a-32 | 4,5-$(CF_3)_2$ |
| R3a-33 | 4,6-$(CF_3)_2$ |
| R3a-34 | 5,6-$(CF_3)_2$ |
| R3a-35 | 2-Br |
| R3a-36 | 4-Br |
| R3a-37 | 5-Br |
| R3a-38 | 6-Br |
| R3a-39 | 2,4-$Br_2$ |
| R3a-40 | 2,5-$Br_2$ |
| R3a-41 | 2,6-$Br_2$ |
| R3a-42 | 4,5-$Br_2$ |
| R3a-43 | 4,6-$Br_2$ |
| R3a-44 | 5,6-$Br_2$ |

*"—" stands for n = 0

It may be preferred, if $(R^3)_n$ is selected from R3a-1, R3a-2, R3a-3, R3a-4, R3a-5, R3a-6, R3a-7, R3a-8, and R3a-9.

In particular with a view to their use, according to one embodiment, preference is given to the compounds of the formula A that are compiled in the following Tables 1d to 44d. Each of the groups mentioned for a substituent in the tables is furthermore per se, independently of the combination in which it is mentioned, a particularly preferred aspect of the substituent in question.

Table 1d Compounds of the formula A in which A is N, Hal is Br and $(R^3)_n$ corresponds to line R3a-1 of Table R3a and the meaning for the combination of $R^1$ and $R^2$ for each individual compound corresponds in each case to one line of Table B (compounds A.R3a-1.B1 to A.R3a1.B352).

Table 2d Compounds of the formula A in which A is N, Hal is Br and $(R^3)_n$ corresponds to line R3a-2 of Table R3a and the meaning for the combination of $R^1$ and $R^2$ for each individual compound corresponds in each case to one line of Table B (compounds A.R3a-2.B1 to A.R3a2.B352).

Table 3d Compounds of the formula A in which A is N, Hal is Br and $(R^3)_n$ corresponds to line R3a-3 of Table R3a and the meaning for the combination of $R^1$ and $R^2$ for each individual compound corresponds in each case to one line of Table B (compounds A.R3a-3.B1 to A.R3a3.B352).

Table 4d Compounds of the formula A in which A is N, Hal is Br and $(R^3)_n$ corresponds to line R3a-4 of Table R3a and the meaning for the combination of $R^1$ and $R^2$ for each individual compound corresponds in each case to one line of Table B (compounds A.R3a-4.B1 to A.R3a4.B352).

Table 5d Compounds of the formula A in which A is N, Hal is Br and $(R^3)_n$ corresponds to line R3a-5 of Table R3a and the meaning for the combination of $R^1$ and $R^2$ for each individual compound corresponds in each case to one line of Table B (compounds A.R3a-5.B1 to A.R3a5.B352).

Table 6d Compounds of the formula A in which A is N, Hal is Br and $(R^3)_n$ corresponds to line R3a-6 of Table R3a and the meaning for the combination of $R^1$ and $R^2$ for each individual compound corresponds in each case to one line of Table B (compounds A.R3a-6.B1 to A.R3a6.B352).

Table 7d Compounds of the formula A in which A is N, Hal is Br and $(R^3)_n$ corresponds to line R3a-7 of Table R3a and the meaning for the combination of $R^1$ and $R^2$ for each individual compound corresponds in each case to one line of Table B (compounds A.R3a-7.B1 to A.R3a7.B352).

Table 8d Compounds of the formula A in which A is N, Hal is Br and $(R^3)_n$ corresponds to line R3a-8 of Table R3a and the meaning for the combination of $R^1$ and $R^2$ for each individual compound corresponds in each case to one line of Table B (compounds A.R3a-8.B1 to A.R3a8.B352).

Table 9d Compounds of the formula A in which A is N, Hal is Br and $(R^3)_n$ corresponds to line R3a-9 of Table R3a and the meaning for the combination of $R^1$ and $R^2$ for each individual compound corresponds in each case to one line of Table B (compounds A.R3a-9.B1 to A.R3a9.B352).

Table 10d Compounds of the formula A in which A is N, Hal is Br and $(R^3)_n$ corresponds to line R3a-10 of Table R3a and the meaning for the combination of $R^1$ and $R^2$ for each individual compound corresponds in each case to one line of Table B (compounds A.R3a-10.B1 to A.R3a10.B352).

Table 11d Compounds of the formula A in which A is N, Hal is Br and $(R^3)_n$ corresponds to line R3a-11 of Table R3a and the meaning for the combination of $R^1$ and $R^2$ for each individual compound corresponds in each case to one line of Table B (compounds A.R3a-11.B1 to A.R3a11.B352).

Table 12d Compounds of the formula A in which A is N, Hal is Br and $(R^3)_n$ corresponds to line R3a-12 of Table R3a and the meaning for the combination of $R^1$ and $R^2$ for each individual compound corresponds in each case to one line of Table B (compounds A.R3a-12.B1 to A.R3a12.B352).

Table 13d Compounds of the formula A in which A is N, Hal is Br and $(R^3)_n$ corresponds to line R3a-13 of Table R3a and the meaning for the combination of $R^1$ and $R^2$ for each individual compound corresponds in each case to one line of Table B (compounds A.R3a-13.B1 to A.R3a13.B352).

Table 14d Compounds of the formula A in which A is N, Hal is Br and $(R^3)_n$ corresponds to line R3a-14 of Table R3a and the meaning for the combination of $R^1$ and $R^2$ for each individual compound corresponds in each case to one line of Table B (compounds A.R3a-14.B1 to A.R3a14.B352).

Table 15d Compounds of the formula A in which A is N, Hal is Br and $(R^3)_n$ corresponds to line R3a-15 of Table R3a and the meaning for the combination of $R^1$ and $R^2$ for each individual compound corresponds in each case to one line of Table B (compounds A.R3a-15.B1 to A.R3a15.B352).

Table 16d Compounds of the formula A in which A is N, Hal is Br and $(R^3)_n$ corresponds to line R3a-16 of Table R3a and the meaning for the combination of $R^1$ and $R^2$ for each individual compound corresponds in each case to one line of Table B (compounds A.R3a-16.B1 to A.R3a16.B352).

Table 17d Compounds of the formula A in which A is N, Hal is Br and $(R^3)_n$ corresponds to line R3a-17 of Table R3a and the meaning for the combination of $R^1$ and $R^2$ for each individual compound corresponds in each case to one line of Table B (compounds A.R3a-17.B1 to A.R3a17.B352).

Table 18d Compounds of the formula A in which A is N, Hal is Br and $(R^3)_n$ corresponds to line R3a-18 of Table R3a and the meaning for the combination of $R^1$ and $R^2$ for each individual compound corresponds in each case to one line of Table B (compounds A.R3a-18.B1 to A.R3a18.B352).

Table 19d Compounds of the formula A in which A is N, Hal is Br and $(R^3)_n$ corresponds to line R3a-19 of Table R3a and the meaning for the combination of $R^1$ and $R^2$ for each individual compound corresponds in each case to one line of Table B (compounds A.R3a-19.B1 to A.R3a19.B352).

Table 20d Compounds of the formula A in which A is N, Hal is Br and $(R^3)_n$ corresponds to line R3a-20 of Table R3a and the meaning for the combination of $R^1$ and $R^2$ for each individual compound corresponds in each case to one line of Table B (compounds A.R3a-20.B1 to A.R3a20.B352).

Table 21d Compounds of the formula A in which A is N, Hal is Br and $(R^3)_n$ corresponds to line R3a-21 of Table R3a and the meaning for the combination of $R^1$ and $R^2$ for each individual compound corresponds in each case to one line of Table B (compounds A.R3a-21.B1 to A.R3a21.B352).

Table 22d Compounds of the formula A in which A is N, Hal is Br and $(R^3)_n$ corresponds to line R3a-22 of Table R3a and the meaning for the combination of $R^1$ and $R^2$ for each individual compound corresponds in each case to one line of Table B (compounds A.R3a-22.B1 to A.R3a22.B352).

Table 23d Compounds of the formula A in which A is N, Hal is Br and $(R^3)_n$ corresponds to line R3a-23 of Table R3a and the meaning for the combination of $R^1$ and $R^2$ for each individual compound corresponds in each case to one line of Table B (compounds A.R3a-23.B1 to A.R3a23.B352).

Table 24d Compounds of the formula A in which A is N, Hal is Br and $(R^3)_n$ corresponds to line R3a-24 of Table R3a and the meaning for the combination of $R^1$ and $R^2$ for each individual compound corresponds in each case to one line of Table B (compounds A.R3a-24.B1 to A.R3a24.B352).

Table 25d Compounds of the formula A in which A is N, Hal is Br and $(R^3)_n$ corresponds to line R3a-25 of Table R3a and the meaning for the combination of $R^1$ and $R^2$ for each individual compound corresponds in each case to one line of Table B (compounds A.R3a-25.B1 to A.R3a25.B352).

Table 26d Compounds of the formula A in which A is N, Hal is Br and $(R^3)_n$ corresponds to line R3a-26 of Table R3a and the meaning for the combination of $R^1$ and $R^2$ for each individual compound corresponds in each case to one line of Table B (compounds A.R3a-26.B1 to A.R3a26.B352).

Table 27d Compounds of the formula A in which A is N, Hal is Br and $(R^3)_n$ corresponds to line R3a-27 of Table R3a and the meaning for the combination of $R^1$ and $R^2$ for each individual compound corresponds in each case to one line of Table B (compounds A.R3a-27.B1 to A.R3a27.B352).

Table 28d Compounds of the formula A in which A is N, Hal is Br and $(R^3)_n$ corresponds to line R3a-28 of Table R3a and the meaning for the combination of $R^1$ and $R^2$ for each individual compound corresponds in each case to one line of Table B (compounds A.R3a-28.B1 to A.R3a28.B352).

Table 29d Compounds of the formula A in which A is N, Hal is Br and $(R^3)_n$ corresponds to line R3a-29 of Table R3a and the meaning for the combination of $R^1$ and $R^2$ for each individual compound corresponds in each case to one line of Table B (compounds A.R3a-29.B1 to A.R3a29.B352).

Table 30d Compounds of the formula A in which A is N, Hal is Br and $(R^3)_n$ corresponds to line R3a-30 of Table R3a and the meaning for the combination of $R^1$ and $R^2$ for each individual compound corresponds in each case to one line of Table B (compounds A.R3a-30.B1 to A.R3a30.B352).

Table 31d Compounds of the formula A in which A is N, Hal is Br and $(R^3)_n$ corresponds to line R3a-31 of Table R3a and the meaning for the combination of $R^1$ and $R^2$ for each individual compound corresponds in each case to one line of Table B (compounds A.R3a-31.B1 to A.R3a31.B352).

Table 32d Compounds of the formula A in which A is N, Hal is Br and $(R^3)_n$ corresponds to line R3a-32 of Table R3a and the meaning for the combination of $R^1$ and $R^2$ for each individual compound corresponds in each case to one line of Table B (compounds A.R3a-32.B1 to A.R3a32.B352).

Table 33d Compounds of the formula A in which A is N, Hal is Br and $(R^3)_n$ corresponds to line R3a-33 of Table R3a and the meaning for the combination of $R^1$ and $R^2$ for each individual compound corresponds in each case to one line of Table B (compounds A.R3a-33.B1 to A.R3a33.B352).

Table 34d Compounds of the formula A in which A is N, Hal is Br and $(R^3)_n$ corresponds to line R3a-34 of Table R3a and the meaning for the combination of $R^1$ and $R^2$ for each individual compound corresponds in each case to one line of Table B (compounds A.R3a-34.B1 to A.R3a34.B352).

Table 35d Compounds of the formula A in which A is N, Hal is Br and $(R^3)_n$ corresponds to line R3a-35 of Table R3a and the meaning for the combination of $R^1$ and $R^2$ for each individual compound corresponds in each case to one line of Table B (compounds A.R3a-35.B1 to A.R3a35.B352).

Table 36d Compounds of the formula A in which A is N, Hal is Br and $(R^3)_n$ corresponds to line R3a-36 of Table R3a and the meaning for the combination of $R^1$ and $R^2$ for each individual compound corresponds in each case to one line of Table B (compounds A.R3a-36.B1 to A.R3a36.B352).

Table 37d Compounds of the formula A in which A is N, Hal is Br and $(R^3)_n$ corresponds to line R3a-37 of Table R3a and the meaning for the combination of $R^1$ and $R^2$ for each individual compound corresponds in each case to one line of Table B (compounds A.R3a-37.B1 to A.R3a37.B352).

Table 38d Compounds of the formula A in which A is N, Hal is Br and $(R^3)_n$ corresponds to line R3a-38 of Table R3a and the meaning for the combination of $R^1$ and $R^2$ for each individual compound corresponds in each case to one line of Table B (compounds A.R3a-38.B1 to A.R3a38.B352).

Table 39d Compounds of the formula A in which A is N, Hal is Br and $(R^3)_n$ corresponds to line R3a-39 of Table R3a and the meaning for the combination of $R^1$ and $R^2$ for each individual compound corresponds in each case to one line of Table B (compounds A.R3a-39.B1 to A.R3a39.B352).

Table 40d Compounds of the formula A in which A is N, Hal is Br and $(R^3)_n$ corresponds to line R3a-40 of Table R3a and the meaning for the combination of $R^1$ and $R^2$ for each individual compound corresponds in each case to one line of Table B (compounds A.R3a-40.B1 to A.R3a40.B352).

Table 41d Compounds of the formula A in which A is N, Hal is Br and $(R^3)_n$ corresponds to line R3a-41 of Table R3a and the meaning for the combination of $R^1$ and $R^2$ for each individual compound corresponds in each case to one line of Table B (compounds A.R3a-41.B1 to A.R3a41.B352).

Table 42d Compounds of the formula A in which A is N, Hal is Br and $(R^3)_n$ corresponds to line R3a-42 of Table R3a and the meaning for the combination of $R^1$ and $R^2$ for each individual compound corresponds in each case to one line of Table B (compounds A.R3a-42.B1 to A.R3a42.B352).

Table 43d Compounds of the formula A in which A is N, Hal is Br and $(R^3)_n$ corresponds to line R3a-43 of Table R3a and the meaning for the combination of $R^1$ and $R^2$ for each individual compound corresponds in each case to one line of Table B (compounds A.R3a-43.B1 to A.R3a43.B352).

Table 44d Compounds of the formula A in which A is N, Hal is Br and $(R^3)_n$ corresponds to line R3a-44 of Table R3a and the meaning for the combination of $R^1$ and $R^2$ for each individual compound corresponds in each case to one line of Table B (compounds A.R3a-44.B1 to A.R3a44.B352).

Particularly preferred $(R^3)_n$ for formula B are the meanings as given in Table R3b:

TABLE R3b

| No. | $(R^3)_n$ |
|---|---|
| R3b-1 | *— |
| R3b-2 | 3-Cl |
| R3b-3 | 4-Cl |
| R3b-4 | 5-Cl |
| R3b-5 | 6-Cl |
| R3b-6 | 3-F |
| R3b-7 | 4-F |
| R3b-8 | 5-F |
| R3b-9 | 6-F |
| R3b-10 | 3,4-$Cl_2$ |
| R3b-11 | 3,5-$Cl_2$ |
| R3b-12 | 3,6-$Cl_2$ |
| R3b-13 | 4,5-$Cl_2$ |
| R3b-14 | 4,6-$Cl_2$ |
| R3b-15 | 5,6-$Cl_2$ |
| R3b-16 | 3,4-$F_2$ |
| R3b-17 | 3,5-$F_2$ |
| R3b-18 | 3,6-$F_2$ |
| R3b-19 | 4,5-$F_2$ |
| R3b-20 | 4,6-$F_2$ |
| R3b-21 | 5,6-$F_2$ |
| R3b-22 | 3-F-4-Cl |
| R3b-23 | 3-F-6-Cl |
| R3b-24 | 3-Cl-3-F |
| R3b-25 | 3-$CF_3$ |
| R3b-26 | 4-$CF_3$ |
| R3b-27 | 5-$CF_3$ |
| R3b-28 | 6-$CF_3$ |
| R3b-29 | 3,4-$(CF_3)_2$ |
| R3b-30 | 3,5-$(CF_3)_2$ |
| R3b-31 | 3,6-$(CF_3)_2$ |
| R3b-32 | 4,5-$(CF_3)_2$ |
| R3b-33 | 4,6-$(CF_3)_2$ |
| R3b-34 | 5,6-$(CF_3)_2$ |
| R3b-35 | 3-Br |
| R3b-36 | 4-Br |
| R3b-37 | 5-Br |
| R3b-38 | 6-Br |
| R3b-39 | 3,4-$Br_2$ |
| R3b-40 | 3,5-$Br_2$ |
| R3b-41 | 3,6-$Br_2$ |
| R3b-42 | 4,5-$Br_2$ |
| R3b-43 | 4,6-$Br_2$ |
| R3b-44 | 5,6-$Br_2$ |

*"—" 2 stands for n = 0

It may be preferred, if $(R^3)_n$ is selected from R3b-1, R3b-2, R3b-3, R3b-4, R3b-5, R3b-6, R3b-7, R3b-8 and R3b-9.

In particular with a view to their use, according to one embodiment, preference is given to the compounds of the formula B that are compiled in the following Tables 1e to 44e. Each of the groups mentioned for a substituent in the tables is furthermore per se, independently of the combination in which it is mentioned, a particularly preferred aspect of the substituent in question.

Table 1e Compounds of the formula B in which A is N, Hal is Br and $(R^3)_n$ corresponds to line R3b-1 of Table R3b and the meaning for the combination of $R^1$ and $R^2$ for each individual compound corresponds in each case to one line of Table B (compounds B.R3b-1.B1 to B.R3b1.B352).

Table 2e Compounds of the formula B in which A is N, Hal is Br and $(R^3)_n$ corresponds to line R3b-2 of Table R3b and the meaning for the combination of $R^1$ and $R^2$ for each individual compound corresponds in each case to one line of Table B (compounds B.R3b-2.B1 to B.R3b2.B352).

Table 3e Compounds of the formula B in which A is N, Hal is Br and $(R^3)_n$ corresponds to line R3b-3 of Table R3b and the meaning for the combination of $R^1$ and $R^2$ for each individual compound corresponds in each case to one line of Table B (compounds B.R3b-3.B1 to B.R3b3.B352).

Table 4e Compounds of the formula B in which A is N, Hal is Br and $(R^3)_n$ corresponds to line R3b-4 of Table R3b and the meaning for the combination of $R^1$ and $R^2$ for each individual compound corresponds in each case to one line of Table B (compounds B.R3b-4.B1 to B.R3b4.B352).

Table 5e Compounds of the formula B in which A is N, Hal is Br and $(R^3)_n$ corresponds to line R3b-5 of Table R3b and the meaning for the combination of $R^1$ and $R^2$ for each individual compound corresponds in each case to one line of Table B (compounds B.R3b-5.B1 to B.R3b5.B352).

Table 6e Compounds of the formula B in which A is N, Hal is Br and $(R^3)_n$ corresponds to line R3b-6 of Table R3b and the meaning for the combination of $R^1$ and $R^2$ for each individual compound corresponds in each case to one line of Table B (compounds B.R3b-6.B1 to B.R3b6.B352).

Table 7e Compounds of the formula B in which A is N, Hal is Br and $(R^3)_n$ corresponds to line R3b-7 of Table R3b and the meaning for the combination of $R^1$ and $R^2$ for each individual compound corresponds in each case to one line of Table B (compounds B.R3b-7.B1 to B.R3b7.B352).

Table 8e Compounds of the formula B in which A is N, Hal is Br and $(R^3)_n$ corresponds to line R3b-8 of Table R3b and the meaning for the combination of $R^1$ and $R^2$ for each individual compound corresponds in each case to one line of Table B (compounds B.R3b-8.B1 to B.R3b8.B352).

Table 9e Compounds of the formula B in which A is N, Hal is Br and $(R^3)_n$ corresponds to line R3b-9 of Table R3b and the meaning for the combination of $R^1$ and $R^2$ for each individual compound corresponds in each case to one line of Table B (compounds B.R3b-9.B1 to B.R3b9.B352).

Table 10e Compounds of the formula B in which A is N, Hal is Br and $(R^3)_n$ corresponds to line R3b-10 of Table R3b and the meaning for the combination of $R^1$ and $R^2$ for each individual compound corresponds in each case to one line of Table B (compounds B.R3b-10.B1 to B.R3b10.B352).

Table 11e Compounds of the formula B in which A is N, Hal is Br and $(R^3)_n$ corresponds to line R3b-11 of Table R3b and the meaning for the combination of $R^1$ and $R^2$ for each individual compound corresponds in each case to one line of Table B (compounds B.R3b-11.B1 to B.R3b11.B352).

Table 12e Compounds of the formula B in which A is N, Hal is Br and $(R^3)_n$ corresponds to line R3b-12 of Table R3b and the meaning for the combination of $R^1$ and $R^2$ for each individual compound corresponds in each case to one line of Table B (compounds B.R3b-12.B1 to B.R3b12.B352).

Table 13e Compounds of the formula B in which A is N, Hal is Br and $(R^3)_n$ corresponds to line R3b-13 of Table R3b and the meaning for the combination of $R^1$ and $R^2$ for each individual compound corresponds in each case to one line of Table B (compounds B.R3b-13.B1 to B.R3b13.B352).

Table 14e Compounds of the formula B in which A is N, Hal is Br and $(R^3)_n$ corresponds to line R3b-14 of Table R3b and the meaning for the combination of $R^1$ and $R^2$ for each individual compound corresponds in each case to one line of Table B (compounds B.R3b-14.B1 to B.R3b14.B352).

Table 15e Compounds of the formula B in which A is N, Hal is Br and $(R^3)_n$ corresponds to line R3b-15 of Table R3b and the meaning for the combination of $R^1$ and $R^2$ for each individual compound corresponds in each case to one line of Table B (compounds B.R3b-15.B1 to B.R3b15.B352).

Table 16e Compounds of the formula B in which A is N, Hal is Br and $(R^3)_n$ corresponds to line R3b-16 of Table R3b and the meaning for the combination of $R^1$ and $R^2$ for each individual compound corresponds in each case to one line of Table B (compounds B.R3b-16.B1 to B.R3b16.B352).

Table 17e Compounds of the formula B in which A is N, Hal is Br and $(R^3)_n$ corresponds to line R3b-17 of Table R3b and the meaning for the combination of $R^1$ and $R^2$ for each individual compound corresponds in each case to one line of Table B (compounds B.R3b-17.B1 to B.R3b17.B352).

Table 18e Compounds of the formula B in which A is N, Hal is Br and $(R^3)_n$ corresponds to line R3b-18 of Table R3b and the meaning for the combination of $R^1$ and $R^2$ for each individual compound corresponds in each case to one line of Table B (compounds B.R3b-18.B1 to B.R3b18.B352).

Table 19e Compounds of the formula B in which A is N, Hal is Br and $(R^3)_n$ corresponds to line R3b-19 of Table R3b and the meaning for the combination of $R^1$ and $R^2$ for each individual compound corresponds in each case to one line of Table B (compounds B.R3b-19.B1 to B.R3b19.B352).

Table 20e Compounds of the formula B in which A is N, Hal is Br and $(R^3)_n$ corresponds to line R3b-20 of Table R3b and the meaning for the combination of $R^1$ and $R^2$ for each individual compound corresponds in each case to one line of Table B (compounds B.R3b-20.B1 to B.R3b20.B352).

Table 21e Compounds of the formula B in which A is N, Hal is Br and $(R^3)_n$ corresponds to line R3b-21 of Table R3b and the meaning for the combination of $R^1$ and $R^2$ for each individual compound corresponds in each case to one line of Table B (compounds B.R3b-21.B1 to B.R3b21.B352).

Table 22e Compounds of the formula B in which A is N, Hal is Br and $(R^3)_n$ corresponds to line R3b-22 of Table R3b and the meaning for the combination of $R^1$ and $R^2$ for each individual compound corresponds in each case to one line of Table B (compounds B.R3b-22.B1 to B.R3b22.B352).

Table 23e Compounds of the formula B in which A is N, Hal is Br and $(R^3)_n$ corresponds to line R3b-23 of Table R3b and the meaning for the combination of $R^1$ and $R^2$ for each individual compound corresponds in each case to one line of Table B (compounds B.R3b-23.B1 to B.R3b23.B352).

Table 24e Compounds of the formula B in which A is N, Hal is Br and $(R^3)_n$ corresponds to line R3b-24 of Table R3b and the meaning for the combination of $R^1$ and $R^2$ for each individual compound corresponds in each case to one line of Table B (compounds B.R3b-24.B1 to B.R3b24.B352).

Table 25e Compounds of the formula B in which A is N, Hal is Br and $(R^3)_n$ corresponds to line R3b-25 of Table R3b and the meaning for the combination of $R^1$ and $R^2$ for each individual compound corresponds in each case to one line of Table B (compounds B.R3b-25.B1 to B.R3b25.B352).

Table 26e Compounds of the formula B in which A is N, Hal is Br and $(R^3)_n$ corresponds to line R3b-26 of Table R3b and the meaning for the combination of $R^1$ and $R^2$ for each individual compound corresponds in each case to one line of Table B (compounds B.R3b-26.B1 to B.R3b26.B352).

Table 27e Compounds of the formula B in which A is N, Hal is Br and $(R^3)_n$ corresponds to line R3b-27 of Table R3b and the meaning for the combination of $R^1$ and $R^2$ for each individual compound corresponds in each case to one line of Table B (compounds B.R3b-27.B1 to B.R3b27.B352).

Table 28e Compounds of the formula B in which A is N, Hal is Br and $(R^3)_n$ corresponds to line R3b-28 of Table R3b and the meaning for the combination of $R^1$ and $R^2$ for each individual compound corresponds in each case to one line of Table B (compounds B.R3b-28.B1 to B.R3b28.B352).

Table 29e Compounds of the formula B in which A is N, Hal is Br and $(R^3)_n$ corresponds to line R3b-29 of Table R3b and the meaning for the combination of $R^1$ and $R^2$ for each individual compound corresponds in each case to one line of Table B (compounds B.R3b-29.B1 to B.R3b29.B352).

Table 30e Compounds of the formula B in which A is N, Hal is Br and $(R^3)_n$ corresponds to line R3b-30 of Table R3b and the meaning for the combination of $R^1$ and $R^2$ for each Table 31e Compounds of the formula B in which A is N, Hal is Br and $(R^3)_n$ corresponds to line R3b-31 of Table R3b and the meaning for the combination of $R^1$ and $R^2$ for each individual compound corresponds in each case to one line of Table B (compounds B.R3b-31.B1 to B.R3b31.B352).

Table 32e Compounds of the formula B in which A is N, Hal is Br and $(R^3)_n$ corresponds to line R3b-32 of Table R3b and the meaning for the combination of $R^1$ and $R^2$ for each individual compound corresponds in each case to one line of Table B (compounds B.R3b-32.B1 to B.R3b32.B352).

Table 33e Compounds of the formula B in which A is N, Hal is Br and $(R^3)_n$ corresponds to line R3b-33 of Table R3b and the meaning for the combination of $R^1$ and $R^2$ for each individual compound corresponds in each case to one line of Table B (compounds B.R3b-33.B1 to B.R3b33.B352).

Table 34e Compounds of the formula B in which A is N, Hal is Br and $(R^3)_n$ corresponds to line R3b-34 of Table R3b and the meaning for the combination of $R^1$ and $R^2$ for each individual compound corresponds in each case to one line of Table B (compounds B.R3b-34.B1 to B.R3b34.B352).

Table 35e Compounds of the formula B in which A is N, Hal is Br and $(R^3)_n$ corresponds to line R3b-35 of Table R3b and the meaning for the combination of $R^1$ and $R^2$ for each individual compound corresponds in each case to one line of Table B (compounds B.R3b-35.B1 to B.R3b35.B352).

Table 36e Compounds of the formula B in which A is N, Hal is Br and $(R^3)_n$ corresponds to line R3b-36 of Table R3b and the meaning for the combination of $R^1$ and $R^2$ for each individual compound corresponds in each case to one line of Table B (compounds B.R3b-36.B1 to B.R3b36.B352).

Table 37e Compounds of the formula B in which A is N, Hal is Br and $(R^3)_n$ corresponds to line R3b-37 of Table R3b and the meaning for the combination of $R^1$ and $R^2$ for each individual compound corresponds in each case to one line of Table B (compounds B.R3b-37.B1 to B.R3b37.B352).

Table 38e Compounds of the formula B in which A is N, Hal is Br and $(R^3)_n$ corresponds to line R3b-38 of Table R3b and the meaning for the combination of $R^1$ and $R^2$ for each individual compound corresponds in each case to one line of Table B (compounds B.R3b-38.B1 to B.R3b38.B352).

Table 39e Compounds of the formula B in which A is N, Hal is Br and $(R^3)_n$ corresponds to line R3b-39 of Table R3b and the meaning for the combination of $R^1$ and $R^2$ for each individual compound corresponds in each case to one line of Table B (compounds B.R3b-39.B1 to B.R3b39.B352).

Table 40e Compounds of the formula B in which A is N, Hal is Br and $(R^3)_n$ corresponds to line R3b-40 of Table R3b and the meaning for the combination of $R^1$ and $R^2$ for each individual compound corresponds in each case to one line of Table B (compounds B.R3b-40.B1 to B.R3b40.B352).

Table 41e Compounds of the formula B in which A is N, Hal is Br and $(R^3)_n$ corresponds to line R3b-41 of Table R3b and the meaning for the combination of $R^1$ and $R^2$ for each individual compound corresponds in each case to one line of Table B (compounds B.R3b-41.B1 to B.R3b41.B352).

Table 42e Compounds of the formula B in which A is N, Hal is Br and $(R^3)_n$ corresponds to line R3b-42 of Table R3b and the meaning for the combination of $R^1$ and $R^2$ for each individual compound corresponds in each case to one line of Table B (compounds B.R3b-42.B1 to B.R3b42.B352).

Table 43e Compounds of the formula B in which A is N, Hal is Br and $(R^3)_n$ corresponds to line R3b-43 of Table R3b and the meaning for the combination of $R^1$ and $R^2$ for each individual compound corresponds in each case to one line of Table B (compounds B.R3b-43.B1 to B.R3b43.B352).

Table 44e Compounds of the formula B in which A is N, Hal is Br and $(R^3)_n$ corresponds to line R3b-44 of Table R3b and the meaning for the combination of $R^1$ and $R^2$ for each individual compound corresponds in each case to one line of Table B (compounds B.R3b-44.B1 to B.R3b44.B352).

Table B can be found below.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-haloalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. 1-alkenyl such as 1-($C_2$-$C_6$)-alkenyl, 1-($C_2$-$C_4$)-alkenyl or 1-$C_3$-alkenyl means that the alkenyl group is attached to the respective skeleton via a carbon atom of the double bond (e.g. CH=CHCH$_3$).

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "phenyl-$C_1$-$C_6$-alkyl" refers to alkyl having 1 to 6 carbon atoms (as defined above), wherein one hydrogen atom of the alkyl radical is replaced by a phenyl radical. Likewise, the terms "phenyl-$C_2$-$C_6$-alkenyl" and "phenyl-$C_2$-$C_6$-alkynyl" refer to alkenyl and alkynyl, respectively, wherein one hydrogen atom of the aforementioned radicals is replaced by a phenyl radical.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "$C_1$-$C_6$-haloalkylsulfinyl" refers to straight-chain or branched haloalkyl group having 1 to 6 carbon atoms (as defined above), bonded through a —S(=O)— moiety, at any position in the haloalkyl group.

The term "$C_1$-$C_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "$C_1$-$C_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "$C_3$-$C_8$-cycloalkyl-$C_3$-$C_8$-cycloalkyl" refers to a cycloalkyl radical having 3 to 8 carbon atoms (as defined above), which is substituted by a further cycloalkyl radical having 3 to 8 carbon atoms.

The term "$C_3$-$C_8$-cycloalkoxy" refers to a cycloalkyl radical having 3 to 8 carbon atoms (as defined above), which is bonded via an oxygen.

The term "C(=O)—$C_1$-$C_4$-alkyl" refers to a radical which is attached through the carbon atom of the group C(=O) as indicated by the number valence of the carbon atom. The number of valence of carbon is 4, that of nitrogen is 3. Likewise the following terms are to be construed: NH($C_1$-$C_4$-alkyl), N($C_1$-$C_4$-alkyl)$_2$, NH($C_3$-$C_6$-cycloalkyl), N($C_3$-$C_6$-cycloalkyl)$_2$, C(=O)OH, C(=O)—O—$C_1$-$C_4$-alkyl, C(=O)—NH($C_1$-$C_4$-alkyl), C(=O)—N($C_1$-$C_4$-alkyl)$_2$, C(=O)—NH($C_3$-$C_6$-cycloalkyl), C(=O)—N($C_3$-$C_6$-cycloalkyl)$_2$.

The term "saturated or partially unsaturated 3-, 4-5-, 6- or 7-membered carbocycle" is to be understood as meaning both saturated or partially unsaturated carbocycles having 3, 4, 5, 6 or 7 ring members. Examples include cyclopropyl, cyclopentyl, cyclopentenyl, cyclopentadienyl, cyclohexyl, cyclohexenyl, cyclohexadienyl, cycloheptyl, cycloheptenyl, cycloheptadienyl, and the like.

The term "saturated or partially unsaturated 3-, 4-, 5-, 6-, or 7-membered heterocycle, wherein the ring member atoms of the heterocycle include besides carbon atoms 1, 2, 3 or 4 heteroatoms independently selected from the group of N, O and S", is to be understood as meaning both saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3- dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and
a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals; and
The term "5- or 6-membered heteroaryl" refers to aromatic ring systems including besides carbon atoms, 1, 2, 3 or 4 heteroatoms independently selected from the group consisting of N, O and S, for example,
a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or
a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

A according to the invention is N or CH. According to one embodiment A is N. According to a further embodiment A is CH.

D according to the present invention is hydrogen, halogen or $SR^D$, wherein $R^D$ is hydrogen, CN, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl.

In a preferred embodiment D is hydrogen, halogen, SH, SCN or S—$CH_2$—CH=$CH_2$ (S-allyl).

According to one embodiment D is hydrogen.

According to a further embodiment, D is halogen, in particular iodine. According to another preferred embodiment D is $SR^D$. According to a particular embodiment, $R^D$ is H. In yet another preferred embodiment $R^D$ is CN. In a further preferred embodiment $R^D$ is —$CH_2$—CH=$CH_2$.

$R^1$ according to the invention is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl-$C_2$-$C_4$-alkenyl or phenyl-$C_2$-$C_4$-alkynyl; wherein the aliphatic moieties of $R^1$ are not further substituted or carry one, two, three or up to the maximum possible number of identical or different groups $R^{1a}$ which independently of one another are selected from $R^{1a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from $R^{1b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to a further embodiment of the invention, $R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl-$C_2$-$C_4$-alkenyl and phenyl-$C_2$-$C_4$-alkynyl, wherein the $R^1$ are in each case unsubstituted or are substituted by $R^{1a}$ and/or $R^{1b}$ as defined and preferably defined herein. Specific embodiments thereof can be found in the below Table P1.

According to a further embodiment of the invention, $R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, wherein the $R^1$ are in each case unsubstituted or are substituted by $R^{1a}$ and/or $R^{1b}$ as defined and preferably defined herein. Specific embodiments thereof can be found in the below Table P1.

According to one particular embodiment, $R^1$ is $C_1$-$C_6$-alkyl, in particular $C_1$-$C_4$-alkyl, such as $CH_3$, $C_2H_5$, $CH(CH_3)_2$ or $C(CH_3)_3$. A further embodiment relates to compounds, wherein $R^1$ is $C_1$-$C_6$-alkyl, in particular $C_1$-$C_4$-alkyl, that is substituted by one, two or three or up to the maximum possible number of identical or different groups $R^{1a}$, as defined and preferably defined herein. According to a specific embodiment thereof, $R^1$ is $C_1$-$C_6$-haloalkyl, in particular $C_1$-$C_4$-haloalkyl, more particularly $C_1$-$C_2$-haloalkyl such as $CF_3$ or $CHF_2$. According to a further specific embodiment thereof, $R^1$ is $C_1$-$C_4$-alkoxy-C, —$C_6$-alkyl, in particular $C_1$-$C_4$-alkoxy-$C_1$-$C_4$-alkyl, such as $CH_2$—$OCH_3$. Further specific embodiments thereof can be found in the below Table P1.

According to still another embodiment, $R^1$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^1$ is $C_3$-$C_8$-cycloalkyl-$C_1$-$C_6$-alkyl, in particular $C_3$-$C_6$-cycloalkyl-$C_1$-$C_4$-alkyl, that is substituted by one, two or three or up to the maximum possible number of identical or different groups $R^{1a}$ in the alkyl moiety and/or substituted by one, two, three four or five or up to the maximum possible number of identical or different groups $R^{1b}$ in the cycloalkyl moiety. $R^{1a}$ are in each case as defined and preferably defined herein. Specific embodiments thereof can be found in the below Table P1.

According to another embodiment, $R^1$ is 1-($C_2$-$C_6$)-alkenyl, in particular 1-($C_2$-$C_4$)-alkenyl, such as $CH$=$CH_2$, $CH$=$CHCH_3$ or $C(CH_3)$=$CH_2$. In a special embodiment $R^1$ is $CH$=$CH_2$. In a further special embodiment $R^1$ is $CH$=$CHCH_3$. In a further special embodiment $R^1$ is $C(CH_3)$=$CH_2$. In a further special embodiment $R^1$ is $C(CH_3)$=$C(CH_3)H$. In a further special embodiment $R^1$ is $C(CH_3)$=$C(CH_3)_2$. In a further special embodiment $R^1$ is $CH$=$C(CH_3)_2$. A further embodiment relates to compounds, wherein $R^1$ is 1-($C_2$-$C_6$)-alkenyl, in particular 1-($C_2$-$C_4$)-alkenyl, that is substituted by one, two or three or up to the maximum possible number of identical or different groups $R^{1a}$ as defined and preferably defined herein. According to a specific embodiment thereof, $R^1$ is 1-($C_2$-$C_6$)-haloalkenyl, in particular 1-($C_2$-$C_4$)-haloalkenyl. In a special embodiment $R^1$ is fully or partially halogenated $C_2$-alkenyl. In a further special embodiment $R^1$ is fully or partially halogenated 1-$C_3$-alkenyl. In a special embodiment $R^1$ is $C(Cl)$=$CH_2$. In a special embodiment $R^1$ is $C(Cl)$=$CClH$. In a further special embodiment $R^1$ is $C(H)$=$CH(Cl)$. In a further special embodiment $R^1$ is $C(H)$=$CCl_2$. In a further special embodiment $R^1$ is $C(Cl)$=$CCl_2$. In a special embodiment $R^1$ is $C(Cl)$=$CH_2$. In a further special embodiment $R^1$ is $C(H)$=$CH(F)$. In a further special embodiment $R^1$ is $C(H)$=$CF_2$. In a further special embodiment $R^1$ is $C(F)$=$CF_2$. In a special embodiment $R^1$ is $C(F)$=$CFH$. According to a further specific embodiment $R^1$ is 1-($C_2$-$C_6$)-alkenyl, preferably 1-($C_2$-$C_4$)-alkenyl, substituted by OH, more preferably, $CH$=$CHCH_2OH$. In a special embodiment $R^1$ is $CH$=$CHOH$. In a further special embodiment $R^1$ is $CH$=$CHCH_2OH$. According to a further specific embodiment $R^1$ is $C_1$-$C_4$-alkoxy-1-($C_2$-$C_6$)-alkenyl, more preferably $C_1$-$C_4$-alkoxy-1-($C_2$-$C_4$)-alkenyl. In a special embodiment $R^1$ is $CH$=$CHOCH_3$. In a further special embodiment $R^1$ is $CH$=$CHCH_2OCH_3$. According to a further specific embodiment $R^1$ is $C_1$-$C_4$-haloalkoxy-1-($C_2$-$C_6$)alkenyl, more preferably $C_1$-$C_4$-haloalkoxy-1-($C_2$-$C_4$)-alkenyl. In a further special embodiment $R^1$ is $CH$=$CHCH_2OCF_3$. In a further special embodiment $R^1$ is $CH$=$CHCH_2OCCl_3$. According to a further specific embodiment $R^1$ is $C_3$-$C_8$-cycloalkyl-1-($C_2$-$C_6$)-alkenyl, preferably $C_3$-$C_6$-cycloalkyl-1-($C_2$-$C_4$)-alkenyl. According to a further specific embodiment $R^1$ is $C_3$-$C_6$-halocycloalkyl-1-($C_2$-$C_4$)alkenyl, preferably $C_3$-$C_8$-halocycloalkyl-1-($C_2$-$C_6$)-alkenyl. In a further special embodiment $R^1$ is $CH$=$CH(C_3H_5)$. In a further special embodiment $R^1$ is $CH$=$CH(C_4H_7)$. In a further special embodiment $R^1$ is $CH$=$C(H)(ClC_3H_4)$. In a further special embodiment $R^1$ is $CH$=$C(H)(FC_3H_4)$. In a further special embodiment $R^1$ is $CH$=$C(H)(ClC_4H_6)$. In a further special embodiment $R^1$ is $CH$=$C(H)(FC_4H_6)$. Further specific embodiments thereof can be found in the below Table P1 According to one specific embodiment thereof, $R^1$ is A, wherein A is #-$CR'$=$CR''R'''$, wherein # is the point of attachment and R', R'' and R''' are independently selected from hydrogen, $C_1$-$C_4$-alkyl, $C_1$-$C_4$-haloalkyl, halogen, CN, nitro, $C_1$-$C_4$-alkoxy, $C_1$-$C_4$-halogenalkoxy, $C_3$-$C_6$-cycloalkyl and $C_3$-$C_8$-halocycloalkyl, in particular Cl, F, $C_1$-$C_4$-alkyl, $C_1$-$C_4$-haloalkyl and $C_3$-cycloalkyl.

According to still another embodiment, $R^1$ is 1-($C_2$-$C_6$)-alkynyl, in particular 1-($C_2$-$C_4$)-alkynyl, such as C≡CH or C≡CCH$_3$. According to one another embodiment $R^1$ is 1-($C_2$-$C_6$)-alkynyl, for example preferably CCH. In a special embodiment $R^1$ is CCH. In a further special embodiment $R^1$ is CCCH$_3$. In a further special embodiment $R^1$ is CCCH$(CH_3)_2$. In a further special embodiment $R^1$ is CCC$(CH_3)_3$. In a further special embodiment $R^1$ is CC($C_2H_5$).

A further embodiment relates to compounds, wherein $R^1$ is 1-($C_2$-$C_6$)-alkynyl, in particular 1-($C_2$-$C_4$)-alkynyl, that is substituted by one, two or three or up to the maximum possible number of identical or different groups $R^{1a}$, as defined and preferably defined herein. According to a specific embodiment thereof, $R^1$ is 1-($C_2$-$C_6$)-haloalkynyl, in particular 1-($C_2$-$C_4$)-haloalkynyl. In a special embodiment $R^1$ is fully or partially halogenated $C_2$-alkynyl. In a further special embodiment $R^1$ is fully or partially halogenated 1-$C_3$-alkynyl. In a further special embodiment $R^1$ is CCCl. In a further special embodiment $R^1$ is CCBr. In a further special embodiment $R^1$ is CC—I. According to a further specific embodiment thereof, $R^1$ is $C_3$-$C_8$-cycloalkyl-1-($C_2$-$C_6$)-alkynyl or $C_3$-$C_8$-halocycloalkyl-1-($C_2$-$C_6$)-alkynyl, in particular $C_3$-$C_6$-cycloalkyl-1-($C_2$-$C_4$)-alkynyl or $C_3$-$C_6$-halocycloalkyl-1-($C_2$-$C_4$)-alkynyl. In a special embodiment $R^1$ is CC($C_3H_5$). In a special embodiment $R^1$ is CC($C_4H_7$). In a special embodiment $R^1$ is CCCH$_2(C_3H_5)$. In a special embodiment $R^1$ is CC—$CH_2$—$C_4H_7$). According to a further specific embodiment $R^1$ is $C_3$-$C_6$-halocycloalkyl-$C_2$-$C_4$-alkynyl, preferably $C_3$-$C_8$-halocycloalkyl-$C_2$-$C_6$-alkynyl. In a special embodiment $R^1$ is CC($C_3H_4Cl$). In a special embodiment $R^1$ is CC($C_3H_4F$). In a special embodiment $R^1$ is CC($C_4H_6Cl$). In a special embodiment $R^1$ is CC($C_4H_6F$). According to a further specific embodiment $R^1$ is 1-($C_2$-$C_6$)-alkynyl, preferably 1-($C_2$-$C_4$)-alkynyl, substituted by OH. In a special embodiment $R^1$ is CC—$C(OH)(CH_3)_2$. According to a further specific embodiment $R^1$ is $C_1$-$C_4$-alkoxy-1-($C_2$-$C_6$)-alkynyl, more preferably $C_1$-$C_4$-alkoxy-1-($C_2$-$C_4$)-alkynyl. In a further special embodiment $R^1$ is CCOCH$_3$. In a special embodiment $R^1$ is CC—$CH_2$—$OCH_3$. In a special embodiment $R^1$ is CC—$C(OCH_3)(CH_3)_2$. According to a further specific embodiment $R^1$ is $C_1$-$C_4$-haloalkoxy-1-($C_2$-$C_6$)-alkynyl, more preferably $C_1$-$C_4$-haloalkoxy-1-($C_2$-$C_4$)-alkynyl. In a further special embodiment $R^1$ is CC—$CH_2OCCl_3$. In a further special embodiment $R^1$ is CC—$CH_2OCF_3$.

According to one specific embodiment thereof, $R^1$ is A, wherein A is

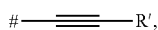

wherein # is the point of attachment and R' is selected from hydrogen, $C_1$-$C_4$-alkyl, $C_1$-$C_4$-haloalkyl, halogen, CN, nitro, $C_1$-$C_4$-alkoxy, $C_1$-$C_4$-halogenalkoxy, $C_3$-$C_6$-cycloalkyl and $C_3$-$C_8$-halocycloalkyl, in particular Cl, F, $C_1$-$C_4$-alkyl, $C_1$-$C_4$-haloalkyl and $C_3$-cycloalkyl. Further specific embodiments thereof can be found in the below Table P1.

According to still another embodiment, $R^1$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{1a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{1b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. According to still another embodiment, $R^1$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{1a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{1b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P1.

According to still another embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{1b}$ as defined and preferably defined herein. According to a specific embodiment thereof, $R^1$ is $C_3$-$C_8$-halocycloalkyl, in particular $C_3$-$C_6$-halocycloalkyl, such as halocyclopropyl, in particular 1-F-cyclopropyl or 1-Cl-cyclopropyl. According to a further specific embodiment thereof, $R^1$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{1b}$ as defined and preferably defined herein, such as 1-cyclopropyl-cyclopropyl or 2-cyclopropyl-cyclopropyl. Specific embodiments thereof can be found in the below Table P1.

In a further embodiment of the invention, $R^1$ is selected from hydrogen, $C_1$-$C_6$-alkyl, 1-($C_2$-$C_6$)alkenyl, 1-($C_2$-$C_6$)-alkynyl and $C_3$-$C_6$-cycloalkyl, wherein the $R^1$ are in each case unsubstituted or are substituted by $R^{1a}$ or $R^{1b}$ as defined and preferably defined herein. In each case, the substituents may also have the preferred meanings for the respective substituent as defined above. Specific embodiments thereof can be found in the below Table P1.

In still a further embodiment of the invention, $R^1$ is selected from $C_1$-$C_6$-alkyl, 1-($C_2$-$C_6$)-alkenyl, 1-($C_2$-$C_6$)-alkynyl and $C_3$-$C_6$-cycloalkyl, wherein the $R^1$ are in each case unsubstituted or are substituted by $R^{1a}$ or $R^{1b}$ as defined and preferably defined herein. In each case, the substituents may also have the preferred meanings for the respective substituent as defined above. Specific embodiments thereof can be found in the below Table P1.

Specifically, it may be preferred, if $R^1$ is selected from $C_1$-$C_4$-alkyl, such as methyl, ethyl, n-propyl, iso-propyl, tert-butyl, $CH_2C(CH_3)_3$ and $CH_2CH(CH_3)_2$, $C_1$-$C_4$-haloalkyl, such as $CF_3$, 1-($C_2$-$C_6$)-alkenyl, 1-($C_2$-$C_6$)-alkynyl, such as C≡$CCH_3$, and $C_3$-$C_6$-cycloalkyl, such as cyclopropyl.

Particularly preferred embodiments of $R^1$ according to the invention are in Table P1 below, wherein each line of lines P1-1 to P1-135 corresponds to one particular embodiment of the invention, wherein P1-1 to P1-135 are also in any combination a preferred embodiment of the present invention.

TABLE P1

| line | $R^1$ |
| --- | --- |
| P1-1 | $CH_3$ |
| P1-2 | $CH_2CH_3$ |
| P1-3 | $CH_2CH_2CH_3$ |
| P1-4 | $CH(CH_3)_2$ |
| P1-5 | $C(CH_3)_3$ |
| P1-6 | $CH(CH_3)CH_2CH_3$ |
| P1-7 | $CH_2CH(CH_3)_2$ |
| P1-8 | $CH_2CH_2CH_2CH_3$ |
| P1-9 | $CF_3$ |
| P1-10 | $CHF_2$ |
| P1-11 | $CH_2F$ |
| P1-12 | $CHCl_2$ |
| P1-13 | $CH_2Cl$ |
| P1-14 | $CH_2OH$ |
| P1-15 | $CH_2CH_2OH$ |
| P1-16 | $CH_2CH_2CH_2OH$ |
| P1-17 | $CH(CH_3)CH_2OH$ |
| P1-18 | $CH_2CH(CH_3)OH$ |
| P1-19 | $CH_2CH_2CH_2CH_2OH$ |
| P1-20 | $CH(CH_3)CN$ |
| P1-21 | $CH_2CH_2CN$ |
| P1-22 | $CH_2CN$ |
| P1-23 | $CH_2CH_2CN$ |
| P1-24 | $CH_2CH_2CH_2CN$, |
| P1-25 | $CH(CH_3)CH_2CN$ |
| P1-26 | $CH_2CH(CH_3)CN$ |
| P1-27 | $CH_2CH_2CH_2CH_2CN$ |
| P1-28 | $CH_2OCH_3$ |
| P1-29 | $CH_2OCH_2CH_3$ |
| P1-30 | $CH(CH_3)OCH_3$ |
| P1-31 | $CH(CH_3)OCH_2CH_3$ |
| P1-32 | $CH_2CH_2OCH_2CH_3$ |
| P1-33 | $CH_2OCF_3$ |
| P1-34 | $CH_2CH_2OCF_3$ |
| P1-35 | $CH_2OCCl_3$ |
| P1-36 | $CH_2CH_2OCCl_3$ |
| P1-37 | CH=$CH_2$ |
| P1-38 | $CH_2$CH=$CH_2$ |
| P1-39 | $CH_2$CH=$CHCH_3$ |
| P1-40 | $CH_2C(CH_3)$=$CH_2$ |
| P1-41 | $CH_2C(CH_3)$=$CHCH_3$ |
| P1-42 | $CH_2C(CH_3)$=$C(CH_3)_2$ |
| P1-43 | CH=$CHCH_3$ |
| P1-44 | C($CH_3$)=$CH_2$ |
| P1-45 | CH=$C(CH_3)_2$ |
| P1-46 | C($CH_3$)=$C(CH_3)_2$ |
| P1-47 | C($CH_3$)=$CH(CH_3)$ |
| P1-48 | C(Cl)=$CH_2$ |
| P1-49 | C(H)=CHCl |
| P1-50 | C(Cl)=CHCl |
| P1-51 | CH=$CCl_2$ |
| P1-52 | C(Cl)=$CCl_2$ |
| P1-53 | C(H)=CH(F) |
| P1-54 | C(H)=$CF_2$ |
| P1-55 | C(F)=$CF_2$ |
| P1-56 | C(F)=CHF |
| P1-57 | CH=$CHCH_2OH$ |

TABLE P1-continued

| line | R$^1$ |
|---|---|
| P1-58 | CH=CHOCH$_3$ |
| P1-59 | CH=CHCH$_2$OCH$_3$ |
| P1-60 | CH=CHCH$_2$OCF$_3$ |
| P1-61 | CH=CHCH$_2$OCCl$_3$ |
| P1-62 | CH=CH(C$_3$H$_5$) |
| P1-63 | CH=CH(C$_4$H$_7$) |
| P1-64 | CH=CH(1-Cl—C$_3$H$_4$) |
| P1-65 | CH=CH(1-F—C$_3$H$_4$) |
| P1-66 | CH=CH(1-Cl—C$_4$H$_6$) |
| P1-67 | CH=CH(1-F—C$_4$H$_6$) |
| P1-68 | C≡CH |
| P1-69 | C≡CCH$_3$ |
| P1-70 | CH$_2$C≡CCH$_3$ |
| P1-71 | CH$_2$C≡CH |
| P1-72 | CH$_2$C≡CCH$_2$CH$_3$ |
| P1-73 | C≡CCH(CH$_3$)$_2$ |
| P1-74 | C≡CC(CH$_3$)$_3$ |
| P1-75 | C≡C(C$_3$H5) |
| P1-76 | C≡C(C$_4$H$_7$) |
| P1-77 | C≡C(1-Cl—C$_3$H$_4$) |
| P1-78 | C≡C(1-Cl—C$_4$H$_6$) |
| P1-79 | C≡CCl |
| P1-80 | C≡CBr |
| P1-81 | C≡C—I |
| P1-82 | CH$_2$C≡CCl |
| P1-83 | CH$_2$C≡CBr |
| P1-84 | CH$_2$C≡C—I |
| P1-85 | C≡CCH$_2$OCH$_3$ |
| P1-86 | C≡CCH(OH)CH$_3$ |
| P1-87 | C≡CCH(OCH$_3$)CH$_3$ |
| P1-88 | C≡COCH$_3$ |
| P1-89 | CH$_2$C≡COCH$_3$ |
| P1-90 | C≡CCH$_2$OCCl$_3$ |
| P1-91 | C≡CCH$_2$OCF$_3$ |
| P1-92 | C≡CCH$_2$(C$_3$H$_5$) |
| P1-93 | C≡CCH$_2$(C$_4$H$_7$) |
| P1-94 | C≡C(1-Cl—C$_3$H$_4$) |
| P1-95 | C≡C(1-F—C$_3$H$_4$) |
| P1-96 | C≡C(1-Cl—C$_4$H$_6$) |
| P1-97 | C≡C(1-F—C$_4$H$_6$) |
| P1-98 | C$_3$H$_5$ (cyclopropyl) |
| P1-99 | C$_4$H$_7$ (cyclobutyl) |
| P1-100 | C$_5$H$_9$ (cyclopentyl) |
| P1-101 | cyclohexyl |
| P1-102 | CH(CH$_3$)—C$_3$H$_5$(CH(CH$_3$)-cyclopropyl) |
| P1-103 | CH$_2$—C$_3$H$_5$ (CH$_2$-cyclopropyl) |
| P1-104 | 1-(Cl)-cyclopropyl |
| P1-105 | 1-(F)-cyclopropyl |
| P1-106 | 1-(CH$_3$)-cyclopropyl |
| P1-107 | 1-(CN)-cyclopropyl |
| P1-108 | 2-(Cl)-cyclopropyl |
| P1-109 | 2-(F)-cyclopropyl |
| P1-110 | 1-(Cl)-cyclobutyl |
| P1-111 | 1-(F)-cyclobutyl |
| P1-112 | 2-(Cl)-cyclobutyl |
| P1-113 | 3-(Cl)-cyclobutyl |
| P1-114 | 2-(F)-cyclobutyl |
| P1-115 | 3-(F)-cyclobutyl |
| P1-116 | 3,3-Cl$_2$-cyclobutyl |
| P1-117 | 3,3-F$_2$-cyclobutyl |
| P1-118 | 2-(CH$_3$)-cyclopropyl |
| P1-119 | 1-(CH$_3$)-cyclobutyl |
| P1-120 | 2-(CH$_3$)-cyclobutyl |
| P1-121 | 3-(CH$_3$)-cyclobutyl |
| P1-122 | 3,3-(CH$_3$)$_2$-cyclobutyl |
| P1-123 | 2-(CN)-cyclopropyl |
| P1-124 | 1-cyclopropyl-cyclopropyl |
| P1-125 | 2-cyclopropyl-cyclopropyl |
| P1-126 | CH(CH$_3$)(cyclobutyl) |
| P1-127 | CH$_2$-(cyclobutyl) |
| P1-128 | CH$_2$CH$_2$-(cyclopropyl) |
| P1-129 | CH$_2$CH$_2$-(cyclobutyl) |
| P1-130 | CH$_2$-(1-Cl-cyclopropyl) |
| P1-131 | CH$_2$-(1-F-cyclopropyl) |
| P1-132 | CH$_2$-(1-Cl-cyclobutyl) |
| P1-133 | CH$_2$-(1-F-cyclobutyl) |
| P1-134 | CHCH$_3$-(1-Cl-cyclopropyl) |
| P1-135 | C(CH$_3$)$_2$-(1-F-cyclopropyl) |

$R^{1a}$ are the possible substituents for the aliphatic moieties of $R^1$.

$R^{1a}$ according to the invention is independently selected from halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy.

According to one embodiment $R^{1a}$ is independently selected from halogen, OH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{1a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

$R^{1b}$ are the possible substituents for the cycloalkyl and/or phenyl moieties of $R^1$.

$R^{1b}$ according to the invention is independently selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to one embodiment thereof $R^{1b}$ is independently selected from halogen, CN, nitro, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{1b}$ is independently selected from F, Cl, OH, CN, nitro, CH$_3$, OCH$_3$, cyclopropyl, 1-F-cyclopropyl, 1-Cl-cyclopropyl and halogenmethoxy.

According to the invention, $R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl, wherein the aliphatic moieties of $R^2$ are not further substituted or carry one, two, three or up to the maximum possible number of identical or different groups $R^{2a}$ which independently of one another are selected from halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy; and wherein the cycloalkyl and/or phenyl moieties of $R^2$ are not further substituted or carry one, two, three, four, five or up to the maximum number of identical or different groups $R^{2b}$ which independently of one another are selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to one embodiment, $R^2$ is H.

According to a further embodiment of the invention, $R^2$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the $R^2$ are in each case unsubstituted or are substituted by $R^{2a}$ and/or $R^{2b}$ as defined and preferably defined herein. Specific embodiments thereof can be found in the below Table P2.

According to a further embodiment of the invention, $R^2$ is selected from H, $C_1$-$C_4$-alkyl, $C_2$-$C_6$-alkenyl, in particular CH$_2$CH=CH$_2$, and $C_2$-$C_6$-alkynyl, in particular CH$_2$C≡CH. Specific embodiments thereof can be found in the below Table P2.

According to one particular embodiment, $R^2$ is $C_1$-$C_6$-alkyl, in particular $C_1$-$C_4$-alkyl, such as CH$_3$, C$_2$H$_5$, CH(CH$_3$)$_2$, CH$_2$CH$_2$CH$_3$, CH$_2$CH$_2$CH$_2$CH$_3$, CH$_2$CH(CH$_3$)$_2$. A further embodiment relates to compounds, wherein $R^2$ is $C_1$-$C_6$-alkyl, in particular $C_1$-$C_4$-alkyl, that is substituted by one, two or three or up to the maximum possible number of identical or different groups $R^{2a}$, as defined and preferably defined herein. According to a specific embodiment thereof, $R^2$ is $C_1$-$C_6$-haloalkyl, in particular $C_1$-$C_4$-haloalkyl, more particularly $C_1$-$C_2$-haloalkyl. According to a further specific embodiment thereof, $R^2$ is $C_1$-$C_4$-alkoxy-$C_1$-$C_6$-alkyl, in particular $C_1$-$C_4$-alkoxy-$C_1$-$C_4$-alkyl, such as $CH_2OCH_3$ or $CH_2CH_2OCH_3$. According to still a further specific embodiment thereof, $R^2$ is hydroxy-$C_1$-$C_6$-alkyl, in particular hydroxyl-$C_1$-$C_4$-alkyl, such as $CH_2CH_2OH$. Further specific embodiments thereof can be found in the below Table P2

According to still another embodiment, $R^2$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^2$ is $C_3$-$C_8$-cycloalkyl-$C_1$-$C_6$-alkyl, in particular $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{2a}$ in the alkyl moiety and/or substituted by one, two, three four or five or up to the maximum possible number of identical or different groups $R^{2b}$ in the cycloalkyl moiety. $R^{2a}$ and $R^{2b}$ are in each case as defined and preferably defined herein. Specific embodiments thereof can be found in the below Table P2.

According to another embodiment, $R^2$ is $C_2$-$C_6$-alkenyl, in particular $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_6$-alkenyl, in particular $C_2$-$C_4$-alkenyl, that is substituted by one, two or three or up to the maximum possible number of identical or different groups $R^{2a}$ as defined and preferably defined herein. According to a specific embodiment thereof, $R^2$ is $C_2$-$C_6$-haloalkenyl, in particular $C_2$-$C_4$-haloalkenyl, such as $CH_2C(Cl)=CH_2$ and $CH_2C(H)=CHCl$. According to a further specific embodiment thereof, $R^2$ is $C_3$-$C_8$-cycloalkyl-$C_2$-$C_6$-alkenyl or $C_3$-$C_8$-halocycloalkyl-$C_2$-$C_6$-alkenyl, in particular $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P2.

According to still another embodiment, $R^2$ is $C_2$-$C_6$-alkynyl, in particular $C_2$-$C_4$-alkynyl, such as $CH_2C\equiv CH$ or $CH_2C\equiv CCH_3$. A further embodiment relates to compounds, wherein $R^2$ is $C_2$-$C_6$-alkynyl, in particular $C_2$-$C_4$-alkynyl, that is substituted by one, two or three or up to the maximum possible number of identical or different groups $R^{2a}$, as defined and preferably defined herein. According to a specific embodiment thereof, $R^2$ is $C_2$-$C_6$-haloalkynyl, in particular $C_2$-$C_4$-haloalkynyl. According to a further specific embodiment thereof, $R^2$ is $C_3$-$C_8$-cycloalkyl-$C_2$-$C_6$-alkynyl or $C_3$-$C_8$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P2.

According to still another embodiment, $R^2$ is phenyl-$C_1$-$C_4$-alkyl, in particular phenyl-$C_1$-$C_2$-alkyl, such as benzyl, wherein the alkyl moiety in each case is unsubstituted or carries one, two or three $R^{2a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{2b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P2.

According to still another embodiment, $R^2$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{2a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{2b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{2a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{2b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^2$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{2b}$ as defined and preferably defined herein. According to a specific embodiment thereof, $R^2$ is $C_3$-$C_8$-halocycloalkyl, in particular $C_3$-$C_6$-halocycloalkyl, such as halocyclopropyl, in particular 1-F-cyclopropyl or 1-Cl-cyclopropyl. According to a further specific embodiment thereof, $R^2$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{2b}$ as defined and preferably defined herein.

According to still another embodiment, $R^2$ is phenyl, wherein the phenyl is unsubstituted or carries one, two, three, four or five independently selected $R^{2b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

In a further embodiment of the invention, $R^2$ is selected from hydrogen, $C_1$-$C_6$-alkyl, $C_2$-$C_6$-alkenyl and $C_2$-$C_6$-alkynyl, wherein the $R^2$ are in each case unsubstituted or are substituted by $R^{2a}$ and/or $R^{2b}$ as defined and preferably defined herein. In each case, the substituents may also have the preferred meanings for the respective substituent as defined above. Specific embodiments thereof can be found in the below Table P2.

Particularly preferred embodiments of $R^2$ according to the invention are in Table P2 below, wherein each line of lines P2-1 to P2-88 corresponds to one particular embodiment of the invention, wherein P2-1 to P2-88 are also in any combination a preferred embodiment of the present invention.

TABLE P2

| line | $R^2$ |
| --- | --- |
| P2-1 | H |
| P2-2 | $CH_3$ |
| P2-3 | $CH_2CH_3$ |
| P2-4 | $CH(CH_3)_2$ |

TABLE P2-continued

| line | $R^2$ |
|---|---|
| P2-5 | $CH_2CH_2CH_3$ |
| P2-6 | $CH_2CH_2CH_2CH_3$ |
| P2-7 | $CH_2CH(CH_3)_2$ |
| P2-8 | $CF_3$ |
| P2-9 | $CHF_2$ |
| P2-10 | $CFH_2$ |
| P2-11 | $CCl_3$. |
| P2-12 | $CHCl_2$ |
| P2-13 | $CClH_2$ |
| P2-14 | $CH_2CF_3$ |
| P2-15 | $CH_2CHF_2$ |
| P2-16 | $CH_2CCl_3$ |
| P2-17 | $CH_2CHCl_2$ |
| P2-18 | $CH_2CH_2OCH_2CH_3$ |
| P2-19 | $CH(CH_3)OCH_2CH_3$ |
| P2-20 | $CH(CH_3)OCH_3$ |
| P2-21 | $CH_2OCH_3$ |
| P2-22 | $CH_2CH_2OCH_3$ |
| P2-23 | $CH_2OCF_3$ |
| P2-24 | $CH_2CH_2OCF_3$ |
| P2-25 | $CH_2OCCl_3$ |
| P2-26 | $CH_2CH_2OCCl_3$ |
| P2-27 | $CH_2CH_2OH$ |
| P2-28 | $CH_2OH$ |
| P2-29 | $CH_2CH_2CH_2OH,$ |
| P2-30 | $CH(CH_3)CH_2OH$ |
| P2-31 | $CH_2CH(CH_3)OH$ |
| P2-32 | $CH_2CH_2CH_2CH_2OH$ |
| P2-33 | $CH_2CN,$ |
| P2-34 | $CH_2CH_2CN,$ |
| P2-35 | $CH_2CH_2CH_2CN,$ |
| P2-36 | $CH(CH_3)CH_2CN,$ |
| P2-37 | $CH_2CH(CH_3)CN,$ |
| P2-38 | $CH_2CH_2CH_2CH_2CN$ |
| P2-39 | $CH=CH_2$ |
| P2-40 | $C(CH_3)=CH_2$ |
| P2-41 | $CH=CHCH_3$ |
| P2-42 | $CH_2CH=CH_2$ |
| P2-43 | $CH_2CH=CHCH_3$ |
| P2-44 | $CH_2C(CH_3)=CH_2$ |
| P2-45 | $C(CH_3)=CH(CH_3)$ |
| P2-46 | $C(CH_3)=C(CH_3)_2$ |
| P2-47 | $CH=C(CH_3)_2$ |
| P2-48 | $CH=C(Cl)_2$ |
| P2-49 | $C(CH_3)=CH_2$ |
| P2-50 | $CH_2C(Cl)=CH_2$ |
| P2-51 | $CH_2C(H)=CHCl$ |
| P2-52 | $CH=CHCH_2OH$ |
| P2-53 | $CH=C(CH_3)OH$ |
| P2-54 | $CH=CHOCH_3$ |
| P2-55 | $CH=CHCH_2OCH_3$ |
| P2-56 | $CH_2CH=CHCH_2OCH_3$ |
| P2-57 | $CH=CHOCF_3$ |
| P2-58 | $CH=CHCH_2OCF_3$ |
| P2-59 | $CH=CHOCCl_3$ |
| P2-60 | $CH=CHCH_2OCCl_3$ |
| P2-61 | $CH_2CH=CH(C_3H_5)$ |
| P2-62 | $CH_2CH=CH(C_4H_7)$ |
| P2-63 | $CH_2CH=CH(1\text{-Cl}-C_3H_4)$ |
| P2-64 | $CH_2CH=CH(1\text{-F}-C_3H_4)$ |
| P2-65 | $CH_2C=CCH(CH_3)_2$ |
| P2-66 | $CH_2C=CH$ |
| P2-67 | $CH_2C=CCH_3$ |
| P2-68 | $CH_2C=CCH_2CH_3$ |
| P2-69 | $CH_2C=CCl$ |
| P2-70 | $CH_2C=CF$ |
| P2-71 | $CH_2C=C-I$ |
| P2-72 | $CH_2C=CCH_2OH$ |
| P2-73 | $CH_2C=CCH_2OCH_3$ |
| P2-74 | $CH_2C=COCH_3$ |
| P2-75 | $CH_2C=CCCH_2OCH_3$ |
| P2-76 | $C=COCF_3$ |
| P2-77 | $CH_2C=COCF_3$ |
| P2-78 | $C=COCCl_3$ |
| P2-79 | $CH_2C=COCCl_3$ |
| P2-80 | $CH_2\text{-(cyclopropyl)}$ |
| P2-81 | $CH_2\text{-(cyclobutyl)}$ |
| P2-82 | $CH_2\text{-(1-Cl-cyclopropyl)}$ |
| P2-83 | $CH_2\text{-(1-F-cyclopropyl)}$ |
| P2-84 | $CH_2C_6H_5$ |
| P2-85 | $CH_2\text{-(4-Cl)-}C_6H_4$ |
| P2-86 | $CH_2\text{-(4-F)-}C_6H_4$ |
| P2-87 | $CH_2\text{-(4-}CH_3\text{)-}C_6H_4$ |
| P2-88 | $CH_2\text{-(4-}OCH_3\text{)}-C_6H_4$ |

According to a further embodiment, $R^1$ is $C_1$-$C_6$-alkyl, $C_2$-$C_6$-alkenyl, $C_2$-$C_6$-alkynyl, $C_3$-$C_8$-cycloalkyl, phenyl-$C_2$-$C_4$-alkenyl or phenyl-$C_2$-$C_4$-alkynyl, wherein the aliphatic moieties of $R^1$ are not further substituted or carry one, two, three or up to the maximum possible number of identical or different groups $R^{1a}$ which independently of one another are selected from halogen, OH, CN, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to still a further embodiment, $R^1$ is $C_1$-$C_3$-alkyl, $C_2$-$C_6$-alkenyl, $C_2$-$C_6$-alkynyl, $C_3$-$C_8$-cycloalkyl, phenyl-$C_2$-$C_4$-alkenyl or phenyl-$C_2$-$C_4$-alkynyl, wherein the aliphatic moieties of $R^1$ are not further substituted or carry one, two, three or up to the maximum possible number of identical or different groups $R^{1a}$ which independently of one another are selected from halogen, OH, CN, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

Each $R^3$ according to the present invention is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O—C_1$-$C_4$-alkyl), $C(=O)(NH(C_1$-$C_4$-alkyl))$, $C(=O)(N(C_1$-$C_4$-alkyl)$_2$)$, $C(=O)(NH(C_3$-$C_6$-cycloalkyl))$ and $C(=O)—(N(C_3$-$C_6$-cycloalkyl)$_2$)$; wherein each of $R^3$ is unsubstituted or further substituted by one, two, three or four $R^{3a}$; wherein $R^{3a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy.

According to the invention, there can be zero, one, two, three or four $R^3$ present, namely for n is 0, 1, 2, 3 or 4.

According to one embodiment, n is 0.

According to a further embodiment, n is 1.

According to a further embodiment, n is 2 or 3. According to one specific embodiment thereof, n is 2, according to a further specific embodiment, n is 3.

According to one embodiment of the invention, one $R^3$ is attached to the 2-position ($R^{31}$). According to one specific embodiment thereof, n is 1, according to a further specific embodiment, n is 2.

According to one embodiment of the invention, one $R^3$ is attached to the 3-position ($R^{32}$). According to one specific embodiment thereof, n is 1, according to a further specific embodiment, n is 2.

According to a further embodiment of the invention, one $R^3$ is attached to the 5-position ($R^{34}$). According to one specific embodiment thereof, n is 1, according to a further specific embodiment, n is 2.

According to still a further embodiment, n is 1, 2 or 3 and one $R^3$ is in 2- or 6-position.

According to a further embodiment of the invention, one $R^3$ is attached to the 6-position ($R^{35}$). According to one specific embodiment thereof, n is 1, according to a further specific embodiment, n is 2.

According to a further embodiment of the invention, two $R^3$ are attached in 2,3-position. According to one specific embodiment thereof, n is 2, according to a further specific embodiment, n is 3.

According to a further embodiment of the invention, two $R^3$ are attached in 2,5-position. According to one specific embodiment thereof, n is 2, according to a further specific embodiment, n is 3.

According to a further embodiment of the invention, two $R^3$ are attached in 2,6-position. According to one specific embodiment thereof, n is 2, according to a further specific embodiment, n is 3.

According to a further embodiment of the invention, two $R^3$ are attached in 3,5-position. According to one specific embodiment thereof, n is 2, according to a further specific embodiment, n is 3.

According to a further embodiment of the invention, two $R^3$ are attached in 3,6-position. According to one specific embodiment thereof, n is 2, according to a further specific embodiment, n is 3.

For every $R^3$ (or $R^{31}$, $R^{32}$, $R^{33}$, $R^{34}$, $R^{35}$, respectively) that is present in the inventive compounds, the following embodiments and preferences apply independently of the meaning of any other $R^3$ (or $R^{31}$, $R^{32}$, $R^{33}$, $R^{34}$, $R^{35}$, respectively) that may be present in the phenyl ring. Furthermore, the particular embodiments and preferences given herein for $R^3$ (or $R^{31}$, $R^{32}$, $R^{34}$, $R^{35}$, respectively) apply independently for each of n=1, n=2, n=3 and n=4.

According to one embodiment, $R^3$ is independently selected from Cl, F, Br, CN, $C_1$-$C_2$-alkyl, in particular $CH_3$, $C_1$-$C_2$-haloalkyl, in particular $CF_3$, $C_1$-$C_2$-alkoxy, in particular $OCH_3$, and $C_1$-$C_2$-haloalkoxy, in particular $OCF_3$.

According to one embodiment, $R^3$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl).

According to a further embodiment, $R^3$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)_2$, $NH(C_3$-$C_6$-cycloalkyl), $N(C_3$-$C_6$-cycloalkyl)_2$, $S(O)_p(C_1$-$C_4$-alkyl) (p=0, 1 or 2), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)_2)$, $C(=O)(NH(C_3$-$C_6$-cycloalkyl))$ and $C(=O)(N(C_3$-$C_6$-cycloalkyl)_2)$; wherein each of $R^3$ is unsubstituted or further substituted by one, two, three or four $R^{3a}$, wherein $R^{3a}$ is as defined and preferably defined herein.

According to still a further embodiment, $R^3$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl).

According to still a further embodiment, $R^3$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to one specific embodiment, $R^3$ is halogen, in particular Br, F or Cl, more specifically F or Cl.

According to a further specific embodiment, $R^3$ is CN.

According to a further specific embodiment, $R^3$ is $C_1$-$C_6$-alkyl, in particular $C_1$-$C_4$-alkyl, such as $CH_3$.

According to a further specific embodiment, $R^3$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment, $R^3$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^3$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^3$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$.

According to still a further embodiment, $R^3$ is $C_2$-$C_6$-alkynyl or $C_2$-$C_6$-haloalkynyl, in particular $C_2$-$C_4$-alkynyl or $C_2$-$C_4$-haloalkynyl, such as $C\equiv CH$.

According to still a further embodiment, $R^3$ is selected from $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)_2)$, $C(=O)(NH(C_3$-$C_6$-cycloalkyl))$ and $C(=O)(N(C_3$-$C_6$-cycloalkyl)_2)$, in particular selected from $C(=O)(C_1$-$C_2$-alkyl), $C(=O)(OH)$, $C(=O)(O-C_1$-$C_2$-alkyl), $C(=O)(NH(C_1$-$C_2$-alkyl))$, $C(=O)(N(C_1$-$C_2$-alkyl)_2)$, $C(=O)(NH(C_3$-$C_6$-cycloalkyl))$ and $C(=O)(N(C_3$-$C_6$-cycloalkyl)_2)$. According to one specific embodiment thereof, $R^3$ is $C(=O)(OH)$ or $C(=O)(O-C_1$-$C_4$-alkyl), in particular $C(=O)(OCH_3)$.

According to still a further embodiment, $R^3$ is selected from $S(C_1$-$C_2$-alkyl), $S(O)(C_1$-$C_2$-alkyl) and $S(O)_2(C_1$-$C_2$-alkyl), in particular $SCH_3$, $S(O)(CH_3)$ and $S(O)_2(CH_3)$.

According to still a further embodiment, $R^3$ is unsubstituted phenyl or phenyl that is substituted by one, two, three or four $R^{3a}$, as defined herein.

According to still a further embodiment, $R^3$ is unsubstituted phenoxy or phenoxy that is substituted by one, two, three or four $R^{3a}$, as defined herein.

According to still a further embodiment, $R^3$ is unsubstituted 5- or 6-membered heteroaryl. According to still a further embodiment, $R^3$ is 5- or 6-membered heteroaryl that is substituted by one, two or three $R^{3a}$, as defined herein. According to one specific embodiment, the heteroaryl in each case is 5-membered such as. According to a further specific embodiment, the heteroaryl in each case is 6-membered such as.

According to still a further embodiment, $R^3$ is unsubstituted 5- or 6-membered heteroaryloxy. According to still a further embodiment, $R^3$ is 5- or 6-membered heteroaryloxy that is substituted by one, two or three $R^{3a}$, as defined herein. According to one specific embodiment, the heteroaryloxy in each case is 5-membered. According to a further specific embodiment, the heteroaryloxy in each case is 6-membered.

$R^{3a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy, in particular selected from halogen, CN, $C_1$-$C_2$-alkyl, $C_1$-$C_2$-haloalkyl, $C_3$-$C_6$-cycloalkyl, $C_3$-$C_6$-halocycloalkyl, $C_1$-$C_2$-alkoxy and $C_1$-$C_2$-halogenalkoxy. Specifically, $R^{3a}$ is independently selected from F, Cl, CN, OH, $CH_3$, halomethyl, cyclopropyl, halocyclopropyl, $OCH_3$ and halogenmethoxy.

Particularly preferred embodiments of $R^3$ according to the invention are in Table P5 below, wherein each line of lines P5-1 to P5-17 corresponds to one particular embodiment of the invention, wherein P5-1 to P5-17 are also in any combination with one another a preferred embodiment of the present invention. Thereby, for every $R^3$ that is present in the inventive compounds, these specific embodiments and preferences apply independently of the meaning of any other $R^3$ that may be present in the phenyl ring:

TABLE P5

| No. | $R^3$ |
|---|---|
| P5-1 | Cl |
| P5-2 | F |
| P5-3 | CN |
| P5-4 | $NO_2$ |
| P5-5 | $CH_3$ |
| P5-6 | $CH_2CH_3$ |
| P5-7 | $CF_3$ |
| P5-8 | $CHF_2$ |
| P5-9 | $OCH_3$ |
| P5-10 | $OCH_2CH_3$ |
| P5-11 | $OCF_3$ |
| P5-12 | $OCHF_2$ |
| P5-13 | $SCH_3$ |
| P5-14 | $SOCH_3$ |
| P5-15 | $SO_2CH_3$ |
| P5-16 | $CO_2CH_3$ |
| P5-17 | Br |

Particularly preferred embodiments of $(R^3)_n$ according to the invention are in Table P6 below, wherein each line of lines P6-1 to P6-166 corresponds to one particular embodiment of the invention, wherein P6-1 to P6-66 are also in any combination a preferred embodiment of the present invention.

TABLE P6

| No. | $(R^3)_n$ |
|---|---|
| P6-1 | —* |
| P6-2 | 2-Cl |
| P6-3 | 3-Cl |
| P6-4 | 2-F |
| P6-5 | 3-F |
| P6-6 | 2-CN |
| P6-7 | 3-CN |
| P6-8 | 2-$NO_2$ |
| P6-9 | 3-$NO_2$ |
| P6-10 | 2-$SCH_3$ |
| P6-11 | 3-$SCH_3$ |
| P6-12 | 2-$SOCH_3$ |
| P6-13 | 3-$SOCH_3$ |
| P6-14 | 2-$SO_2CH_3$ |
| P6-15 | 3-$SO_2CH_3$ |
| P6-16 | 2-$CO_2CH_3$ |
| P6-17 | 3-$CO_2CH_3$ |
| P6-18 | 2,3-$Cl_2$ |
| P6-19 | 2,5-$Cl_2$ |
| P6-20 | 3,5-$Cl_2$ |
| P6-21 | 2,6-$Cl_2$ |
| P6-22 | 2,3-$F_2$ |
| P6-23 | 2,5-$F_2$ |
| P6-24 | 3,5-$F_2$ |
| P6-25 | 2,6-$F_2$ |
| P6-26 | 2-F-3-Cl |
| P6-27 | 2-F-6-Cl |
| P6-28 | 2-Cl-3-F |
| P6-29 | 2-$CH_3$ |
| P6-30 | 3-$CH_3$ |
| P6-31 | 2-$CH_2CH_3$ |
| P6-32 | 3-$CH_2CH_3$ |
| P6-33 | 2-$CF_3$ |
| P6-34 | 3-$CF_3$ |
| P6-35 | 2-$CHF_2$ |
| P6-36 | 3-$CHF_2$ |
| P6-37 | 2-$OCH_3$ |
| P6-38 | 3-$OCH_3$ |
| P6-39 | 2-$OCH_2CH_3$ |
| P6-40 | 3-$OCH_2CH_3$ |
| P6-41 | 2-$OCF_3$ |
| P6-42 | 3-$OCF_3$ |
| P6-43 | 2-$OCHF_2$ |
| P6-44 | 3-$OCHF_2$ |
| P6-45 | 2,3-$(CH_3)_2$ |
| P6-46 | 2,6-$(CH_3)_2$ |
| P6-47 | 2,3-$(CH_2CH_3)_2$ |
| P6-48 | 2,6-$(CH_2CH_3)_2$ |
| P6-49 | 2,3-$(CF_3)_2$ |
| P6-50 | 2,6-$(CF_3)_2$ |
| P6-51 | 2,3-$(CHF_2)_2$ |
| P6-52 | 2,6-$(CHF_2)_2$ |
| P6-53 | 2,3-$(OCH_3)_2$ |
| P6-54 | 2,6-$(OCH_3)_2$ |
| P6-55 | 2,3-$(OCH_2CH_3)_2$ |
| P6-56 | 2,6-$(OCH_2CH_3)_2$ |
| P6-57 | 2,3-$(OCF_3)_2$ |
| P6-58 | 2,6-$(OCF_3)_2$ |
| P6-59 | 2,3-$(OCHF_2)_2$ |
| P6-60 | 2,6-$(OCHF_2)_2$ |
| P6-61 | 2-Br |
| P6-62 | 3-Br |
| P6-63 | 2,3-$Br_2$ |
| P6-64 | 2,5-$Br_2$ |
| P6-65 | 3,5-$Br_2$ |
| P6-66 | 2,6-$Br_2$ |

—* means that n = 0

Y is a direct bond or a divalent group selected from the group consisting of —S—, SO—, —$SO_2$—, —NH—, —N($C_1$-$C_4$-alkyl)-, —$CR^7R^8$—, —$CR^9R^{10}$—$CR^{11}R^{12}$—, —$CR^{13}$=$CR^{14}$— and —C≡C—; wherein $R^7$, $R^8$, $R^9$, $R^{10}$, $R^{11}$, $R^{12}$, $R^{13}$, $R^{14}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

According to an embodiment, Y is selected from a direct bond, —$CR^{12}R^{13}$—, —$CR^{12}R^{13}$—$CR^{14}R^{15}$—, —$CR^{16}$=$CR^{17}$— and —C≡C—; wherein $R^{12}$, $R^{13}$, $R^{14}$, $R^{15}$, $R^{16}$ and $R^{17}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

According to one embodiment, Y is a direct bond.
According to still a further embodiment, Y is —S—.
According to still a further embodiment, Y is —SO—.
According to still a further embodiment, Y is —$SO_2$—.
According to still a further embodiment, Y is —NH—.
According to still a further embodiment, Y is —N($C_1$-$C_4$-alkyl)-.
According to still a further embodiment, Y is —$CR^{12}R^{13}$—.

$R^{12}$ and $R^{13}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^{12}$ and $R^{13}$ are independently selected from hydrogen and halogen, in particular hydrogen, fluorine and chlorine. In a further preferred embodiment $R^{12}$ and $R^{13}$ are independently selected from hydrogen and $C_1$-$C_4$-alkyl, in particular hydrogen, methyl and ethyl. In a preferred embodiment, $R^{12}$ and $R^{13}$ are independently selected from hydrogen and $C_1$-$C_4$-alkoxy, in particular hydrogen, methoxy and ethoxy. In another preferred embodiment, $R^{12}$ and $R^{13}$ are independently selected from hydrogen and CN. In yet another preferred embodiment $R^{12}$ and $R^{13}$ are independently selected from hydrogen and OH.

According to still a further embodiment, Y is —$CR^{12}R^{13}$—$CR^{14}R^{15}$—.

$R^{12}$, $R^{13}$, $R^{14}$ and $R^{15}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^{12}$, $R^{13}$, $R^{14}$ and $R^{15}$ are independently selected from hydrogen and halogen, in particular hydrogen, fluorine and chlorine. In a further preferred embodiment $R^{12}$, $R^{13}$, $R^{14}$ and $R^{15}$ are independently selected from hydrogen and $C_1$-$C_4$-alkyl, in particular hydrogen, methyl and ethyl. In a preferred embodiment, $R^{12}$, $R^{13}$, $R^{14}$ and $R^{15}$ are independently selected from hydrogen and $C_1$-$C_4$-alkoxy, in particular hydrogen, methoxy and ethoxy. In another preferred embodiment, $R^{12}$, $R^{13}$, $R^{14}$ and $R^{15}$ are independently selected from hydrogen and CN. In yet another preferred embodiment $R^{12}$, $R^{13}$, $R^{14}$ and $R^{15}$ are independently selected from hydrogen and OH.

According to still a further embodiment, Y is —$CR^{16}$=$CR^{17}$—.

$R^{16}$ and $R^{17}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^{16}$ and $R^{17}$ are independently selected from hydrogen and halogen, in particular hydrogen, fluorine and chlorine. In a further preferred embodiment $R^{16}$ and $R^{17}$ are independently selected from hydrogen and $C_1$-$C_4$-alkyl, in particular hydrogen, methyl and ethyl. In a preferred embodiment, $R^{16}$ and $R^{17}$ are independently selected from hydrogen and $C_1$-$C_4$-alkoxy, in particular hydrogen, methoxy and ethoxy. In another preferred embodiment, $R^{16}$ and $R^{17}$ are independently selected from hydrogen and CN. In yet another preferred embodiment $R^{16}$ and $R^{17}$ are independently selected from hydrogen and OH.

According to still a further embodiment, Y is —C≡C—.

In general, $R^{12}$, $R^{13}$, $R^{14}$, $R^{15}$, $R^{16}$, $R^{17}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy. In one preferred embodiment of the invention $R^{12}$, $R^{13}$, $R^{14}$, $R^{15}$, $R^{16}$ and $R^{17}$ are independently selected from hydrogen and halogen, in particular hydrogen, fluorine and chlorine. In a further preferred embodiment $R^{12}$, $R^{13}$, $R^{14}$, $R^{15}$, $R^{16}$ and $R^{17}$ are independently selected from hydrogen and $C_1$-$C_4$-alkyl, in particular hydrogen, methyl and ethyl. In a preferred embodiment, $R^{12}$, $R^{13}$, $R^{14}$, $R^{15}$, $R^{16}$ and $R^{17}$ are independently selected from hydrogen and $C_1$-$C_4$-alkoxy, in particular hydrogen, methoxy and ethoxy. In another preferred embodiment, $R^{12}$, $R^{13}$, $R^{14}$, $R^{15}$, $R^{16}$ and $R^{17}$ are independently selected from hydrogen and CN. In yet another preferred embodiment $R^{12}$, $R^{13}$, $R^{14}$, $R^{15}$, $R^{16}$ and $R^{17}$ are independently selected from hydrogen and OH.

Z is five or six-membered heteroaryl, wherein the heteroaryl contains 1, 2, 3 or 4 heteroatoms selected from the group consisting of O, N and S, wherein the heteroaryl is unsubstituted ($m_1$=0) or substituted by $(R^{41})_{m1}$; or is phenyl, that is substituted by $(R^{42})_{m2}$; wherein m1 is 0, 1, 2, 3 or 4; and m2 is 1, 2, 3, 4 or 5; and $R^{41}$ and $R^{42}$ are in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl$)_2$, $NH(C_3$-$C_6$-cycloalkyl), $N(C_3$-$C_6$-cycloalkyl$)_2$, $S(O)_p(C_1$-$C_4$-alkyl), C(=O)($C_1$-$C_4$-alkyl), C(=O)(OH), C(=O)(O—$C_1$-$C_4$-alkyl), C(=O)(NH($C_1$-$C_4$-alkyl)), C(=O)(N($C_1$-$C_4$-alkyl$)_2$), C(=O)(NH($C_3$-$C_6$-cycloalkyl)) and C(=O)—(N($C_3$-$C_6$-cycloalkyl$)_2$); wherein each of $R^{41}$ or $R^{42}$ is unsubstituted or further substituted by one, two, three or four $R^{41a}$ or $R^{42a}$ wherein $R^{41a}$ and $R^{42a}$ are independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy; and wherein p is 0, 1 or 2.

According to one embodiment, Z is phenyl, substituted by $(R^{42})_{m2}$. According to the invention, there can be one, two, three, four or five $R^{42}$ present, namely for m2 is 1, 2, 3, 4 or 5. In particular, m2 is 1, 2, 3 or 4.

According to a further embodiment, m2 is 1, 2, 3 or 4, in particular 1, 2 or 3, more specifically 1 or 2. According to one specific embodiment thereof, m2 is 1, according to a further specific embodiment, m2 is 2.

According to still a further embodiment, m2 is 2, 3 or 4.

According to still a further embodiment, m2 is 3.

According to one embodiment of the invention, one $R^{42}$ is attached to the para-position (4-position).

According to a further embodiment of the invention, one $R^{42}$ is attached to the meta-position (3-position).

According to a further embodiment of the invention, one $R^{42}$ is attached to the ortho-position (2-position).

According to a further embodiment of the invention, two $R^{42}$ are attached in 2,4-position.

According to a further embodiment of the invention, two $R^{42}$ are attached in 2,3-position.

According to a further embodiment of the invention, two $R^{42}$ are attached in 2,5-position.

According to a further embodiment of the invention, two $R^{42}$ are attached in 2,6-position.

According to a further embodiment of the invention, two $R^{42}$ are attached in 3,4-position.

According to a further embodiment of the invention, two $R^{42}$ are attached in 3,5-position.

According to a further embodiment of the invention, three $R^{42}$ are attached in 2,4,6-position.

For every $R^{42}$ that is present in the inventive compounds, the following embodiments and preferences apply independently of the meaning of any other $R^{42}$ that may be present in the phenyl ring. Furthermore, the particular embodiments and preferences given herein for $R^{42}$ apply independently for each of m=1, m=2, m=3, m=4 and m=5.

Each $R^{42}$ is independently selected from halogen, CN, $NO_2$, OH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, $C_3$-$C_8$-cycloalkyloxy, $NH_2$, $NH(C_1$-$C_4$-alkyl), $N(C_1$-$C_4$-alkyl$)_2$, $NH(C_3$-$C_6$-cycloalkyl), $N(C_3$-$C_6$-cycloalkyl$)_2$, C(=O)—$C_1$-$C_4$-alkyl, C(=O)OH, C(=O)—O—$C_1$-$C_4$-alkyl, C(=O)—NH($C_1$-$C_4$-alkyl), C(=O)—N($C_1$-$C_4$-alkyl$)_2$, C(=O)—NH($C_3$-$C_6$-cycloalkyl), C(=O)N($C_3$-$C_6$-cycloalkyl$)_2$, phenyl and phenyl-$C_1$-$C_4$-alkyl, wherein the aliphatic, alicyclic and aromatic moieties of $R^{42}$ are unsubstituted or substituted by one, two, three or four or up to the maximum possible number of $R^{42a}$; wherein $R^{42a}$ is independently selected from halogen, CN, $NO_2$, OH, SH, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio and $C_1$-$C_6$-haloalkylthio.

According to one embodiment, $R^{42}$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)$—$N(C_3$-$C_6$-cycloalkyl)$_2$); wherein each of $R^{42}$ is unsubstituted or further substituted by one, two, three or four independently selected $R^{42a}$, wherein $R^{42a}$ is as defined and preferably defined herein.

According to a further embodiment, $R^{42}$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, $NH_2$, $NH(C_1$-$C_{42}$-alkyl), $N(C_1$-$C_2$-alkyl)$_2$, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl), wherein each of $R^{42}$ is unsubstituted or further substituted by one, two, three or four independently selected $R^{42a}$, wherein $R^{42a}$ is as defined and preferably defined herein.

According to a further embodiment, $R^{42}$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl).

According to a further embodiment, $R^{42}$ is independently selected from halogen, CN, $NO_2$, $C_1$-$C_2$-alkyl, $C_1$-$C_2$-haloalkyl, $C_1$-$C_2$-alkoxy, $C_1$-$C_2$-haloalkoxy, $S(C_1$-$C_2$-alkyl), $S(O)(C_1$-$C_2$-alkyl), $S(O)_2(C_1$-$C_2$-alkyl), $C(=O)(OH)$ and $C(=O)(O-C_1$-$C_2$-alkyl).

According to a further embodiment, $R^{42}$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to a further embodiment, $R^{42}$ is independently selected from F, Cl, Br, CN, $C_1$-haloalkyl, $C_1$-alkoxy and $C_1$-haloalkoxy.

According to still a further specific embodiment, $R^{42}$ is independently selected from halogen, in particular from Br, F and Cl, more specifically from F and Cl.

According to a further specific embodiment, $R^{42}$ is CN.
According to one further embodiment $R^{42}$ is $NO_2$.
According to one further embodiment $R^{42}$ is OH.
According to one further embodiment $R^{42}$ is SH.

According to a further specific embodiment, $R^{42}$ is $C_1$-$C_6$-alkyl, in particular $C_1$-$C_4$-alkyl, such as $CH_3$. Further appropriate alkyls are ethyl, n-propyl, i-propyl, n-butyl, i-butyl and t-butyl.

According to a further specific embodiment, $R^{42}$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment $R^{42}$ is $C_1$-$C_6$-alkyl, preferably $C_1$-$C_4$-alkyl, substituted by OH, more preferably $CH_2OH$, $CH_2CH_2OH$, $CH_2CH_2CH_2OH$, $CH(CH_3)CH_2OH$, $CH_2CH(CH_3)OH$, $CH_2CH_2CH_2CH_2OH$. In a special embodiment $R^{42}$ is $CH_2OH$. According to a further specific embodiment $R^{42}$ is $C_1$-$C_6$-alkyl, preferably $C_1$-$C_4$-alkyl substituted by CN, more preferably $CH_2CN$, $CH_2CH_2CN$, $CH_2CH_2CH_2CN$, $CH(CH_3)CH_2CN$, $CH_2CH(CH_3)CN$, $CH_2CH_2CH_2CH_2CN$. In a special embodiment $R^{42}$ is $CH_2CH_2CN$. In a further special embodiment $R^{42}$ is $CH(CH_3)CN$. According to a further specific embodiment $R^{42}$ is $C_1$-$C_4$-alkoxy-$C_1$-$C_6$-alkyl, more preferably $C_1$-$C_4$-alkoxy-$C_1$-$C_4$-alkyl. In a special embodiment $R^{42}$ is $CH_2OCH_3$. In a further special embodiment $R^{42}$ is $CH_2CH_2OCH_3$. In a further special embodiment $R^{42}$ is $CH(CH_3)OCH_3$. In a further special embodiment $R^{42}$ is $CH(CH_3)OCH_2CH_3$. In a further special embodiment $R^{42}$ is $CH_2CH_2OCH_2CH_3$. According to a further specific embodiment $R^{42}$ is $C_1$-$C_4$-haloalkoxy-$C_1$-$C_6$-alkyl, more preferably $C_1$-$C_4$-alkoxy-$C_1$-$C_4$-alkyl. In a special embodiment $R^{42}$ is $CH_2OCF_3$. In a further special embodiment $R^{42}$ is $CH_2CH_2OCF_3$. In a further special embodiment $R^{42}$ is $CH_2OCCl_3$. In a further special embodiment $R^{42}$ is $CH_2CH_2OCCl_3$.

According to a further specific embodiment, $R^{42}$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^{42}$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^{42}$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$, $CH_2CH=CH_2$, $CH=CHCH_3$ or $C(CH_3)=CH_2$.

According to a further specific embodiment $R^{42}$ is $C_2$-$C_6$-alkenyl, preferably $C_2$-$C_4$-alkenyl, substituted by OH, more preferably, $CH=CHOH$, $CH=CHCH_2OH$, $C(CH_3)=CHOH$, $CH=C(CH_3)OH$. In a special embodiment $R^{42}$ is $CH=CHOH$. In a further special embodiment $R^{42}$ is $CH=CHCH_2OH$. According to a further specific embodiment $R^{42}$ is $C_1$-$C_4$-alkoxy-$C_2$-$C_6$-alkenyl, more preferably $C_1$-$C_4$-alkoxy-$C_2$-$C_4$-alkenyl. In a special embodiment $R^{42}$ is $CH=CHOCH_3$. In a further special embodiment $R^{42}$ is $CH=CHCH_2OCH_3$. According to a further specific embodiment $R^{42}$ is $C_1$-$C_4$-haloalkoxy-$C_2$-$C_6$-alkenyl, more preferably $C_1$-$C_4$-haloalkoxy-$C_2$-$C_4$-alkenyl. In a special embodiment $R^{42}$ is $CH=CHOCF_3$. In a further special embodiment $R^{42}$ is $CH=CHCH_2OCF_3$. In a further special embodiment $R^{42}$ is $CH=CHOCCl_3$. In a further special embodiment $R^{42}$ is $CH=CHCH_2OCCl_3$. According to a further specific embodiment $R^{42}$ is $C_3$-$C_8$-cycloalkyl-$C_2$-$C_6$-alkenyl, preferably $C_3$-$C_6$-cycloalkyl-$C_2$-$C_4$-alkenyl. According to a further specific embodiment $R^{42}$ is $C_3$-$C_6$-halocycloalkyl-$C_2$-$C_4$-alkenyl, preferably $C_3$-$C_8$-halocycloalkyl-$C_2$-$C_6$-alkenyl.

According to still a further embodiment, $R^{42}$ is $C_2$-$C_6$-alkynyl or $C_2$-$C_6$-haloalkynyl, in particular $C_2$-$C_4$-alkynyl or $C_2$-$C_4$-haloalkynyl, such as $C\equiv CH$, $CH_2CCH$ or $CH_2CCCH_3$.

According to a further specific embodiment $R^{42}$ is $C_2$-$C_6$-alkynyl, preferably $C_2$-$C_4$-alkynyl, substituted by OH, more preferably, CCOH, $CH_2CCOH$. In a special embodiment $R^{42}$ is CCOH. In a further special embodiment $R^{42}$ is $CH_2CCOH$. According to a further specific embodiment $R^{42}$ is $C_1$-$C_4$-alkoxy-$C_2$-$C_6$-alkynyl, more preferably $C_1$-$C_4$-alkoxy-$C_2$-$C_4$-alkynyl. In a special embodiment $R^{42}$ is $CCOCH_3$. In a further special embodiment $R^{42}$ is $CH_2CCOCH_3$. According to a further specific embodiment $R^{42}$ is $C_1$-$C_4$-haloalkoxy-$C_2$-$C_6$-alkynyl, more preferably $C_1$-$C_4$-haloalkoxy-$C_2$-$C_4$-alkynyl. In a special embodiment $R^{42}$ is $CCOCF_3$. In a further special embodiment $R^{42}$ is $CH_2CCOCF_3$. In a further special embodiment $R^{42}$ is $CCOCCl_3$. In a further special embodiment $R^{42}$ is $CH_2CCOCCl_3$. According to a further specific embodiment $R^{42}$ is $C_3$-$C_8$-cycloalkyl-$C_2$-$C_6$-alkynyl, preferably $C_3$-$C_6$- cycloalkyl-$C_2$-$C_4$-alkynyl. According to a further specific embodiment $R^{42}$ is $C_3$-$C_6$-halocycloalkyl-$C_2$-$C_4$-alkynyl, preferably $C_3$-$C_8$-halocycloalkyl-$C_2$-$C_6$-alkynyl.

According to one another embodiment $R^{42}$ is $C_3$-$C_8$-cycloalkyl, preferably cyclopropyl, cyclobutyl, cyclopentyl or cyclohexyl, in particular cyclopropyl or cyclobutyl. In a special embodiment $R^{42}$ is cyclopropyl. In a further special embodiment $R^{42}$ is cyclobutyl. In a further special embodiment $R^{42}$ is cyclopentyl. In a further special embodiment $R^{42}$ is cyclohexyl.

According to one another embodiment $R^{42}$ is $C_3$-$C_8$-cycloalkoxy, preferably $C_3$-$C_6$-cycloalkoxy. In a special embodiment $R^{42}$ is O-cyclopropyl.

According to a specific embodiment $R^{42}$ is $C_3$-$C_8$-halocycloalkyl, more preferably fully or partially halogenated $C_3$-$C_6$-cycloalkyl. In a special embodiment $R^{42}$ is fully or partially halogenated cyclopropyl. In a further special embodiment $R^{42}$ is 1-Cl-cyclopropyl. In a further special embodiment $R^{42}$ is 2-Cl-cyclopropyl. In a further special embodiment $R^{42}$ is 1-F-cyclopropyl. In a further special embodiment $R^{42}$ is 2-F-cyclopropyl. In a further special embodiment $R^{42}$ is fully or partially halogenated cyclobutyl. In a further special embodiment $R^{42}$ is 1-Cl-cyclobutyl. In a further special embodiment $R^{42}$ is 1-F-cyclobutyl. In a further special embodiment $R^{42}$ is 3,3-$Cl_2$-cyclobutyl. In a further special embodiment $R^{42}$ is 3,3-$F_2$-cyclobutyl. According to a specific embodiment $R^{42}$ is $C_3$-$C_8$-cycloalkyl substituted by $C_1$-$C_4$-alkyl, more preferably is $C_3$-$C_6$-cycloalkyl substituted by $C_1$-$C_4$-alkyl. In a special embodiment $R^{42}$ is 1-$CH_3$-cyclopropyl. According to a specific embodiment $R^{42}$ is $C_3$-$C_8$-cycloalkyl substituted by CN, more preferably is $C_3$-$C_6$-cycloalkyl substituted by CN. In a special embodiment $R^{42}$ is 1-CN-cyclopropyl. According to a further specific embodiment $R^{42}$ is $C_3$-$C_8$-cycloalkyl-$C_3$-$C_8$-cycloalkyl, preferably $C_3$-$C_6$-cycloalkyl-$C_3$-$C_6$-cycloalkyl. In a special embodiment $R^{42}$ is cyclopropyl-cyclopropyl. In a special embodiment $R^{42}$ is 2-cyclopropyl-cyclopropyl. According to a further specific embodiment $R^{42}$ is $C_3$-$C_8$-cycloalkyl-$C_3$-$C_8$-halocycloalkyl, preferably $C_3$-$C_6$-cycloalkyl-$C_3$-$C_6$-halocycloalkyl.

According to one another embodiment $R^{42}$ is $C_3$-$C_8$-cycloalkyl-$C_1$-$C_4$-alkyl, preferably $C_3$-$C_6$-cycloalkyl-$C_1$-$C_4$-alkyl. In a special embodiment $R^{42}$ is $CH(CH_3)$(cyclopropyl). In a further special embodiment $R^{42}$ is $CH_2$-(cyclopropyl).

According to a further preferred embodiment $R^{42}$ is $C_3$-$C_8$-cycloalkyl-$C_1$-$C_4$-alkyl wherein the alkyl moiety can be substituted by one, two, three or up to the maximum possible number of identical or different groups $R^a$ as defined and preferably herein and the cycloalkyl moiety can be substituted by one, two, three or up to the maximum possible number of identical or different groups $R^b$ as defined and preferably herein.

According to a specific embodiment $R^{42}$ is $C_3$-$C_8$-cycloalkyl-$C_1$-$C_4$-haloalkyl, $C_3$-$C_6$-cycloalkyl-$C_1$-$C_4$-haloalkyl. According to a specific embodiment $R^{42}$ is $C_3$-$C_8$-halocycloalkyl-$C_1$-$C_4$-alkyl, $C_3$-$C_6$-halocycloalkyl-$C_1$-$C_4$-alkyl. In a special embodiment $R^{42}$ is fully or partially halogenated cyclopropyl-$C_1$-$C_4$-alkyl. In a further special embodiment $R^{42}$ is 1-Cl-cyclopropyl-$C_1$-$C_4$-alkyl. In a further special embodiment $R^{42}$ is 1-F-cyclopropyl-$C_1$-$C_4$-alkyl.

According to one another embodiment $R^{42}$ is $NH_2$.

According to one another embodiment $R^{42}$ is $NH(C_1$-$C_4$-alkyl). According to a specific embodiment $R^{42}$ is $NH(CH_3)$. According to a specific embodiment $R^{42}$ is $NH(CH_2CH_3)$. According to a specific embodiment $R^{42}$ is $NH(CH_2CH_2CH_3)$. According to a specific embodiment $R^{42}$ is $NH(CH(CH_3)_2)$. According to a specific embodiment $R^{42}$ is $NH(CH_2CH_2CH_2CH_3)$. According to a specific embodiment $R^{42}$ is $NH(C(CH_3)_3)$.

According to one another embodiment $R^{42}$ is $N(C_1$-$C_4$-alkyl)$_2$. According to a specific embodiment $R^{42}$ is $N(CH_3)_2$. According to a specific embodiment $R^{42}$ is $N(CH_2CH_3)_2$. According to a specific embodiment $R^{42}$ is $N(CH_2CH_2CH_3)_2$. According to a specific embodiment $R^{42}$ is $N(CH(CH_3)_2)_2$. According to a specific embodiment $R^{42}$ is $N(CH_2CH_2CH_2CH_3)_2$. According to a specific embodiment $R^{42}$ is $NH(C(CH_3)_3)_2$.

According to one another embodiment $R^{42}$ is $NH(C_3$-$C_8$-cycloalkyl) preferably $NH(C_3$-$C_6$-cycloalkyl). According to a specific embodiment $R^{42}$ is NH(cyclopropyl). According to a specific embodiment $R^{42}$ is NH(cyclobutyl). According to a specific embodiment $R^{42}$ is NH(cyclopentyl). According to a specific embodiment $R^{42}$ is NH(cyclohexyl).

According to one another embodiment $R^{42}$ is $N(C_3$-$C_8$-cycloalkyl)$_2$ preferably $N(C_3$-$C_6$-cycloalkyl)$_2$. According to a specific embodiment $R^{42}$ is $N(cyclopropyl)_2$. According to a specific embodiment $R^{42}$ is $N(cyclobutyl)_2$. According to a specific embodiment $R^{42}$ is $N(cyclopentyl)_2$. According to a specific embodiment $R^{42}$ is $N(cyclohexyl)_2$.

According to still a further embodiment, $R^{42}$ is selected from $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)(N(C_3$-$C_6$-cycloalkyl)$_2$), in particular selected from $C(=O)(C_1$-$C_2$-alkyl), $C(=O)(OH)$, $C(=O)(O-C_1$-$C_2$-alkyl), $C(=O)(NH(C_1$-$C_2$-alkyl))$, $C(=O)(N(C_1$-$C_2$-alkyl)$_2$), $C(=O)(NH(C_3$-$C_6$-cycloalkyl))$ and $C(=O)(N(C_3$-$C_6$-cycloalkyl)$_2$). According to one specific embodiment thereof, $R^{42}$ is $C(=O)(OH)$ or $C(=O)(O-C_1$-$C_4$-alkyl), in particular $C(=O)(OCH_3)$.

According to one another embodiment $R^{42}$ is $C(=O)(C_1$-$C_4$-alkyl). According to a specific embodiment $R^{42}$ is $C(=O)CH_3$. According to a further specific embodiment $R^{42}$ is $C(=O)CH_2CH_3$. According to a further specific embodiment $R^{42}$ is $C(=O)CH_2CH_2CH_3$. According to a further specific embodiment $R^{42}$ is $C(=O)CH(CH_3)_2$. According to a further specific embodiment $R^{42}$ is $C(=O)C(CH_3)_3$.

According to one another embodiment $R^{42}$ is $C(=O)OH$.

According to one another embodiment $R^{42}$ is $C(=O)(-O-C_1$-$C_4$-alkyl). According to a specific embodiment $R^{42}$ is $C(=O)OCH_3$. According to a further specific embodiment $R^{42}$ is $C(=O)OCH_2CH_3$.

According to a further specific embodiment $R^{42}$ is $C(=O)OCH_2CH_2CH_3$. According to a further specific embodiment $R^{42}$ is $C(=O)OCH(CH_3)_2$. According to a further specific embodiment $R^{42}$ is $C(=O)OC(CH_3)_3$.

According to one another embodiment $R^{42}$ is $C(=O)-NH(C_1$-$C_4$-alkyl). According to a specific embodiment $R^{42}$ is $C(=O)NHCH_3$. According to a further specific embodiment $R^{42}$ is $C(=O)NHCH_2CH_3$. According to a further specific embodiment $R^{42}$ is $C(=O)NHCH_2CH_2CH_3$. According to a further specific embodiment $R^{42}$ is $C(=O)NHCH(CH_3)_2$. According to a further specific embodiment $R^{42}$ is $C(=O)NHC(CH_3)_3$.

According to one another embodiment $R^{42}$ is $C(=O)-N(C_1$-$C_4$-alkyl)$_2$. According to a specific embodiment $R^{42}$ is $C(=O)N(CH_3)_2$. According to a further specific embodiment $R^{42}$ is $C(=O)N(CH_2CH_3)_2$. According to a further specific embodiment $R^{42}$ is $C(=O)N(CH_2CH_2CH_3)_2$.

According to a further specific embodiment $R^{42}$ is C(=O)N(CH(CH$_3$)$_2$)$_2$. According to a further specific embodiment $R^{42}$ is C(=O)N(C(CH$_3$)$_3$)$_2$.

According to one another embodiment $R^{42}$ is C(=O)—NH(C$_3$-C$_6$-cycloalkyl). According to a specific embodiment $R^{42}$ is C(=O)NH(cyclopropyl). According to a further specific embodiment $R^{42}$ is C(=O)NH(cyclobutyl). According to a further specific embodiment $R^{42}$ is C(=O)NH(cyclopentyl). According to a further specific embodiment $R^{42}$ is C(=O)NH(cyclohexyl).

According to one another embodiment $R^{42}$ is C(=O)—N(C$_3$-C$_6$-cycloalkyl)$_2$. According to a specific embodiment $R^{42}$ is C(=O)N(cyclopropyl)$_2$. According to a further specific embodiment $R^{42}$ is C(=O)N(cyclobutyl)$_2$. According to a further specific embodiment $R^{42}$ is C(=O)N(cyclopentyl)$_2$. According to a further specific embodiment $R^{42}$ is C(=O)N(cyclohexyl)$_2$.

According to still a further embodiment, $R^{42}$ is selected from S(C$_1$-C$_2$-alkyl), S(O)(C$_1$-C$_2$-alkyl) and S(O)$_2$(C$_1$-C$_2$-alkyl), in particular SCH$_3$, S(O)(CH$_3$) and S(O)$_2$(CH$_3$). According to a specific embodiment $R^{42}$ is selected from S(C$_1$-C$_2$-haloalkyl), S(O)(C$_1$-C$_2$-haloalkyl) and S(O)$_2$(C$_1$-C$_2$-haloalkyl), such as SO$_2$CF$_3$.

Particularly preferred embodiments of $R^{42}$ according to the invention are in Table PL below, wherein each line of lines PL-1 to PL-17 corresponds to one particular embodiment of the invention, wherein PL-1 to PL-17 are also in any combination with one another a preferred embodiment of the present invention. Thereby, for every $R^{42}$ that is present in the inventive compounds, these specific embodiments and preferences apply independently of the meaning of any other $R^{42}$ that may be present in the phenyl ring:

TABLE PL

| No. | $R^{42}$ |
|---|---|
| PL-1 | Cl |
| PL-2 | F |
| PL-3 | CN |
| PL-4 | NO$_2$ |
| PL-5 | CH$_3$ |
| PL-6 | CH$_2$CH$_3$ |
| PL-7 | CF$_3$ |
| PL-8 | CHF$_2$ |
| PL-9 | OCH$_3$ |
| PL-10 | OCH$_2$CH$_3$ |
| PL-11 | OCF$_3$ |
| PL-12 | OCHF$_2$ |
| PL-13 | SCH$_3$ |
| PL-14 | SOCH$_3$ |
| PL-15 | SO$_2$CH$_3$ |
| PL-16 | CO$_2$CH$_3$ |
| PL-17 | Br |

Particularly preferred embodiments of $(R^{42})_{m2}$ if Z is phenyl according to the invention are in Table P4 below, wherein each line of lines P4-1 to P4-154 corresponds to one particular embodiment of the invention, wherein P4-1 to P4-154 are also in any combination a preferred embodiment of the present invention.

TABLE P4

| No. | $(R^{42})_{m2}$ |
|---|---|
| P4-1 | 2-Cl |
| P4-2 | 3-Cl |
| P4-3 | 4-Cl |
| P4-4 | 2-F |
| P4-5 | 3-F |
| P4-6 | 4-F |
| P4-7 | 2-CN |
| P4-8 | 3-CN |
| P4-9 | 4-CN |
| P4-10 | 2-NO$_2$ |
| P4-11 | 3-NO$_2$ |
| P4-12 | 4-NO$_2$ |
| P4-13 | 2-SCH$_3$ |
| P4-14 | 3-SCH$_3$ |
| P4-15 | 4-SCH$_3$ |
| P4-16 | 2-SOCH$_3$ |
| P4-17 | 3-SOCH$_3$ |
| P4-18 | 4-SOCH$_3$ |
| P4-19 | 2-SO$_2$CH$_3$ |
| P4-20 | 3-SO$_2$CH$_3$ |
| P4-21 | 4-SO$_2$CH$_3$ |
| P4-22 | 2-CO$_2$CH$_3$ |
| P4-23 | 3-CO$_2$CH$_3$ |
| P4-24 | 4-CO$_2$CH$_3$ |
| P4-25 | 2,3-Cl$_2$ |
| P4-26 | 2,4-Cl$_2$ |
| P4-27 | 2,5-Cl$_2$ |
| P4-28 | 3,4-Cl$_2$ |
| P4-29 | 3,5-Cl$_2$ |
| P4-30 | 2,6-Cl$_2$ |
| P4-31 | 2,3-F$_2$ |
| P4-32 | 2,4-F$_2$ |
| P4-33 | 2,5-F$_2$ |
| P4-34 | 3,4-F$_2$ |
| P4-35 | 3,5-F$_2$ |
| P4-36 | 2,6-F$_2$ |
| P4-37 | 2-F-3-Cl |
| P4-38 | 2-F-4-Cl |
| P4-39 | 3-F-4-Cl |
| P4-40 | 2-F-6-Cl |
| P4-41 | 2-Cl-3-F |
| P4-42 | 2-Cl-4-F |
| P4-43 | 3-Cl-4-F |
| P4-44 | 2,3,4-Cl$_3$ |
| P4-45 | 2,4,5-Cl$_3$ |
| P4-46 | 3,4,5-Cl$_3$ |
| P4-47 | 2,4,6-Cl$_3$ |
| P4-48 | 2,3,4-F$_3$ |
| P4-49 | 2,4,5-F$_3$ |
| P4-50 | 3,4,5-F$_3$ |
| P4-51 | 2,4,6-F$_3$ |
| P4-52 | 2,3-4-F$_3$ |
| P4-53 | 2,4-F$_2$-3-Cl |
| P4-54 | 2,6-F$_2$-4-Cl |
| P4-55 | 2,5-F$_2$-4-Cl |
| P4-56 | 2,4-Cl$_2$-3-F |
| P4-57 | 2,6-Cl$_2$-4-F |
| P4-58 | 2,5-Cl$_2$-4-F |
| P4-59 | 2-CH$_3$ |
| P4-60 | 3-CH$_3$ |
| P4-61 | 4-CH$_3$ |
| P4-62 | 2-CH$_2$CH$_3$ |
| P4-63 | 3-CH$_2$CH$_3$ |
| P4-64 | 4-CH$_2$CH$_3$ |
| P4-65 | 2-CF$_3$ |
| P4-66 | 3-CF$_3$ |
| P4-67 | 4-CF$_3$ |
| P4-68 | 2-CHF$_2$ |
| P4-69 | 3-CHF$_2$ |
| P4-70 | 4-CHF$_2$ |
| P4-71 | 2-OCH$_3$ |
| P4-72 | 3-OCH$_3$ |
| P4-73 | 4-OCH$_3$ |
| P4-74 | 2-OCH$_2$CH$_3$ |
| P4-75 | 3-OCH$_2$CH$_3$ |
| P4-76 | 4-OCH$_2$CH$_3$ |
| P4-77 | 2-OCF$_3$ |
| P4-78 | 3-OCF$_3$ |
| P4-79 | 4-OCF$_3$ |
| P4-80 | 2-OCHF$_2$ |
| P4-81 | 3-OCHF$_2$ |
| P4-82 | 4-OCHF$_2$ |
| P4-83 | 2,3-(CH$_3$)$_2$ |

TABLE P4-continued

| No. | $(R^{42})_{m2}$ |
|---|---|
| P4-84 | 2,4-$(CH_3)_2$ |
| P4-85 | 3,4-$(CH_3)_2$ |
| P4-86 | 2,6-$(CH_3)_2$ |
| P4-87 | 2,3-$(CH_2CH_3)_2$ |
| P4-88 | 2,4-$(CH_2CH_3)_2$ |
| P4-89 | 3,4-$(CH_2CH_3)_2$ |
| P4-90 | 2,6-$(CH_2CH_3)_2$ |
| P4-91 | 2,3-$(CF_3)_2$ |
| P4-92 | 2,4-$(CF_3)_2$ |
| P4-93 | 3,4-$(CF_3)_2$ |
| P4-94 | 2,6-$(CF_3)_2$ |
| P4-95 | 2,3-$(CHF_2)_2$ |
| P4-96 | 2,4-$(CHF_2)_2$ |
| P4-97 | 3,4-$(CHF_2)_2$ |
| P4-98 | 2,6-$(CHF_2)_2$ |
| P4-99 | 2,3-$(OCH_3)_2$ |
| P4-100 | 2,4-$(OCH_3)_2$ |
| P4-101 | 3,4-$(OCH_3)_2$ |
| P4-102 | 2,6-$(OCH_3)_2$ |
| P4-103 | 2,3-$(OCH_2CH_3)_2$ |
| P4-104 | 2,4-$(OCH_2CH_3)_2$ |
| P4-105 | 3,4-$(OCH_2CH_3)_2$ |
| P4-106 | 2,6-$(OCH_2CH_3)_2$ |
| P4-107 | 2,3-$(OCF_3)_2$ |
| P4-108 | 2,4-$(OCF_3)_2$ |
| P4-109 | 3,4-$(OCF_3)_2$ |
| P4-110 | 2,6-$(OCF_3)_2$ |
| P4-111 | 2,3-$(OCHF_2)_2$ |
| P4-112 | 2,4-$(OCHF_2)_2$ |
| P4-113 | 3,4-$(OCHF_2)_2$ |
| P4-114 | 2,6-$(OCHF_2)_2$ |
| P4-115 | 2,3,4-$(CH_3)_3$ |
| P4-116 | 2,4,5-$(CH_3)_3$ |
| P4-117 | 3,4,5-$(CH_3)_3$ |
| P4-118 | 2,4,6-$(CH_3)_3$ |
| P4-119 | 2,3,4-$(CH_2CH_3)_3$ |
| P4-120 | 2,4,5-$(CH_2CH_3)_3$ |
| P4-121 | 3,4,5-$(CH_2CH_3)_3$ |
| P4-122 | 2,4,6-$(CH_2CH_3)_3$ |
| P4-123 | 2,3,4-$(CF_3)_3$ |
| P4-124 | 2,4,5-$(CF_3)_3$ |
| P4-125 | 3,4,5-$(CF_3)_3$ |
| P4-126 | 2,4,6-$(CF_3)_3$ |
| P4-127 | 2,3,4-$(CHF_2)_3$ |
| P4-128 | 2,4,5-$(CHF_2)_3$ |
| P4-129 | 3,4,5-$(CHF_2)_3$ |
| P4-130 | 2,4,6-$(CHF_2)_3$ |
| P4-131 | 2,3,4-$(OCH_3)_3$ |
| P4-132 | 2,4,5-$(OCH_3)_3$ |
| P4-133 | 3,4,5-$(OCH_3)_3$ |
| P4-134 | 2,4,6-$(OCH_3)_3$ |
| P4-135 | 2,3,4-$(OCH_2CH_3)_3$ |
| P4-136 | 2,4,5-$(OCH_2CH_3)_3$ |
| P4-137 | 3,4,5-$(OCH_2CH_3)_3$ |
| P4-138 | 2,4,6-$(OCH_2CH_3)_3$ |
| P4-139 | 2,3,4-$(OCF_3)_3$ |
| P4-140 | 2,4,5-$(OCF_3)_3$ |
| P4-141 | 3,4,5-$(OCF_3)_3$ |
| P4-142 | 2,4,6-$(OCF_3)_3$ |
| P4-143 | 2,3,4-$(OCHF_2)_3$ |
| P4-144 | 2,4,5-$(OCHF_2)_3$ |
| P4-145 | 3,4,5-$(OCHF_2)_3$ |
| P4-146 | 2,4,6-$(OCHF_2)_3$ |
| P4-147 | 2-$CF_3$-4-Cl |
| P4-148 | 2-$CF_3$-4-F |
| P4-149 | 2-Cl-4-$CF_3$ |
| P4-150 | 2-F-4-$CF_3$ |
| P4-151 | 2-CN-4-Cl |
| P4-152 | 2-CN-4-F |
| P4-153 | 2-Cl-4-CN |
| P4-154 | 2-F-4-CN |

In another embodiment Z is a five- or six-membered heteroaryl that is unsubstituted (m1=0) or substituted by $(R^{41})_{m1}$.

According to the invention, there can be zero, one, two, three, four or five $R^{42}$ present, namely for m1 is 0, 1, 2, 3, 4 or 5. In particular, m1 is 0, 1, 2, 3 or 4.

According to a further embodiment, m1 is 1, 2, 3 or 4, in particular 1, 2 or 3, more specifically 1 or 2. According to one specific embodiment thereof, m1 is 1, according to a further specific embodiment, m1 is 2.

According to still a further embodiment, m1 is 2, 3 or 4. According to still a further embodiment, m1 is 3.

According to one embodiment thereof, Z is a five-membered heteroaryl which is unsubstituted or carries one, two or three independently selected radicals $R^{41}$ as defined or preferably defined below. According to a further embodiment thereof, Z is a six-membered heteroaryl which is unsubstituted or carries one, two or three independently selected radicals $R^{41}$ as defined or preferably defined below.

According to one embodiment thereof, Z is selected from the group consisting of pyrimidin-2-yl, pyrimidin-3-yl, pyrimidin-4-yl, pyridin-2-yl, pyridin-3-yl, pyridin-4-yl, thiazol-2-yl, thiazol-4-yl, thiazol-5-yl, isothiazol-3-yl, isothiazol-4-yl, isothiazol-5-yl, pyrazin-2-yl, pyridazin-3-yl, 1,3,5-triazin-2-yl and 1,2,4-triazin-3-yl; wherein said heteroaryl is unsubstituted or carrie one, two, three or four independently selected radicals $R^{41}$ as defined or preferably defined below.

According to one specific embodiment of the invention Z is selected from the group consisting of pyrimidin-2-yl, pyrimidin-3-yl, pyrimidin-4-yl, pyridin-2-yl, pyridin-3-yl, pyridin-4-yl, thiazol-2-yl, pyrazin-2-yl, pyridazin-3-yl, 1,3,5-triazin-2-yl, and 1,2,4-triazin-3-yl; preferably Z is pyrimidin-2-yl, pyridin-2-yl, pyridin-3-yl, pyridin-4-yl and thiazol-2-yl, that are unsubstituted or carry one, two, three or four independently selected radicals $R^{41}$ as defined or preferably defined below.

According to the invention, there can be zero, one, two, three, four or five $R^{41}$ present, namely for m is 0, 1, 2, 3, 4 or 5. The number of m also depends on the kind of heteroaryl. In particular, m is 0, 1, 2 or 3. According to one embodiment, m is 0. According to a further embodiment, m is 1, 2 or 3, in particular 1 or 2. According to one specific embodiment thereof, m is 1, according to a further specific embodiment, m is 2.

For every $R^{41}$ that is present in the inventive compounds, the following embodiments and preferences apply independently of the meaning of any other $R^{41}$ that may be present in the heteroaryl ring. Furthermore, the particular embodiments and preferences given herein for $R^{41}$ apply independently for each of m=1, m=2, m=3, m=4 and m=5.

Each $R^{41}$ is independently selected from halogen, CN, $NO_2$, OH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, $C_3$-$C_8$-cycloalkyloxy, $NH_2$, NH($C_1$-$C_4$-alkyl), N($C_1$-$C_4$-alkyl)$_2$, NH($C_3$-$C_6$-cycloalkyl), N($C_3$-$C_6$-cycloalkyl)$_2$, C(=O)—$C_1$-$C_4$-alkyl, C(=O)OH, C(=O)—O—$C_1$-$C_4$-alkyl, C(=O)—NH($C_1$-$C_4$-alkyl), C(=O)—N($C_1$-$C_4$-alkyl)$_2$, C(=O)—NH($C_3$-$C_6$-cycloalkyl), C(=O)N($C_3$-$C_6$-cycloalkyl)$_2$, phenyl and phenyl-$C_1$-$C_4$-alkyl, wherein the aliphatic, alicyclic and aromatic moieties of $R^{41}$ are unsubstituted or substituted by one, two, three or four or up to the maximum possible number of $R^{41a}$; wherein $R^{41a}$ is independently selected from halogen, CN, $NO_2$, OH, SH, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio and $C_1$-$C_6$-haloalkylthio.

According to one embodiment, $R^{41}$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O$—$C_1$-$C_4$-alkyl), $C(=O)$ $(NH(C_1$-$C_4$-alkyl))$, $C(=O)(N(C_1$-$C_4$-alkyl)$_2)$, $C(=O)(NH$ $(C_3$-$C_6$-cycloalkyl))$ and $C(=O)$—$(N(C_3$-$C_6$-cycloalkyl)$_2)$; wherein each of $R^{41}$ is unsubstituted or further substituted by one, two, three or four independently selected $R^{41a}$, wherein $R^{41a}$ is as defined and preferably defined herein.

According to a further embodiment, $R^{41}$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, $NH_2$, $NH(C_1$-$C_{42}$-alkyl), $N(C_1$-$C_2$-alkyl)$_2$, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl), wherein each of $R^{41}$ is unsubstituted or further substituted by one, two, three or four independently selected $R^{41a}$, wherein $R^{41a}$ is as defined and preferably defined herein.

According to a further embodiment, $R^{41}$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl).

According to a further embodiment, $R^{41}$ is independently selected from halogen, CN, $NO_2$, $C_1$-$C_2$-alkyl, $C_1$-$C_2$-haloalkyl, $C_1$-$C_2$-alkoxy, $C_1$-$C_2$-haloalkoxy, $S(C_1$-$C_2$-alkyl), $S(O)(C_1$-$C_2$-alkyl), $S(O)_2(C_1$-$C_2$-alkyl), $C(=O)(OH)$ and $C(=O)(O$—$C_1$-$C_2$-alkyl).

According to a further embodiment, $R^{41}$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to still a further specific embodiment, $R^{41}$ is independently selected from halogen, in particular from Br, F and Cl, more specifically from F and Cl.

According to a further specific embodiment, $R^{41}$ is CN.
According to one further embodiment $R^{41}$ is $NO_2$.
According to one further embodiment $R^{41}$ is OH.
According to one further embodiment $R^{41}$ is SH.
According to a further specific embodiment, $R^{41}$ is $C_1$-$C_6$-alkyl, in particular $C_1$-$C_4$-alkyl, such as $CH_3$. Further appropriate alkyls are ethyl, n-propyl, i-propyl, n-butyl, i-butyl and t-butyl.

According to a further specific embodiment, $R^{41}$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment $R^{41}$ is $C_1$-$C_6$-alkyl, preferably $C_1$-$C_4$-alkyl, substituted by OH, more preferably $CH_2OH$, $CH_2CH_2OH$, $CH_2CH_2CH_2OH$, $CH(CH_3)CH_2OH$, $CH_2CH(CH_3)OH$, $CH_2CH_2CH_2CH_2OH$. In a special embodiment $R^{41}$ is $CH_2OH$. According to a further specific embodiment $R^{41}$ is $C_1$-$C_6$-alkyl, preferably $C_1$-$C_4$-alkyl substituted by CN, more preferably $CH_2CN$, $CH_2CH_2CN$, $CH_2CH_2CH_2CN$, $CH(CH_3)CH_2CN$, $CH_2CH$ $(CH_3)CN$, $CH_2CH_2CH_2CH_2CN$. In a special embodiment $R^{41}$ is $CH_2CH_2CN$. In a further embodiment $R^{41}$ is $CH(CH_3)CN$. According to a further specific embodiment $R^{41}$ is $C_1$-$C_4$-alkoxy-$C_1$-$C_6$-alkyl, more preferably $C_1$-$C_4$-alkoxy-$C_1$-$C_4$-alkyl. In a special embodiment $R^{41}$ is $CH_2OCH_3$. In a further special embodiment $R^{41}$ is $CH_2CH_2OCH_3$. In a further special embodiment $R^{41}$ is $CH(CH_3)OCH_3$. In a further special embodiment $R^{41}$ is $CH(CH_3)OCH_2CH_3$. In a further special embodiment $R^{41}$ is $CH_2CH_2OCH_2CH_3$. According to a further specific embodiment $R^{41}$ is $C_1$-$C_4$-haloalkoxy-$C_1$-$C_6$-alkyl, more preferably $C_1$-$C_4$-alkoxy-$C_1$-$C_4$-alkyl. In a special embodiment $R^{41}$ is $CH_2OCF_3$. In a further special embodiment $R^{41}$ is $CH_2CH_2OCF_3$. In a further special embodiment $R^{41}$ is $CH_2OCCl_3$. In a further special embodiment $R^{41}$ is $CH_2CH_2OCCl_3$.

According to a further specific embodiment, $R^{41}$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^{41}$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further specific embodiment, $R^{41}$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$, $CH_2CH=CH_2$, $CH=CHCH_3$ or $C(CH_3)=CH_2$.

According to a further specific embodiment $R^{41}$ is $C_2$-$C_6$-alkenyl, preferably $C_2$-$C_4$-alkenyl, substituted by OH, more preferably, $CH=CHOH$, $CH=CHCH_2OH$, $C(CH_3)=CHOH$, $CH=C(CH_3)OH$. In a special embodiment $R^{41}$ is $CH=CHOH$. In a further special embodiment $R^{41}$ is $CH=CHCH_2OH$. According to a further specific embodiment $R^{41}$ is $C_1$-$C_4$-alkoxy-$C_2$-$C_6$-alkenyl, more preferably $C_1$-$C_4$-alkoxy-$C_2$-$C_4$-alkenyl. In a special embodiment $R^{41}$ is $CH=CHOCH_3$. In a further special embodiment $R^{41}$ is $CH=CHCH_2OCH_3$. According to a further specific embodiment $R^{41}$ is $C_1$-$C_4$-haloalkoxy-$C_2$-$C_6$-alkenyl, more preferably $C_1$-$C_4$-haloalkoxy-$C_2$-$C_4$-alkenyl. In a special embodiment $R^{41}$ is $CH=CHOCF_3$. In a further special embodiment $R^{41}$ is $CH=CHCH_2OCF_3$. In a further special embodiment $R^{41}$ is $CH=CHOCCl_3$. In a further special embodiment $R^{41}$ is $CH=CHCH_2OCCl_3$. According to a further specific embodiment $R^{41}$ is $C_3$-$C_8$-cycloalkyl-$C_2$-$C_6$-alkenyl, preferably $C_3$-$C_6$-cycloalkyl-$C_2$-$C_4$-alkenyl. According to a further specific embodiment $R^{41}$ is $C_3$-$C_6$-halocycloalkyl-$C_2$-$C_4$-alkenyl, preferably $C_3$-$C_8$-halocycloalkyl-$C_2$-$C_6$-alkenyl.

According to still a further specific embodiment, $R^{41}$ is $C_2$-$C_6$-alkynyl or $C_2$-$C_6$-haloalkynyl, in particular $C_2$-$C_4$-alkynyl or $C_2$-$C_4$-haloalkynyl, such as $C\equiv CH$, $CH_2CCH$ or $CH_2CCCH_3$.

According to a further specific embodiment $R^{41}$ is $C_2$-$C_6$-alkynyl, preferably $C_2$-$C_4$-alkynyl, substituted by OH, more preferably, $CCOH$, $CH_2CCOH$. In a special embodiment $R^{41}$ is $CCOH$. In a further special embodiment $R^{41}$ is $CH_2CCOH$. According to a further specific embodiment $R^{41}$ is $C_1$-$C_4$-alkoxy-$C_2$-$C_6$-alkynyl, more preferably $C_1$-$C_4$-alkoxy-$C_2$-$C_4$-alkynyl. In a special embodiment $R^{41}$ is $CCOCH_3$. In a further special embodiment $R^{41}$ is $CH_2CCOCH_3$. According to a further specific embodiment $R^{41}$ is $C_1$-$C_4$-haloalkoxy-$C_2$-$C_6$-alkynyl, more preferably $C_1$-$C_4$-haloalkoxy-$C_2$-$C_4$-alkynyl. In a special embodiment $R^{41}$ is $CCOCF_3$. In a further special embodiment $R^{41}$ is $CH_2CCOCF_3$. In a further special embodiment $R^{41}$ is $CCOCCl_3$. In a further special embodiment $R^{41}$ is $CH_2CCOCCl_3$. According to a further specific embodiment $R^{41}$ is $C_3$-$C_8$-cycloalkyl-$C_2$-$C_6$-alkynyl, preferably $C_3$-$C_6$-cycloalkyl-$C_2$-$C_4$-alkynyl. According to a further specific embodiment $R^{41}$ is $C_3$-$C_6$-halocycloalkyl-$C_2$-$C_4$-alkynyl, preferably $C_3$-$C_8$-halocycloalkyl-$C_2$-$C_6$-alkynyl.

According to one another embodiment $R^{41}$ is $C_3$-$C_8$-cycloalkyl, preferably cyclopropyl, cyclobutyl, cyclopentyl or cyclohexyl, in particular cyclopropyl or cyclobutyl. In a special embodiment $R^{41}$ is cyclopropyl. In a further special embodiment $R^{41}$ is cyclobutyl. In a further special embodiment $R^{41}$ is cyclopentyl. In a further special embodiment $R^{41}$ is cyclohexyl.

According to one another embodiment $R^{41}$ is $C_3$-$C_8$-cycloalkoxy, preferably $C_3$-$C_6$-cycloalkoxy. In a special embodiment $R^{41}$ is O-cyclopropyl.

According to a specific embodiment $R^{41}$ is $C_3$-$C_8$-halocycloalkyl, more preferably fully or partially halogenated $C_3$-$C_6$-cycloalkyl. In a special embodiment $R^{41}$ is fully or partially halogenated cyclopropyl. In a further special embodiment $R^{41}$ is 1-Cl-cyclopropyl. In a further special embodiment $R^{41}$ is 2-Cl-cyclopropyl. In a further special embodiment $R^{41}$ is 1-F-cyclopropyl. In a further special embodiment $R^{41}$ is 2-F-cyclopropyl. In a further special embodiment $R^{41}$ is fully or partially halogenated cyclobutyl. In a further special embodiment $R^{41}$ is 1-Cl-cyclobutyl. In a further special embodiment $R^{41}$ is 1-F-cyclobutyl. In a further special embodiment $R^{41}$ is 3,3-$Cl_2$-cyclobutyl. In a further special embodiment $R^{41}$ is 3,3-$F_2$-cyclobutyl. According to a specific embodiment $R^{41}$ is $C_3$-$C_8$-cycloalkyl substituted by $C_1$-$C_4$-alkyl, more preferably is $C_3$-$C_6$-cycloalkyl substituted by $C_1$-$C_4$-alkyl. In a special embodiment $R^{41}$ is 1-$CH_3$-cyclopropyl. According to a specific embodiment $R^{41}$ is $C_3$-$C_8$-cycloalkyl substituted by CN, more preferably is $C_3$-$C_6$-cycloalkyl substituted by CN. In a special embodiment $R^{41}$ is 1-CN-cyclopropyl. According to a further specific embodiment $R^{41}$ is $C_3$-$C_8$-cycloalkyl-$C_3$-$C_8$-cycloalkyl, preferably $C_3$-$C_6$-cycloalkyl-$C_3$-$C_6$-cycloalkyl. In a special embodiment $R^{41}$ is cyclopropyl-cyclopropyl. In a special embodiment $R^{41}$ is 2-cyclopropyl-cyclopropyl. According to a further specific embodiment $R^{41}$ is $C_3$-$C_8$-cycloalkyl-$C_3$-$C_8$-halocycloalkyl, preferably $C_3$-$C_6$-cycloalkyl-$C_3$-$C_6$-halocycloalkyl.

According to one another embodiment $R^{41}$ is $C_3$-$C_8$-cycloalkyl-$C_1$-$C_4$-alkyl, preferably $C_3$-$C_6$-cycloalkyl-$C_1$-$C_4$-alkyl. In a special embodiment $R^{41}$ is $CH(CH_3)$(cyclopropyl). In a further special embodiment $R^{41}$ is $CH_2$-(cyclopropyl).

According to a further preferred embodiment $R^{41}$ is $C_3$-$C_8$-cycloalkyl-$C_1$-$C_4$-alkyl wherein the alkyl moiety can be substituted by one, two, three or up to the maximum possible number of identical or different groups $R^a$ as defined and preferably herein and the cycloalkyl moiety can be substituted by one, two, three or up to the maximum possible number of identical or different groups $R^b$ as defined and preferably herein.

According to a specific embodiment $R^{41}$ is $C_3$-$C_8$-cycloalkyl-$C_1$-$C_4$-haloalkyl, $C_3$-$C_6$-cycloalkyl-$C_1$-$C_4$-haloalkyl. According to a specific embodiment $R^{41}$ is $C_3$-$C_8$-halocycloalkyl-$C_1$-$C_4$-alkyl, $C_3$-$C_6$-halocycloalkyl-$C_1$-$C_4$-alkyl. In a special embodiment $R^{41}$ is fully or partially halogenated cyclopropyl-$C_1$-$C_4$-alkyl. In a further special embodiment $R^{41}$ is 1-Cl-cyclopropyl-$C_1$-$C_4$-alkyl. In a further special embodiment $R^{41}$ is 1-F-cyclopropyl-$C_1$-$C_4$-alkyl.

According to one another embodiment $R^{41}$ is $NH_2$.

According to one another embodiment $R^{41}$ is $NH(C_1$-$C_4$-alkyl). According to a specific embodiment $R^{41}$ is $NH(CH_3)$. According to a specific embodiment $R^{41}$ is $NH(CH_2CH_3)$. According to a specific embodiment $R^{41}$ is $NH(CH_2CH_2CH_3)$. According to a specific embodiment $R^{41}$ is $NH(CH(CH_3)_2)$. According to a specific embodiment $R^{41}$ is $NH(CH_2CH_2CH_2CH_3)$. According to a specific embodiment $R^{41}$ is $NH(C(CH_3)_3)$.

According to one another embodiment $R^{41}$ is $N(C_1$-$C_4$-alkyl)$_2$. According to a specific embodiment $R^{41}$ is $N(CH_3)_2$. According to a specific embodiment $R^{41}$ is $N(CH_2CH_3)_2$. According to a specific embodiment $R^{41}$ is $N(CH_2CH_2CH_3)_2$. According to a specific embodiment $R^{41}$ is $N(CH(CH_3)_2)_2$. According to a specific embodiment $R^{41}$ is $N(CH_2CH_2CH_2CH_3)_2$. According to a specific embodiment $R^{41}$ is $NH(C(CH_3)_3)_2$.

According to one another embodiment $R^{41}$ is $NH(C_3$-$C_8$-cycloalkyl) preferably $NH(C_3$-$C_6$-cycloalkyl). According to a specific embodiment $R^{41}$ is $NH$(cyclopropyl). According to a specific embodiment $R^{41}$ is $NH$(cyclobutyl). According to a specific embodiment $R^{41}$ is $NH$(cyclopentyl). According to a specific embodiment $R^{41}$ is $NH$(cyclohexyl).

According to one another embodiment $R^{41}$ is $N(C_3$-$C_8$-cycloalkyl)$_2$ preferably $N(C_3$-$C_6$-cycloalkyl)$_2$. According to a specific embodiment $R^{41}$ is $N$(cyclopropyl)$_2$. According to a specific embodiment $R^{41}$ is $N$(cyclobutyl)$_2$. According to a specific embodiment $R^{41}$ is $N$(cyclopentyl)$_2$. According to a specific embodiment $R^{41}$ is $N$(cyclohexyl)$_2$.

According to still a further embodiment, $R^{41}$ is selected from $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl)) and $C(=O)(N(C_3$-$C_6$-cycloalkyl)$_2$), in particular selected from $C(=O)(C_1$-$C_2$-alkyl), $C(=O)(OH)$, $C(=O)(O$—$C_1$-$C_2$-alkyl), $C(=O)(NH(C_1$-$C_2$-alkyl))$, $C(=O)(N(C_1$-$C_2$-alkyl)$_2$), $C(=O)(NH(C_3$-$C_6$-cycloalkyl)) and $C(=O)(N(C_3$-$C_6$-cycloalkyl)$_2$). According to one specific embodiment thereof, $R^{41}$ is $C(=O)(OH)$ or $C(=O)(O$—$C_1$-$C_4$-alkyl), in particular $C(=O)(OCH_3)$.

According to one another embodiment $R^{41}$ is $C(=O)($—$C_1$-$C_4$-alkyl). According to a specific embodiment $R^{41}$ is $C(=O)CH_3$. According to a further specific embodiment $R^{41}$ is $C(=O)CH_2CH_3$. According to a further specific embodiment $R^{41}$ is $C(=O)CH_2CH_2CH_3$. According to a further specific embodiment $R^{41}$ is $C(=O)CH(CH_3)_2$. According to a further specific embodiment $R^{41}$ is $C(=O)C(CH_3)_3$.

According to one another embodiment $R^{41}$ is $C(=O)OH$.

According to one another embodiment $R^{41}$ is $C(=O)($—$O$—$C_1$-$C_4$-alkyl). According to a specific embodiment $R^{41}$ is $C(=O)OCH_3$. According to a further specific embodiment $R^{41}$ is $C(=O)OCH_2CH_3$. According to a further specific embodiment $R^{41}$ is $C(=O)OCH_2CH_2CH_3$. According to a further specific embodiment $R^{41}$ is $C(=O)OCH(CH_3)_2$. According to a further specific embodiment $R^{41}$ is $C(=O)OC(CH_3)_3$.

According to one another embodiment $R^{41}$ is $C(=O)$—$NH(C_1$-$C_4$-alkyl). According to a specific embodiment $R^{41}$ is $C(=O)NHCH_3$. According to a further specific embodiment $R^{41}$ is $C(=O)NHCH_2CH_3$. According to a further specific embodiment $R^{41}$ is $C(=O)NHCH_2CH_2CH_3$. According to a further specific embodiment $R^{41}$ is $C(=O)NHCH(CH_3)_2$. According to a further specific embodiment $R^{41}$ is $C(=O)NHC(CH_3)_3$.

According to one another embodiment $R^{41}$ is $C(=O)$—$N(C_1$-$C_4$-alkyl)$_2$. According to a specific embodiment $R^{41}$ is $C(=O)N(CH_3)_2$. According to a further specific embodiment $R^{41}$ is $C(=O)N(CH_2CH_3)_2$. According to a further specific embodiment $R^{41}$ is $C(=O)N(CH_2CH_2CH_3)_2$. According to a further specific embodiment $R^{41}$ is $C(=O)N(CH(CH_3)_2)_2$. According to a further specific embodiment $R^{41}$ is $C(=O)N(C(CH_3)_3)_2$.

According to one another embodiment $R^{41}$ is $C(=O)$—$NH(C_3$-$C_6$-cycloalkyl). According to a specific embodiment $R^{41}$ is $C(=O)NH$(cyclopropyl). According to a further specific embodiment $R^{41}$ is $C(=O)NH$(cyclobutyl). According to a further specific embodiment $R^{41}$ is C(=O)NH(cyclopentyl). According to a further specific embodiment $R^{41}$ is C(=O)NH(cyclohexyl).

According to one another embodiment $R^{41}$ is C(=O)—N($C_3$-$C_6$-cycloalkyl)$_2$. According to a specific embodiment $R^{41}$ is C(=O)N(cyclopropyl)$_2$. According to a further specific embodiment $R^{41}$ is C(=O)N(cyclobutyl)$_2$. According to a further specific embodiment $R^{41}$ is C(=O)N(cyclopentyl)$_2$. According to a further specific embodiment $R^{41}$ is C(=O)N(cyclohexyl)$_2$.

According to still a further embodiment, $R^{41}$ is selected from S($C_1$-$C_2$-alkyl), S(O)($C_1$-$C_2$-alkyl) and S(O)$_2$($C_1$-$C_2$-alkyl), in particular SCH$_3$, S(O)(CH$_3$) and S(O)$_2$(CH$_3$). According to a specific embodiment $R^{41}$ is selected from S($C_1$-$C_2$-haloalkyl), S(O)($C_1$-$C_2$-haloalkyl) and S(O)$_2$($C_1$-$C_2$-haloalkyl), such as SO$_2$CF$_3$.

Particularly preferred embodiments of $R^{41}$ present in the heteroaryl according to the invention are in Table PL above, wherein each line of lines PL-1 to PL-16 corresponds to one particular embodiment of the invention, wherein PL-1 to PL-16 are also in any combination with one another a preferred embodiment of the present invention. Thereby, for every $R^{41}$ that is present in the inventive compounds, these specific embodiments and preferences apply independently of the meaning of any other $R^{41}$ that may be present in the heteroaryl ring.

Particularly preferred embodiments of $(R^{41})_{m1}$ if Z is heteroaryl according to the invention are in Table H below, wherein each line of lines H-1 to H-109 corresponds to one particular embodiment of the invention, wherein H-1 to H-109 are also in any combination a preferred embodiment of the present invention.

TABLE H

| line | Z |
|---|---|
| H-1 | (2-pyridyl) |
| H-2 | (3-pyridyl) |
| H-3 | (4-pyridyl) |
| H-4 | (3-F-2-pyridyl) |
| H-5 | (4-F-2-pyridyl) |
| H-6 | (5-F-2-pyridyl) |
| H-7 | (6-F-2-pyridyl) |
| H-8 | (4-F-3-pyridyl) |
| H-9 | (5-F-3-pyridyl) |
| H-10 | (6-F-3-pyridyl) |
| H-11 | (5-F-3-pyridyl variant) |
| H-12 | (3-F-4-pyridyl) |
| H-13 | (2-F-4-pyridyl) |
| H-14 | (3-Cl-2-pyridyl) |

TABLE H-continued
| line | Z |
|---|---|
| H-15 | 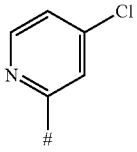 |
| H-16 | 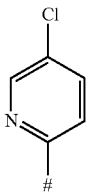 |
| H-17 | 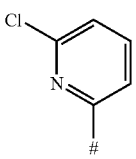 |
| H-18 | 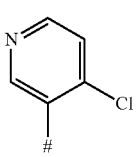 |
| H-19 | 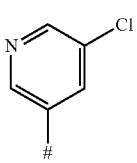 |
| H-20 | 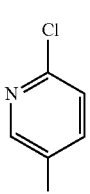 |
| H-21 | 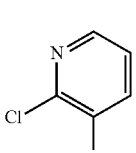 |
| H-22 | 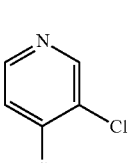 |
| H-23 | 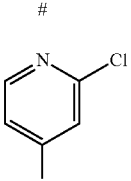 |
TABLE H-continued
| line | Z |
|---|---|
| H-24 | 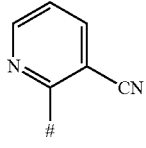 |
| H-25 | 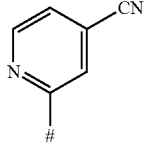 |
| H-26 | 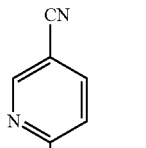 |
| H-27 | 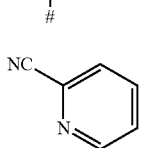 |
| H-28 | 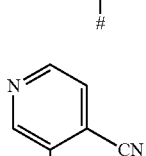 |
| H-29 | 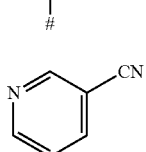 |
| H-30 | 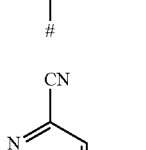 |
| H-31 | 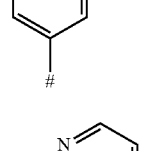 |
| H-32 | 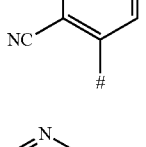 |

TABLE H-continued
| line | Z |
|---|---|
| H-33 | 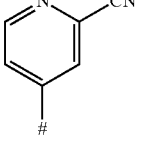 |
| H-34 | 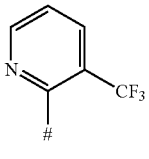 |
| H-35 | 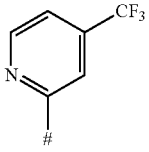 |
| H-36 | 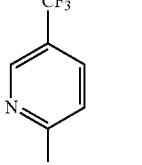 |
| H-37 | 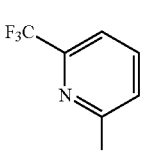 |
| H-38 | 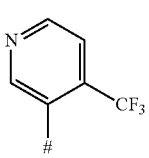 |
| H-39 | 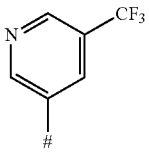 |
| H-40 | 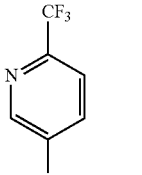 |
| H-41 |  |
| H-42 | 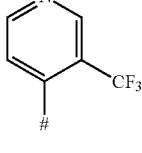 |
| H-43 | 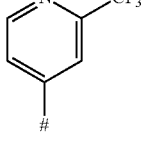 |
| H-44 | 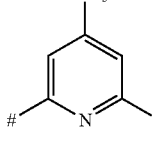 |
| H-45 | 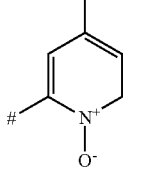 |
| H-46 | 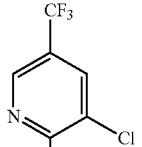 |
| H-47 | 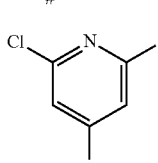 |
| H-48 | 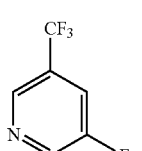 |
| H-49 | 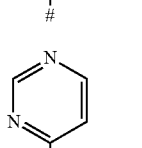 |
| H-50 | 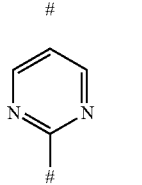 |

TABLE H-continued

| line | Z |
|---|---|
| H-51 | 2-(trifluoromethyl)pyrimidin-4-yl (#) |
| H-52 | 4-(trifluoromethyl)pyrimidin-6-yl (#) |
| H-53 | 2-chloropyrimidin-4-yl (#) |
| H-54 | 4-chloropyrimidin-6-yl (#) |
| H-55 | 2,4-dichloropyrimidin-6-yl (#) |
| H-56 | 2,4-bis(trifluoromethyl)pyrimidin-6-yl (#) |
| H-57 | 2-(trifluoromethyl)-4-chloropyrimidin-6-yl (#) |
| H-58 | 5-methoxy-6-chloropyrimidin-4-yl (#) |
| H-59 | 2-methyl-6-chloropyrimidin-4-yl (#) |
| H-60 | 6-chloro-2-phenylpyrimidin-4-yl (#) |
| H-61 | methyl 6-chloropyrimidine-5-carboxylate-4-yl (#) |
| H-62 | 4-methyl-2-chloropyrimidin-6-yl (#) |
| H-63 | 2,5-dimethyl-6-chloropyrimidin-4-yl (#) |
| H-64 | 5-methyl-6-chloropyrimidin-4-yl (#) |
| H-65 | 4-chloro-2-(dimethylamino)pyrimidin-6-yl (#) |
| H-66 | 6-chloro-2-methoxypyrimidin-4-yl (#) |
| H-67 | 6-chloro-5-fluoropyrimidin-4-yl (#) |
| H-68 | 5-cyano-6-chloropyrimidin-4-yl (#) |

TABLE H-continued

| line | Z |
|------|---|
| H-69 | 4,5-dichloropyrimidin-6-yl (# at 6) |
| H-70 | 2-(trifluoromethyl)-6-chloropyrimidin-4-yl (# at 4) |
| H-71 | 4-methoxypyrimidin-6-yl (# at 6) |
| H-72 | 2-methoxypyrimidin-4-yl (# at 4) |
| H-73 | 4-(trifluoromethyl)pyrimidin-2-yl (# at 2) |
| H-74 | 4,6-dichloropyrimidin-2-yl (# at 2) |
| H-75 | 4,6-bis(trifluoromethyl)pyrimidin-2-yl (# at 2) |
| H-76 | 4-chloro-6-(trifluoromethyl)pyrimidin-2-yl (# at 2) |
| H-77 | 4-chloro-6-(trifluoromethyl)pyrimidin-2-yl (# at 2) |
| H-78 | pyridazin-3-yl (# at 3) |
| H-79 | 3,6-bis-substituted pyridazine with CF₃ (# at 6) |
| H-80 | 3-chloropyridazin-6-yl (# at 6) |
| H-81 | 3-methoxypyridazin-6-yl (# at 6) |
| H-82 | 3-(trifluoromethyl)-1-methyl-1H-pyrazol-5-yl (# at 5) |
| H-83 | 4-chloro-3-(trifluoromethyl)-1-methyl-1H-pyrazol-5-yl (# at 5) |
| H-84 | 3-methyl-1-methyl-1H-pyrazol-5-yl (# at 5) |
| H-85 | 4-chloro-3-methyl-1-methyl-1H-pyrazol-5-yl (# at 5) |

TABLE H-continued
| line | Z |
|---|---|
| H-86 | 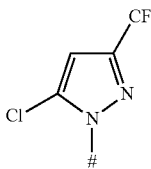 |
| H-87 | 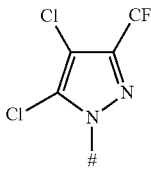 |
| H-88 | 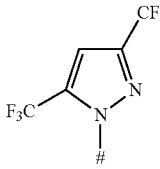 |
| H-89 | 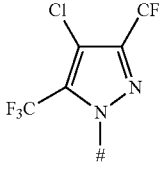 |
| H-90 | 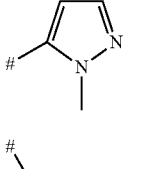 |
| H-91 | 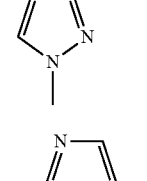 |
| H-92 | 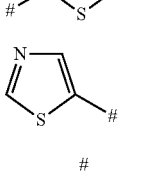 |
| H-93 | 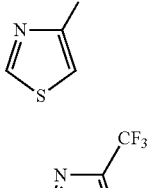 |
| H-94 | 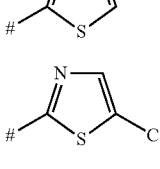 |
| H-95 |  |
| H-96 |  |
TABLE H-continued
| line | Z |
|---|---|
| H-97 | 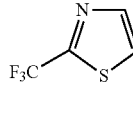 |
| H-98 | 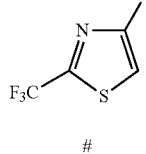 |
| H-99 | 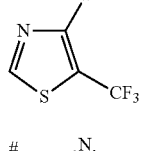 |
| H-100 | 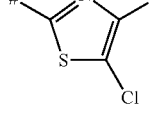 |
| H-101 | 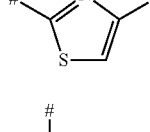 |
| H-102 | 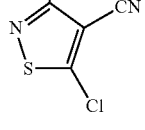 |
| H-103 | 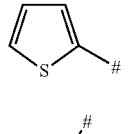 |
| H-104 | 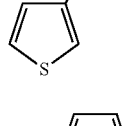 |
| H-105 | 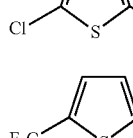 |
| H-106 | 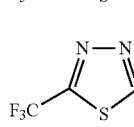 |
| H-107 |  |
| H-108 |  |

TABLE H-continued

| line | Z |
|---|---|
| H-109 | 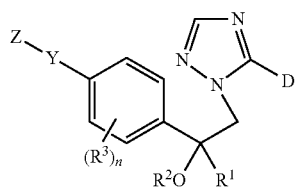 |

One embodiment relates to compounds I, wherein A is N (I.A).

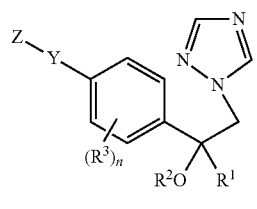

I.A

In one embodiment thereof, Z is phenyl as defined and preferably defined herein. In another embodiment thereof, Z is heteroaryl, as defined and preferably defined herein. Specifically, D is H. Furthermore, it may be particularly preferred in these embodiments, if Y is a direct bond. Specific embodiment are compounds I.A1 (D=H, A=N) and I.A2 (D=SH, A=N):

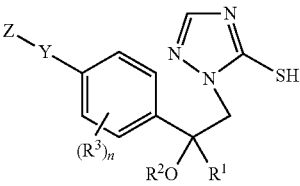

I.A1

I.A2

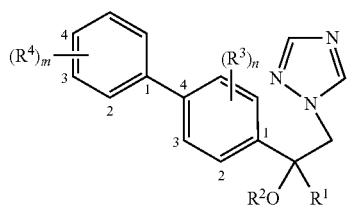

In one embodiment thereof, Z is phenyl as defined and preferably defined herein. In another embodiment thereof, Z is heteroaryl, as defined and preferably defined herein.

One specific embodiment are compounds I.Aa:

I.Aa

A further embodiment of the invention are compounds I.B, wherein A is CH.

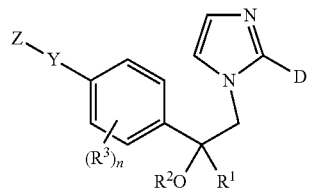

I.B

In one embodiment thereof, Z is phenyl as defined and preferably defined herein. In another embodiment thereof, Z is heteroaryl, as defined and preferably defined herein.

Specific embodiment are compounds I.B1 (D=H, A=CH) and I.B2 (D=SH, A=CH):

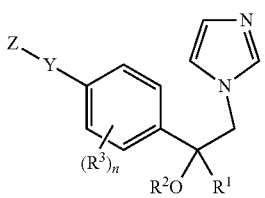

I.B1

I.B2

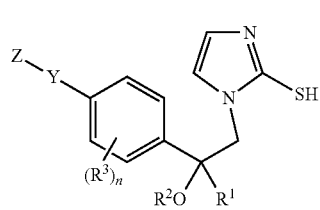

One specific embodiment are compounds I.Ba:

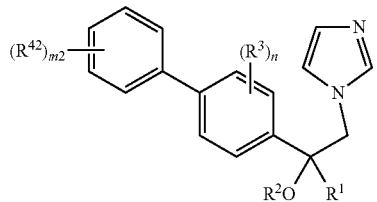

I.Ba

In particular with a view to their use, according to one embodiment, preference is given to the compounds of the formula I.Aa and I.Ba that are compiled in the Tables 1a to 140a and Tables 1b to 140b below. Each of the groups mentioned for a substituent in the tables is furthermore per se, independently of the combination in which it is mentioned, a particularly preferred aspect of the substituent in question.

Table 1a Compounds of the formula I.Aa in which the combination of $(R^3)_n$ and $(R^{42})_{m2}$ corresponds to line D1-1 of Table D1 and the meaning for the combination of $R^1$ and $R^2$ for each individual compound corresponds in each case to one line of Table B (compounds I.Aa.D1-1.B1 to I.Aa.D1-1.B352).

Table 2a Compounds of the formula I.Aa in which the combination of $(R^3)_n$ and $(R^{42})_{m2}$ corresponds to line D1-2 of Table D1 and the meaning for the combination of $R^1$ and $R^2$ for each individual compound corresponds in each case to one line of Table B (compounds I.Aa.D1-2.B1 to I.Aa.D1-2.B352).

Table 3a Compounds of the formula I.Aa in which the combination of $(R^3)_n$ and $(R^{42})_{m2}$ corresponds to line D1-3 of Table D1 and the meaning for the combination of $R^1$ and $R^2$ for each individual compound corresponds in each case to one line of Table B (compounds I.Aa.D1-3.B1 to I.Aa.D1-3.B352).

Table 4a Compounds of the formula I.Aa in which the combination of $(R^3)_n$ and $(R^{42})_{m2}$ corresponds to line D1-4 of Table D1 and the meaning for the combination of $R^1$ and $R^2$ for each individual compound corresponds in each case to one line of Table B (compounds I.Aa.D1-4.B1 to I.Aa.D1-4.B352).

Table 5a Compounds of the formula I.Aa in which the combination of $(R^3)_n$ and $(R^{42})_{m2}$ corresponds to line D1-5 of Table D1 and the meaning for the combination of $R^1$ and $R^2$ for each individual compound corresponds in each case to one line of Table B (compounds I.Aa.D1-5.B1 to I.Aa.D1-5.B352).

Table 6a Compounds of the formula I.Aa in which the combination of $(R^3)_n$ and $(R^{42})_{m2}$ corresponds to line D1-6 of Table D1 and the meaning for the combination of $R^1$ and $R^2$ for each individual compound corresponds in each case to one line of Table B (compounds I.Aa.D1-6.B1 to I.Aa.D1-6.B352).

Table 7a Compounds of the formula I.Aa in which the combination of $(R^3)_n$ and $(R^{42})_{m2}$ corresponds to line D1-7 of Table D1 and the meaning for the combination of $R^1$ and $R^2$ for each individual compound corresponds in each case to one line of Table B (compounds I.Aa.D1-7.B1 to I.Aa.D1-7.B352).

Table 8a Compounds of the formula I.Aa in which the combination of $(R^3)_n$ and $(R^{42})_{m2}$ corresponds to line D1-8 of Table D1 and the meaning for the combination of $R^1$ and $R^2$ for each individual compound corresponds in each case to one line of Table B (compounds I.Aa.D1-8.B1 to I.Aa.D1-8.B352).

Table 9a Compounds of the formula I.Aa in which the combination of $(R^3)_n$ and $(R^{42})_{m2}$ corresponds to line D1-9 of Table D1 and the meaning for the combination of $R^1$ and $R^2$ for each individual compound corresponds in each case to one line of Table B (compounds I.Aa.D1-9.B1 to I.Aa.D1-9.B352).

Table 10a Compounds of the formula I.Aa in which the combination of $(R^3)_n$ and $(R^{42})_{m2}$ corresponds to line D1-10 of Table D1 and the meaning for the combination of $R^1$ and $R^2$ for each individual compound corresponds in each case to one line of Table B (compounds I.Aa.D1-10.B1 to I.Aa.D1-10.B352).

Table 11a Compounds of the formula I.Aa in which the combination of $(R^3)_n$ and $(R^{42})_{m2}$ corresponds to line D1-11 of Table D1 and the meaning for the combination of $R^1$ and $R^2$ for each individual compound corresponds in each case to one line of Table B (compounds I.Aa.D1-11.B1 to I.Aa.D1-11.B352).

Table 12a Compounds of the formula I.Aa in which the combination of $(R^3)_n$ and $(R^{42})_{m2}$ corresponds to line D1-12 of Table D1 and the meaning for the combination of $R^1$ and $R^2$ for each individual compound corresponds in each case to one line of Table B (compounds I.Aa.D1-12.B1 to I.Aa.D1-12.B352).

Table 13a Compounds of the formula I.Aa in which the combination of $(R^3)_n$ and $(R^{42})_{m2}$ corresponds to line D1-13 of Table D1 and the meaning for the combination of $R^1$ and $R^2$ for each individual compound corresponds in each case to one line of Table B (compounds I.Aa.D1-13.B1 to I.Aa.D1-13.B352).

Table 14a Compounds of the formula I.Aa in which the combination of $(R^3)_n$ and $(R^{42})_{m2}$ corresponds to line D1-14 of Table D1 and the meaning for the combination of $R^1$ and $R^2$ for each individual compound corresponds in each case to one line of Table B (compounds I.Aa.D1-14.B1 to I.Aa.D1-14.B352).

Table 15a Compounds of the formula I.Aa in which the combination of $(R^3)_n$ and $(R^{42})_{m2}$ corresponds to line D1-15 of Table D1 and the meaning for the combination of $R^1$ and $R^2$ for each individual compound corresponds in each case to one line of Table B (compounds I.Aa.D1-15.B1 to I.Aa.D1-15.B352).

Table 16a Compounds of the formula I.Aa in which the combination of $(R^3)_n$ and $(R^{42})_{m2}$ corresponds to line D1-16 of Table D1 and the meaning for the combination of $R^1$ and $R^2$ for each individual compound corresponds in each case to one line of Table B (compounds I.Aa.D1-16.B1 to I.Aa.D1-16.B352).

Table 17a Compounds of the formula I.Aa in which the combination of $(R^3)_n$ and $(R^{42})_{m2}$ corresponds to line D1-17 of Table D1 and the meaning for the combination of $R^1$ and $R^2$ for each individual compound corresponds in each case to one line of Table B (compounds I.Aa.D1-17.B1 to I.Aa.D1-17.B352).

Table 18a Compounds of the formula I.Aa in which the combination of $(R^3)_n$ and $(R^{42})_{m2}$ corresponds to line D1-18 of Table D1 and the meaning for the combination of $R^1$ and $R^2$ for each individual compound corresponds in each case to one line of Table B (compounds I.Aa.D1-18.B1 to I.Aa.D1-18.B352).

Table 19a Compounds of the formula I.Aa in which the combination of $(R^3)_n$ and $(R^{42})_{m2}$ corresponds to line D1-19 of Table D1 and the meaning for the combination of $R^1$ and $R^2$ for each individual compound corresponds in each case to one line of Table B (compounds I.Aa.D1-19.B1 to I.Aa.D1-19.B352).

Table 20a Compounds of the formula I.Aa in which the combination of $(R^3)_n$ and $(R^{42})_{m2}$ corresponds to line D1-20 of Table D1 and the meaning for the combination of $R^1$ and $R^2$ for each individual compound corresponds in each case to one line of Table B (compounds I.Aa.D1-20.B1 to I.Aa.D1-20.B352).

Table 21a Compounds of the formula I.Aa in which the combination of $(R^3)_n$ and $(R^{42})_{m2}$ corresponds to line D1-21 of Table D1 and the meaning for the combination of $R^1$ and $R^2$ for each individual compound corresponds in each case to one line of Table B (compounds I.Aa.D1-21.B1 to I.Aa.D1-21.B352).

Table 22a Compounds of the formula I.Aa in which the combination of $(R^3)_n$ and $(R^{42})_{m2}$ corresponds to line D1-22 of Table D1 and the meaning for the combination of $R^1$ and $R^2$ for each individual compound corresponds in each case to one line of Table B (compounds I.Aa.D1-22.B1 to I.Aa.D1-22.B352).

Table 23a Compounds of the formula I.Aa in which the combination of $(R^3)_n$ and $(R^{42})_{m2}$ corresponds to line D1-23 of Table D1 and the meaning for the combination of $R^1$ and $R^2$ for each individual compound corresponds in each case to one line of Table B (compounds I.Aa.D1-23.B1 to I.Aa.D1-23.B352).

Table 24a Compounds of the formula I.Aa in which the combination of $(R^3)_n$ and $(R^{42})_{m2}$ corresponds to line D1-24 of Table D1 and the meaning for the combination of $R^1$ and $R^2$ for each individual compound corresponds in each case to one line of Table B (compounds I.Aa.D1-24.B1 to I.Aa.D1-24.B352).

Table 25a Compounds of the formula I.Aa in which the combination of $(R^3)_n$ and $(R^{42})_{m2}$ corresponds to line D1-25 of Table D1 and the meaning for the combination of $R^1$ and $R^2$ for each individual compound corresponds in each case to one line of Table B (compounds I.Aa.D1-25.B1 to I.Aa.D1-25.B352).

Table 26a Compounds of the formula I.Aa in which the combination of $(R^3)_n$ and $(R^{42})_{m2}$ corresponds to line D1-26 of Table D1 and the meaning for the combination of $R^1$ and $R^2$ for each individual compound corresponds in each case to one line of Table B (compounds I.Aa.D1-26.B1 to I.Aa.D1-26.B352).

Table 27a Compounds of the formula I.Aa in which the combination of $(R^3)_n$ and $(R^{42})_{m2}$ corresponds to line D1-27 of Table D1 and the meaning for the combination of $R^1$ and $R^2$ for each individual compound corresponds in each case to one line of Table B (compounds I.Aa.D1-27.B1 to I.Aa.D1-27.B352).

Table 28a Compounds of the formula I.Aa in which the combination of $(R^3)_n$ and $(R^{42})_{m2}$ corresponds to line D1-28 of Table D1 and the meaning for the combination of $R^1$ and $R^2$ for each individual compound corresponds in each case to one line of Table B (compounds I.Aa.D1-28.B1 to I.Aa.D1-28.B352).

Table 29a Compounds of the formula I.Aa in which the combination of $(R^3)_n$ and $(R^{42})_{m2}$ corresponds to line D1-29 of Table D1 and the meaning for the combination of $R^1$ and $R^2$ for each individual compound corresponds in each case to one line of Table B (compounds I.Aa.D1-29.B1 to I.Aa.D1-29.B352).

Table 30a Compounds of the formula I.Aa in which the combination of $(R^3)_n$ and $(R^{42})_{m2}$ corresponds to line D1-30 of Table D1 and the meaning for the combination of $R^1$ and $R^2$ for each individual compound corresponds in each case to one line of Table B (compounds I.Aa.D1-30.B1 to I.Aa.D1-30.B352).

Table 31a Compounds of the formula I.Aa in which the combination of $(R^3)_n$ and $(R^{42})_{m2}$ corresponds to line D1-31 of Table D1 and the meaning for the combination of $R^1$ and $R^2$ for each individual compound corresponds in each case to one line of Table B (compounds I.Aa.D1-31.B1 to I.Aa.D1-31.B352).

Table 32a Compounds of the formula I.Aa in which the combination of $(R^3)_n$ and $(R^{42})_{m2}$ corresponds to line D1-32 of Table D1 and the meaning for the combination of $R^1$ and $R^2$ for each individual compound corresponds in each case to one line of Table B (compounds I.Aa.D1-32.B1 to I.Aa.D1-32.B352).

Table 33a Compounds of the formula I.Aa in which the combination of $(R^3)_n$ and $(R^{42})_{m2}$ corresponds to line D1-33 of Table D1 and the meaning for the combination of $R^1$ and $R^2$ for each individual compound corresponds in each case to one line of Table B (compounds I.Aa.D1-33.B1 to I.Aa.D1-33.B352).

Table 34a Compounds of the formula I.Aa in which the combination of $(R^3)_n$ and $(R^{42})_{m2}$ corresponds to line D1-34 of Table D1 and the meaning for the combination of $R^1$ and $R^2$ for each individual compound corresponds in each case to one line of Table B (compounds I.Aa.D1-34.B1 to I.Aa.D1-34.B352).

Table 35a Compounds of the formula I.Aa in which the combination of $(R^3)_n$ and $(R^{42})_{m2}$ corresponds to line D1-35 of Table D1 and the meaning for the combination of $R^1$ and $R^2$ for each individual compound corresponds in each case to one line of Table B (compounds I.Aa.D1-35.B1 to I.Aa.D1-35.B352).

Table 36a Compounds of the formula I.Aa in which the combination of $(R^3)_n$ and $(R^{42})_{m2}$ corresponds to line D1-36 of Table D1 and the meaning for the combination of $R^1$ and $R^2$ for each individual compound corresponds in each case to one line of Table B (compounds I.Aa.D1-36.B1 to I.Aa.D1-36.B352).

Table 37a Compounds of the formula I.Aa in which the combination of $(R^3)_n$ and $(R^{42})_{m2}$ corresponds to line D1-37 of Table D1 and the meaning for the combination of $R^1$ and $R^2$ for each individual compound corresponds in each case to one line of Table B (compounds I.Aa.D1-37.B1 to I.Aa.D1-37.B352).

Table 38a Compounds of the formula I.Aa in which the combination of $(R^3)_n$ and $(R^{42})_{m2}$ corresponds to line D1-38 of Table D1 and the meaning for the combination of $R^1$ and $R^2$ for each individual compound corresponds in each case to one line of Table B (compounds I.Aa.D1-38.B1 to I.Aa.D1-38.B352).

Table 39a Compounds of the formula I.Aa in which the combination of $(R^3)_n$ and $(R^{42})_{m2}$ corresponds to line D1-39 of Table D1 and the meaning for the combination of $R^1$ and $R^2$ for each individual compound corresponds in each case to one line of Table B (compounds I.Aa.D1-39.B1 to I.Aa.D1-39.B352).

Table 40a Compounds of the formula I.Aa in which the combination of $(R^3)_n$ and $(R^{42})_{m2}$ corresponds to line D1-40 of Table D1 and the meaning for the combination of $R^1$ and $R^2$ for each individual compound corresponds in each case to one line of Table B (compounds I.Aa.D1-40.B1 to I.Aa.D1-40.B352).

Table 41a Compounds of the formula I.Aa in which the combination of $(R^3)_n$ and $(R^{42})_{m2}$ corresponds to line D1-41 of Table D1 and the meaning for the combination of $R^1$ and $R^2$ for each individual compound corresponds in each case to one line of Table B (compounds I.Aa.D1-41.B1 to I.Aa.D1-41.B352).

Table 42a Compounds of the formula I.Aa in which the combination of $(R^3)_n$ and $(R^{42})_{m2}$ corresponds to line D1-42 of Table D1 and the meaning for the combination of $R^1$ and $R^2$ for each individual compound corresponds in each case to one line of Table B (compounds I.Aa.D1-42.B1 to I.Aa.D1-42.B352).

Table 43a Compounds of the formula I.Aa in which the combination of $(R^3)_n$ and $(R^{42})_{m2}$ corresponds to line D1-43 of Table D1 and the meaning for the combination of $R^1$ and $R^2$ for each individual compound corresponds in each case to one line of Table B (compounds I.Aa.D1-43.B1 to I.Aa.D1-43.B352).

Table 44a Compounds of the formula I.Aa in which the combination of $(R^3)_n$ and $(R^{42})_{m2}$ corresponds to line D1-44 of Table D1 and the meaning for the combination of $R^1$ and $R^2$ for each individual compound corresponds in each case to one line of Table B (compounds I.Aa.D1-44.B1 to I.Aa.D1-44.B352).

Table 45a Compounds of the formula I.Aa in which the combination of $(R^3)_n$ and $(R^{42})_{m2}$ corresponds to line D1-45 of Table D1 and the meaning for the combination of $R^1$ and $R^2$ for each individual compound corresponds in each case to one line of Table B (compounds I.Aa.D1-45.B1 to I.Aa.D1-45.B352).

Table 46a Compounds of the formula I.Aa in which the combination of $(R^3)_n$ and $(R^{42})_{m2}$ corresponds to line D1-46 of Table D1 and the meaning for the combination of $R^1$ and $R^2$ for each individual compound corresponds in each case to one line of Table B (compounds I.Aa.D1-46.B1 to I.Aa.D1-46.B352).

Table 47a Compounds of the formula I.Aa in which the combination of $(R^3)_n$ and $(R^{42})_{m2}$ corresponds to line D1-47 of Table D1 and the meaning for the combination of $R^1$ and $R^2$ for each individual compound corresponds in each case to one line of Table B (compounds I.Aa.D1-47.B1 to I.Aa.D1-47.B352).

Table 48a Compounds of the formula I.Aa in which the combination of $(R^3)_n$ and $(R^{42})_{m2}$ corresponds to line D1-48 of Table D1 and the meaning for the combination of $R^1$ and $R^2$ for each individual compound corresponds in each case to one line of Table B (compounds I.Aa.D1-48.B1 to I.Aa.D1-48.B352).

Table 49a Compounds of the formula I.Aa in which the combination of $(R^3)_n$ and $(R^{42})_{m2}$ corresponds to line D1-49 of Table D1 and the meaning for the combination of $R^1$ and $R^2$ for each individual compound corresponds in each case to one line of Table B (compounds I.Aa.D1-49.B1 to I.Aa.D1-49.B352).

Table 50a Compounds of the formula I.Aa in which the combination of $(R^3)_n$ and $(R^{42})_{m2}$ corresponds to line D1-50 of Table D1 and the meaning for the combination of $R^1$ and $R^2$ for each individual compound corresponds in each case to one line of Table B (compounds I.Aa.D1-50.B1 to I.Aa.D1-50.B352).

Table 51a Compounds of the formula I.Aa in which the combination of $(R^3)_n$ and $(R^{42})_{m2}$ corresponds to line D1-51 of Table D1 and the meaning for the combination of $R^1$ and $R^2$ for each individual compound corresponds in each case to one line of Table B (compounds I.Aa.D1-51.B1 to I.Aa.D1-51.B352).

Table 52a Compounds of the formula I.Aa in which the combination of $(R^3)_n$ and $(R^{42})_{m2}$ corresponds to line D1-52 of Table D1 and the meaning for the combination of $R^1$ and $R^2$ for each individual compound corresponds in each case to one line of Table B (compounds I.Aa.D1-52.B1 to I.Aa.D1-52.B352).

Table 53a Compounds of the formula I.Aa in which the combination of $(R^3)_n$ and $(R^{42})_{m2}$ corresponds to line D1-53 of Table D1 and the meaning for the combination of $R^1$ and $R^2$ for each individual compound corresponds in each case to one line of Table B (compounds I.Aa.D1-53.B1 to I.Aa.D1-53.B352).

Table 54a Compounds of the formula I.Aa in which the combination of $(R^3)_n$ and $(R^{42})_{m2}$ corresponds to line D1-54 of Table D1 and the meaning for the combination of $R^1$ and $R^2$ for each individual compound corresponds in each case to one line of Table B (compounds I.Aa.D1-54.B1 to I.Aa.D1-54.B352).

Table 55a Compounds of the formula I.Aa in which the combination of $(R^3)_n$ and $(R^{42})_{m2}$ corresponds to line D1-55 of Table D1 and the meaning for the combination of $R^1$ and $R^2$ for each individual compound corresponds in each case to one line of Table B (compounds I.Aa.D1-55.B1 to I.Aa.D1-55.B352).

Table 56a Compounds of the formula I.Aa in which the combination of $(R^3)_n$ and $(R^{42})_{m2}$ corresponds to line D1-56 of Table D1 and the meaning for the combination of $R^1$ and $R^2$ for each individual compound corresponds in each case to one line of Table B (compounds I.Aa.D1-56.B1 to I.Aa.D1-56.B352).

Table 57a Compounds of the formula I.Aa in which the combination of $(R^3)_n$ and $(R^{42})_{m2}$ corresponds to line D1-57 of Table D1 and the meaning for the combination of $R^1$ and $R^2$ for each individual compound corresponds in each case to one line of Table B (compounds I.Aa.D1-57.B1 to I.Aa.D1-57.B352).

Table 58a Compounds of the formula I.Aa in which the combination of $(R^3)_n$ and $(R^{42})_{m2}$ corresponds to line D1-58 of Table D1 and the meaning for the combination of $R^1$ and $R^2$ for each individual compound corresponds in each case to one line of Table B (compounds I.Aa.D1-58.B1 to I.Aa.D1-58.B352).

Table 59a Compounds of the formula I.Aa in which the combination of $(R^3)_n$ and $(R^{42})_{m2}$ corresponds to line D1-59 of Table D1 and the meaning for the combination of $R^1$ and $R^2$ for each individual compound corresponds in each case to one line of Table B (compounds I.Aa.D1-59.B1 to I.Aa.D1-59.B352).

Table 60a Compounds of the formula I.Aa in which the combination of $(R^3)_n$ and $(R^{42})_{m2}$ corresponds to line D1-60 of Table D1 and the meaning for the combination of $R^1$ and $R^2$ for each individual compound corresponds in each case to one line of Table B (compounds I.Aa.D1-60.B1 to I.Aa.D1-60.B352).

Table 61a Compounds of the formula I.Aa in which the combination of $(R^3)_n$ and $(R^{42})_{m2}$ corresponds to line D1-61 of Table D1 and the meaning for the combination of $R^1$ and $R^2$ for each individual compound corresponds in each case to one line of Table B (compounds I.Aa.D1-61.B1 to I.Aa.D1-61.B352).

Table 62a Compounds of the formula I.Aa in which the combination of $(R^3)_n$ and $(R^{42})_{m2}$ corresponds to line D1-62 of Table D1 and the meaning for the combination of $R^1$ and $R^2$ for each individual compound corresponds in each case to one line of Table B (compounds I.Aa.D1-62.B1 to I.Aa.D1-62.B352).

Table 63a Compounds of the formula I.Aa in which the combination of $(R^3)_n$ and $(R^{42})_{m2}$ corresponds to line D1-63 of Table D1 and the meaning for the combination of $R^1$ and $R^2$ for each individual compound corresponds in each case to one line of Table B (compounds I.Aa.D1-63.B1 to I.Aa.D1-63.B352).

Table 64a Compounds of the formula I.Aa in which the combination of $(R^3)_n$ and $(R^{42})_{m2}$ corresponds to line D1-64 of Table D1 and the meaning for the combination of $R^1$ and $R^2$ for each individual compound corresponds in each case to one line of Table B (compounds I.Aa.D1-64.B1 to I.Aa.D1-64.B352).

Table 65a Compounds of the formula I.Aa in which the combination of $(R^3)_n$ and $(R^{42})_{m2}$ corresponds to line D1-65 of Table D1 and the meaning for the combination of $R^1$ and $R^2$ for each individual compound corresponds in each case to one line of Table B (compounds I.Aa.D1-65.B1 to I.Aa.D1-65.B352).

Table 66a Compounds of the formula I.Aa in which the combination of $(R^3)_n$ and $(R^{42})_{m2}$ corresponds to line D1-66 of Table D1 and the meaning for the combination of $R^1$ and $R^2$ for each individual compound corresponds in each case to one line of Table B (compounds I.Aa.D1-66.B1 to I.Aa.D1-66.B352).

Table 67a Compounds of the formula I.Aa in which the combination of $(R^3)_n$ and $(R^{42})_{m2}$ corresponds to line D1-67 of Table D1 and the meaning for the combination of $R^1$ and $R^2$ for each individual compound corresponds in each case to one line of Table B (compounds I.Aa.D1-67.B1 to I.Aa.D1-67.B352).

Table 68a Compounds of the formula I.Aa in which the combination of $(R^3)_n$ and $(R^{42})_{m2}$ corresponds to line D1-68 of Table D1 and the meaning for the combination of $R^1$ and $R^2$ for each individual compound corresponds in each case to one line of Table B (compounds I.Aa.D1-68.B1 to I.Aa.D1-68.B352).

Table 69a Compounds of the formula I.Aa in which the combination of $(R^3)_n$ and $(R^{42})_{m2}$ corresponds to line D1-69 of Table D1 and the meaning for the combination of $R^1$ and $R^2$ for each individual compound corresponds in each case to one line of Table B (compounds I.Aa.D1-69.B1 to I.Aa.D1-69.B352).

Table 70a Compounds of the formula I.Aa in which the combination of $(R^3)_n$ and $(R^{42})_{m2}$ corresponds to line D1-70 of Table D1 and the meaning for the combination of $R^1$ and $R^2$ for each individual compound corresponds in each case to one line of Table B (compounds I.Aa.D1-70.B1 to I.Aa.D1-70.B352).

Table 71a Compounds of the formula I.Aa in which the combination of $(R^3)_n$ and $(R^{42})_{m2}$ corresponds to line D2-1 of Table D2 and the meaning for the combination of $R^1$ and $R^2$ for each individual compound corresponds in each case to one line of Table B (compounds I.Aa.D2-1.B1 to I.Aa.D2-1.B352).

Table 72a Compounds of the formula I.Aa in which the combination of $(R^3)_n$ and $(R^{42})_{m2}$ corresponds to line D2-2 of Table D2 and the meaning for the combination of $R^1$ and $R^2$ for each individual compound corresponds in each case to one line of Table B (compounds I.Aa.D2-2.B1 to I.Aa.D2-2.B352).

Table 73a Compounds of the formula I.Aa in which the combination of $(R^3)_n$ and $(R^{42})_{m2}$ corresponds to line D2-3 of Table D2 and the meaning for the combination of $R^1$ and $R^2$ for each individual compound corresponds in each case to one line of Table B (compounds I.Aa.D2-3.B1 to I.Aa.D2-3.B352).

Table 74a Compounds of the formula I.Aa in which the combination of $(R^3)_n$ and $(R^{42})_{m2}$ corresponds to line D2-4 of Table D2 and the meaning for the combination of $R^1$ and $R^2$ for each individual compound corresponds in each case to one line of Table B (compounds I.Aa.D2-4.B1 to I.Aa.D2-4.B352).

Table 75a Compounds of the formula I.Aa in which the combination of $(R^3)_n$ and $(R^{42})_{m2}$ corresponds to line D2-5 of Table D2 and the meaning for the combination of $R^1$ and $R^2$ for each individual compound corresponds in each case to one line of Table B (compounds I.Aa.D2-5.B1 to I.Aa.D2-5.B352).

Table 76a Compounds of the formula I.Aa in which the combination of $(R^3)_n$ and $(R^{42})_{m2}$ corresponds to line D2-6 of Table D2 and the meaning for the combination of $R^1$ and $R^2$ for each individual compound corresponds in each case to one line of Table B (compounds I.Aa.D2-6.B1 to I.Aa.D2-6.B352).

Table 77a Compounds of the formula I.Aa in which the combination of $(R^3)_n$ and $(R^{42})_{m2}$ corresponds to line D2-7 of Table D2 and the meaning for the combination of $R^1$ and $R^2$ for each individual compound corresponds in each case to one line of Table B (compounds I.Aa.D2-7.B1 to I.Aa.D2-7.B352).

Table 78a Compounds of the formula I.Aa in which the combination of $(R^3)_n$ and $(R^{42})_{m2}$ corresponds to line D2-8 of Table D2 and the meaning for the combination of $R^1$ and $R^2$ for each individual compound corresponds in each case to one line of Table B (compounds I.Aa.D2-8.B1 to I.Aa.D2-8.B352).

Table 79a Compounds of the formula I.Aa in which the combination of $(R^3)_n$ and $(R^{42})_{m2}$ corresponds to line D2-9 of Table D2 and the meaning for the combination of $R^1$ and $R^2$ for each individual compound corresponds in each case to one line of Table B (compounds I.Aa.D2-9.B1 to I.Aa.D2-9.B352).

Table 80a Compounds of the formula I.Aa in which the combination of $(R^3)_n$ and $(R^{42})_{m2}$ corresponds to line D2-10 of Table D2 and the meaning for the combination of $R^1$ and $R^2$ for each individual compound corresponds in each case to one line of Table B (compounds I.Aa.D2-10.B1 to I.Aa.D2-10.B352).

Table 81a Compounds of the formula I.Aa in which the combination of $(R^3)_n$ and $(R^{42})_{m2}$ corresponds to line D2-11 of Table D2 and the meaning for the combination of $R^1$ and $R^2$ for each individual compound corresponds in each case to one line of Table B (compounds I.Aa.D2-11.B1 to I.Aa.D2-11.B352).

Table 82a Compounds of the formula I.Aa in which the combination of $(R^3)_n$ and $(R^{42})_{m2}$ corresponds to line D2-12 of Table D2 and the meaning for the combination of $R^1$ and $R^2$ for each individual compound corresponds in each case to one line of Table B (compounds I.Aa.D2-12.B1 to I.Aa.D2-12.B352).

Table 83a Compounds of the formula I.Aa in which the combination of $(R^3)_n$ and $(R^{42})_{m2}$ corresponds to line D2-13 of Table D2 and the meaning for the combination of $R^1$ and $R^2$ for each individual compound corresponds in each case to one line of Table B (compounds I.Aa.D2-13.B1 to I.Aa.D2-13.B352).

Table 84a Compounds of the formula I.Aa in which the combination of $(R^3)_n$ and $(R^{42})_{m2}$ corresponds to line D2-14 of Table D2 and the meaning for the combination of $R^1$ and $R^2$ for each individual compound corresponds in each case to one line of Table B (compounds I.Aa.D2-14.B1 to I.Aa.D2-14.B352).

Table 85a Compounds of the formula I.Aa in which the combination of $(R^3)_n$ and $(R^{42})_{m2}$ corresponds to line D2-15 of Table D2 and the meaning for the combination of $R^1$ and $R^2$ for each individual compound corresponds in each case to one line of Table B (compounds I.Aa.D2-15.B1 to I.Aa.D2-15.B352).

Table 86a Compounds of the formula I.Aa in which the combination of $(R^3)_n$ and $(R^{42})_{m2}$ corresponds to line D2-16 of Table D2 and the meaning for the combination of $R^1$ and $R^2$ for each individual compound corresponds in each case to one line of Table B (compounds I.Aa.D2-16.B1 to I.Aa.D2-16.B352).

Table 87a Compounds of the formula I.Aa in which the combination of $(R^3)_n$ and $(R^{42})_{m2}$ corresponds to line D2-17 of Table D2 and the meaning for the combination of $R^1$ and $R^2$ for each individual compound corresponds in each case to one line of Table B (compounds I.Aa.D2-17.B1 to I.Aa.D2-17.B352).

Table 88a Compounds of the formula I.Aa in which the combination of $(R^3)_n$ and $(R^{42})_{m2}$ corresponds to line D2-18 of Table D2 and the meaning for the combination of $R^1$ and $R^2$ for each individual compound corresponds in each case to one line of Table B (compounds I.Aa.D2-18.B1 to I.Aa.D2-18.B352).

Table 89a Compounds of the formula I.Aa in which the combination of $(R^3)_n$ and $(R^{42})_{m2}$ corresponds to line D2-19 of Table D2 and the meaning for the combination of $R^1$ and $R^2$ for each individual compound corresponds in each case to one line of Table B (compounds I.Aa.D2-19.B1 to I.Aa.D2-19.B352).

Table 90a Compounds of the formula I.Aa in which the combination of $(R^3)_n$ and $(R^{42})_{m2}$ corresponds to line D2-20 of Table D2 and the meaning for the combination of $R^1$ and $R^2$ for each individual compound corresponds in each case to one line of Table B (compounds I.Aa.D2-20.B1 to I.Aa.D2-20.B352).

Table 91a Compounds of the formula I.Aa in which the combination of $(R^3)_n$ and $(R^{42})_{m2}$ corresponds to line D2-21 of Table D2 and the meaning for the combination of $R^1$ and $R^2$ for each individual compound corresponds in each case to one line of Table B (compounds I.Aa.D2-21.B1 to I.Aa.D2-21.B352).

Table 92a Compounds of the formula I.Aa in which the combination of $(R^3)_n$ and $(R^{42})_{m2}$ corresponds to line D2-22 of Table D2 and the meaning for the combination of $R^1$ and $R^2$ for each individual compound corresponds in each case to one line of Table B (compounds I.Aa.D2-22.B1 to I.Aa.D2-22.B352).

Table 93a Compounds of the formula I.Aa in which the combination of $(R^3)_n$ and $(R^{42})_{m2}$ corresponds to line D2-23 of Table D2 and the meaning for the combination of $R^1$ and $R^2$ for each individual compound corresponds in each case to one line of Table B (compounds I.Aa.D2-23.B1 to I.Aa.D2-23.B352).

Table 94a Compounds of the formula I.Aa in which the combination of $(R^3)_n$ and $(R^{42})_{m2}$ corresponds to line D2-24 of Table D2 and the meaning for the combination of $R^1$ and $R^2$ for each individual compound corresponds in each case to one line of Table B (compounds I.Aa.D2-24.B1 to I.Aa.D2-24.B352).

Table 95a Compounds of the formula I.Aa in which the combination of $(R^3)_n$ and $(R^{42})_{m2}$ corresponds to line D2-25 of Table D2 and the meaning for the combination of $R^1$ and $R^2$ for each individual compound corresponds in each case to one line of Table B (compounds I.Aa.D2-25.B1 to I.Aa.D2-25.B352).

Table 96a Compounds of the formula I.Aa in which the combination of $(R^3)_n$ and $(R^{42})_{m2}$ corresponds to line D2-26 of Table D2 and the meaning for the combination of $R^1$ and $R^2$ for each individual compound corresponds in each case to one line of Table B (compounds I.Aa.D2-26.B1 to I.Aa.D2-26.B352).

Table 97a Compounds of the formula I.Aa in which the combination of $(R^3)_n$ and $(R^{42})_{m2}$ corresponds to line D2-27 of Table D2 and the meaning for the combination of $R^1$ and $R^2$ for each individual compound corresponds in each case to one line of Table B (compounds I.Aa.D2-27.B1 to I.Aa.D2-27.B352).

Table 98a Compounds of the formula I.Aa in which the combination of $(R^3)_n$ and $(R^{42})_{m2}$ corresponds to line D2-28 of Table D2 and the meaning for the combination of $R^1$ and $R^2$ for each individual compound corresponds in each case to one line of Table B (compounds I.Aa.D2-28.B1 to I.Aa.D2-28.B352).

Table 99a Compounds of the formula I.Aa in which the combination of $(R^3)_n$ and $(R^{42})_{m2}$ corresponds to line D2-29 of Table D2 and the meaning for the combination of $R^1$ and $R^2$ for each individual compound corresponds in each case to one line of Table B (compounds I.Aa.D2-29.B1 to I.Aa.D2-29.B352).

Table 100a Compounds of the formula I.Aa in which the combination of $(R^3)_n$ and $(R^{42})_{m2}$ corresponds to line D2-30 of Table D2 and the meaning for the combination of $R^1$ and $R^2$ for each individual compound corresponds in each case to one line of Table B (compounds I.Aa.D2-30.B1 to I.Aa.D2-30.B352).

Table 101a Compounds of the formula I.Aa in which the combination of $(R^3)_n$ and $(R^{42})_{m2}$ corresponds to line D2-31 of Table D2 and the meaning for the combination of $R^1$ and $R^2$ for each individual compound corresponds in each case to one line of Table B (compounds I.Aa.D2-31.B1 to I.Aa.D2-31.B352).

Table 102a Compounds of the formula I.Aa in which the combination of $(R^3)_n$ and $(R^{42})_{m2}$ corresponds to line D2-32 of Table D2 and the meaning for the combination of $R^1$ and $R^2$ for each individual compound corresponds in each case to one line of Table B (compounds I.Aa.D2-32.B1 to I.Aa.D2-32.B352).

Table 103a Compounds of the formula I.Aa in which the combination of $(R^3)_n$ and $(R^{42})_{m2}$ corresponds to line D2-33 of Table D2 and the meaning for the combination of $R^1$ and $R^2$ for each individual compound corresponds in each case to one line of Table B (compounds I.Aa.D2-33.B1 to I.Aa.D2-33.B352).

Table 104a Compounds of the formula I.Aa in which the combination of $(R^3)_n$ and $(R^{42})_{m2}$ corresponds to line D2-34 of Table D2 and the meaning for the combination of $R^1$ and $R^2$ for each individual compound corresponds in each case to one line of Table B (compounds I.Aa.D2-34.B1 to I.Aa.D2-34.B352).

Table 105a Compounds of the formula I.Aa in which the combination of $(R^3)_n$ and $(R^{42})_{m2}$ corresponds to line D2-35 of Table D2 and the meaning for the combination of $R^1$ and $R^2$ for each individual compound corresponds in each case to one line of Table B (compounds I.Aa.D2-35.B1 to I.Aa.D2-35.B352).

Table 106a Compounds of the formula I.Aa in which the combination of $(R^3)_n$ and $(R^{42})_{m2}$ corresponds to line D2-36 of Table D2 and the meaning for the combination of $R^1$ and $R^2$ for each individual compound corresponds in each case to one line of Table B (compounds I.Aa.D2-36.B1 to I.Aa.D2-36.B352).

Table 107a Compounds of the formula I.Aa in which the combination of $(R^3)_n$ and $(R^{42})_{m2}$ corresponds to line D2-37 of Table D2 and the meaning for the combination of $R^1$ and $R^2$ for each individual compound corresponds in each case to one line of Table B (compounds I.Aa.D2-37.B1 to I.Aa.D2-37.B352).

Table 108a Compounds of the formula I.Aa in which the combination of $(R^3)_n$ and $(R^{42})_{m2}$ corresponds to line D2-38 of Table D2 and the meaning for the combination of $R^1$ and $R^2$ for each individual compound corresponds in each case to one line of Table B (compounds I.Aa.D2-38.B1 to I.Aa.D2-38.B352).

Table 109a Compounds of the formula I.Aa in which the combination of $(R^3)_n$ and $(R^{42})_{m2}$ corresponds to line D2-39 of Table D2 and the meaning for the combination of $R^1$ and $R^2$ for each individual compound corresponds in each case to one line of Table B (compounds I.Aa.D2-39.B1 to I.Aa.D2-39.B352).

Table 110a Compounds of the formula I.Aa in which the combination of $(R^3)_n$ and $(R^{42})_{m2}$ corresponds to line D2-40 of Table D2 and the meaning for the combination of $R^1$ and $R^2$ for each individual compound corresponds in each case to one line of Table B (compounds I.Aa.D2-40.B1 to I.Aa.D2-40.B352).

Table 111a Compounds of the formula I.Aa in which the combination of $(R^3)_n$ and $(R^{42})_{m2}$ corresponds to line D2-41 of Table D2 and the meaning for the combination of $R^1$ and $R^2$ for each individual compound corresponds in each case to one line of Table B (compounds I.Aa.D2-41.B1 to I.Aa.D2-41.B352).

Table 112a Compounds of the formula I.Aa in which the combination of $(R^3)_n$ and $(R^{42})_{m2}$ corresponds to line D2-42 of Table D2 and the meaning for the combination of $R^1$ and $R^2$ for each individual compound corresponds in each case to one line of Table B (compounds I.Aa.D2-42.B1 to I.Aa.D2-42.B352).

Table 113a Compounds of the formula I.Aa in which the combination of $(R^3)_n$ and $(R^{42})_{m2}$ corresponds to line D2-43 of Table D2 and the meaning for the combination of $R^1$ and $R^2$ for each individual compound corresponds in each case to one line of Table B (compounds I.Aa.D2-43.B1 to I.Aa.D2-43.B352).

Table 114a Compounds of the formula I.Aa in which the combination of $(R^3)_n$ and $(R^{42})_{m2}$ corresponds to line D2-44 of Table D2 and the meaning for the combination of $R^1$ and $R^2$ for each individual compound corresponds in each case to one line of Table B (compounds I.Aa.D2-44.B1 to I.Aa.D2-44.B352).

Table 115a Compounds of the formula I.Aa in which the combination of $(R^3)_n$ and $(R^{42})_{m2}$ corresponds to line D2-45 of Table D2 and the meaning for the combination of $R^1$ and $R^2$ for each individual compound corresponds in each case to one line of Table B (compounds I.Aa.D2-45.B1 to I.Aa.D2-45.B352).

Table 116a Compounds of the formula I.Aa in which the combination of $(R^3)_n$ and $(R^{42})_{m2}$ corresponds to line D2-46 of Table D2 and the meaning for the combination of $R^1$ and $R^2$ for each individual compound corresponds in each case to one line of Table B (compounds I.Aa.D2-46.B1 to I.Aa.D2-46.B352).

Table 117a Compounds of the formula I.Aa in which the combination of $(R^3)_n$ and $(R^{42})_{m2}$ corresponds to line D2-47 of Table D2 and the meaning for the combination of $R^1$ and $R^2$ for each individual compound corresponds in each case to one line of Table B (compounds I.Aa.D2-47.B1 to I.Aa.D2-47.B352).

Table 118a Compounds of the formula I.Aa in which the combination of $(R^3)_n$ and $(R^{42})_{m2}$ corresponds to line D2-48 of Table D2 and the meaning for the combination of $R^1$ and $R^2$ for each individual compound corresponds in each case to one line of Table B (compounds I.Aa.D2-48.B1 to I.Aa.D2-48.B352).

Table 119a Compounds of the formula I.Aa in which the combination of $(R^3)_n$ and $(R^{42})_{m2}$ corresponds to line D2-49 of Table D2 and the meaning for the combination of $R^1$ and $R^2$ for each individual compound corresponds in each case to one line of Table B (compounds I.Aa.D2-49.B1 to I.Aa.D2-49.B352).

Table 120a Compounds of the formula I.Aa in which the combination of $(R^3)_n$ and $(R^{42})_{m2}$ corresponds to line D2-50 of Table D2 and the meaning for the combination of $R^1$ and $R^2$ for each individual compound corresponds in each case to one line of Table B (compounds I.Aa.D2-50.B1 to I.Aa.D2-50.B352).

Table 121a Compounds of the formula I.Aa in which the combination of $(R^3)_n$ and $(R^{42})_{m2}$ corresponds to line D2-51 of Table D2 and the meaning for the combination of $R^1$ and $R^2$ for each individual compound corresponds in each case to one line of Table B (compounds I.Aa.D2-51.B1 to I.Aa.D2-51.B352).

Table 122a Compounds of the formula I.Aa in which the combination of $(R^3)_n$ and $(R^{42})_{m2}$ corresponds to line D2-52 of Table D2 and the meaning for the combination of $R^1$ and $R^2$ for each individual compound corresponds in each case to one line of Table B (compounds I.Aa.D2-52.B1 to I.Aa.D2-52.B352).

Table 123a Compounds of the formula I.Aa in which the combination of $(R^3)_n$ and $(R^{42})_{m2}$ corresponds to line D2-53 of Table D2 and the meaning for the combination of $R^1$ and $R^2$ for each individual compound corresponds in each case to one line of Table B (compounds I.Aa.D2-53.B1 to I.Aa.D2-53.B352).

Table 124a Compounds of the formula I.Aa in which the combination of $(R^3)_n$ and $(R^{42})_{m2}$ corresponds to line D2-54 of Table D2 and the meaning for the combination of $R^1$ and $R^2$ for each individual compound corresponds in each case to one line of Table B (compounds I.Aa.D2-54.B1 to I.Aa.D2-54.B352).

Table 125a Compounds of the formula I.Aa in which the combination of $(R^3)_n$ and $(R^{42})_{m2}$ corresponds to line D2-55 of Table D2 and the meaning for the combination of $R^1$ and $R^2$ for each individual compound corresponds in each case to one line of Table B (compounds I.Aa.D2-55.B1 to I.Aa.D2-55.B352).

Table 126a Compounds of the formula I.Aa in which the combination of $(R^3)_n$ and $(R^{42})_{m2}$ corresponds to line D2-56 of Table D2 and the meaning for the combination of $R^1$ and $R^2$ for each individual compound corresponds in each case to one line of Table B (compounds I.Aa.D2-56.B1 to I.Aa.D2-56.B352).

Table 127a Compounds of the formula I.Aa in which the combination of $(R^3)_n$ and $(R^{42})_{m2}$ corresponds to line D2-57 of Table D2 and the meaning for the combination of $R^1$ and $R^2$ for each individual compound corresponds in each case to one line of Table B (compounds I.Aa.D2-57.B1 to I.Aa.D2-57.B352).

Table 128a Compounds of the formula I.Aa in which the combination of $(R^3)_n$ and $(R^{42})_{m2}$ corresponds to line D2-58 of Table D2 and the meaning for the combination of $R^1$ and $R^2$ for each individual compound corresponds in each case to one line of Table B (compounds I.Aa.D2-58.B1 to I.Aa.D2-58.B352).

Table 129a Compounds of the formula I.Aa in which the combination of $(R^3)_n$ and $(R^{42})_{m2}$ corresponds to line D2-59 of Table D2 and the meaning for the combination of $R^1$ and $R^2$ for each individual compound corresponds in each case to one line of Table B (compounds I.Aa.D2-59.B1 to I.Aa.D2-59.B352).

Table 130a Compounds of the formula I.Aa in which the combination of $(R^3)_n$ and $(R^{42})_{m2}$ corresponds to line D2-60 of Table D2 and the meaning for the combination of $R^1$ and $R^2$ for each individual compound corresponds in each case to one line of Table B (compounds I.Aa.D2-60.B1 to I.Aa.D2-60.B352).

Table 131a Compounds of the formula I.Aa in which the combination of $(R^3)_n$ and $(R^{42})_{m2}$ corresponds to line D2-61 of Table D2 and the meaning for the combination of $R^1$ and $R^2$ for each individual compound corresponds in each case to one line of Table B (compounds I.Aa.D2-61.B1 to I.Aa.D2-61.B352).

Table 132a Compounds of the formula I.Aa in which the combination of $(R^3)_n$ and $(R^{42})_{m2}$ corresponds to line D2-62 of Table D2 and the meaning for the combination of $R^1$ and $R^2$ for each individual compound corresponds in each case to one line of Table B (compounds I.Aa.D2-62.B1 to I.Aa.D2-62.B352).

Table 133a Compounds of the formula I.Aa in which the combination of $(R^3)_n$ and $(R^{42})_{m2}$ corresponds to line D2-63 of Table D2 and the meaning for the combination of $R^1$ and $R^2$ for each individual compound corresponds in each case to one line of Table B (compounds I.Aa.D2-63.B1 to I.Aa.D2-63.B352).

Table 134a Compounds of the formula I.Aa in which the combination of $(R^3)_n$ and $(R^{42})_{m2}$ corresponds to line D2-64 of Table D2 and the meaning for the combination of $R^1$ and $R^2$ for each individual compound corresponds in each case to one line of Table B (compounds I.Aa.D2-64.B1 to I.Aa.D2-64.B352).

Table 135a Compounds of the formula I.Aa in which the combination of $(R^3)_n$ and $(R^{42})_{m2}$ corresponds to line D2-65 of Table D2 and the meaning for the combination of $R^1$ and $R^2$ for each individual compound corresponds in each case to one line of Table B (compounds I.Aa.D2-65.B1 to I.Aa.D2-65.B352).

Table 136a Compounds of the formula I.Aa in which the combination of $(R^3)_n$ and $(R^{42})_{m2}$ corresponds to line D2-66 of Table D2 and the meaning for the combination of $R^1$ and $R^2$ for each individual compound corresponds in each case to one line of Table B (compounds I.Aa.D2-66.B1 to I.Aa.D2-66.B352).

Table 137a Compounds of the formula I.Aa in which the combination of $(R^3)_n$ and $(R^{42})_{m2}$ corresponds to line D2-67 of Table D2 and the meaning for the combination of $R^1$ and $R^2$ for each individual compound corresponds in each case to one line of Table B (compounds I.Aa.D2-67.B1 to I.Aa.D2-67.B352).

Table 138a Compounds of the formula I.Aa in which the combination of $(R^3)_n$ and $(R^{42})_{m2}$ corresponds to line D2-68 of Table D2 and the meaning for the combination of $R^1$ and $R^2$ for each individual compound corresponds in each case to one line of Table B (compounds I.Aa.D2-68.B1 to I.Aa.D2-68.B352).

Table 139a Compounds of the formula I.Aa in which the combination of $(R^3)_n$ and $(R^{42})_{m2}$ corresponds to line D2-69 of Table D2 and the meaning for the combination of $R^1$ and $R^2$ for each individual compound corresponds in each case to one line of Table B (compounds I.Aa.D2-69.B1 to I.Aa.D2-69.B352).

Table 140a Compounds of the formula I.Aa in which the combination of $(R^3)_n$ and $(R^{42})_{m2}$ corresponds to line D2-70 of Table D2 and the meaning for the combination of $R^1$ and $R^2$ for each individual compound corresponds in each case to one line of Table B (compounds I.Aa.D2-70.B1 to I.Aa.D2-70.B352).

Table 1b Compounds of the formula I.Ba in which the combination of $(R^3)_n$ and $(R^{42})_{m2}$ corresponds to line D1-1 of Table D1 and the meaning for the combination of $R^1$ and $R^2$ for each individual compound corresponds in each case to one line of Table B (compounds I.Ba.D1-1.B1 to I.Ba.D1-1.B352).

Table 2b Compounds of the formula I.Ba in which the combination of $(R^3)_n$ and $(R^{42})_{m2}$ corresponds to line D1-2 of Table D1 and the meaning for the combination of $R^1$ and $R^2$ for each individual compound corresponds in each case to one line of Table B (compounds I.Ba.D1-2.B1 to I.Ba.D1-2.B352).

Table 3b Compounds of the formula I.Ba in which the combination of $(R^3)_n$ and $(R^{42})_{m2}$ corresponds to line D1-3 of Table D1 and the meaning for the combination of $R^1$ and $R^2$ for each individual compound corresponds in each case to one line of Table B (compounds I.Ba.D1-3.B1 to I.Ba.D1-3.B352).

Table 4b Compounds of the formula I.Ba in which the combination of $(R^3)_n$ and $(R^{42})_{m2}$ corresponds to line D1-4 of Table D1 and the meaning for the combination of $R^1$ and $R^2$ for each individual compound corresponds in each case to one line of Table B (compounds I.Ba.D1-4.B1 to I.Ba.D1-4.B352).

Table 5b Compounds of the formula I.Ba in which the combination of $(R^3)_n$ and $(R^{42})_{m2}$ corresponds to line D1-5 of Table D1 and the meaning for the combination of $R^1$ and $R^2$ for each individual compound corresponds in each case to one line of Table B (compounds I.Ba.D1-5.B1 to I.Ba.D1-5.B352).

Table 6b Compounds of the formula I.Ba in which the combination of $(R^3)_n$ and $(R^{42})_{m2}$ corresponds to line D1-6 of Table D1 and the meaning for the combination of $R^1$ and $R^2$ for each individual compound corresponds in each case to one line of Table B (compounds I.Ba.D1-6.B1 to I.Ba.D1-6.B352).

Table 7b Compounds of the formula I.Ba in which the combination of $(R^3)_n$ and $(R^{42})_{m2}$ corresponds to line D1-7 of Table D1 and the meaning for the combination of $R^1$ and $R^2$ for each individual compound corresponds in each case to one line of Table B (compounds I.Ba.D1-7.B1 to I.Ba.D1-7.B352).

Table 8b Compounds of the formula I.Ba in which the combination of $(R^3)_n$ and $(R^{42})_{m2}$ corresponds to line D1-8 of Table D1 and the meaning for the combination of $R^1$ and $R^2$ for each individual compound corresponds in each case to one line of Table B (compounds I.Ba.D1-8.B1 to I.Ba.D1-8.B352).

Table 9b Compounds of the formula I.Ba in which the combination of $(R^3)_n$ and $(R^{42})_{m2}$ corresponds to line D1-9 of Table D1 and the meaning for the combination of $R^1$ and $R^2$ for each individual compound corresponds in each case to one line of Table B (compounds I.Ba.D1-9.B1 to I.Ba.D1-9.B352).

Table 10b Compounds of the formula I.Ba in which the combination of $(R^3)_n$ and $(R^{42})_{m2}$ corresponds to line D1-10 of Table D1 and the meaning for the combination of $R^1$ and $R^2$ for each individual compound corresponds in each case to one line of Table B (compounds I.Ba.D1-10.B1 to I.Ba.D1-10.B352).

Table 11b Compounds of the formula I.Ba in which the combination of $(R^3)_n$ and $(R^{42})_{m2}$ corresponds to line D1-11 of Table D1 and the meaning for the combination of $R^1$ and $R^2$ for each individual compound corresponds in each case to one line of Table B (compounds I.Ba.D1-11.B1 to I.Ba.D1-11.B352).

Table 12b Compounds of the formula I.Ba in which the combination of $(R^3)_n$ and $(R^{42})_{m2}$ corresponds to line D1-12 of Table D1 and the meaning for the combination of $R^1$ and $R^2$ for each individual compound corresponds in each case to one line of Table B (compounds I.Ba.D1-12.B1 to I.Ba.D1-12.B352).

Table 13b Compounds of the formula I.Ba in which the combination of $(R^3)_n$ and $(R^{42})_{m2}$ corresponds to line D1-13 of Table D1 and the meaning for the combination of $R^1$ and $R^2$ for each individual compound corresponds in each case to one line of Table B (compounds I.Ba.D1-13.B1 to I.Ba.D1-13.B352).

Table 14b Compounds of the formula I.Ba in which the combination of $(R^3)_n$ and $(R^{42})_{m2}$ corresponds to line D1-14 of Table D1 and the meaning for the combination of $R^1$ and $R^2$ for each individual compound corresponds in each case to one line of Table B (compounds I.Ba.D1-14.B1 to I.Ba.D1-14.B352).

Table 15b Compounds of the formula I.Ba in which the combination of $(R^3)_n$ and $(R^{42})_{m2}$ corresponds to line D1-15 of Table D1 and the meaning for the combination of $R^1$ and $R^2$ for each individual compound corresponds in each case to one line of Table B (compounds I.Ba.D1-15.B1 to I.Ba.D1-15.B352).

Table 16b Compounds of the formula I.Ba in which the combination of $(R^3)_n$ and $(R^{42})_{m2}$ corresponds to line D1-16 of Table D1 and the meaning for the combination of $R^1$ and $R^2$ for each individual compound corresponds in each case to one line of Table B (compounds I.Ba.D1-16.B1 to I.Ba.D1-16.B352).

Table 17b Compounds of the formula I.Ba in which the combination of $(R^3)_n$ and $(R^{42})_{m2}$ corresponds to line D1-17 of Table D1 and the meaning for the combination of $R^1$ and $R^2$ for each individual compound corresponds in each case to one line of Table B (compounds I.Ba.D1-17.B1 to I.Ba.D1-17.B352).

Table 18b Compounds of the formula I.Ba in which the combination of $(R^3)_n$ and $(R^{42})_{m2}$ corresponds to line D1-18 of Table D1 and the meaning for the combination of $R^1$ and $R^2$ for each individual compound corresponds in each case to one line of Table B (compounds I.Ba.D1-18.B1 to I.Ba.D1-18.B352).

Table 19b Compounds of the formula I.Ba in which the combination of $(R^3)_n$ and $(R^{42})_{m2}$ corresponds to line D1-19 of Table D1 and the meaning for the combination of $R^1$ and $R^2$ for each individual compound corresponds in each case to one line of Table B (compounds I.Ba.D1-19.B1 to I.Ba.D1-19.B352).

Table 20b Compounds of the formula I.Ba in which the combination of $(R^3)_n$ and $(R^{42})_{m2}$ corresponds to line D1-20 of Table D1 and the meaning for the combination of $R^1$ and $R^2$ for each individual compound corresponds in each case to one line of Table B (compounds I.Ba.D1-20.B1 to I.Ba.D1-20.B352).

Table 21b Compounds of the formula I.Ba in which the combination of $(R^3)_n$ and $(R^{42})_{m2}$ corresponds to line D1-21 of Table D1 and the meaning for the combination of $R^1$ and $R^2$ for each individual compound corresponds in each case to one line of Table B (compounds I.Ba.D1-21.B1 to I.Ba.D1-21.B352).

Table 22b Compounds of the formula I.Ba in which the combination of $(R^3)_n$ and $(R^{42})_{m2}$ corresponds to line D1-22 of Table D1 and the meaning for the combination of $R^1$ and $R^2$ for each individual compound corresponds in each case to one line of Table B (compounds I.Ba.D1-22.B1 to I.Ba.D1-22.B352).

Table 23b Compounds of the formula I.Ba in which the combination of $(R^3)_n$ and $(R^{42})_{m2}$ corresponds to line D1-23 of Table D1 and the meaning for the combination of $R^1$ and $R^2$ for each individual compound corresponds in each case to one line of Table B (compounds I.Ba.D1-23.B1 to I.Ba.D1-23.B352).

Table 24b Compounds of the formula I.Ba in which the combination of $(R^3)_n$ and $(R^{42})_{m2}$ corresponds to line D1-24 of Table D1 and the meaning for the combination of $R^1$ and $R^2$ for each individual compound corresponds in each case to one line of Table B (compounds I.Ba.D1-24.B1 to I.Ba.D1-24.B352).

Table 25b Compounds of the formula I.Ba in which the combination of $(R^3)_n$ and $(R^{42})_{m2}$ corresponds to line D1-25 of Table D1 and the meaning for the combination of $R^1$ and $R^2$ for each individual compound corresponds in each case to one line of Table B (compounds I.Ba.D1-25.B1 to I.Ba.D1-25.B352).

Table 26b Compounds of the formula I.Ba in which the combination of $(R^3)_n$ and $(R^{42})_{m2}$ corresponds to line D1-26 of Table D1 and the meaning for the combination of $R^1$ and $R^2$ for each individual compound corresponds in each case to one line of Table B (compounds I.Ba.D1-26.B1 to I.Ba.D1-26.B352).

Table 27b Compounds of the formula I.Ba in which the combination of $(R^3)_n$ and $(R^{42})_{m2}$ corresponds to line D1-27 of Table D1 and the meaning for the combination of $R^1$ and $R^2$ for each individual compound corresponds in each case to one line of Table B (compounds I.Ba.D1-27.B1 to I.Ba.D1-27.B352).

Table 28b Compounds of the formula I.Ba in which the combination of $(R^3)_n$ and $(R^{42})_{m2}$ corresponds to line D1-28 of Table D1 and the meaning for the combination of $R^1$ and $R^2$ for each individual compound corresponds in each case to one line of Table B (compounds I.Ba.D1-28.B1 to I.Ba.D1-28.B352).

Table 29b Compounds of the formula I.Ba in which the combination of $(R^3)_n$ and $(R^{42})_{m2}$ corresponds to line D1-29 of Table D1 and the meaning for the combination of $R^1$ and $R^2$ for each individual compound corresponds in each case to one line of Table B (compounds I.Ba.D1-29.B1 to I.Ba.D1-29.B352).

Table 30b Compounds of the formula I.Ba in which the combination of $(R^3)_n$ and $(R^{42})_{m2}$ corresponds to line D1-30 of Table D1 and the meaning for the combination of $R^1$ and $R^2$ for each individual compound corresponds in each case to one line of Table B (compounds I.Ba.D1-30.B1 to I.Ba.D1-30.B352).

Table 31b Compounds of the formula I.Ba in which the combination of $(R^3)_n$ and $(R^{42})_{m2}$ corresponds to line D1-31 of Table D1 and the meaning for the combination of $R^1$ and $R^2$ for each individual compound corresponds in each case to one line of Table B (compounds I.Ba.D1-31.B1 to I.Ba.D1-31.B352).

Table 32b Compounds of the formula I.Ba in which the combination of $(R^3)_n$ and $(R^{42})_{m2}$ corresponds to line D1-32 of Table D1 and the meaning for the combination of $R^1$ and $R^2$ for each individual compound corresponds in each case to one line of Table B (compounds I.Ba.D1-32.B1 to I.Ba.D1-32.B352).

Table 33b Compounds of the formula I.Ba in which the combination of $(R^3)_n$ and $(R^{42})_{m2}$ corresponds to line D1-33 of Table D1 and the meaning for the combination of $R^1$ and $R^2$ for each individual compound corresponds in each case to one line of Table B (compounds I.Ba.D1-33.B1 to I.Ba.D1-33.B352).

Table 34b Compounds of the formula I.Ba in which the combination of $(R^3)_n$ and $(R^{42})_{m2}$ corresponds to line D1-34 of Table D1 and the meaning for the combination of $R^1$ and $R^2$ for each individual compound corresponds in each case to one line of Table B (compounds I.Ba.D1-34.B1 to I.Ba.D1-34.B352).

Table 35b Compounds of the formula I.Ba in which the combination of $(R^3)_n$ and $(R^{42})_{m2}$ corresponds to line D1-35 of Table D1 and the meaning for the combination of $R^1$ and $R^2$ for each individual compound corresponds in each case to one line of Table B (compounds I.Ba.D1-35.B1 to I.Ba.D1-35.B352).

Table 36b Compounds of the formula I.Ba in which the combination of $(R^3)_n$ and $(R^{42})_{m2}$ corresponds to line D1-36 of Table D1 and the meaning for the combination of $R^1$ and $R^2$ for each individual compound corresponds in each case to one line of Table B (compounds I.Ba.D1-36.B1 to I.Ba.D1-36.B352).

Table 37b Compounds of the formula I.Ba in which the combination of $(R^3)_n$ and $(R^{42})_{m2}$ corresponds to line D1-37 of Table D1 and the meaning for the combination of $R^1$ and $R^2$ for each individual compound corresponds in each case to one line of Table B (compounds I.Ba.D1-37.B1 to I.Ba.D1-37.B352).

Table 38b Compounds of the formula I.Ba in which the combination of $(R^3)_n$ and $(R^{42})_{m2}$ corresponds to line D1-38 of Table D1 and the meaning for the combination of $R^1$ and $R^2$ for each individual compound corresponds in each case to one line of Table B (compounds I.Ba.D1-38.B1 to I.Ba.D1-38.B352).

Table 39b Compounds of the formula I.Ba in which the combination of $(R^3)_n$ and $(R^{42})_{m2}$ corresponds to line D1-39 of Table D1 and the meaning for the combination of $R^1$ and $R^2$ for each individual compound corresponds in each case to one line of Table B (compounds I.Ba.D1-39.B1 to I.Ba.D1-39.B352).

Table 40b Compounds of the formula I.Ba in which the combination of $(R^3)_n$ and $(R^{42})_{m2}$ corresponds to line D1-40 of Table D1 and the meaning for the combination of $R^1$ and $R^2$ for each individual compound corresponds in each case to one line of Table B (compounds I.Ba.D1-40.B1 to I.Ba.D1-40.B352).

Table 41b Compounds of the formula I.Ba in which the combination of $(R^3)_n$ and $(R^{42})_{m2}$ corresponds to line D1-41 of Table D1 and the meaning for the combination of $R^1$ and $R^2$ for each individual compound corresponds in each case to one line of Table B (compounds I.Ba.D1-41.B1 to I.Ba.D1-41.B352).

Table 42b Compounds of the formula I.Ba in which the combination of $(R^3)_n$ and $(R^{42})_{m2}$ corresponds to line D1-42 of Table D1 and the meaning for the combination of $R^1$ and $R^2$ for each individual compound corresponds in each case to one line of Table B (compounds I.Ba.D1-42.B1 to I.Ba.D1-42.B352).

Table 43b Compounds of the formula I.Ba in which the combination of $(R^3)_n$ and $(R^{42})_{m2}$ corresponds to line D1-43 of Table D1 and the meaning for the combination of $R^1$ and $R^2$ for each individual compound corresponds in each case to one line of Table B (compounds I.Ba.D1-43.B1 to I.Ba.D1-43.B352).

Table 44b Compounds of the formula I.Ba in which the combination of $(R^3)_n$ and $(R^{42})_{m2}$ corresponds to line D1-44 of Table D1 and the meaning for the combination of $R^1$ and $R^2$ for each individual compound corresponds in each case to one line of Table B (compounds I.Ba.D1-44.B1 to I.Ba.D1-44.B352).

Table 45b Compounds of the formula I.Ba in which the combination of $(R^3)_n$ and $(R^{42})_{m2}$ corresponds to line D1-45 of Table D1 and the meaning for the combination of $R^1$ and $R^2$ for each individual compound corresponds in each case to one line of Table B (compounds I.Ba.D1-45.B1 to I.Ba.D1-45.B352).

Table 46b Compounds of the formula I.Ba in which the combination of $(R^3)_n$ and $(R^{42})_{m2}$ corresponds to line D1-46 of Table D1 and the meaning for the combination of $R^1$ and $R^2$ for each individual compound corresponds in each case to one line of Table B (compounds I.Ba.D1-46.B1 to I.Ba.D1-46.B352).

Table 47b Compounds of the formula I.Ba in which the combination of $(R^3)_n$ and $(R^{42})_{m2}$ corresponds to line D1-47 of Table D1 and the meaning for the combination of $R^1$ and $R^2$ for each individual compound corresponds in each case to one line of Table B (compounds I.Ba.D1-47.B1 to I.Ba.D1-47.B352).

Table 48b Compounds of the formula I.Ba in which the combination of $(R^3)_n$ and $(R^{42})_{m2}$ corresponds to line D1-48 of Table D1 and the meaning for the combination of $R^1$ and $R^2$ for each individual compound corresponds in each case to one line of Table B (compounds I.Ba.D1-48.B1 to I.Ba.D1-48.B352).

Table 49b Compounds of the formula I.Ba in which the combination of $(R^3)_n$ and $(R^{42})_{m2}$ corresponds to line D1-49 of Table D1 and the meaning for the combination of $R^1$ and $R^2$ for each individual compound corresponds in each case to one line of Table B (compounds I.Ba.D1-49.B1 to I.Ba.D1-49.B352).

Table 50b Compounds of the formula I.Ba in which the combination of $(R^3)_n$ and $(R^{42})_{m2}$ corresponds to line D1-50 of Table D1 and the meaning for the combination of $R^1$ and $R^2$ for each individual compound corresponds in each case to one line of Table B (compounds I.Ba.D1-50.B1 to I.Ba.D1-50.B352).

Table 51b Compounds of the formula I.Ba in which the combination of $(R^3)_n$ and $(R^{42})_{m2}$ corresponds to line D1-51 of Table D1 and the meaning for the combination of $R^1$ and $R^2$ for each individual compound corresponds in each case to one line of Table B (compounds I.Ba.D1-51.B1 to I.Ba.D1-51.B352).

Table 52b Compounds of the formula I.Ba in which the combination of $(R^3)_n$ and $(R^{42})_{m2}$ corresponds to line D1-52 of Table D1 and the meaning for the combination of $R^1$ and $R^2$ for each individual compound corresponds in each case to one line of Table B (compounds I.Ba.D1-52.B1 to I.Ba.D1-52.B352).

Table 53b Compounds of the formula I.Ba in which the combination of $(R^3)_n$ and $(R^{42})_{m2}$ corresponds to line D1-53 of Table D1 and the meaning for the combination of $R^1$ and $R^2$ for each individual compound corresponds in each case to one line of Table B (compounds I.Ba.D1-53.B1 to I.Ba.D1-53.B352).

Table 54b Compounds of the formula I.Ba in which the combination of $(R^3)_n$ and $(R^{42})_{m2}$ corresponds to line D1-54 of Table D1 and the meaning for the combination of $R^1$ and $R^2$ for each individual compound corresponds in each case to one line of Table B (compounds I.Ba.D1-54.B1 to I.Ba.D1-54.B352).

Table 55b Compounds of the formula I.Ba in which the combination of $(R^3)_n$ and $(R^{42})_{m2}$ corresponds to line D1-55 of Table D1 and the meaning for the combination of $R^1$ and $R^2$ for each individual compound corresponds in each case to one line of Table B (compounds I.Ba.D1-55.B1 to I.Ba.D1-55.B352).

Table 56b Compounds of the formula I.Ba in which the combination of $(R^3)_n$ and $(R^{42})_{m2}$ corresponds to line D1-56 of Table D1 and the meaning for the combination of $R^1$ and $R^2$ for each individual compound corresponds in each case to one line of Table B (compounds I.Ba.D1-56.B1 to I.Ba.D1-56.B352).

Table 57b Compounds of the formula I.Ba in which the combination of $(R^3)_n$ and $(R^{42})_{m2}$ corresponds to line D1-57 of Table D1 and the meaning for the combination of $R^1$ and $R^2$ for each individual compound corresponds in each case to one line of Table B (compounds I.Ba.D1-57.B1 to I.Ba.D1-57.B352).

Table 58b Compounds of the formula I.Ba in which the combination of $(R^3)_n$ and $(R^{42})_{m2}$ corresponds to line D1-58 of Table D1 and the meaning for the combination of $R^1$ and $R^2$ for each individual compound corresponds in each case to one line of Table B (compounds I.Ba.D1-58.B1 to I.Ba.D1-58.B352).

Table 59b Compounds of the formula I.Ba in which the combination of $(R^3)_n$ and $(R^{42})_{m2}$ corresponds to line D1-59 of Table D1 and the meaning for the combination of $R^1$ and $R^2$ for each individual compound corresponds in each case to one line of Table B (compounds I.Ba.D1-59.B1 to I.Ba.D1-59.B352).

Table 60b Compounds of the formula I.Ba in which the combination of $(R^3)_n$ and $(R^{42})_{m2}$ corresponds to line D1-60 of Table D1 and the meaning for the combination of $R^1$ and $R^2$ for each individual compound corresponds in each case to one line of Table B (compounds I.Ba.D1-60.B1 to I.Ba.D1-60.B352).

Table 61b Compounds of the formula I.Ba in which the combination of $(R^3)_n$ and $(R^{42})_{m2}$ corresponds to line D1-61 of Table D1 and the meaning for the combination of $R^1$ and $R^2$ for each individual compound corresponds in each case to one line of Table B (compounds I.Ba.D1-61.B1 to I.Ba.D1-61.B352).

Table 62b Compounds of the formula I.Ba in which the combination of $(R^3)_n$ and $(R^{42})_{m2}$ corresponds to line D1-62 of Table D1 and the meaning for the combination of $R^1$ and $R^2$ for each individual compound corresponds in each case to one line of Table B (compounds I.Ba.D1-62.B1 to I.Ba.D1-62.B352).

Table 63b Compounds of the formula I.Ba in which the combination of $(R^3)_n$ and $(R^{42})_{m2}$ corresponds to line D1-63 of Table D1 and the meaning for the combination of $R^1$ and $R^2$ for each individual compound corresponds in each case to one line of Table B (compounds I.Ba.D1-63.B1 to I.Ba.D1-63.B352).

Table 64b Compounds of the formula I.Ba in which the combination of $(R^3)_n$ and $(R^{42})_{m2}$ corresponds to line D1-64 of Table D1 and the meaning for the combination of $R^1$ and $R^2$ for each individual compound corresponds in each case to one line of Table B (compounds I.Ba.D1-64.B1 to I.Ba.D1-64.B352).

Table 65b Compounds of the formula I.Ba in which the combination of $(R^3)_n$ and $(R^{42})_{m2}$ corresponds to line D1-65 of Table D1 and the meaning for the combination of $R^1$ and $R^2$ for each individual compound corresponds in each case to one line of Table B (compounds I.Ba.D1-65.B1 to I.Ba.D1-65.B352).

Table 66b Compounds of the formula I.Ba in which the combination of $(R^3)_n$ and $(R^{42})_{m2}$ corresponds to line D1-66 of Table D1 and the meaning for the combination of $R^1$ and $R^2$ for each individual compound corresponds in each case to one line of Table B (compounds I.Ba.D1-66.B1 to I.Ba.D1-66.B352).

Table 67b Compounds of the formula I.Ba in which the combination of $(R^3)_n$ and $(R^{42})_{m2}$ corresponds to line D1-67 of Table D1 and the meaning for the combination of $R^1$ and $R^2$ for each individual compound corresponds in each case to one line of Table B (compounds I.Ba.D1-67.B1 to I.Ba.D1-67.B352).

Table 68b Compounds of the formula I.Ba in which the combination of $(R^3)_n$ and $(R^{42})_{m2}$ corresponds to line D1-68 of Table D1 and the meaning for the combination of $R^1$ and $R^2$ for each individual compound corresponds in each case to one line of Table B (compounds I.Ba.D1-68.B1 to I.Ba.D1-68.B352).

Table 69b Compounds of the formula I.Ba in which the combination of $(R^3)_n$ and $(R^{42})_{m2}$ corresponds to line D1-69 of Table D1 and the meaning for the combination of $R^1$ and $R^2$ for each individual compound corresponds in each case to one line of Table B (compounds I.Ba.D1-69.B1 to I.Ba.D1-69.B352).

Table 70b Compounds of the formula I.Ba in which the combination of $(R^3)_n$ and $(R^{42})_{m2}$ corresponds to line D1-70 of Table D1 and the meaning for the combination of $R^1$ and $R^2$ for each individual compound corresponds in each case to one line of Table B (compounds I.Ba.D1-70.B1 to I.Ba.D1-70.B352).

Table 71b Compounds of the formula I.Ba in which the combination of $(R^3)_n$ and $(R^{42})_{m2}$ corresponds to line D2-1 of Table D2 and the meaning for the combination of $R^1$ and $R^2$ for each individual compound corresponds in each case to one line of Table B (compounds I.Ba.D2-1.B1 to I.Ba.D2-1.B352).

Table 72b Compounds of the formula I.Ba in which the combination of $(R^3)_n$ and $(R^{42})_{m2}$ corresponds to line D2-2 of Table D2 and the meaning for the combination of $R^1$ and $R^2$ for each individual compound corresponds in each case to one line of Table B (compounds I.Ba.D2-2.B1 to I.Ba.D2-2.B352).

Table 73b Compounds of the formula I.Ba in which the combination of $(R^3)_n$ and $(R^{42})_{m2}$ corresponds to line D2-3 of Table D2 and the meaning for the combination of $R^1$ and $R^2$ for each individual compound corresponds in each case to one line of Table B (compounds I.Ba.D2-3.B1 to I.Ba.D2-3.B352).

Table 74b Compounds of the formula I.Ba in which the combination of $(R^3)_n$ and $(R^{42})_{m2}$ corresponds to line D2-4 of Table D2 and the meaning for the combination of $R^1$ and $R^2$ for each individual compound corresponds in each case to one line of Table B (compounds I.Ba.D2-4.B1 to I.Ba.D2-4.B352).

Table 75b Compounds of the formula I.Ba in which the combination of $(R^3)_n$ and $(R^{42})_{m2}$ corresponds to line D2-5 of Table D2 and the meaning for the combination of $R^1$ and $R^2$ for each individual compound corresponds in each case to one line of Table B (compounds I.Ba.D2-5.B1 to I.Ba.D2-5.B352).

Table 76b Compounds of the formula I.Ba in which the combination of $(R^3)_n$ and $(R^{42})_{m2}$ corresponds to line D2-6 of Table D2 and the meaning for the combination of $R^1$ and $R^2$ for each individual compound corresponds in each case to one line of Table B (compounds I.Ba.D2-6.B1 to I.Ba.D2-6.B352).

Table 77b Compounds of the formula I.Ba in which the combination of $(R^3)_n$ and $(R^{42})_{m2}$ corresponds to line D2-7 of Table D2 and the meaning for the combination of $R^1$ and $R^2$ for each individual compound corresponds in each case to one line of Table B (compounds I.Ba.D2-7.B1 to I.Ba.D2-7.B352).

Table 78b Compounds of the formula I.Ba in which the combination of $(R^3)_n$ and $(R^{42})_{m2}$ corresponds to line D2-8 of Table D2 and the meaning for the combination of $R^1$ and $R^2$ for each individual compound corresponds in each case to one line of Table B (compounds I.Ba.D2-8.B1 to I.Ba.D2-8.B352).

Table 79b Compounds of the formula I.Ba in which the combination of $(R^3)_n$ and $(R^{42})_{m2}$ corresponds to line D2-9 of Table D2 and the meaning for the combination of $R^1$ and $R^2$ for each individual compound corresponds in each case to one line of Table B (compounds I.Ba.D2-9.B1 to I.Ba.D2-9.B352).

Table 80b Compounds of the formula I.Ba in which the combination of $(R^3)_n$ and $(R^{42})_{m2}$ corresponds to line D2-10 of Table D2 and the meaning for the combination of $R^1$ and $R^2$ for each individual compound corresponds in each case to one line of Table B (compounds I.Ba.D2-10.B1 to I.Ba.D2-10.B352).

Table 81b Compounds of the formula I.Ba in which the combination of $(R^3)_n$ and $(R^{42})_{m2}$ corresponds to line D2-11 of Table D2 and the meaning for the combination of $R^1$ and $R^2$ for each individual compound corresponds in each case to one line of Table B (compounds I.Ba.D2-11.B1 to I.Ba.D2-11.B352).

Table 82b Compounds of the formula I.Ba in which the combination of $(R^3)_n$ and $(R^{42})_{m2}$ corresponds to line D2-12 of Table D2 and the meaning for the combination of $R^1$ and $R^2$ for each individual compound corresponds in each case to one line of Table B (compounds I.Ba.D2-12.B1 to I.Ba.D2-12.B352).

Table 83b Compounds of the formula I.Ba in which the combination of $(R^3)_n$ and $(R^{42})_{m2}$ corresponds to line D2-13 of Table D2 and the meaning for the combination of $R^1$ and $R^2$ for each individual compound corresponds in each case to one line of Table B (compounds I.Ba.D2-13.B1 to I.Ba.D2-13.B352).

Table 84b Compounds of the formula I.Ba in which the combination of $(R^3)_n$ and $(R^{42})_{m2}$ corresponds to line D2-14 of Table D2 and the meaning for the combination of $R^1$ and $R^2$ for each individual compound corresponds in each case to one line of Table B (compounds I.Ba.D2-14.B1 to I.Ba.D2-14.B352).

Table 85b Compounds of the formula I.Ba in which the combination of $(R^3)_n$ and $(R^{42})_{m2}$ corresponds to line D2-15 of Table D2 and the meaning for the combination of $R^1$ and $R^2$ for each individual compound corresponds in each case to one line of Table B (compounds I.Ba.D2-15.B1 to I.Ba.D2-15.B352).

Table 86b Compounds of the formula I.Ba in which the combination of $(R^3)_n$ and $(R^{42})_{m2}$ corresponds to line D2-16 of Table D2 and the meaning for the combination of $R^1$ and $R^2$ for each individual compound corresponds in each case to one line of Table B (compounds I.Ba.D2-16.B1 to I.Ba.D2-16.B352).

Table 87b Compounds of the formula I.Ba in which the combination of $(R^3)_n$ and $(R^{42})_{m2}$ corresponds to line D2-17 of Table D2 and the meaning for the combination of $R^1$ and $R^2$ for each individual compound corresponds in each case to one line of Table B (compounds I.Ba.D2-17.B1 to I.Ba.D2-17.B352).

Table 88b Compounds of the formula I.Ba in which the combination of $(R^3)_n$ and $(R^{42})_{m2}$ corresponds to line D2-18 of Table D2 and the meaning for the combination of $R^1$ and $R^2$ for each individual compound corresponds in each case to one line of Table B (compounds I.Ba.D2-18.B1 to I.Ba.D2-18.B352).

Table 89b Compounds of the formula I.Ba in which the combination of $(R^3)_n$ and $(R^{42})_{m2}$ corresponds to line D2-19 of Table D2 and the meaning for the combination of $R^1$ and $R^2$ for each individual compound corresponds in each case to one line of Table B (compounds I.Ba.D2-19.B1 to I.Ba.D2-19.B352).

Table 90b Compounds of the formula I.Ba in which the combination of $(R^3)_n$ and $(R^{42})_{m2}$ corresponds to line D2-20 of Table D2 and the meaning for the combination of $R^1$ and $R^2$ for each individual compound corresponds in each case to one line of Table B (compounds I.Ba.D2-20.B1 to I.Ba.D2-20.B352).

Table 91b Compounds of the formula I.Ba in which the combination of $(R^3)_n$ and $(R^{42})_{m2}$ corresponds to line D2-21 of Table D2 and the meaning for the combination of $R^1$ and $R^2$ for each individual compound corresponds in each case to one line of Table B (compounds I.Ba.D2-21.B1 to I.Ba.D2-21.B352).

Table 92b Compounds of the formula I.Ba in which the combination of $(R^3)_n$ and $(R^{42})_{m2}$ corresponds to line D2-22 of Table D2 and the meaning for the combination of $R^1$ and $R^2$ for each individual compound corresponds in each case to one line of Table B (compounds I.Ba.D2-22.B1 to I.Ba.D2-22.B352).

Table 93b Compounds of the formula I.Ba in which the combination of $(R^3)_n$ and $(R^{42})_{m2}$ corresponds to line D2-23 of Table D2 and the meaning for the combination of $R^1$ and $R^2$ for each individual compound corresponds in each case to one line of Table B (compounds I.Ba.D2-23.B1 to I.Ba.D2-23.B352).

Table 94b Compounds of the formula I.Ba in which the combination of $(R^3)_n$ and $(R^{42})_{m2}$ corresponds to line D2-24 of Table D2 and the meaning for the combination of $R^1$ and $R^2$ for each individual compound corresponds in each case to one line of Table B (compounds I.Ba.D2-24.B1 to I.Ba.D2-24.B352).

Table 95b Compounds of the formula I.Ba in which the combination of $(R^3)_n$ and $(R^{42})_{m2}$ corresponds to line D2-25 of Table D2 and the meaning for the combination of $R^1$ and $R^2$ for each individual compound corresponds in each case to one line of Table B (compounds I.Ba.D2-25.B1 to I.Ba.D2-25.B352).

Table 96b Compounds of the formula I.Ba in which the combination of $(R^3)_n$ and $(R^{42})_{m2}$ corresponds to line D2-26 of Table D2 and the meaning for the combination of $R^1$ and $R^2$ for each individual compound corresponds in each case to one line of Table B (compounds I.Ba.D2-26.B1 to I.Ba.D2-26.B352).

Table 97b Compounds of the formula I.Ba in which the combination of $(R^3)_n$ and $(R^{42})_{m2}$ corresponds to line D2-27 of Table D2 and the meaning for the combination of $R^1$ and $R^2$ for each individual compound corresponds in each case to one line of Table B (compounds I.Ba.D2-27.B1 to I.Ba.D2-27.B352).

Table 98b Compounds of the formula I.Ba in which the combination of $(R^3)_n$ and $(R^{42})_{m2}$ corresponds to line D2-28 of Table D2 and the meaning for the combination of $R^1$ and $R^2$ for each individual compound corresponds in each case to one line of Table B (compounds I.Ba.D2-28.B1 to I.Ba.D2-28.B352).

Table 99b Compounds of the formula I.Ba in which the combination of $(R^3)_n$ and $(R^{42})_{m2}$ corresponds to line D2-29 of Table D2 and the meaning for the combination of $R^1$ and $R^2$ for each individual compound corresponds in each case to one line of Table B (compounds I.Ba.D2-29.B1 to I.Ba.D2-29.B352).

Table 100b Compounds of the formula I.Ba in which the combination of $(R^3)_n$ and $(R^{42})_{m2}$ corresponds to line D2-30 of Table D2 and the meaning for the combination of $R^1$ and $R^2$ for each individual compound corresponds in each case to one line of Table B (compounds I.Ba.D2-30.B1 to I.Ba.D2-30.B352).

Table 101b Compounds of the formula I.Ba in which the combination of $(R^3)_n$ and $(R^{42})_{m2}$ corresponds to line D2-31 of Table D2 and the meaning for the combination of $R^1$ and $R^2$ for each individual compound corresponds in each case to one line of Table B (compounds I.Ba.D2-31.B1 to I.Ba.D2-31.B352).

Table 102b Compounds of the formula I.Ba in which the combination of $(R^3)_n$ and $(R^{42})_{m2}$ corresponds to line D2-32 of Table D2 and the meaning for the combination of $R^1$ and $R^2$ for each individual compound corresponds in each case to one line of Table B (compounds I.Ba.D2-32.B1 to I.Ba.D2-32.B352).

Table 103b Compounds of the formula I.Ba in which the combination of $(R^3)_n$ and $(R^{42})_{m2}$ corresponds to line D2-33 of Table D2 and the meaning for the combination of $R^1$ and $R^2$ for each individual compound corresponds in each case to one line of Table B (compounds I.Ba.D2-33.B1 to I.Ba.D2-33.B352).

Table 104b Compounds of the formula I.Ba in which the combination of $(R^3)_n$ and $(R^{42})_{m2}$ corresponds to line D2-34 of Table D2 and the meaning for the combination of $R^1$ and $R^2$ for each individual compound corresponds in each case to one line of Table B (compounds I.Ba.D2-34.B1 to I.Ba.D2-34.B352).

Table 105b Compounds of the formula I.Ba in which the combination of $(R^3)_n$ and $(R^{42})_{m2}$ corresponds to line D2-35 of Table D2 and the meaning for the combination of $R^1$ and $R^2$ for each individual compound corresponds in each case to one line of Table B (compounds I.Ba.D2-35.B1 to I.Ba.D2-35.B352).

Table 106b Compounds of the formula I.Ba in which the combination of $(R^3)_n$ and $(R^{42})_{m2}$ corresponds to line D2-36 of Table D2 and the meaning for the combination of $R^1$ and $R^2$ for each individual compound corresponds in each case to one line of Table B (compounds I.Ba.D2-36.B1 to I.Ba.D2-36.B352).

Table 107b Compounds of the formula I.Ba in which the combination of $(R^3)_n$ and $(R^{42})_{m2}$ corresponds to line D2-37 of Table D2 and the meaning for the combination of $R^1$ and $R^2$ for each individual compound corresponds in each case to one line of Table B (compounds I.Ba.D2-37.B1 to I.Ba.D2-37.B352).

Table 108b Compounds of the formula I.Ba in which the combination of $(R^3)_n$ and $(R^{42})_{m2}$ corresponds to line D2-38 of Table D2 and the meaning for the combination of $R^1$ and $R^2$ for each individual compound corresponds in each case to one line of Table B (compounds I.Ba.D2-38.B1 to I.Ba.D2-38.B352).

Table 109b Compounds of the formula I.Ba in which the combination of $(R^3)_n$ and $(R^{42})_{m2}$ corresponds to line D2-39 of Table D2 and the meaning for the combination of $R^1$ and $R^2$ for each individual compound corresponds in each case to one line of Table B (compounds I.Ba.D2-39.B1 to I.Ba.D2-39.B352).

Table 110b Compounds of the formula I.Ba in which the combination of $(R^3)_n$ and $(R^{42})_{m2}$ corresponds to line D2-40 of Table D2 and the meaning for the combination of $R^1$ and $R^2$ for each individual compound corresponds in each case to one line of Table B (compounds I.Ba.D2-40.B1 to I.Ba.D2-40.B352).

Table 111b Compounds of the formula I.Ba in which the combination of $(R^3)_n$ and $(R^{42})_{m2}$ corresponds to line D2-41 of Table D2 and the meaning for the combination of $R^1$ and $R^2$ for each individual compound corresponds in each case to one line of Table B (compounds I.Ba.D2-41.B1 to I.Ba.D2-41.B352).

Table 112b Compounds of the formula I.Ba in which the combination of $(R^3)_n$ and $(R^{42})_{m2}$ corresponds to line D2-42 of Table D2 and the meaning for the combination of $R^1$ and $R^2$ for each individual compound corresponds in each case to one line of Table B (compounds I.Ba.D2-42.B1 to I.Ba.D2-42.B352).

Table 113b Compounds of the formula I.Ba in which the combination of $(R^3)_n$ and $(R^{42})_{m2}$ corresponds to line D2-43 of Table D2 and the meaning for the combination of $R^1$ and $R^2$ for each individual compound corresponds in each case to one line of Table B (compounds I.Ba.D2-43.B1 to I.Ba.D2-43.B352).

Table 114b Compounds of the formula I.Ba in which the combination of $(R^3)_n$ and $(R^{42})_{m2}$ corresponds to line D2-44 of Table D2 and the meaning for the combination of $R^1$ and $R^2$ for each individual compound corresponds in each case to one line of Table B (compounds I.Ba.D2-44.B1 to I.Ba.D2-44.B352).

Table 115b Compounds of the formula I.Ba in which the combination of $(R^3)_n$ and $(R^{42})_{m2}$ corresponds to line D2-45 of Table D2 and the meaning for the combination of $R^1$ and $R^2$ for each individual compound corresponds in each case to one line of Table B (compounds I.Ba.D2-45.B1 to I.Ba.D2-45.B352).

Table 116b Compounds of the formula I.Ba in which the combination of $(R^3)_n$ and $(R^{42})_{m2}$ corresponds to line D2-46 of Table D2 and the meaning for the combination of $R^1$ and $R^2$ for each individual compound corresponds in each case to one line of Table B (compounds I.Ba.D2-46.B1 to I.Ba.D2-46.B352).

Table 117b Compounds of the formula I.Ba in which the combination of $(R^3)_n$ and $(R^{42})_{m2}$ corresponds to line D2-47 of Table D2 and the meaning for the combination of $R^1$ and $R^2$ for each individual compound corresponds in each case to one line of Table B (compounds I.Ba.D2-47.B1 to I.Ba.D2-47.B352).

Table 118b Compounds of the formula I.Ba in which the combination of $(R^3)_n$ and $(R^{42})_{m2}$ corresponds to line D2-48 of Table D2 and the meaning for the combination of $R^1$ and $R^2$ for each individual compound corresponds in each case to one line of Table B (compounds I.Ba.D2-48.B1 to I.Ba.D2-48.B352).

Table 119b Compounds of the formula I.Ba in which the combination of $(R^3)_n$ and $(R^{42})_{m2}$ corresponds to line D2-49 of Table D2 and the meaning for the combination of $R^1$ and $R^2$ for each individual compound corresponds in each case to one line of Table B (compounds I.Ba.D2-49.B1 to I.Ba.D2-49.B352).

Table 120b Compounds of the formula I.Ba in which the combination of $(R^3)_n$ and $(R^{42})_{m2}$ corresponds to line D2-50 of Table D2 and the meaning for the combination of $R^1$ and $R^2$ for each individual compound corresponds in each case to one line of Table B (compounds I.Ba.D2-50.B1 to I.Ba.D2-50.B352).

Table 121b Compounds of the formula I.Ba in which the combination of $(R^3)_n$ and $(R^{42})_{m2}$ corresponds to line D2-51 of Table D2 and the meaning for the combination of $R^1$ and $R^2$ for each individual compound corresponds in each case to one line of Table B (compounds I.Ba.D2-51.B1 to I.Ba.D2-51.B352).

Table 122b Compounds of the formula I.Ba in which the combination of $(R^3)_n$ and $(R^{42})_{m2}$ corresponds to line D2-52 of Table D2 and the meaning for the combination of $R^1$ and $R^2$ for each individual compound corresponds in each case to one line of Table B (compounds I.Ba.D2-52.B1 to I.Ba.D2-52.B352).

Table 123b Compounds of the formula I.Ba in which the combination of $(R^3)_n$ and $(R^{42})_{m2}$ corresponds to line D2-53 of Table D2 and the meaning for the combination of $R^1$ and $R^2$ for each individual compound corresponds in each case to one line of Table B (compounds I.Ba.D2-53.B1 to I.Ba.D2-53.B352).

Table 124b Compounds of the formula I.Ba in which the combination of $(R^3)_n$ and $(R^{42})_{m2}$ corresponds to line D2-54 of Table D2 and the meaning for the combination of $R^1$ and $R^2$ for each individual compound corresponds in each case to one line of Table B (compounds I.Ba.D2-54.B1 to I.Ba.D2-54.B352).

Table 125b Compounds of the formula I.Ba in which the combination of $(R^3)_n$ and $(R^{42})_{m2}$ corresponds to line D2-55 of Table D2 and the meaning for the combination of $R^1$ and $R^2$ for each individual compound corresponds in each case to one line of Table B (compounds I.Ba.D2-55.B1 to I.Ba.D2-55.B352).

Table 126b Compounds of the formula I.Ba in which the combination of $(R^3)_n$ and $(R^{42})_{m2}$ corresponds to line D2-56 of Table D2 and the meaning for the combination of $R^1$ and $R^2$ for each individual compound corresponds in each case to one line of Table B (compounds I.Ba.D2-56.B1 to I.Ba.D2-56.B352).

Table 127b Compounds of the formula I.Ba in which the combination of $(R^3)_n$ and $(R^{42})_{m2}$ corresponds to line D2-57 of Table D2 and the meaning for the combination of $R^1$ and $R^2$ for each individual compound corresponds in each case to one line of Table B (compounds I.Ba.D2-57.B1 to I.Ba.D2-57.B352).

Table 128b Compounds of the formula I.Ba in which the combination of $(R^3)_n$ and $(R^{42})_{m2}$ corresponds to line D2-58 of Table D2 and the meaning for the combination of $R^1$ and $R^2$ for each individual compound corresponds in each case to one line of Table B (compounds I.Ba.D2-58.B1 to I.Ba.D2-58.B352).

Table 129b Compounds of the formula I.Ba in which the combination of $(R^3)_n$ and $(R^{42})_{m2}$ corresponds to line D2-59 of Table D2 and the meaning for the combination of $R^1$ and $R^2$ for each individual compound corresponds in each case to one line of Table B (compounds I.Ba.D2-59.B1 to I.Ba.D2-59.B352).

Table 130b Compounds of the formula I.Ba in which the combination of $(R^3)_n$ and $(R^{42})_{m2}$ corresponds to line D2-60 of Table D2 and the meaning for the combination of $R^1$ and $R^2$ for each individual compound corresponds in each case to one line of Table B (compounds I.Ba.D2-60.B1 to I.Ba.D2-60.B352).

Table 131b Compounds of the formula I.Ba in which the combination of $(R^3)_n$ and $(R^{42})_{m2}$ corresponds to line D2-61 of Table D2 and the meaning for the combination of $R^1$ and $R^2$ for each individual compound corresponds in each case to one line of Table B (compounds I.Ba.D2-61.B1 to I.Ba.D2-61.B352).

Table 132b Compounds of the formula I.Ba in which the combination of $(R^3)_n$ and $(R^{42})_{m2}$ corresponds to line D2-62 of Table D2 and the meaning for the combination of $R^1$ and $R^2$ for each individual compound corresponds in each case to one line of Table B (compounds I.Ba.D2-62.B1 to I.Ba.D2-62.B352).

Table 133b Compounds of the formula I.Ba in which the combination of $(R^3)_n$ and $(R^{42})_{m2}$ corresponds to line D2-63 of Table D2 and the meaning for the combination of $R^1$ and $R^2$ for each individual compound corresponds in each case to one line of Table B (compounds I.Ba.D2-63.B1 to I.Ba.D2-63.B352).

Table 134b Compounds of the formula I.Ba in which the combination of $(R^3)_n$ and $(R^{42})_{m2}$ corresponds to line D2-64 of Table D2 and the meaning for the combination of $R^1$ and $R^2$ for each individual compound corresponds in each case to one line of Table B (compounds I.Ba.D2-64.B1 to I.Ba.D2-64.B352).

Table 135b Compounds of the formula I.Ba in which the combination of $(R^3)_n$ and $(R^{42})_{m2}$ corresponds to line D2-65 of Table D2 and the meaning for the combination of $R^1$ and $R^2$ for each individual compound corresponds in each case to one line of Table B (compounds I.Ba.D2-65.B1 to I.Ba.D2-65.B352).

Table 136b Compounds of the formula I.Ba in which the combination of $(R^3)_n$ and $(R^{42})_{m2}$ corresponds to line D2-66 of Table D2 and the meaning for the combination of $R^1$ and $R^2$ for each individual compound corresponds in each case to one line of Table B (compounds I.Ba.D2-66.B1 to I.Ba.D2-66.B352).

Table 137b Compounds of the formula I.Ba in which the combination of $(R^3)_n$ and $(R^{42})_{m2}$ corresponds to line D2-67 of Table D2 and the meaning for the combination of $R^1$ and $R^2$ for each individual compound corresponds in each case to one line of Table B (compounds I.Ba.D2-67.B1 to I.Ba.D2-67.B352).

Table 138b Compounds of the formula I.Ba in which the combination of $(R^3)_n$ and $(R^{42})_{m2}$ corresponds to line D2-68 of Table D2 and the meaning for the combination of $R^1$ and $R^2$ for each individual compound corresponds in each case to one line of Table B (compounds I.Ba.D2-68.B1 to I.Ba.D2-68.B352).

Table 139b Compounds of the formula I.Ba in which the combination of $(R^3)_n$ and $(R^{42})_{m2}$ corresponds to line D2-69 of Table D2 and the meaning for the combination of $R^1$ and $R^2$ for each individual compound corresponds in each case to one line of Table B (compounds I.Ba.D2-69.B1 to I.Ba.D2-69.B352).

Table 140b Compounds of the formula I.Ba in which the combination of $(R^3)_n$ and $(R^{42})_{m2}$ corresponds to line D2-70 of Table D2 and the meaning for the combination of $R^1$ and $R^2$ for each individual compound corresponds in each case to one line of Table B (compounds I.Ba.D2-70.B1 to I.Ba.D2-70.B352).

TABLE D1

| line | $(R^3)_n$ | $(R^{42})_m$ |
|---|---|---|
| D-1 | —* | 2-OCH$_3$ |
| D-2 | 2-Cl | 2-OCH$_3$ |
| D-3 | 2-F | 2-OCH$_3$ |
| D-4 | 2-CF$_3$ | 2-OCH$_3$ |
| D-5 | 3-Cl | 2-OCH$_3$ |
| D-6 | 3-F | 2-OCH$_3$ |
| D-7 | 3-CF$_3$ | 2-OCH$_3$ |
| D-8 | —* | 2-Cl |
| D-9 | 2-Cl | 2-Cl |
| D-10 | 2-F | 2-Cl |
| D-11 | 3-CF$_3$ | 2-Cl |
| D-12 | 3-Cl | 2-Cl |
| D-13 | 3-F | 2-Cl |
| D-14 | 3-CF$_3$ | 2-Cl |
| D-15 | —* | 3-Cl |
| D-16 | 2-Cl | 3-Cl |
| D-17 | 2-F | 3-Cl |
| D-18 | 3-CF$_3$ | 3-Cl |
| D-19 | 3-Cl | 3-Cl |
| D-20 | 3-F | 3-Cl |
| D-21 | 3-CF$_3$ | 3-Cl |
| D-22 | —* | 4-Cl |
| D-23 | 2-Cl | 4-Cl |
| D-24 | 2-F | 4-Cl |
| D-25 | 3-CF$_3$ | 4-Cl |
| D-26 | 3-Cl | 4-Cl |
| D-27 | 3-F | 4-Cl |
| D-28 | 3-CF$_3$ | 4-Cl |
| D-29 | —* | 2-F |
| D-30 | 2-Cl | 2-F |
| D-31 | 2-F | 2-F |
| D-32 | 3-CF$_3$ | 2-F |
| D-33 | 3-Cl | 2-F |
| D-34 | 3-F | 2-F |
| D-35 | 3-CF$_3$ | 2-F |
| D-36 | —* | 3-F |
| D-37 | 2-Cl | 3-F |
| D-38 | 2-F | 3-F |
| D-39 | 3-CF$_3$ | 3-F |
| D-40 | 3-Cl | 3-F |
| D-41 | 3-F | 3-F |
| D-42 | 3-CF$_3$ | 3-F |
| D-43 | —* | 4-F |
| D-44 | 2-Cl | 4-F |
| D-45 | 2-F | 4-F |
| D-46 | 3-CF$_3$ | 4-F |
| D-47 | 3-Cl | 4-F |
| D-48 | 3-F | 4-F |
| D-49 | 3-CF$_3$ | 4-F |
| D-50 | —* | 2-CN |
| D-51 | 2-Cl | 2-CN |
| D-52 | 2-F | 2-CN |
| D-53 | 3-CF$_3$ | 2-CN |
| D-54 | 3-Cl | 2-CN |

TABLE D1-continued

| line | $(R^3)_n$ | $(R^{42})_m$ |
|---|---|---|
| D-55 | 3-F | 2-CN |
| D-56 | 3-CF$_3$ | 2-CN |
| D-57 | —* | 3-CN |
| D-58 | 2-Cl | 3-CN |
| D-59 | 2-F | 3-CN |
| D-60 | 3-CF$_3$ | 3-CN |
| D-61 | 3-Cl | 3-CN |
| D-62 | 3-F | 3-CN |
| D-63 | 3-CF$_3$ | 3-CN |
| D-64 | —* | 4-CN |
| D-65 | 2-Cl | 4-CN |
| D-66 | 2-F | 4-CN |
| D-67 | 3-CF$_3$ | 4-CN |
| D-68 | 3-Cl | 4-CN |
| D-69 | 3-F | 4-CN |
| D-70 | 3-CF$_3$ | 4-CN |

—* means that n is 0

TABLE D2

| line | $(R^3)_n$ | $(R^{42})_{m2}$ |
|---|---|---|
| D2-1 | —* | 2-CF$_3$ |
| D2-2 | 2-Cl | 2-CF$_3$ |
| D2-3 | 2-F | 2-CF$_3$ |
| D2-4 | 2-CF$_3$ | 2-CF$_3$ |
| D2-5 | 3-Cl | 2-CF$_3$ |
| D2-6 | 3-F | 2-CF$_3$ |
| D2-7 | 3-CF$_3$ | 2-CF$_3$ |
| D2-8 | —* | 3-CF$_3$ |
| D2-9 | 2-Cl | 3-CF$_3$ |
| D2-10 | 2-F | 3-CF$_3$ |
| D2-11 | 2-CF$_3$ | 3-CF$_3$ |
| D2-12 | 3-Cl | 3-CF$_3$ |
| D2-13 | 3-F | 3-CF$_3$ |
| D2-14 | 3-CF$_3$ | 3-CF$_3$ |
| D2-15 | —* | 4-CF$_3$ |
| D2-16 | 2-Cl | 4-CF$_3$ |
| D2-17 | 2-F | 4-CF$_3$ |
| D2-18 | 2-CF$_3$ | 4-CF$_3$ |
| D2-19 | 3-Cl | 4-CF$_3$ |
| D2-20 | 3-F | 4-CF$_3$ |
| D2-21 | 3-CF$_3$ | 4-CF$_3$ |
| D2-22 | —* | 2,4-Cl$_2$ |
| D2-23 | 2-Cl | 2,4-Cl$_2$ |
| D2-24 | 2-F | 2,4-Cl$_2$ |
| D2-25 | 2-CF$_3$ | 2,4-Cl$_2$ |
| D2-26 | 3-Cl | 2,4-Cl$_2$ |
| D2-27 | 3-F | 2,4-Cl$_2$ |
| D2-28 | 3-CF$_3$ | 2,4-Cl$_2$ |
| D2-29 | —* | 2,6-Cl$_2$ |
| D2-30 | 2-Cl | 2,6-Cl$_2$ |
| D2-31 | 2-F | 2,6-Cl$_2$ |
| D2-32 | 2-CF$_3$ | 2,6-Cl$_2$ |
| D2-33 | 3-Cl | 2,6-Cl$_2$ |
| D2-34 | 3-F | 2,6-Cl$_2$ |
| D2-35 | 3-CF$_3$ | 2,6-Cl$_2$ |
| D2-36 | —* | 2,4-F$_2$ |
| D2-37 | 2-Cl | 2,4-F$_2$ |
| D2-38 | 2-F | 2,4-F$_2$ |
| D2-39 | 2-CF$_3$ | 2,4-F$_2$ |
| D2-40 | 3-Cl | 2,4-F$_2$ |
| D2-41 | 3-F | 2,4-F$_2$ |
| D2-42 | 3-CF$_3$ | 2,4-F$_2$ |
| D2-43 | —* | 2,4-F$_2$ |
| D2-44 | 2-Cl | 2-F-4-CN |
| D2-45 | 2-F | 2-F-4-CN |
| D2-46 | 2-CF$_3$ | 2-F-4-CN |
| D2-47 | 3-Cl | 2-F-4-CN |
| D2-48 | 3-F | 2-F-4-CN |
| D2-49 | 3-CF$_3$ | 2-F-4-CN |
| D2-50 | —* | 2-Cl-4-CN |
| D2-51 | 2-Cl | 2-Cl-4-CN |
| D2-52 | 2-F | 2-Cl-4-CN |
| D2-53 | 2-CF$_3$ | 2-Cl-4-CN |

TABLE D2-continued

| line | $(R^3)_n$ | $(R^{42})_{m2}$ |
|---|---|---|
| D2-54 | 3-Cl | 2-Cl-4-CN |
| D2-55 | 3-F | 2-Cl-4-CN |
| D2-56 | 3-CF$_3$ | 2-Cl-4-CN |
| D2-57 | —* | 2-Cl-4-CF$_3$ |
| D2-58 | 2-Cl | 2-Cl-4-CF$_3$ |
| D2-59 | 2-F | 2-Cl-4-CF$_3$ |
| D2-60 | 2-CF$_3$ | 2-Cl-4-CF$_3$ |
| D2-61 | 3-Cl | 2-Cl-4-CF$_3$ |
| D2-62 | 3-F | 2-Cl-4-CF$_3$ |
| D2-63 | 3-CF$_3$ | 2-Cl-4-CF$_3$ |
| D2-64 | —* | 2-F-4-CF$_3$ |
| D2-65 | 2-Cl | 2-F-4-CF$_3$ |
| D2-66 | 2-F | 2-F-4-CF$_3$ |
| D2-67 | 2-CF$_3$ | 2-F-4-CF$_3$ |
| D2-68 | 3-Cl | 2-F-4-CF$_3$ |
| D2-69 | 3-F | 2-F-4-CF$_3$ |
| D2-70 | 3-CF$_3$ | 2-F-4-CF$_3$ |

—* means that m = 0

TABLE B

| line | $R^1$ | $R^2$ |
|---|---|---|
| B-1 | CH$_3$ | H |
| B-2 | CH$_2$CH$_3$ | H |
| B-3 | CH$_2$CH$_2$CH$_3$ | H |
| B-4 | CH(CH$_3$)$_2$ | H |
| B-5 | C(CH$_3$)$_3$ | H |
| B-6 | CH(CH$_3$)CH$_2$CH$_3$ | H |
| B-7 | CH$_2$CH(CH$_3$)$_2$ | H |
| B-8 | CH$_2$CH$_2$CH$_2$CH$_3$ | H |
| B-9 | CF$_3$ | H |
| B-10 | CHF$_2$ | H |
| B-11 | CH$_2$F | H |
| B-12 | CHCl$_2$ | H |
| B-13 | CH$_2$Cl | H |
| B-14 | CH$_2$OH | H |
| B-15 | CH$_2$CH$_2$OH | H |
| B-16 | CH$_2$CH$_2$CH$_2$OH | H |
| B-17 | CH(CH$_3$)CH$_2$OH | H |
| B-18 | CH$_2$CH(CH$_3$)OH | H |
| B-19 | n-C$_4$H$_8$OH | H |
| B-20 | CH$_2$OCH$_3$ | H |
| B-21 | CH$_2$OCH$_2$CH$_3$ | H |
| B-22 | CH(CH$_3$)OCH$_3$ | H |
| B-23 | CH$_2$OCF$_3$ | H |
| B-24 | CH$_2$CH$_2$OCF$_3$ | H |
| B-25 | CH$_2$OCCl$_3$ | H |
| B-26 | CH$_2$CH$_2$OCCl$_3$ | H |
| B-27 | CH=CH$_2$ | H |
| B-28 | CH$_2$CH=CH$_2$ | H |
| B-29 | CH$_2$CH=CHCH$_3$ | H |
| B-30 | CH$_2$C(CH$_3$)=CH$_2$ | H |
| B-31 | CH=CHCH$_3$ | H |
| B-32 | C(CH$_3$)=CH$_2$ | H |
| B-33 | CH=C(CH$_3$)$_2$ | H |
| B-34 | C(CH$_3$)=C(CH$_3$)$_2$ | H |
| B-35 | C(CH$_3$)=CH(CH$_3$) | H |
| B-36 | C(Cl)=CH$_2$ | H |
| B-37 | C(H)=CHCl | H |
| B-38 | C(Cl)=CHCl | H |
| B-39 | CH=CCl$_2$ | H |
| B-40 | C(Cl)=CCl$_2$ | H |
| B-41 | C(H)=CH(F) | H |
| B-42 | C(H)=CF$_2$ | H |
| B-43 | C(F)=CF$_2$ | H |
| B-44 | C(F)=CHF | H |
| B-45 | CH=CHCH$_2$OH | H |
| B-46 | CH=CHOCH$_3$ | H |
| B-47 | CH=CHCH$_2$OCH$_3$ | H |
| B-48 | CH=CHCH$_2$OCF$_3$ | H |
| B-49 | CH=CH(C$_3$H$_5$) | H |
| B-50 | C≡CH | H |
| B-51 | C≡CCH$_3$ | H |
| B-52 | CH$_2$C≡CCH$_3$ | H |

TABLE B-continued

| line | R¹ | R² |
|---|---|---|
| B-53 | CH₂C≡CH | H |
| B-54 | CH₂C≡CCH₃ | H |
| B-55 | C≡CCH(CH₃)₂ | H |
| B-56 | C≡CC(CH₃)₃ | H |
| B-57 | C≡C(C₃H₅) | H |
| B-58 | C≡C(C₄H₇) | H |
| B-59 | C≡C(1-Cl—C₃H₄) | H |
| B-60 | C≡C(1-Cl—C₄H₆) | H |
| B-61 | C≡CCl | H |
| B-62 | C≡CBr | H |
| B-63 | C≡C—I | H |
| B-64 | CH₂C≡CCl | H |
| B-65 | CH₂C≡CBr | H |
| B-66 | CH₂C≡C—I | H |
| B-67 | C≡CCH₂OCH₃ | H |
| B-68 | C≡CCH(OH)CH₃ | H |
| B-69 | C≡COCH₃ | H |
| B-70 | CH₂C≡COCH₃ | H |
| B-71 | C≡CCH₂OCCl₃ | H |
| B-72 | C≡CCH₂OCF₃ | H |
| B-73 | C≡CCH₂(C₃H₅) | H |
| B-74 | C≡C(1-Cl—C₃H4) | H |
| B-75 | C≡C(1-F—C₃H4) | H |
| B-76 | C₃H₅ (cyclopropyl) | H |
| B-77 | CH(CH₃)-C₃H₅ | H |
| B-78 | CH₂—C₃H₅ | H |
| B-79 | 1-(Cl)-C₃H₅ | H |
| B-80 | 1-(F)-C₃H₅ | H |
| B-81 | 1-(CH₃)-C₃H₅ | H |
| B-82 | 1-(CN)-C₃H₅ | H |
| B-83 | 2-(Cl)-C₃H₅ | H |
| B-84 | 2-(F)-C₃H₅ | H |
| B-85 | 1-C₃H₅—C₃H₅ | H |
| B-86 | 2-C₃H₅—C₃H₅ | H |
| B-87 | CH₂-(1-Cl—C₃H₅) | H |
| B-88 | CH₂-(1-F—C₃H₅) | H |
| B-89 | CH₃ | CH₃ |
| B-90 | CH₂CH₃ | CH₃ |
| B-91 | CH₂CH₂CH₃ | CH₃ |
| B-92 | CH(CH₃)₂ | CH₃ |
| B-93 | C(CH₃)₃ | CH₃ |
| B-94 | CH(CH₃)CH₂CH₃ | CH₃ |
| B-95 | CH₂CH(CH₃)₂ | CH₃ |
| B-96 | CH₂CH₂CH₂CH₃ | CH₃ |
| B-97 | CF₃ | CH₃ |
| B-98 | CHF₂ | CH₃ |
| B-99 | CH₂F | CH₃ |
| B-100 | CHCl₂ | CH₃ |
| B-101 | CH₂Cl | CH₃ |
| B-102 | CH₂OH | CH₃ |
| B-103 | CH₂CH₂OH | CH₃ |
| B-104 | CH₂CH₂CH₂OH | CH₃ |
| B-105 | CH(CH₃)CH₂OH | CH₃ |
| B-106 | CH₂CH(CH₃)OH | CH₃ |
| B-107 | n-C₄H₈OH | CH₃ |
| B-108 | CH₂OCH₃ | CH₃ |
| B-109 | CH₂OCH₂CH₃ | CH₃ |
| B-110 | CH(CH₃)OCH₃ | CH₃ |
| B-111 | CH₂OCF₃ | CH₃ |
| B-112 | CH₂CH₂OCF₃ | CH₃ |
| B-113 | CH₂OCCl₃ | CH₃ |
| B-114 | CH₂CH₂OCCl₃ | CH₃ |
| B-115 | CH=CH₂ | CH₃ |
| B-116 | CH₂CH=CH₂ | CH₃ |
| B-117 | CH₂CH=CHCH₃ | CH₃ |
| B-118 | CH₂C(CH₃)=CH₂ | CH₃ |
| B-119 | CH=CHCH₃ | CH₃ |
| B-120 | C(CH₃)=CH₂ | CH₃ |
| B-121 | CH=C(CH₃)₂ | CH₃ |
| B-122 | C(CH₃)=C(CH₃)₂ | CH₃ |
| B-123 | C(CH₃)=CH(CH₃) | CH₃ |
| B-124 | C(Cl)=CH₂ | CH₃ |
| B-125 | C(H)=CHCl | CH₃ |
| B-126 | C(Cl)=CHCl | CH₃ |
| B-127 | CH=CCl₂ | CH₃ |
| B-128 | C(Cl)=CCl₂ | CH₃ |
| B-129 | C(H)=CH(F) | CH₃ |
| B-130 | C(H)=CF₂ | CH₃ |
| B-131 | C(F)=CF₂ | CH₃ |
| B-132 | C(F)=CHF | CH₃ |
| B-133 | CH=CHCH₂OH | CH₃ |
| B-134 | CH=CHOCH₃ | CH₃ |
| B-135 | CH=CHCH₂OCH₃ | CH₃ |
| B-136 | CH=CHCH₂OCF₃ | CH₃ |
| B-137 | CH=CH(C₃H₅) | CH₃ |
| B-138 | C≡CH | CH₃ |
| B-139 | C≡CCH₃ | CH₃ |
| B-140 | CH₂C≡CCH₃ | CH₃ |
| B-141 | CH₂C≡CH | CH₃ |
| B-142 | CH₂C≡CCH₂CH₃ | CH₃ |
| B-143 | C≡CCH(CH₃)₂ | CH₃ |
| B-144 | C≡CC(CH₃)₃ | CH₃ |
| B-145 | C≡C(C₃H₅) | CH₃ |
| B-146 | C≡C(C₄H₇) | CH₃ |
| B-147 | C≡C(1-Cl—C₃H₄) | CH₃ |
| B-148 | C≡C(1-Cl—C₄H₆) | CH₃ |
| B-149 | C≡CCl | CH₃ |
| B-150 | C≡CBr | CH₃ |
| B-151 | C≡C—I | CH₃ |
| B-152 | CH₂C≡CCl | CH₃ |
| B-153 | CH₂C≡CBr | CH₃ |
| B-154 | CH₂C≡C—I | CH₃ |
| B-155 | C≡CCH₂OCH₃ | CH₃ |
| B-156 | C≡CCH(OH)CH₃ | CH₃ |
| B-157 | C≡COCH₃ | CH₃ |
| B-158 | CH₂C≡COCH₃ | CH₃ |
| B-159 | C≡CCH₂OCCl₃ | CH₃ |
| B-160 | C≡CCH₂OCF₃ | CH₃ |
| B-161 | C≡CCH₂(C₃H₅) | CH₃ |
| B-162 | C≡C(1-Cl—C₃H₄) | CH₃ |
| B-163 | C≡C(1-F—C₃H₄) | CH₃ |
| B-164 | C₃H₅ (cyclopropyl) | CH₃ |
| B-165 | CH(CH₃)-C₃H₅ | CH₃ |
| B-166 | CH₂—C₃H₅ | CH₃ |
| B-167 | 1-(Cl)-C₃H₅ | CH₃ |
| B-168 | 1-(F)-C₃H₅ | CH₃ |
| B-169 | 1-(CH₃)-C₃H₅ | CH₃ |
| B-170 | 1-(CN)-C₃H₅ | CH₃ |
| B-171 | 2-(Cl)-C₃H₅ | CH₃ |
| B-172 | 2-(F)-C₃H₅ | CH₃ |
| B-173 | 1-C₃H₅—C₃H₅ | CH₃ |
| B-174 | 2-C₃H₅—C₃H₅ | CH₃ |
| B-175 | CH₂-(1-Cl—C₃H₅) | CH₃ |
| B-176 | CH₂-(1-F—C₃H₅) | CH₃ |
| B-177 | CH₃ | CH₂CH=CH₂ |
| B-178 | CH₂CH₃ | CH₂CH=CH₂ |
| B-179 | CH₂CH₂CH₃ | CH₂CH=CH₂ |
| B-180 | CH(CH₃)₂ | CH₂CH=CH₂ |
| B-181 | C(CH₃)3 | CH₂CH=CH₂ |
| B-182 | CH(CH₃)CH₂CH₃ | CH₂CH=CH₂ |
| B-183 | CH₂CH(CH₃)₂ | CH₂CH=CH₂ |
| B-184 | CH₂CH₂CH₂CH₃ | CH₂CH=CH₂ |
| B-185 | CF₃ | CH₂CH=CH₂ |
| B-186 | CHF₂ | CH₂CH=CH₂ |
| B-187 | CH₂F | CH₂CH=CH₂ |
| B-188 | CHCl₂ | CH₂CH=CH₂ |
| B-189 | CH₂Cl | CH₂CH=CH₂ |
| B-190 | CH₂OH | CH₂CH=CH₂ |
| B-191 | CH₂CH₂OH | CH₂CH=CH₂ |
| B-192 | CH₂CH₂CH₂OH | CH₂CH=CH₂ |
| B-193 | CH(CH₃)CH₂OH | CH₂CH=CH₂ |
| B-194 | CH₂CH(CH₃)OH | CH₂CH=CH₂ |
| B-195 | n-C₄H₈OH | CH₂CH=CH₂ |
| B-196 | CH₂OCH₃ | CH₂CH=CH₂ |
| B-197 | CH₂OCH₂CH₃ | CH₂CH=CH₂ |
| B-198 | CH(CH₃)OCH₃ | CH₂CH=CH₂ |
| B-199 | CH₂OCF₃ | CH₂CH=CH₂ |
| B-200 | CH₂CH₂OCF₃ | CH₂CH=CH₂ |
| B-201 | CH₂OCCl₃ | CH₂CH=CH₂ |
| B-202 | CH₂CH₂OCCl₃ | CH₂CH=CH₂ |
| B-203 | CH=CH₂ | CH₂CH=CH₂ |
| B-204 | CH₂CH=CH₂ | CH₂CH=CH₂ |
| B-205 | CH₂CH=CHCH₃ | CH₂CH=CH₂ |
| B-206 | CH₂C(CH₃)=CH₂ | CH₂CH=CH₂ |

TABLE B-continued

| line | R$^1$ | R$^2$ |
|---|---|---|
| B-207 | CH=CHCH$_3$ | CH$_2$CH=CH$_2$ |
| B-208 | C(CH$_3$)=CH$_2$ | CH$_2$CH=CH$_2$ |
| B-209 | CH=C(CH$_3$)$_2$ | CH$_2$CH=CH$_2$ |
| B-210 | C(CH$_3$)=C(CH$_3$)$_2$ | CH$_2$CH=CH$_2$ |
| B-211 | C(CH$_3$)=CH(CH$_3$) | CH$_2$CH=CH$_2$ |
| B-212 | C(Cl)=CH$_2$ | CH$_2$CH=CH$_2$ |
| B-213 | C(H)=CHCl | CH$_2$CH=CH$_2$ |
| B-214 | C(Cl)=CHCl | CH$_2$CH=CH$_2$ |
| B-215 | CH=CCl$_2$ | CH$_2$CH=CH$_2$ |
| B-216 | C(Cl)=CCl$_2$ | CH$_2$CH=CH$_2$ |
| B-217 | C(H)=CH(F) | CH$_2$CH=CH$_2$ |
| B-218 | C(H)=CF$_2$ | CH$_2$CH=CH$_2$ |
| B-219 | C(F)=CF$_2$ | CH$_2$CH=CH$_2$ |
| B-220 | C(F)=CHF | CH$_2$CH=CH$_2$ |
| B-221 | CH=CHCH$_2$OH | CH$_2$CH=CH$_2$ |
| B-222 | CH=CHOCH$_3$ | CH$_2$CH=CH$_2$ |
| B-223 | CH=CHCH$_2$OCH$_3$ | CH$_2$CH=CH$_2$ |
| B-224 | CH=CHCH$_2$OCF$_3$ | CH$_2$CH=CH$_2$ |
| B-225 | CH=CH(C$_3$H$_5$) | CH$_2$CH=CH$_2$ |
| B-226 | C≡CH | CH$_2$CH=CH$_2$ |
| B-227 | C≡CCH$_3$ | CH$_2$CH=CH$_2$ |
| B-228 | CH$_2$C≡CCH$_3$ | CH$_2$CH=CH$_2$ |
| B-229 | CH$_2$C≡CH | CH$_2$CH=CH$_2$ |
| B-230 | CH$_2$C≡CCH$_2$CH$_3$ | CH$_2$CH=CH$_2$ |
| B-231 | C≡CCH(CH$_3$)$_2$ | CH$_2$CH=CH$_2$ |
| B-232 | C≡CC(CH$_3$)$_3$ | CH$_2$CH=CH$_2$ |
| B-233 | C≡C(C$_3$H$_5$) | CH$_2$CH=CH$_2$ |
| B-234 | C≡C(C$_4$H$_7$) | CH$_2$CH=CH$_2$ |
| B-235 | C≡C(1-Cl—C$_3$H$_4$) | CH$_2$CH=CH$_2$ |
| B-236 | C≡C(1-Cl—C$_4$H$_6$) | CH$_2$CH=CH$_2$ |
| B-237 | C≡CCl | CH$_2$CH=CH$_2$ |
| B-238 | C≡CBr | CH$_2$CH=CH$_2$ |
| B-239 | C≡C—I | CH$_2$CH=CH$_2$ |
| B-240 | CH$_2$C≡CCl | CH$_2$CH=CH$_2$ |
| B-241 | CH$_2$C≡CBr | CH$_2$CH=CH$_2$ |
| B-242 | CH$_2$C≡C—I | CH$_2$CH=CH$_2$ |
| B-243 | C≡CCH$_2$OCH$_3$ | CH$_2$CH=CH$_2$ |
| B-244 | C≡CCH(OH)CH$_3$ | CH$_2$CH=CH$_2$ |
| B-245 | C≡COCH$_3$ | CH$_2$CH=CH$_2$ |
| B-246 | CH$_2$C≡COCH$_3$ | CH$_2$CH=CH$_2$ |
| B-247 | C≡CCH$_2$OCCl$_3$ | CH$_2$CH=CH$_2$ |
| B-248 | C≡CCH$_2$OCF$_3$ | CH$_2$CH=CH$_2$ |
| B-249 | C≡CCH$_2$(C$_3$H$_5$) | CH$_2$CH=CH$_2$ |
| B-250 | C≡C(1-Cl—C$_3$H$_4$) | CH$_2$CH=CH$_2$ |
| B-251 | C≡C(1-F—C$_3$H$_4$) | CH$_2$CH=CH$_2$ |
| B-252 | C$_3$H$_5$ (cyclopropyl) | CH$_2$CH=CH$_2$ |
| B-253 | CH(CH$_3$)—C$_3$H$_5$ | CH$_2$CH=CH$_2$ |
| B-254 | CH$_2$—C$_3$H$_5$ | CH$_2$CH=CH$_2$ |
| B-255 | 1-(Cl)-C$_3$H$_5$ | CH$_2$CH=CH$_2$ |
| B-256 | 1-(F)-C$_3$H$_5$ | CH$_2$CH=CH$_2$ |
| B-257 | 1-(CH$_3$)-C$_3$H$_5$ | CH$_2$CH=CH$_2$ |
| B-258 | 1-(CN)-C$_3$H$_5$ | CH$_2$CH=CH$_2$ |
| B-259 | 2-(Cl)-C$_3$H$_5$ | CH$_2$CH=CH$_2$ |
| B-260 | 2-(F)-C$_3$H$_5$ | CH$_2$CH=CH$_2$ |
| B-261 | 1-C$_3$H$_5$—C$_3$H$_5$ | CH$_2$CH=CH$_2$ |
| B-262 | 2-C$_3$H$_5$—C$_3$H$_5$ | CH$_2$CH=CH$_2$ |
| B-263 | CH$_2$-(1-Cl—C$_3$H$_5$) | CH$_2$CH=CH$_2$ |
| B-264 | CH$_2$-(1-F—C$_3$H$_5$) | CH$_2$CH=CH$_2$ |
| B-265 | CH$_3$ | CH$_2$C≡CH |
| B-266 | CH$_2$CH$_3$ | CH$_2$C≡CH |
| B-267 | CH$_2$CH$_2$CH$_3$ | CH$_2$C≡CH |
| B-268 | CH(CH$_3$)$_2$ | CH$_2$C≡CH |
| B-269 | C(CH$_3$)$_3$ | CH$_2$C≡CH |
| B-270 | CH(CH$_3$)CH$_2$CH$_3$ | CH$_2$C≡CH |
| B-271 | CH$_2$CH(CH$_3$)$_2$ | CH$_2$C≡CH |
| B-272 | CH$_2$CH$_2$CH$_2$CH$_3$ | CH$_2$C≡CH |
| B-273 | CF$_3$ | CH$_2$C≡CH |
| B-274 | CHF$_2$ | CH$_2$C≡CH |
| B-275 | CH$_2$F | CH$_2$C≡CH |
| B-276 | CHCl$_2$ | CH$_2$C≡CH |
| B-277 | CH$_2$Cl | CH$_2$C≡CH |
| B-278 | CH$_2$OH | CH$_2$C≡CH |
| B-279 | CH$_2$CH$_2$OH | CH$_2$C≡CH |
| B-280 | CH$_2$CH$_2$CH$_2$OH | CH$_2$C≡CH |
| B-281 | CH(CH$_3$)CH$_2$OH | CH$_2$C≡CH |
| B-282 | CH$_2$CH(CH$_3$)OH | CH$_2$C≡CH |
| B-283 | n-C$_4$H$_8$OH | CH$_2$C≡CH |
| B-284 | CH$_2$OCH$_3$ | CH$_2$C≡CH |
| B-285 | CH$_2$OCH$_2$CH$_3$ | CH$_2$C≡CH |
| B-286 | CH(CH$_3$)OCH$_3$ | CH$_2$C≡CH |
| B-287 | CH$_2$OCF$_3$ | CH$_2$C≡CH |
| B-288 | CH$_2$CH$_2$OCF$_3$ | CH$_2$C≡CH |
| B-289 | CH$_2$OCCl$_3$ | CH$_2$C≡CH |
| B-290 | CH$_2$CH$_2$OCCl$_3$ | CH$_2$C≡CH |
| B-291 | CH=CH$_2$ | CH$_2$C≡CH |
| B-292 | CH$_2$CH=CH$_2$ | CH$_2$C≡CH |
| B-293 | CH$_2$CH=CHCH$_3$ | CH$_2$C≡CH |
| B-294 | CH$_2$C(CH$_3$)=CH$_2$ | CH$_2$C≡CH |
| B-295 | CH=CHCH$_3$ | CH$_2$C≡CH |
| B-296 | C(CH$_3$)=CH$_2$ | CH$_2$C≡CH |
| B-297 | CH=C(CH$_3$)$_2$ | CH$_2$C≡CH |
| B-298 | C(CH$_3$)=C(CH$_3$)$_2$ | CH$_2$C≡CH |
| B-299 | C(CH$_3$)=CH(CH$_3$) | CH$_2$C≡CH |
| B-300 | C(Cl)=CH$_2$ | CH$_2$C≡CH |
| B-301 | C(H)=CHCl | CH$_2$C≡CH |
| B-302 | C(Cl)=CHCl | CH$_2$C≡CH |
| B-303 | CH=CCl$_2$ | CH$_2$C≡CH |
| B-304 | C(Cl)=CCl$_2$ | CH$_2$C≡CH |
| B-305 | C(H)=CH(F) | CH$_2$C≡CH |
| B-306 | C(H)=CF$_2$ | CH$_2$C≡CH |
| B-307 | C(F)=CF$_2$ | CH$_2$C≡CH |
| B-308 | C(F)=CHF | CH$_2$C≡CH |
| B-309 | CH=CHCH$_2$OH | CH$_2$C≡CH |
| B-310 | CH=CHOCH$_3$ | CH$_2$C≡CH |
| B-311 | CH=CHCH$_2$OCH$_3$ | CH$_2$C≡CH |
| B-312 | CH=CHCH$_2$OCF$_3$ | CH$_2$C≡CH |
| B-313 | CH=CH(C$_3$H$_5$) | CH$_2$C≡CH |
| B-314 | C≡CH | CH$_2$C≡CH |
| B-315 | C≡CCH$_3$ | CH$_2$C≡CH |
| B-316 | CH$_2$C≡CCH$_3$ | CH$_2$C≡CH |
| B-317 | CH$_2$C≡CH | CH$_2$C≡CH |
| B-318 | CH$_2$C≡CCH$_2$CH$_3$ | CH$_2$C≡CH |
| B-319 | C≡CCH(CH$_3$)$_2$ | CH$_2$C≡CH |
| B-320 | C≡CC(CH$_3$)$_3$ | CH$_2$C≡CH |
| B-321 | C≡C(C$_3$H$_5$) | CH$_2$C≡CH |
| B-322 | C≡C(C$_4$H$_7$) | CH$_2$C≡CH |
| B-323 | C≡C(1-Cl—C$_3$H4) | CH$_2$C≡CH |
| B-324 | C≡C(1-Cl—C$_4$H$_6$) | CH$_2$C≡CH |
| B-325 | C≡CCl | CH$_2$C≡CH |
| B-326 | C≡CBr | CH$_2$C≡CH |
| B-327 | C≡C—I | CH$_2$C≡CH |
| B-328 | CH$_2$C≡CCl | CH$_2$C≡CH |
| B-329 | CH$_2$C≡CBr | CH$_2$C≡CH |
| B-330 | CH$_2$C≡C—I | CH$_2$C≡CH |
| B-331 | C≡CCH$_2$OCH$_3$ | CH$_2$C≡CH |
| B-332 | C≡CCH(OH)CH$_3$ | CH$_2$C≡CH |
| B-333 | C≡COCH$_3$ | CH$_2$C≡CH |
| B-334 | CH$_2$C≡COCH$_3$ | CH$_2$C≡CH |
| B-335 | C≡CCH$_2$OCCl$_3$ | CH$_2$C≡CH |
| B-336 | C≡CCH$_2$OCF$_3$ | CH$_2$C≡CH |
| B-337 | C≡CCH$_2$(C$_3$H$_5$) | CH$_2$C≡CH |
| B-338 | C≡C(1-Cl—C$_3$H4) | CH$_2$C≡CH |
| B-339 | C≡C(1-F—C$_3$H4) | CH$_2$C≡CH |
| B-340 | C$_3$H$_5$ (cyclopropyl) | CH$_2$C≡CH |
| B-341 | CH(CH$_3$)-C$_3$H$_5$ | CH$_2$C≡CH |
| B-342 | CH$_2$—C$_3$H$_5$ | CH$_2$C≡CH |
| B-343 | 1-(Cl)-C$_3$H$_5$ | CH$_2$C≡CH |
| B-344 | 1-(F)-C$_3$H$_5$ | CH$_2$C≡CH |
| B-345 | 1-(CH$_3$)-C$_3$H$_5$ | CH$_2$C≡CH |
| B-346 | 1-(CN)-C$_3$H$_5$ | CH$_2$C≡CH |
| B-347 | 2-(Cl)-C$_3$H$_5$ | CH$_2$C≡CH |
| B-348 | 2-(F)-C$_3$H$_5$ | CH$_2$C≡CH |
| B-349 | 1-C$_3$H$_5$—C$_3$H$_5$ | CH$_2$C≡CH |
| B-350 | 2-C$_3$H$_5$—C$_3$H$_5$ | CH$_2$C≡CH |
| B-351 | CH$_2$-(1-Cl—C$_3$H$_5$) | CH$_2$C≡CH |
| B-352 | CH$_2$-(1-F—C$_3$H$_5$) | CH$_2$C≡CH |

The compounds I and the compositions according to the invention, respectively, are suitable as fungicides.

Furthermore, also the compounds IV according to the invention, are suitable as fungicides. The following description referring to compounds I also applies to the compounds of formula IV.

Furthermore, also the compounds A and B of the further aspect of the invention, are suitable as fungicides. The following description referring to compounds I also applies to the compounds of formula A and B.

Consequently, according to a further aspect, the present invention relates to the use of compounds of formula I, the N-oxides and the agriculturally acceptable salts thereof or of the compositions of the invention for combating phytopathogenic fungi.

Accordingly, the present invention also encompasses a method for combating harmful fungi, comprising treating the fungi or the materials, plants, the soil or seeds to be protected against fungal attack with an effective amount of at least one compound of formula I or with a composition comprising according to the invention.

They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e.g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. indemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylin-*

*drocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*. Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasilliense* each causing sudden death syndrome on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*. Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monlinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritic, Septoria blotch*) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. P. destructor), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humilion* hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii*(orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. scerotiorum*) and soybeans (e. g. *S. rolfsii* or *S. scerotiorum*); *Septoria* spp. on various plants, e. g. *S. glycines* (brown spot) on soybeans, *S. tritici*(*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*]*nodorum*) on wheat; *Synchytrum endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and nonliving materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to compositions comprising one compound I according to the invention. In particular, such composition further comprises an auxiliary as defined below.

The term "effective amount" used denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e.g. finely divided kaolin) ad 100 wt %.

xii) Granules (GR, FG)

0.5-30 wt % of a compound I is ground finely and associated with solid carrier (e.g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 g to 10 kg, in particular 0.1 to 1000 g, more particularly from 1 to 1000 g, specifically from 1 to 100 g and most specifically from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as a virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes.

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a composition comprising two or three active ingredients, may be mixed by the user himself in a spray tank or any other kind of vessel used for applications (e.g seed treater drums, seed pelleting machinery, knapsack sprayer) and further auxiliaries may be added, if appropriate.

When living microorganisms, such as pesticides from groups L1), L3) and L5), form part of such kit, it must be taken care that choice and amounts of the components (e.g. chemical pesticidal agents) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides (e.g. pesticidally active substances and biopesticides), in conjunction with which the compounds I can be used, is intended to illustrate the possible combinations but does not limit them:

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S, 7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol; 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-

(trifluoromethyl)phenyl]-1-(1,2,4-triazol-1-yl)propan-2-ol, 2-[2-chloro-4-(4-chlorophenoxyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, 3-(4-chloro-2-fluoro-phenyl)-5-(2,4-difluorophenyl)isoxazol-4-yl]-(3-pyridyl)methanol;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy) pyrimidin-4-amine, 5-fluoro-2-(4-fluorophenyl-methoxyl)pyrimidin-4-amine;

D) Inhibitors of Cell Division and Cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

compounds affecting cell membrane permeability and fatty acids: propamocarb, propamocarb-hydrochlorid fatty acid amide hydrolase inhibitors: oxathiapiprolin, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 2-{3-[2-(1-{[3,5-bis(difluoromethyl-1H-pyrazol-1-yl] acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl] acetyl}piperidin-4-yl) 1,3-thiazol-4-yl]-4,5-dihydro-1,2-oxazol-5-yl}-3-chlorophenyl methanesulfonate;

H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors inhibitors of glucan synthesis: validamycin, polyoxin B;

melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts;

K) Unknown Mode of Action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, oxin-copper, proquinazid, tebufloquin, tecloftalam, triazoxide, 2-butoxy-6-iodo-3-propylchromen-4-one, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy) phenyl]-4,5-dihydro-1,2-oxazol-3-yl}-1,3-thiazol-2-yl) piperidin-1-yl]ethanone, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)N-[4-(3,4-dimethoxy-phenyl)-isoxazol-5-yl]-2-prop-2-ynyloxy-acetamide;

ethyl (Z)-3-amino-2-cyano-3-phenyl-prop-2-enoate, picarbutrazox, pentyl N-[6-[[(Z)-[(1-methyltetrazol-5-yl)-phenyl-methylene]amino]oxymethyl]-2-pyridyl] carbamate, 2-[2-[(7,8-difluoro-2-methyl-3-quinolyl) oxy]-6-fluoro-phenyl]propan-2-ol, 2-[2-fluoro-6-[(8-fluoro-2-methyl-3-quinolyl)oxy]phen-yl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

L) Biopesticides
- L1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum;* mixture of *T. harzianum* and *T. viride;* mixture of *T. polysporum* and *T. harzianum; T. stromaticum, T. virens* (also named *Gliocladium virens*), *T. viride, Typhula phacorrhiza, Ulocladium oudemansii, Verticillium dahlia,* zucchini yellow mosaic virus (avirulent strain);
- L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;
- L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai,* B. t. ssp. *israelensis,* B. t. ssp. *galleriae,* B. t. ssp. *kurstaki,* B. t. ssp. *tenebrionis, Beauveria bassiana, B. brongniartii, Burkholderia* sp., *Chromobacterium subtsugae, Cydia pomonella granulosis virus, Cryptophlebia leucotreta granulovirus* (CrleGV), *Isaria fumosorosea, Heterorhabditis bacteriophora, Lecanicillium longisporum, L. muscarium* (formerly *Verticillium lecanii*), *Metarhizium anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramose, P. reneformis, P. thornea, P. usgae, Pseudomonas fluorescens, Steinernema carpocapsae, S. feltiae, S. kraussei;*
- L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodae,* Catnip oil, Neem oil, Quillay extract, *Tagetes* oil;
- L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* sp., *B. elkanii, B. japonicum, B. liaoningense, B. lupini, Delftia acidovorans, Glomus intraradices, Mesorhizobium* sp., *Paenibacillus alvei, Penicillium bilaiae, Rhizobium leguminosarum* bv. *phaseoli,* R. l. *trifolii,* R. l. bv. *viciae, R. tropici, Sinorhizobium meliloti;*
- L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract; M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides
- acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
- amino acid derivatives: bilanafos, glyphosate, glufosinate, sulfosate;
- aryloxyphenoxypropionates: clodinafop, cyhalofop-butyl, fenoxaprop, fluazifop, haloxyfop, metamifop, propaquizafop, quizalofop, quizalofop-P-tefuryl;
- Bipyridyls: diquat, paraquat;
- (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
- cyclohexanediones: butroxydim, clethodim, cycloxydim, profoxydim, sethoxydim, tepraloxydim, tralkoxydim;
- dinitroanilines: benfluralin, ethalfluralin, oryzalin, pendimethalin, prodiamine, trifluralin;
- diphenyl ethers: acifluorfen, aclonifen, bifenox, diclofop, ethoxyfen, fomesafen, lactofen, oxyfluorfen;
- hydroxybenzonitriles: bomoxynil, dichlobenil, ioxynil;
- imidazolinones: imazamethabenz, imazamox, imazapic, imazapyr, imazaquin, imazethapyr;
- phenoxy acetic acids: clomeprop, 2,4-dichlorophenoxyacetic acid (2,4-D), 2,4-DB, dichlorprop, MCPA, MCPA-thioethyl, MCPB, Mecoprop;
- pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methylphenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and Ill compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4- sulfanylidene)carbamoyl]-phenyl]-2-(3-chloro-2-pyridyl)-5-(trifluoromethyl)pyrazole-3-carboxamide);

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]cyclopropaneacetic acid ester.

The present invention furthermore relates to compositions comprising a compound I (component 1) and at least one further active substance useful for plant protection, e. g. selected from the groups A) to O) (component 2), in particular one further fungicide, e. g. fungicide from the groups A) to K), as described above, and if desired one suitable solvent or solid carrier. Those compositions are of particular interest, since many of them at the same application rate show higher efficiencies against harmful fungi. Furthermore, combating harmful fungi with a composition comprising a compound I and a fungicide from groups A) to K), as described above, is more efficient than combating those fungi with individual compounds I or individual fungicides from groups A) to K). By applying compounds I together with at least one active substance from groups A) to O) a synergistic effect can be obtained, i.e. more then simple addition of the individual effects is obtained (synergistic compositions).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying a compound of the present invention and a pesticide II sequentially the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a composition or mixture comprising a pesticide II selected from group L), it is preferred that the pesticide II is applied as last treatment.

According to the invention, the solid material (dry matter) of the biopesticides (with the exception of oils such as Neem oil, *Tagetes* oil, etc.) are considered as active components (e.g. to be obtained after drying or evaporation of the extraction medium or the suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^9$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

In compositions according to the invention comprising one compound I (component 1) and one further pesticidally active substance (component 2), e. g. one active substance from groups A) to O), the weight ratio of component 1 and component 2 generally depends on the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In compositions according to the invention comprising one compound I (component 1) and a first further pesticidally active substance (component 2) and a second further pesticidally active substance (component 3), e. g. two active substances from groups A) to O), the weight ratio of component 1 and component 2 depends on the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to compositions comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; benzovindiflupyr, bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to compositions comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to compositions comprising a compound of formula I (component 1) and at least one active substance selected from group C) (component 2) and particularly selected from metalaxyl, (metalaxyl-M) mefenoxam, ofurace.

Preference is given to compositions comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to compositions comprising a compound I (component 1) and at least one active substance selected from group E) (component 2) and particularly selected from cyprodinil, mepanipyrim, pyrimethanil.

Preference is also given to compositions comprising a compound I (component 1) and at least one active substance selected from group F) (component 2) and particularly selected from iprodione, fludioxonil, vinclozolin, quinoxyfen.

Preference is also given to compositions comprising a compound I (component 1) and at least one active substance selected from group G) (component 2) and particularly selected from dimethomorph, flumorph, iprovalicarb, benthiavalicarb, mandipropamid, propamocarb.

Preference is also given to compositions comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to compositions comprising a compound I (component 1) and at least one active substance selected from group I) (component 2) and particularly selected from carpropamid and fenoxanil.

Preference is also given to compositions comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to compositions comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

The biopesticides from group L) of pesticides II, their preparation and their pesticidal activity e.g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) and/or L6) may also have fungicidal, bactericidal, viricidal, plant defense activator, insecticidal, acaricidal, molluscidal, pheromone and/or nematicidal activity.

Many of these biopesticides are registered and/or are commercially available: aluminium silicate (Screen™ Duo from Certis LLC, USA), *Agrobacterium radiobacter* K1026 (e.g. NoGall® from Becker Underwood Pty Ltd., Australia), *A. radiobacter* K84 (Nature 280, 697-699, 1979; e.g. Gall-Troll® from AG Biochem, Inc., C, USA), *Ampelomyces quisqualis* M-10 (e.g. AQ 10® from Intrachem Bio GmbH & Co. KG, Germany), *Ascophyllum nodosum* (Norwegian kelp, Brown kelp) extract or filtrate (e.g. ORKA GOLD from Becker Underwood, South Africa; or Goemar® from Laboratoires Goemar, France), *Aspergillus flavus* NRRL 21882 isolated from a peanut in Georgia in 1991 by the USDA, National Peanut Research Laboratory (e.g. in AflaGuard® from Syngenta, CH), mixtures of *Aureobasidium pullulans* DSM14940 and DSM 14941 (e.g. blastospores in Blossom-Protect® from bio-ferm GmbH, Germany), *Azospirillum amazonense* BR 11140 (SpY2$^T$) (Proc. 9$^{th}$ Int. and 1$^{st}$ Latin American PGPR meeting, Quimara, Medellin, Colombia 2012, p. 60, ISBN 978-958-46-0908-3), *A. brasilense* AZ39 (Eur. J. Soil Biol 45(1), 28-35, 2009), *A. brasilense* XOH (e.g. AZOS from Xtreme Gardening, USA or RTI Reforestation Technologies International; USA), *A. brasilense* BR 11002 (Proc. 9$^{th}$ Int. and 1$^{st}$ Latin American PGPR meeting, Quimara, Medellin, Colombia 2012, p. 60, ISBN 978-958-46-0908-3), *A. brasilense* BR 11005 (SP245; e.g. in GEL-FIX Gramineas from BASF Agricultural Specialties Ltd., Brazil), *A. lipoferum* BR 11646 (Sp31) (Proc. 9$^{th}$ Int. and 1$^{st}$ Latin American PGPR meeting, Quimara, Medellin, Colombia 2012, p. 60), *Bacillus amyloliquefaciens* FZB42 (e.g. in RhizoVital® 42 from AbiTEP GmbH, Berlin, Germany), *B. amyloliquefaciens* IN937a (J. Microbiol. Biotechnol. 17(2), 280-286, 2007; e.g. in BioYield® from Gustafson LLC, TX, USA), *B. amyloliquefaciens* IT-45 (CNCM I-3800) (e.g. Rhizocell C from ITHEC, France), *B. amyloliquefaciens* subsp. *plantarum* MBI600 (NRRL B-50595, deposited at United States Department of Agriculture) (e.g. Integral®, Subtilex® NG from Becker Underwood, USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *B. pumilus* GB34 (ATCC 700814; e.g. in YieldShield® from Gustafson LLC, TX, USA), and *Bacillus pumilus* KFP9F (NRRL B-50754) (e.g. in BAC-UP or FUSION-P from Becker Underwood South Africa), *B. pumilus* QST 2808

(NRRL B-30087) (e.g. Sonata® and Ballad® Plus from AgraQuest Inc., USA), *B. subtilis* GB03 (e.g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B-21661 in Rhapsody®, Serenade® MAX and Serenade® ASO from AgraQuest Inc., USA), *B. subtilis* var. *amyloliquefaciens* FZB24 (e.g. Taegro® from Novozyme Biologicals, Inc., USA), *B. subtilis* var. *amyloliquefaciens* D747 (e.g. Double Nickel 55 from Certis LLC, USA), *B. thuringiensis* ssp. *aizawai* ABTS-1857 (e.g. in XenTari® from BioFa AG, Munsingen, Germany), B. t. ssp. *aizawai* SAN 401 I, ABG-6305 and ABG-6346, *Bacillus t.* ssp. *israelensis* AM65-52 (e.g. in VectoBac® from Valent BioSciences, IL, USA), *Bacillus thuringiensis* ssp. *kurstaki* SB4 (NRRL B-50753; e.g. Beta Pro® from Becker Underwood, South Africa), B. t. ssp. *kurstaki* ABTS-351 identical to HD-1 (ATCC SD-1275; e.g. in Dipel® DF from Valent BioSciences, IL, USA), B. t. ssp. *kurstaki* EG 2348 (e.g. in Lepinox® or Rapax® from CBC (Europe) S.r.l., Italy), B. t. ssp. *tenebrionis* DSM 2803 (EP 0 585 215 B1; identical to NRRL B-15939; Mycogen Corp.), B. t. ssp. *tenebrionis* NB-125 (DSM 5526; EP 0 585 215 B1; also referred to as SAN 418 I or ABG-6479; former production strain of Novo-Nordisk), B. t. ssp. *tenebrionis* NB-176 (or NB176-1) a gamma-irradiated, induced high-yielding mutant of strain NB-125 (DSM 5480; EP 585 215 B1; Novodor® from Valent BioSciences, Switzerland), *Beauveria bassiana* ATCC 74040 (e.g. in Naturalis® from CBC (Europe) S.r.l., Italy), *B. bassiana* DSM 12256 (US 200020031495; e.g. BioExpert® SC from Live Systems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e.g. BroadBand® from Becker Underwood, South Africa), *B. brongniartii* (e.g. in Melocont® from Agrifutur, Agrianello, Italy, for control of cockchafer; J. Appl. Microbiol. 100(5), 1063-72, 2006), *Bradyrhizobium* sp. (e.g. Vault® from Becker Underwood, USA), *B. japonicum* (e.g. VAULT® from Becker Underwood, USA), *Candida oleophila* 1-182 (NRRL Y-18846; e.g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e.g. Biocure® (in mixture with lysozyme) and BioCoat® from Micro Flo Company, USA (BASF SE) and Arysta), Chitosan (e.g. ArmourZen® from BotriZen Ltd., NZ), *Clonostachys rosea* f. *catenulata*, also named *Gliocladium catenulatum* (e.g. isolate J 1446: Prestop® from Verdera Oy, Finland), *Chromobacterium subtsugae* PRAA4-1 isolated from soil under an eastern hemlock (*Tsuga canadensis*) in the Catoctin Mountain region of central Maryland (e.g. in GRANDEVO from Marrone Bio Innovations, USA), *Coniothyrium minitans* CON/M/91-08 (e.g. Contans® WG from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Cryptophlebia leucotreta* granulovirus (CrleGV) (e.g. in CRYPTEX from Adermatt Biocontrol, Switzerland), *Cydia pomonella* granulovirus (CpGV) V03 (DSM GV-0006; e.g. in MADEX Max from Andermatt Biocontrol, Switzerland), CpGV V22 (DSM GV-0014; e.g. in MADEX Twin from Adermatt Biocontrol, Switzerland), *Delftia acidovorans* RAY209 (ATCC PTA-4249; WO 2003/57861; e.g. in BIO-BOOST from Brett Young, Winnipeg, Canada), *Dilophosphora alopecuri* (Twist Fungus from Becker Underwood, Australia), *Ecklonia maxima* (kelp) extract (e.g. KELPAK SL from Kelp Products Ltd, South Africa), formononetin (e.g. in MYCONATE from Plant Health Care plc, U.K.), *Fusarium oxysporum* (e.g. BIOFOX® from S.I.A.P.A., Italy, FUSACLEAN® from Natural Plant Protection, France), *Glomus intraradices* (e.g. MYC 4000 from ITHEC, France), *Glomus intraradices* RTI801 (e.g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e.g. MESSENGER or HARP-N-Tek from Plant Health Care plc, U.K.; Science 257, 1-132, 1992), *Heterorhabditis bacteriophaga* (e.g. Nemasys® G from Becker Underwood Ltd., UK), *Isaria fumosorosea* Apopka-97 (ATCC 20874) (PFR-97™ from Certis LLC, USA), cis-jasmone (U.S. Pat. No. 8,221,736), laminarin (e.g. in VACCIPLANT from Laboratoires Goemar, St. Malo, France or Stähler SA, Switzerland), *Lecanicillium longisporum* KV42 and KV71 (e.g. VERTALEC® from Koppert BV, Netherlands), *L. muscarium* KV01 (formerly *Verticillium lecanii*) (e.g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in *Niger*; also NRRL 50758) (e.g. GREEN MUSCLE® from Becker Underwood, South Africa), *M. a.* var. *acridum* FI-985 (e.g. GREEN GUARD® SC from Becker Underwood Pty Ltd, Australia), *M. anisopliae* FI-1045 (e.g. BIOCANE® from Becker Underwood Pty Ltd, Australia), *M. anisopliae* F52 (DSM 3884, ATCC 90448; e.g. MET52® Novozymes Biologicals BioAg Group, Canada), *M. anisopliae* ICIPE 69 (e.g. METATHRIPOL from ICIPE, Nairobe, Kenya), *Metschnikowia fructicola* (NRRL Y-30752; e.g. SHEMER® from Agrogreen, Israel, now distributed by Bayer CropSciences, Germany; U.S. Pat. No. 6,994,849), *Microdochium dimerum* (e.g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e.g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e.g. NO FLY™ from Natural Industries, Inc., USA), *P. lilacinus* 251 (e.g. in BioAct®/MeloCon® from Prophyta, Germany; Crop Protection 27, 352-361, 2008; originally isolated from infected nematode eggs in the Philippines), *P. lilacinus* DSM 15169 (e.g. NEMATA® SC from Live Systems Technology S.A., Colombia), *P. lilacinus* BCP2 (NRRL 50756; e.g. PL GOLD from Becker Underwood BioAg SA Ltd, South Africa), mixture of *Paenibacillus alvei* NAS6G6 (NRRL B-50755), *Pantoea vagans* (formerly *agglomerans*) C$_9$-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* spp. ATCC PTA-9643 (WO 2010/085795), *Pasteuria* spp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e.g. Jump Start® from Novozymes Biologicals BioAg Group, Canada, originally isolated from soil in southern Alberta; Fertilizer Res. 39, 97-103, 1994), *Phlebiopsis gigantea* (e.g. RotStop® from Verdera Oy, Finland), *Pichia anomala* WRL-076 (NRRL Y30842; U.S. Pat. No. 8,206,972), potassium bicarbonate (e.g. Amicarb® from Stähler SA, Switzerland), potassium silicate (e.g. Sil-MATRIX™ from Certis LLC, USA), *Pseudozyma flocculosa* PF-A22 UL (e.g. Sporodex® from Plant Products Co. Ltd., Canada), *Pseudomonas* sp. DSM 13134 (WO 2001/40441, e.g. in PRORADIX from Sourcon Padena GmbH & Co. KG, Hechinger Str. 262, 72072 Tubingen, Germany), *P. chloraphis* MA 342 (e.g. in CER-ALL or CEDEMON from BioAgri AB, Uppsala, Sweden), *P. fluorescens* CL 145A (e.g. in ZEQUANOX from Marrone BioInnovations, Davis, Calif., USA; J. Invertebr. Pathol. 113(1):104-14, 2013), *Pythium oligandrum* DV 74 (ATCC 38472; e.g. POLYVERSUM® from Remeslo SSRO, Biopreparaty, Czech Rep. and GOWAN, USA; US 2013/0035230), *Reynoutria sachlinensis* extract (e.g. REGALIA® SC from Marrone BioInnovations, Davis, Calif., USA), *Rhizobium leguminosarum* bv. *phaseoli* (e.g. RHIZO-STICK from Becker Underwood, USA), R. l. *trifolii* RP113-7 (e.g. DORMAL from Becker Underwood, USA; Appl. Environ. Microbiol. 44(5), 1096-1101), R. l. bv. *viciae* P1NP3Cst (also referred to as 1435; New Phytol 179(1), 224-235, 2008; e.g. in NODULATOR PL Peat Granule from Becker Underwood, USA; or in NODULATOR XL PL from Becker Underwood, Canada), R. l. bv. *viciae* SU303 (e.g. NODULAID Group E from Becker Underwood, Australia), R. l. bv. *viciae* WSM1455 (e.g. NODULAID Group F from Becker Underwood, Australia), *R. tropici* SEMIA 4080 (identical to PRF 81; Soil Biology & Biochemistry 39, 867-876, 2007), Sinorhizobium *meliloti* MSDJ0848 (INRA, France) also referred to as strain 2011 or RCR2011 (Mol Gen Genomics (2004) 272: 1-17; e.g. DORMAL ALFALFA from Becker Underwood, USA; NITRAGIN® Gold from Novozymes Biologicals BioAg Group, Canada), *Sphaerodes mycoparasitica* IDAC 301008-01 (WO 2011/022809), *Steinernema carpocapsae* (e.g. MILLENIUM® from Becker Underwood Ltd., UK), *S. feltiae* (NEM-ASHIELD® from BioWorks, Inc., USA; NEMASYS® from Becker Underwood Ltd., UK), *S. kraussei* L137 (NEMA-SYS® L from Becker Underwood Ltd., UK), *Streptomyces griseoviridis* K61 (e.g. MYCOSTOP® from Verdera Oy, Espoo, Finland; Crop Protection 25, 468-475, 2006), *S. lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968,503), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. asperellum* ICC 012 (e.g. in TENET WP, REMDIER WP, BIOTEN WP from Isagro NC, USA, BIO-TAM from AgraQuest, USA), *T. atroviride* LC52 (e.g. SENTINEL® from Agrimm Technologies Ltd, NZ), *T. atroviride* CNCM 1-1237 (e.g. in Esquive WG from Agrauxine S.A., France, e.g. against pruning wound diseases on vine and plant root pathogens), *T. fertile* JM41R (NRRL 50759; e.g. RICHPLUS™ from Becker Underwood Bio Ag SA Ltd, South Africa), *T. gamsii* ICC 080 (e.g. in TENET WP, REMDIER WP, BIOTEN WP from Isagro NC, USA, BIO-TAM from AgraQuest, USA), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (also named *Gliocladium virens*) (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy) and *Ulocladium oudemansii* HRU3 (e.g. in BOTRY-ZEN® from Botry-Zen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-lnstitut DSMZ-Deutsche Sammlung von Mikroorganismen und Zellkulturen GmbH, Inhoffenstraße 7 B, 38124 Braunschweig, Germany (strains with prefix DSM); International Depositary Authority of Canada Collection, Canada (strains with prefix IDAC); International Collection of Micro-organisms from Plants, Landcare Research, Private Bag 92170, Auckland Mail Centre, Auckland 1142, New Zealand (strains with prefix ICMP); IITA, PMB 5320, Ibadan, Nigeria (straisn with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuária, Rua Gonçalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Room 19-9, Beltsville, Md. 20705, USA (strains with prefix USDA: Beltsville *Rhizobium* Culture Collection Catalog March 1987 USDA-ARS ARS-30: http://pdf.usaid.gov/pdf_docs/PNAAW891.pdf); and Murdoch University, Perth, Western Australia (strains with prefix WSM). Further strains may be found at the Global catalogue of Microorganisms: http://gcm.wfcc.info/ and http://www.landcareresearch.co.nz/resources/collections/icmp and further references to strain collections and their prefixes at http://refs.wdcm.org/collections.htm.

*Bacillus amyloliquefaciens* subsp. *plantarum* MBI600 (NRRL B-50595) is deposited under accession number NRRL B-50595 with the strain designation *Bacillus subtilis* 1430 (and identical to NCIMB 1237). Recently, MBI 600 has been re-classified as *Bacillus amyloliquefaciens* subsp. *plantarum* based on polyphasic testing which combines classical microbiological methods relying on a mixture of traditional tools (such as culture-based methods) and molecular tools (such as genotyping and fatty acids analysis). Thus, *Bacillus subtilis* MBI600 (or MBI 600 or MBI-600) is identical to *Bacillus amyloliquefaciens* subsp. *plantarum* MBI600, formerly *Bacillus subtilis* MBI600. *Bacillus amyloliquefaciens* MBI600 is known as plant growth-promoting rice seed treatment from Int. J. Microbiol. Res. 3(2) (2011), 120-130 and further described e.g. in US 2012/0149571 A1. This strain MBI600 is e.g. commercially available as liquid formulation product INTEGRAL® (Becker-Underwood Inc., USA).

*Bacillus subtilis* strain FB17 was originally isolated from red beet roots in North America (System Appl. Microbiol 27 (2004) 372-379). This *B. subtilis* strain promotes plant health (US 2010/0260735 A1; WO 2011/109395 A2). *B. subtilis* FB17 has also been deposited at ATCC under number PTA-11857 on Apr. 26, 2011. *Bacillus subtilis* strain FB17 may be referred elsewhere to as UD1022 or UD10-22.

*Bacillus amyloliquefaciens* AP-136 (NRRL B-50614), *B. amyloliquefaciens* AP-188 (NRRL B50615), *B. amyloliquefaciens* AP-218 (NRRL B-50618), *B. amyloliquefaciens* AP-219 (NRRL B50619), *B. amyloliquefaciens* AP-295 (NRRL B-50620), *B. japonicum* SEMIA 5079 (e.g. Gelfix 5 or Adhere 60 from Nitral Urbana Laoboratories, Brazil, a BASF Company), *B. japonicum* SEMIA 5080 (e.g. GELFIX 5 or ADHERE 60 from Nitral Urbana Laoboratories, Brazil, a BASF Company), *B. mojavensis* AP-209 (NRRL B-50616), *B. solisalsi* AP-217 (NRRL B-50617), *B. pumilus* strain INR-7 (otherwise referred to as BU-F22 (NRRL B-50153) and BU-F33 (NRRL B-50185)), *B. simplex* ABU 288 (NRRL B-50340) and *B. amyloliquefaciens* subsp. *plantarum* MBI600 (NRRL B-50595) have been mentioned i.a. in US patent appl. 20120149571, U.S. Pat. No. 8,445,255, WO 2012/079073. *Bradyrhizobium japonicum* USDA 3 is known from U.S. Pat. No. 7,262,151.

Jasmonic acid or salts (jasmonates) or derivatives include without limitation potassium jasmonate, sodium jasmonate, lithium jasmonate, ammonium jasmonate, dimethylammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl-pentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

According to one embodiment, the microbial pesticides selected from groups L1), L3) and L5) embrace not only the isolated, pure cultures of the respective micro-organism as defined herein, but also its cell-free extract, its suspensions in a whole broth culture or as a metabolite-containing supernatant or a purified metabolite obtained from a whole broth culture of the microorganism or microorganism strain.

According to a further embodiment, the microbial pesticides selected from groups L1), L3 and L5) embraces not only the isolated, pure cultures of the respective micro-organism as defined herein, but also a cell-free extract thereof or at least one metabolite thereof, and/or a mutant of the respective micro-organism having all the identifying characteristics thereof and also a cell-free extract or at least one metabolite of the mutant.

"Whole broth culture" refers to a liquid culture containing both cells and media.

"Supernatant" refers to the liquid broth remaining when cells grown in broth are removed by centrifugation, filtration, sedimentation, or other means well known in the art.

The term "cell-free extract" refers to an extract of the vegetative cells, spores and/or the whole culture broth of a microorganism comprising cellular metabolites produced by the respective microorganism obtainable by cell disruption methods known in the art such as solvent-based (e.g. organic solvents such as alcohols sometimesin combination with suitable salts), temperature-based, application of shear forces, cell disruption with an ultrasonicator. The desired extract may be concentrated by conventional concentration techniques such as drying, evaporation, centrifugation or alike. Certain washing steps using organic solvents and/or water-based media may also be applied to the crude extract preferably prior to use.

The term "metabolite" refers to any compound, substance or byproduct produced by a microorganism (such as fungi and bacteria) that has improves plant growth, water use efficiency of the plant, plant health, plant appearance, or the population of beneficial microorganisms in the soil around the plant activity.

The term "mutant" refers a microorganism obtained by direct mutant selection but also includes microorganisms that have been further mutagenized or otherwise manipulated (e.g., via the introduction of a plasmid). Accordingly, embodiments include mutants, variants, and or derivatives of the respective microorganism, both naturally occurring and artificially induced mutants. For example, mutants may be induced by subjecting the microorganism to known mutagens, such as N-methyl-nitrosoguanidine, using conventional methods.

Suitable bactericides are bronopol and isothiazolinone derivatives such as alkylisothiazolinones and benzisothiazolinones. Suitable anti-freezing agents are ethylene glycol, propylene glycol, urea and glycerin. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants). Suitable tackifiers or binders are polyvinylpyrrolidons, polyvinylacetates, polyvinyl alcohols, polyacrylates, biological or synthetic waxes, and cellulose ethers.

In the case of mixtures comprising microbial pesticides II selected from groups L1), L3) and L5), the microorganisms as used according to the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

When living microorganisms, such as pesticides II from groups L1), L3) and L5), form part of the compositions, such compositions can be prepared as compositions comprising besides the active ingredients at least one auxiliary (inert ingredient) by usual means (see e.g. H. D. Burges: Formulation of Microbial Biopesticides, Springer, 1998). Suitable customary types of such compositions are suspensions, dusts, powders, pastes, granules, pressings, capsules, and mixtures thereof. Examples for composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). Herein, it has to be taken into account that each formulation type or choice of auxiliary should not influence the viability of the microorganism during storage of the composition and when finally applied to the soil, plant or plant propagation material. Suitable formulations are e.g. mentioned in WO 2008/002371, U.S. Pat. No. 6,955,912, U.S. Pat. No. 5,422,107.

Examples for suitable auxiliaries are those mentioned earlier herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants. Suitable stabilizers or nutrients are e.g. alpha-tocopherol, trehalose, glutamate, potassium sorbate, various sugars like glucose, sucrose, lactose and maltodextrine (H. D. Burges: Formulation of Microbial Biopesticides, Springer, 1998). Suitable UV protectants are e.g. inorganic compounds like titan dioxide, zinc oxide and iron oxide pigments or organic compounds like benzophenones, benzotriazoles and phenyltriazines. The compositions may in addition to auxiliaries mentioned for compositions comprising compounds I herein optionally comprise 0.1-80% stabilizers or nutrients and 0.1-10% UV protectants.

When mixtures comprising microbial pesticides are employed in crop protection, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e.g. *Steinernema feltiae*), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e.g. in the form of eggs, juvenile or any other live stages, preferably in an infective juvenile stage) per ha.

When mixtures comprising microbial pesticides are employed in seed treatment, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of the microbial pesticides II, the application rates with respect to plant propagation material also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

Accordingly, the present invention furthermore relates to compositions comprising one compound I (component 1) and one further active substance (component 2), which further active substance is selected from the column "Component 2" of the lines C-1 to C-398 of Table C.

A further embodiment relates to the compositions C-1 to C-398 listed in Table C, wherein one row of Table C corresponds in each case to a composition comprising one of the compounds I that are individualized compounds of formula I (component 1) and the respective further active substance from groups A) to O) (component 2) stated in the respective row. According to a preferred embodiment, the "individualized compound I" is one of the compounds as individualized in Tables 1a to 140a and Tables 1b to 140b or in Table I below. Preferably, the compositions described comprise the active substances in synergistically effective amounts.

TABLE C

Composition comprising one individualized compound of the present invention and one further active substance from groups A) to O)

| composition | Component 1 | Component 2 |
|---|---|---|
| C-1 | one individualized compound I | Azoxystrobin |
| C-2 | one individualized compound I | Coumethoxystrobin |
| C-3 | one individualized compound I | Coumoxystrobin |
| C-4 | one individualized compound I | Dimoxystrobin |
| C-5 | one individualized compound I | Enestroburin |
| C-6 | one individualized compound I | Fenaminstrobin |
| C-7 | one individualized compound I | Fenoxystrobin/Flufenoxystrobin |
| C-8 | one individualized compound I | Fluoxastrobin |
| C-9 | one individualized compound I | Kresoxim-methyl |
| C-10 | one individualized compound I | Metominostrobin |
| C-11 | one individualized compound I | Orysastrobin |
| C-12 | one individualized compound I | Picoxystrobin |
| C-13 | one individualized compound I | Pyraclostrobin |
| C-14 | one individualized compound I | Pyrametostrobin |
| C-15 | one individualized compound I | Pyraoxystrobin |
| C-16 | one individualized compound I | Pyribencarb |
| C-17 | one individualized compound I | Trifloxystrobin |
| C-18 | one individualized compound I | Triclopyricarb/Chlorodincarb |
| C-19 | one individualized compound I | 2-[2-(2,5-dimethyl-phenoxymethyl)-phenyl]-3-methoxy-acrylic acid methyl ester |
| C-20 | one individualized compound I | 2-(2-(3-(2,6-dichlorophenyl)-1-methyl-allylideneaminooxymethyl)-phenyl)-2-methoxyimino-N-methyl-acetamide |
| C-21 | one individualized compound I | Benalaxyl |
| C-22 | one individualized compound I | Benalaxyl-M |
| C-23 | one individualized compound I | Benodanil |
| C-24 | one individualized compound I | Benzovindiflupyr |

TABLE C-continued

Composition comprising one individualized compound of the present invention and one further active substance from groups A) to O)

| composition | Component 1 | Component 2 |
| --- | --- | --- |
| C-25 | one individualized compound I | Bixafen |
| C-26 | one individualized compound I | Boscalid |
| C-27 | one individualized compound I | Carboxin |
| C-28 | one individualized compound I | Fenfuram |
| C-29 | one individualized compound I | Fenhexamid |
| C-30 | one individualized compound I | Flutolanil |
| C-31 | one individualized compound I | Fluxapyroxad |
| C-32 | one individualized compound I | Furametpyr |
| C-33 | one individualized compound I | Isopyrazam |
| C-34 | one individualized compound I | Isotianil |
| C-35 | one individualized compound I | Kiralaxyl |
| C-36 | one individualized compound I | Mepronil |
| C-37 | one individualized compound I | Metalaxyl |
| C-38 | one individualized compound I | Metalaxyl-M |
| C-39 | one individualized compound I | Ofurace |
| C-40 | one individualized compound I | Oxadixyl |
| C-41 | one individualized compound I | Oxycarboxin |
| C-42 | one individualized compound I | Penflufen |
| C-43 | one individualized compound I | Penthiopyrad |
| C-44 | one individualized compound I | Sedaxane |
| C-45 | one individualized compound I | Tecloftalam |
| C-46 | one individualized compound I | Thifluzamide |
| C-47 | one individualized compound I | Tiadinil |
| C-48 | one individualized compound I | 2-Amino-4-methyl-thiazole-5-carboxylic acid anilide |
| C-49 | one individualized compound I | N-(4'-trifluoromethylthiobiphenyl-2-yl)-3-difluoromethyl-1-methyl-1H-pyrazole-4-carboxamide |
| C-50 | one individualized compound I | N-(2-(1,3,3-trimethyl-butyl)-phenyl)-1,3-dimethyl-5-fluoro-1H-pyrazole-4-carboxamide |
| C-51 | one individualized compound I | 3-(difluoromethyl)-1-methyl-N-(1,1,3-trimethylindan-4-yl)pyrazole-4-carboxamide |
| C-52 | one individualized compound I | 3-(trifluoromethyl)-1-methyl-N-(1,1,3-trimethylindan-4-yl)pyrazole-4-carboxamide |
| C-53 | one individualized compound I | 1,3-dimethyl-N-(1,1,3-trimethylindan-4-yl)pyrazole-4-carboxamide |
| C-54 | one individualized compound I | 3-(trifluoromethyl)-1,5-dimethyl-N-(1,1,3-trimethylindan-4-yl)pyrazole-4-carboxamide |
| C-55 | one individualized compound I | 3-(difluoromethyl)-1,5-dimethyl-N-(1,1,3-trimethylindan-4-yl)pyrazole-4-carboxamide |
| C-56 | one individualized compound I | 1,3,5-trimethyl-N-(1,1,3-trimethylindan-4-yl)pyrazole-4-carboxamide |
| C-57 | one individualized compound I | Dimethomorph |
| C-58 | one individualized compound I | Flumorph |
| C-59 | one individualized compound I | Pyrimorph |
| C-60 | one individualized compound I | Flumetover |
| C-61 | one individualized compound I | Fluopicolide |
| C-62 | one individualized compound I | Fluopyram |
| C-63 | one individualized compound I | Zoxamide |
| C-64 | one individualized compound I | Carpropamid |
| C-65 | one individualized compound I | Diclocymet |
| C-66 | one individualized compound I | Mandipropamid |
| C-67 | one individualized compound I | Oxytetracyclin |
| C-68 | one individualized compound I | Silthiofam |
| C-69 | one individualized compound I | N-(6-methoxy-pyridin-3-yl)cyclopropanecarboxylic acid amide |
| C-70 | one individualized compound I | Azaconazole |
| C-71 | one individualized compound I | Bitertanol |
| C-72 | one individualized compound I | Bromuconazole |
| C-73 | one individualized compound I | Cyproconazole |
| C-74 | one individualized compound I | Difenoconazole |
| C-75 | one individualized compound I | Diniconazole |
| C-76 | one individualized compound I | Diniconazole-M |
| C-77 | one individualized compound I | Epoxiconazole |
| C-78 | one individualized compound I | Fenbuconazole |
| C-79 | one individualized compound I | Fluquinconazole |
| C-80 | one individualized compound I | Flusilazole |
| C-81 | one individualized compound I | Flutriafol |
| C-82 | one individualized compound I | Hexaconazol |

TABLE C-continued

Composition comprising one individualized compound of the present invention and one further active substance from groups A) to O)

| composition | Component 1 | Component 2 |
| --- | --- | --- |
| C-83 | one individualized compound I | Imibenconazole |
| C-84 | one individualized compound I | Ipconazole |
| C-85 | one individualized compound I | Metconazole |
| C-86 | one individualized compound I | Myclobutanil |
| C-87 | one individualized compound I | Oxpoconazol |
| C-88 | one individualized compound I | Paclobutrazol |
| C-89 | one individualized compound I | Penconazole |
| C-90 | one individualized compound I | Propiconazole |
| C-91 | one individualized compound I | Prothioconazole |
| C-92 | one individualized compound I | Simeconazole |
| C-93 | one individualized compound I | Tebuconazole |
| C-94 | one individualized compound I | Tetraconazole |
| C-95 | one individualized compound I | Triadimefon |
| C-96 | one individualized compound I | Triadimenol |
| C-97 | one individualized compound I | Triticonazole |
| C-98 | one individualized compound I | Uniconazole |
| C-99 | one individualized compound I | 1-[rel-(2S;3R)-3-(2-chlorophenyl)-2-(2,4-difluorophenyl)-oxiranylmethyl]-5-thiocyanato-1H-[1,2,4]triazole, |
| C-100 | one individualized compound I | 2-[rel-(2S,3R)-3-(2-chlorophenyl)-2-(2,4-difluorophenyl)-oxiranylmethyl]-2H-[1,2,4]triazole-3-thiol |
| C-101 | one individualized compound I | Cyazofamid |
| C-102 | one individualized compound I | Amisulbrom |
| C-103 | one individualized compound I | Imazalil |
| C-104 | one individualized compound I | Imazalil-sulfate |
| C-105 | one individualized compound I | Pefurazoate |
| C-106 | one individualized compound I | Prochloraz |
| C-107 | one individualized compound I | Triflumizole |
| C-108 | one individualized compound I | Benomyl |
| C-109 | one individualized compound I | Carbendazim |
| C-110 | one individualized compound I | Fuberidazole |
| C-111 | one individualized compound I | Thiabendazole |
| C-112 | one individualized compound I | Ethaboxam |
| C-113 | one individualized compound I | Etridiazole |
| C-114 | one individualized compound I | Hymexazole |
| C-115 | one individualized compound I | 2-(4-Chloro-phenyl)-N-[4-(3,4-dimethoxy-phenyl)-isoxazol-5-yl]-2-prop-2-ynyloxy-acetamide |
| C-116 | one individualized compound I | Fluazinam |
| C-117 | one individualized compound I | Pyrifenox |
| C-118 | one individualized compound I | 3-[5-(4-Chloro-phenyl)-2,3-dimethyl-isoxazolidin-3-yl]-pyridine (Pyrisoxazole) |
| C-119 | one individualized compound I | 3-[5-(4-Methyl-phenyl)-2,3-dimethyl-isoxazolidin-3-yl]-pyridine |
| C-120 | one individualized compound I | Bupirimate |
| C-121 | one individualized compound I | Cyprodinil |
| C-122 | one individualized compound I | 5-Fluorocytosine |
| C-123 | one individualized compound I | 5-Fluoro-2-(p-tolylmethoxy)pyrimidin-4-amine |
| C-124 | one individualized compound I | 5-Fluoro-2-(4-fluorophenylmethoxy)-pyrimidin-4-amine |
| C-125 | one individualized compound I | Diflumetorim |
| C-126 | one individualized compound I | (5,8-Difluoroquinazolin-4-yl)-{2-[2-fluoro-4-(4-trifluoromethylpyridin-2-yloxy)-phenyl]-ethyl}-amine |
| C-127 | one individualized compound I | Fenarimol |
| C-128 | one individualized compound I | Ferimzone |
| C-129 | one individualized compound I | Mepanipyrim |
| C-130 | one individualized compound I | Nitrapyrin |
| C-131 | one individualized compound I | Nuarimol |
| C-132 | one individualized compound I | Pyrimethanil |
| C-133 | one individualized compound I | Triforine |
| C-134 | one individualized compound I | Fenpiclonil |
| C-135 | one individualized compound I | Fludioxonil |
| C-136 | one individualized compound I | Aldimorph |
| C-137 | one individualized compound I | Dodemorph |
| C-138 | one individualized compound I | Dodemorph-acetate |
| C-139 | one individualized compound I | Fenpropimorph |
| C-140 | one individualized compound I | Tridemorph |
| C-141 | one individualized compound I | Fenpropidin |
| C-142 | one individualized compound I | Fluoroimid |
| C-143 | one individualized compound I | Iprodione |
| C-144 | one individualized compound I | Procymidone |

TABLE C-continued

Composition comprising one individualized compound of the present invention and one further active substance from groups A) to O)

| composition | Component 1 | Component 2 |
| --- | --- | --- |
| C-145 | one individualized compound I | Vinclozolin |
| C-146 | one individualized compound I | Famoxadone |
| C-147 | one individualized compound I | Fenamidone |
| C-148 | one individualized compound I | Flutianil |
| C-149 | one individualized compound I | Octhilinone |
| C-150 | one individualized compound I | Probenazole |
| C-151 | one individualized compound I | Fenpyrazamine |
| C-152 | one individualized compound I | Acibenzolar-S-methyl |
| C-153 | one individualized compound I | Ametoctradin |
| C-154 | one individualized compound I | Amisulbrom |
| C-155 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| C-156 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| C-157 | one individualized compound I | [(3S,6S,7R,8R)-8-benzyl-3-[[3-(acet-oxymethoxy)-4-methoxy-pyridine-2-carbonyl]amino]-6-methyl-4,9-dioxo-1,5-dioxonan-7-yl]2-methylpropanoate |
| C-158 | one individualized compound I | [(3S,6S,7R,8R)-8-benzyl-3-[(3-isobut-oxycarbonyloxy-4-methoxy-pyridine-2-carbonyl)amino]-6-methyl-4,9-dioxo-1,5-dioxonan-7-yl]2-methylpropanoate |
| C-159 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methyl-propanoate |
| C-160 | one individualized compound I | (3S,6S,7R,8R)-3-[[(3-hydroxy-4-meth-oxy-2-pyridinyl)carbonyl]amino]-6-methyl-4,9-dioxo-8-(phenylmethyl)-1,5-dioxonan-7-yl2-methylpropanoate |
| C-161 | one individualized compound I | Anilazin |
| C-162 | one individualized compound I | Blasticidin-S |
| C-163 | one individualized compound I | Captafol |
| C-164 | one individualized compound I | Captan |
| C-165 | one individualized compound I | Chinomethionat |
| C-166 | one individualized compound I | Dazomet |
| C-167 | one individualized compound I | Debacarb |
| C-168 | one individualized compound I | Diclomezine |
| C-169 | one individualized compound I | Difenzoquat, |
| C-170 | one individualized compound I | Difenzoquat-methylsulfate |
| C-171 | one individualized compound I | Fenoxanil |
| C-172 | one individualized compound I | Folpet |
| C-173 | one individualized compound I | Oxolinsäure |
| C-174 | one individualized compound I | Piperalin |
| C-175 | one individualized compound I | Proquinazid |
| C-176 | one individualized compound I | Pyroquilon |
| C-177 | one individualized compound I | Quinoxyfen |
| C-178 | one individualized compound I | Triazoxid |
| C-179 | one individualized compound I | Tricyclazole |
| C-180 | one individualized compound I | 2-Butoxy-6-iodo-3-propyl-chromen-4-one |
| C-181 | one individualized compound I | 5-Chloro-1-(4,6-dimethoxy-pyrimidin-2-yl)-2-methyl-1H-benzoimidazole |
| C-182 | one individualized compound I | 5-Chloro-7-(4-methyl-piperidin-1-yl)-6-(2,4,6-trifluoro-phenyl)-[1,2,4]tri-azolo[1,5-a]pyrimidine |
| C-183 | one individualized compound I | Ferbam |
| C-184 | one individualized compound I | Mancozeb |
| C-185 | one individualized compound I | Maneb |
| C-186 | one individualized compound I | Metam |
| C-187 | one individualized compound I | Methasulphocarb |
| C-188 | one individualized compound I | Metiram |
| C-189 | one individualized compound I | Propineb |
| C-190 | one individualized compound I | Thiram |
| C-191 | one individualized compound I | Zineb |
| C-192 | one individualized compound I | Ziram |

TABLE C-continued

Composition comprising one individualized compound of the present invention and one further active substance from groups A) to O)

| composition | Component 1 | Component 2 |
| --- | --- | --- |
| C-193 | one individualized compound I | Diethofencarb |
| C-194 | one individualized compound I | Benthiavalicarb |
| C-195 | one individualized compound I | Iprovalicarb |
| C-196 | one individualized compound I | Propamocarb |
| C-197 | one individualized compound I | Propamocarb hydrochlorid |
| C-198 | one individualized compound I | Valifenalate |
| C-199 | one individualized compound I | N-(1-(1-(4-cyanophenyl)ethanesulfon-yl)-but-2-yl) carbamic acid-(4-fluoro-phenyl) ester |
| C-200 | one individualized compound I | Dodine |
| C-201 | one individualized compound I | Dodine free base |
| C-202 | one individualized compound I | Guazatine |
| C-203 | one individualized compound I | Guazatine-acetate |
| C-204 | one individualized compound I | Iminoctadine |
| C-205 | one individualized compound I | Iminoctadine-triacetate |
| C-206 | one individualized compound I | Iminoctadine-tris(albesilate) |
| C-207 | one individualized compound I | Kasugamycin |
| C-208 | one individualized compound I | Kasugamycin-hydrochloride-hydrate |
| C-209 | one individualized compound I | Polyoxine |
| C-210 | one individualized compound I | Streptomycin |
| C-211 | one individualized compound I | Validamycin A |
| C-212 | one individualized compound I | Binapacryl |
| C-213 | one individualized compound I | Dicloran |
| C-214 | one individualized compound I | Dinobuton |
| C-215 | one individualized compound I | Dinocap |
| C-216 | one individualized compound I | Nitrothal-isopropyl |
| C-217 | one individualized compound I | Tecnazen |
| C-218 | one individualized compound I | Fentin salts |
| C-219 | one individualized compound I | Dithianon |
| C-220 | one individualized compound I | 2,6-dimethyl-1H,5H-[1,4]dithiino [2,3-c:5,6-c']dipyrrole-1,3,5,7(2H,6H)-tetraone |
| C-221 | one individualized compound I | Isoprothiolane |
| C-222 | one individualized compound I | Edifenphos |
| C-223 | one individualized compound I | Fosetyl, Fosetyl-aluminium |
| C-224 | one individualized compound I | Iprobenfos |
| C-225 | one individualized compound I | Phosphorous acid ($H_3PO_3$) and derivatives |
| C-226 | one individualized compound I | Pyrazophos |
| C-227 | one individualized compound I | Tolclofos-methyl |
| C-228 | one individualized compound I | Chlorothalonil |
| C-229 | one individualized compound I | Dichlofluanid |
| C-230 | one individualized compound I | Dichlorophen |
| C-231 | one individualized compound I | Flusulfamide |
| C-232 | one individualized compound I | Hexachlorbenzene |
| C-233 | one individualized compound I | Pencycuron |
| C-234 | one individualized compound I | Pentachlorophenol and salts |
| C-235 | one individualized compound I | Phthalide |
| C-236 | one individualized compound I | Quintozene |
| C-237 | one individualized compound I | Thiophanate Methyl |
| C-238 | one individualized compound I | Tolylfluanid |
| C-239 | one individualized compound I | N-(4-chloro-2-nitro-phenyl)-N-ethyl-4-methyl-benzenesulfonamide |
| C-240 | one individualized compound I | Bordeaux mixture |
| C-241 | one individualized compound I | Copper acetate |
| C-242 | one individualized compound I | Copper hydroxide |
| C-243 | one individualized compound I | Copper oxychloride |
| C-244 | one individualized compound I | basic Copper sulfate |
| C-245 | one individualized compound I | Sulfur |
| C-246 | one individualized compound I | Biphenyl |
| C-247 | one individualized compound I | Bronopol |
| C-248 | one individualized compound I | Cyflufenamid |
| C-249 | one individualized compound I | Cymoxanil |
| C-250 | one individualized compound I | Diphenylamin |
| C-251 | one individualized compound I | Metrafenone |
| C-252 | one individualized compound I | Pyriofenone |
| C-253 | one individualized compound I | Mildiomycin |
| C-254 | one individualized compound I | Oxin-copper |
| C-255 | one individualized compound I | Oxathiapiprolin |
| C-256 | one individualized compound I | Prohexadione calcium |
| C-257 | one individualized compound I | Spiroxamine |
| C-258 | one individualized compound I | Tebufloquin |

TABLE C-continued

Composition comprising one individualized compound of the present invention and one further active substance from groups A) to O)

| composition | Component 1 | Component 2 |
|---|---|---|
| C-259 | one individualized compound I | Tolylfluanid |
| C-260 | one individualized compound I | N-(Cyclopropylmethoxyimino-(6-difluoromethoxy-2,3-difluoro-phenyl)-methyl)-2-phenyl acetamide |
| C-261 | one individualized compound I | N'-(4-(4-chloro-3-trifluoromethyl-phenoxy)-2,5-dimethyl-phenyl)-N-ethyl-N-methyl formamidine |
| C-262 | one individualized compound I | N'-(4-(4-fluoro-3-trifluoromethyl-phenoxy)-2,5-dimethyl-phenyl)-N-ethyl-N-methyl formamidine |
| C-263 | one individualized compound I | N'-(2-methyl-5-trifluoromethyl-4-(3-tri-methylsilanyl-propoxy)-phenyl)-N-ethyl-N-methyl formamidine |
| C-264 | one individualized compound I | N'-(5-difluoromethyl-2-methyl-4-(3-tri-methylsilanyl-propoxy)-phenyl)-N-ethyl-N-methyl formamidine |
| C-265 | one individualized compound I | Methoxy-acetic acid 6-tert-butyl-8-fluoro-2,3-dimethyl-quinolin-4-ylester |
| C-266 | one individualized compound I | *Bacillus subtilis* NRRL No. B-21661 |
| C-267 | one individualized compound I | *Bacillus pumilus* NRRL No. B-30087 |
| C-268 | one individualized compound I | *Ulocladium oudemansii* |
| C-269 | one individualized compound I | Carbaryl |
| C-270 | one individualized compound I | Carbofuran |
| C-271 | one individualized compound I | Carbosulfan |
| C-272 | one individualized compound I | Methomylthiodicarb |
| C-273 | one individualized compound I | Bifenthrin |
| C-274 | one individualized compound I | Cyfluthrin |
| C-275 | one individualized compound I | Cypermethrin |
| C-276 | one individualized compound I | alpha-Cypermethrin |
| C-277 | one individualized compound I | zeta-Cypermethrin |
| C-278 | one individualized compound I | Deltamethrin |
| C-279 | one individualized compound I | Esfenvalerate |
| C-280 | one individualized compound I | Lambda-cyhalothrin |
| C-281 | one individualized compound I | Permethrin |
| C-282 | one individualized compound I | Tefluthrin |
| C-283 | one individualized compound I | Diflubenzuron |
| C-284 | one individualized compound I | Flufenoxuron |
| C-285 | one individualized compound I | Lufenuron |
| C-286 | one individualized compound I | Teflubenzuron |
| C-287 | one individualized compound I | Spirotetramate |
| C-288 | one individualized compound I | Clothianidin |
| C-289 | one individualized compound I | Dinotefuran |
| C-290 | one individualized compound I | Imidacloprid |
| C-291 | one individualized compound I | Thiamethoxam |
| C-292 | one individualized compound I | Flupyradifurone |
| C-293 | one individualized compound I | Acetamiprid |
| C-294 | one individualized compound I | Thiacloprid |
| C-295 | one individualized compound I | Endosulfan |
| C-296 | one individualized compound I | Fipronil |
| C-297 | one individualized compound I | Abamectin |
| C-298 | one individualized compound I | Emamectin |
| C-299 | one individualized compound I | Spinosad |
| C-300 | one individualized compound I | Spinetoram |
| C-301 | one individualized compound I | Hydramethylnon |
| C-302 | one individualized compound I | Chlorfenapyr |
| C-303 | one individualized compound I | Fenbutatin oxide |
| C-304 | one individualized compound I | Indoxacarb |
| C-305 | one individualized compound I | Metaflumizone |
| C-306 | one individualized compound I | Flonicamid |
| C-307 | one individualized compound I | Lubendiamide |
| C-308 | one individualized compound I | Chlorantraniliprole |
| C-309 | one individualized compound I | Cyazypyr (HGW86) |
| C-310 | one individualized compound I | Cyflumetofen |
| C-311 | one individualized compound I | Acetochlor |
| C-312 | one individualized compound I | Dimethenamid |
| C-313 | one individualized compound I | metolachlor |
| C-314 | one individualized compound I | Metazachlor |
| C-315 | one individualized compound I | Glyphosate |
| C-316 | one individualized compound I | Glufosinate |
| C-317 | one individualized compound I | Sulfosate |
| C-318 | one individualized compound I | Clodinafop |
| C-319 | one individualized compound I | Fenoxaprop |
| C-320 | one individualized compound I | Fluazifop |
| C-321 | one individualized compound I | Haloxyfop |
| C-322 | one individualized compound I | Paraquat |

TABLE C-continued

Composition comprising one individualized compound of the present invention and one further active substance from groups A) to O)

| composition | Component 1 | Component 2 |
|---|---|---|
| C-323 | one individualized compound I | Phenmedipham |
| C-324 | one individualized compound I | Clethodim |
| C-325 | one individualized compound I | Cycloxydim |
| C-326 | one individualized compound I | Profoxydim |
| C-327 | one individualized compound I | Sethoxydim |
| C-328 | one individualized compound I | Tepraloxydim |
| C-329 | one individualized compound I | Pendimethalin |
| C-330 | one individualized compound I | Prodiamine |
| C-331 | one individualized compound I | Trifluralin |
| C-332 | one individualized compound I | Acifluorfen |
| C-333 | one individualized compound I | Bromoxynil |
| C-334 | one individualized compound I | Imazamethabenz |
| C-335 | one individualized compound I | Imazamox |
| C-336 | one individualized compound I | Imazapic |
| C-337 | one individualized compound I | Imazapyr |
| C-338 | one individualized compound I | Imazaquin |
| C-339 | one individualized compound I | Imazethapyr |
| C-340 | one individualized compound I | 2,4-Dichlorophenoxyacetic acid (2,4-D) |
| C-341 | one individualized compound I | Chloridazon |
| C-342 | one individualized compound I | Clopyralid |
| C-343 | one individualized compound I | Fluroxypyr |
| C-344 | one individualized compound I | Picloram |
| C-345 | one individualized compound I | Picolinafen |
| C-346 | one individualized compound I | Bensulfuron |
| C-347 | one individualized compound I | Chlorimuron-ethyl |
| C-348 | one individualized compound I | Cyclosulfamuron |
| C-349 | one individualized compound I | Iodosulfuron |
| C-350 | one individualized compound I | Mesosulfuron |
| C-351 | one individualized compound I | Metsulfuron-methyl |
| C-352 | one individualized compound I | Nicosulfuron |
| C-353 | one individualized compound I | Rimsulfuron |
| C-354 | one individualized compound I | Triflusulfuron |
| C-355 | one individualized compound I | Atrazine |
| C-356 | one individualized compound I | Hexazinone |
| C-357 | one individualized compound I | Diuron |
| C-358 | one individualized compound I | Florasulam |
| C-359 | one individualized compound I | Pyroxasulfone |
| C-360 | one individualized compound I | Bentazone |
| C-361 | one individualized compound I | Cinidon-ethyl |
| C-362 | one individualized compound I | Cinmethylin |
| C-363 | one individualized compound I | Dicamba |
| C-364 | one individualized compound I | Diflufenzopyr |
| C-365 | one individualized compound I | Quinclorac |
| C-366 | one individualized compound I | Quinmerac |
| C-367 | one individualized compound I | Mesotrione |
| C-368 | one individualized compound I | Saflufenacil |
| C-369 | one individualized compound I | Topramezone |
| C-370 | one individualized compound I | 1,1'-[(3S,4R,4aR,6S,6aS,12R,12aS,12bS)-4-[[(2-cyclopropylacetyl)oxy]methyl]-1,3,4,4a,5,6,6a,12,12a,12b-deca-hydro-12-hydroxy-4,6a,12b-trimethyl-11-oxo-9-(3-pyridinyl)-2H,11H-naph-tho[2,1-b]pyrano[3,4-e]pyran-3,6-diyl] cyclopropaneacetic acid ester |
| C-371 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| C-372 | one individualized compound I | isofetamid |
| C-373 | one individualized compound I | N-(7-fluoro-1,1,3-trimethyl-indan-4-yl)-1,3-dimethyl-pyrazole-4-carboxamide |
| C-374 | one individualized compound I | N-[2-(2,4-dichlorophenyl)-2-methoxy-1-methyl-ethyl]-3-(difluoromethyl)-1-methyl-pyrazole-4-carboxamide |
| C-375 | one individualized compound I | 2-[2-chloro-4-(4-chlorophenoxy)-phenyl]-1-(1,2,4-triazol-1-yl)pentan-2-ol |
| C-376 | one individualized compound I | 1-[4-(4-chlorophenoxy)-2-(trifluoro-methyl)phenyl]-1-cyclopropyl-2-(1,2,4-triazol-1-yl)ethanol |
| C-377 | one individualized compound I | 2-[4-(4-chlorophenoxy)-2-(trifluoromethyl)phenyl]-1-(1,2,4-triazol-1-yl)butan-2-ol |

TABLE C-continued

Composition comprising one individualized compound of the present invention and one further active substance from groups A) to O)

| composition | Component 1 | Component 2 |
|---|---|---|
| C-378 | one individualized compound I | 2-[2-chloro-4-(4-chlorophenoxy)phenyl]-1-(1,2,4-triazol-1-yl)butan-2-ol |
| C-379 | one individualized compound I | 2-[4-(4-chlorophenoxy)-2-(trifluoromethyl)phenyl]-3-methyl-1-(1,2,4-triazol-1-yl)butan-2-ol |
| C-380 | one individualized compound I | 2-[4-(4-chlorophenoxy)-2-(trifluoromethyl)phenyl]-1-(1,2,4-triazol-1-yl)propan-2-ol |
| C-381 | one individualized compound I | 2-[2-chloro-4-(4-chlorophenoxy)phenyl]-3-methyl-1-(1,2,4-triazol-1-yl)butan-2-ol |
| C-382 | one individualized compound I | 2-[4-(4-chlorophenoxy)-2-(trifluoromethyl)phenyl]-1-(1,2,4-triazol-1-yl)pentan-2-ol |
| C-383 | one individualized compound I | 2-[4-(4-fluorophenoxy)-2-(trifluoromethyl)phenyl]-1-(1,2,4-triazol-1-yl)propan-2-ol |
| C-384 | one individualized compound I | 3-(4-chloro-2-fluoro-phenyl)-5-(2,4-difluorophenyl)isoxazol-4-yl]-(3-pyridyl)methanol |
| C-385 | one individualized compound I | 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate |
| C-386 | one individualized compound I | 2-{3-[2-(1-{[3,5-bis(difluoromethyl)-1H-pyrazol-1-yl]acetyl}piperidin-4-yl)1,3-thiazol-4-yl]-4,5-dihydro-1,2-oxazol-5-yl}-3-chlorophenyl methanesulfonate |
| C-387 | one individualized compound I | tolprocarb |
| C-388 | one individualized compound I | 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone |
| C-389 | one individualized compound I | 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone |
| C-390 | one individualized compound I | 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone |
| C-391 | one individualized compound I | ethyl (Z)-3-amino-2-cyano-3-phenyl-prop-2-enoate, |
| C-392 | one individualized compound I | picarbutrazox |
| C-393 | one individualized compound I | pentyl N-[6-[[(Z)-[(1-methyltetrazol-5-yl)-phenyl-methylene]amino]oxymethyl]-2-pyridyl]carbamate, |
| C-394 | one individualized compound I | 2-[2-[(7,8-difluoro-2-methyl-3-quinolyl)oxy]-6-fluoro-phenyl]propan-2-ol |
| C-395 | one individualized compound I | 2-[2-fluoro-6-[(8-fluoro-2-methyl-3-quinolyl)oxy]phen-yl]propan-2-ol, |
| C-396 | one individualized compound I | 3-(5-fluoro-3,3,4,4-tetramethyl-3,4-dihydroisoquinolin-1-yl)quinoline |
| C-397 | one individualized compound I | 3-(4,4-difluoro-3,3-dimethyl-3,4-dihydroisoquinolin-1-yl)quinoline |
| C-398 | one individualized compound I | 3-(4,4,5-trifluoro-3,3-dimethyl-3,4-dihydroisoquinolin-1-yl)quinoline |

The active substances referred to as component 2, their preparation and their activity e.g. against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009 and WO 13/024010).

The composition of active substances can be prepared as compositions comprising besides the active ingredients at least one inert ingredient by usual means, e. g. by the means given for the compositions of compounds I.

Concerning usual ingredients of such compositions reference is made to the explanations given for the compositions containing compounds I.

The compositions of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

Example 1

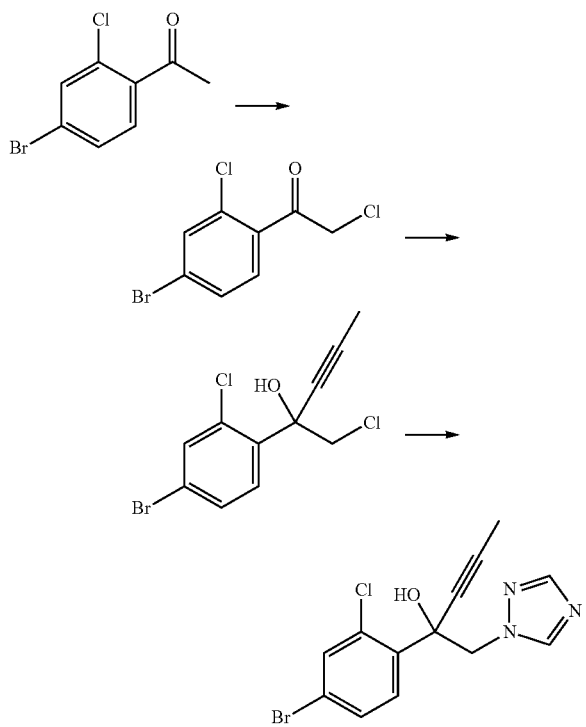

Step 1-1 1-(4-bromo-2-chloro-phenyl)-2-chloroethanone

To a mixture 2-chloro-4-bromo acetophenone (500 g), MeOH (137 g) in $CH_2Cl_2$ (4 L), $SO_2Cl_2$ (578 g in 1 L of $CH_2Cl_2$) was added dropwise, maintaining the temperature below 30° C. After gas evolution stopped, HPLC indicated full conversion. $H_2O$ (3 L) was added carefully and the pH was adjusted to 6.5 using 50% NaOH. The phases were separated and the aqueous phase extracted with $CH_2Cl_2$ (2*1 L). The combined organic phases were washed with brine and dried with $Na_2SO_4$. The crude compound was obtained as a viscous oil (608 g) and was used without further purification. HPLC: RT=3.096 min. $^1$H-NMR (300 MHz, $CDCl_3$): δ=4.65 (2H), 7.40-7.65 (3H).

Step 1-2 2-(4-bromo-2-chloro-phenyl)-1-chloro-pent-3-yn-2-ol

A solution of 1-(4-bromo-2-chloro-phenyl)-2-chloroethanone (267 g in 500 mL $CH_2Cl_2$) was added dropwise to prop-1-inyl magnesium bromide (1915 mL of a 0.5M solution in THF) at −20° C. and warmed to RT. The reaction mixture was added to sat aqu $NH_4Cl$-solution (5 L) and extracted with $CH_2Cl_2$ (3*2 L). the combined organic phases were washed with brine and dried with $Na_2SO_4$ and evaporated. The crude product was used in the next reaction without any further purification. HPLC: RT=3.271 min, $^1$H-NMR (300 MHz, $CDCl_3$): δ=1.85 (3H), 3.95 (1H), 4.20 (1H), 7.45 (1H), 7.55 (1H), 7.80 (1H).

Step 1-3 2-(4-bromo-2-chloro-phenyl)-1-(1,2,4-triazol-1-yl)pent-3-yn-2-ol 2-(4-bromo-2-chloro-phenyl)-1-chloro-pent-3-yn-2-ol (305 g), 1,2,4-triazole (191 g) and NaOH (83.2 g) were stirred in NMP (2 L) at 100° C. for 30 min. HPLC indicated full conversion. The reaction mixture was diluted with sat aqu $NH_4Cl$ (2 L) and extracted with MTBE (4*2 L) washed with brine (1 L) and dried with $Na_2SO_4$. After evaporation, crystallization from $iPr_2O$ enabled the target compound as colorless crystals (322.6 g). HPLC: RT=2.629 min, $^1$H-NMR (300 MHz, $CDCl_3$): δ=1.80 (3H), 4.70 (1H), 4.90 (1H), 7.40 (1H), 7.60 (1H), 7.75 (1H), 7.90 (1H), 8.10 (1H).

Step 1-4 2-[2-chloro-4-(4,4,5,5-tetramethyl-1,3,2-dioxaborolan-2-yl)phenyl]-1-(1,2,4-triazol-1-yl)pent-3-yn-2-ol A mixture of 2-(4-bromo-2-chloro-phenyl)-1-(1,2,4-triazol-1-yl)pent-3-yn-2-ol (22 g), bis(pinacolato)-diboron (19.2 g) KOAc (5.7 g) and $PdCl_2dppf$ (470 mg) in dioxane (200 mL) was heated to 100° C. for 5 h. HPLC indicated full conversion. The reaction mixture was added to brine (200 mL) and extracted with EtOAc (3*300 mL). the combined organic phases were dried with $Na_2SO_4$ and filtered over a plug of celite. The crude compound (43 g) was used in the next step without further purification. HPLC-MS (MSD5): RT=1.099 [M=389.8, [M+H$^+$]]

The coupling to the respective end product has been carried out analogously to the procedure as described below.

Example 2: [ss1]

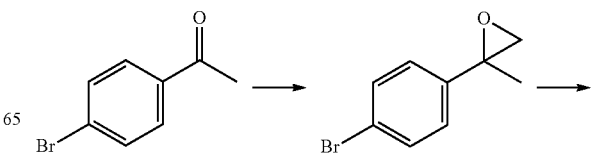

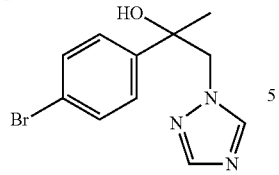

Step 2-1 2-(4-bromophenyl)-2-methyl-oxirane

To a suspension of NaH (150 g) in THF (2 L) at 10-15° C., DMSO (2.0 L) was added and stirred for 10 min. A solution of Me$_3$SI (160 g in 3.0 L DMSO) was added over a period of 90 min keeping the temperature at 10-15° C. after 1 h, a solution of 4-Bromo acetophenone (500 g in 2.5 L THF) was slowly added dropwise. Stirring was continued for 16 h and monitored by HPLC. After full conversion, sat aq NH$_4$Cl-solution (5.0 L) was added and extracted with MTBE (2*5.0 L). the combined organic phases were washed with H$_2$O (5.0 L) and brine (2.0 L) dried over Na$_2$SO$_4$ and evaporated to obtain the crude product as a yellow oil (650 g), that was used in the next step without further purification.

Step 2-2 2-(4-bromophenyl)-1-(1,2,4-triazol-1-yl)propan-2-ol

To a solution of 2-(4-bromophenyl)-2-methyl-oxirane (650 g) in NMP (8.0 L) was added NaOH (610 g) and 1,2,4-triazole (1895 g) at RT. The reaction mixture was heated to 100° C. for 8 h. after full conversion (indicated by HPLC) sat aqu. NH$_4$Cl (10 L) was added and extracted with EtOAc (2*6 L). The collected organic phases were washed with H2O (2*5 L) and brine (5 L). After drying over Na2SO4, all solvent was removed and recrystallized from MTBE (1 L) and petrolether (4 L) to give the title compound as a off-white solid (515 g, 40% for 2 steps, mp: 83° C.).

The coupling to the respective end product has been carried out analogously to the procedure as described below.

Example 3 Synthesis of 1-[2-chloro-4-(2-thienyl)phenyl]-1-cyclopropyl-2-(1,2,4-triazol-1-yl)ethanol

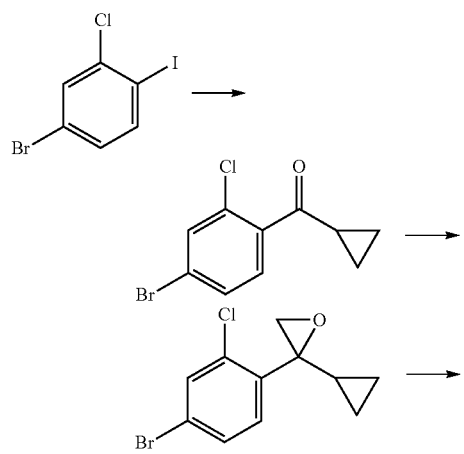

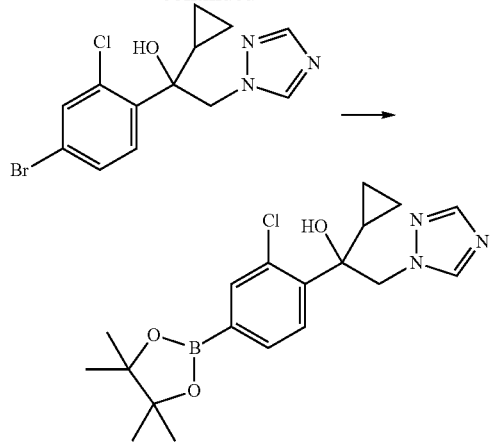

Step 3-1 (4-bromo-2-chloro-phenyl)-cyclopropyl-methanone

A solution of 4-bromo-2-chloro-1-iodo-benzene (250 g) in 0.5 L THF was cooled to −20° C. and a solution of iPrMgCl (780 mL, 1.3 eq) was added keeping the reaction temperature at −20° C. After HPLC control indicated full conversion, the Grignard solution was transferred to a previously prepared mixture of cyclopropanecarbonyl chloride (107 g), AlCl$_3$ (3.2 g), LiCl (2.0 g) and CuCl (2.34 g) in 1 L THF at 25-35° C. with slight cooling. After HPLC indicated full conversion the reaction mixture was added to sat aq. NH$_4$Cl (1 L). extraction with MTBE (3*1 L), extraction of the combined organic phases with brine (500 mL) and Na$_2$SO$_4$ yielded the target compound that was used in the next reaction without further purification. $^1$H-NMR (300 MHz, CDCl$_3$): δ=0.8-1.2 (4H), 2.40 (1H), 7.25-7.60 (3H).

Step 3-2 2-(4-bromo-2-chloro-phenyl)-2-cyclopropyl-oxirane

To KOtBu (90.4 g) in DMSO (800 mL) was added Me$_3$SI (195 g) in several portions. After stirring for 1 h, a solution of (4-bromo-2-chloro-phenyl)-cyclopropyl-methanone (220 g) was added. After 48 h, the reaction mixture was added to water (3 L) and extracted with EtOAc (3*1 L). The combined organic phases were dried with brine (1 L) and Na$_2$SO$_4$. The compound was used without further purification in the next step. $^1$H-NMR (300 MHz, CDCl$_3$): δ=0.4-1.2 (5H), 2.8 (1H), 3.00 (1H), 7.20-7.65 (3H).

Step 3-3 1-(4-bromo-2-chloro-phenyl)-1-cyclopropyl-2-(1,2,4-triazol-1-yl)ethanol 2-(4-bromo-2-chloro-phenyl)-2-cyclopropyl-oxirane (211 g, crude), NaOH (62 g) and 1,2,4 triazole (213 g) in NMP (1 L) were heated to 120° C. for 1 h. HPLC indicated full conversion. The reaction mixture was added to sat aq. NH$_4$Cl sol. (1 L) and extracted with MTBE (3*1 L). The combined organic phases were dried with brine and Na$_2$SO$_4$ to obtain the crude product. Crystallization from iPr$_2$O yielded the product (108 g) as off-white solid. $^1$H-NMR (300 MHz, CDCl$_3$): δ=0.2 (1H), 0.4 (2H), 0.6 (1H), 2.75 (1H), 4.55 (2H), 5.35 (1H), 7.25 (1H), 7.50 (2H), 7.85 (1H), 8.00 (1H).

Step 3-4 1-[2-chloro-4-(4,4,5,5-tetramethyl-1,3,2-dioxaborolan-2-yl)phenyl]-1-cyclopropyl-2-(1,2,4-triazol-1-yl)ethanol 1-(4-bromo-2-chloro-phenyl)-1-cyclopropyl-2-(1,2,4-triazol-1-yl)ethanol (30 g), KOAcH (5.7 g) and Bis-pinacolato-diboron (17.3 g) were heated to reflux in 1,4-dioxane (50 mL) for 4 h. The reaction mixture was added to ice cold NH$_4$Cl-sol. and extracted with MTBE (2*200 mL). The organic phase was washed with NH$_4$Cl-sol and brine, dried over Na$_2$SO$_4$ and evaporated. The crude product was crystallized with MeCN (150 mL) and the product was obtained as off-white solid (13.2 g). $^1$H-NMR (300 MHz, CDCl$_3$): δ=0.20 (1H), 0.40 (2H), 0.70 (1H), 1.30 (12H), 1.80 (1H), 4.55 (2H), 5.45 (1H), 7.60 (2H), 7.75 (1H), 7.80 (1H), 7.95 (1H).

Step 3-5 1-[2-chloro-4-(2-thienyl)phenyl]-1-cyclopropyl-2-(1,2,4-triazol-1-yl)ethanol

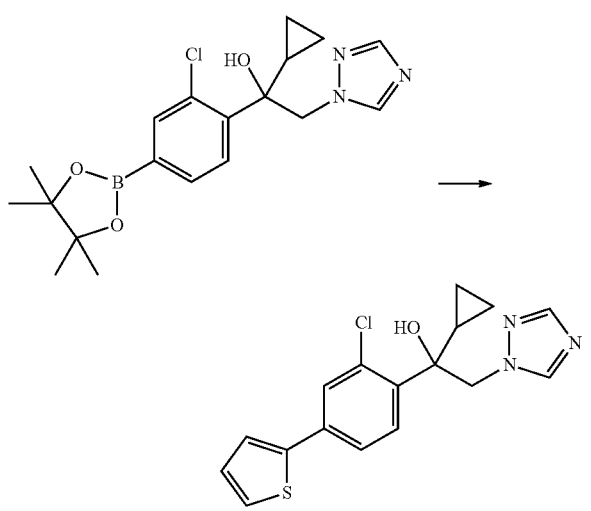

1-[2-chloro-4-(4,4,5,5-tetramethyl-1,3,2-dioxaborolan-2-yl)phenyl]-1-cyclopropyl-2-(1,2,4-triazol-1-yl)ethanol (700 mg), 2-bromothiophene (400 mg), Na$_2$CO3 (2.5 mL of a 10% solution in H$_2$O) and PdCl$_2$dppf (20 mg) in DME (10 mL) were heated to reflux for 4 h. the reaction mixture was added to NH$_4$Cl and extracted with MTBE (2*30 mL). the combined organic phases were dried with brine and Na$_2$SO$_4$ to obtain the crude product. Purification by means of MPLC (MeCN/H$_2$O 60:40) gave the title compound (450 mg). $^1$H-NMR (300 MHz, CDCl$_3$): δ=0.25 (1H), 0.45 (2H), 0.80 (1H), 1.30 (12H), 1.80 (1H), 4.50 (1H), 4.60 (1H), 5.45 (1H), 7.05 (1H), 7.30 (2H), 7.40 (1H), 7.55 (1H), 7.65 (1H), 7.85 (1H), 8.05 (1H).

Example 4 Synthesis of 1-[2-chloro-4-[4-(trifluoromethyl)phenyl]phenyl]-1-cyclopropyl-2-(1,2,4-triazol-1-yl)ethanol (Compound I-67 of Table I)

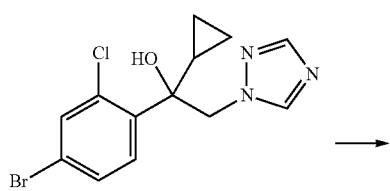

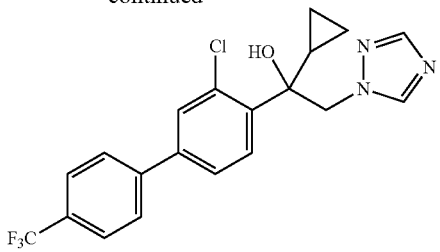

1-(4-bromo-2-chloro-phenyl)-1-cyclopropyl-2-(1,2,4-triazol-1-yl)ethanol (700 mg), [(4-trifluoromethyl)benzene]boronic acid (580 mg), PdCl$_2$dppf (10 mol %), Pd(PPh$_3$)$_4$ (10 mol %), Na$_2$CO$_3$ (1080 mg in 2 mL H$_2$O) were heated to reflux in DME (10 mL) for 12 h. HPLC indicated full conversion. The reaction mixture was added to NH$_4$Cl-sol and extracted with MTBE (3*10 mL). the combined organic phases were filtered over plug of silica and the eluent evaporated. The product was obtained as solid. HPLC-MS (MSD5): RT=1.253 [M=408 [M$^+$]]. $^1$H-NMR (500 MHz, CDCl$_3$): δ=0.30 (1H), 0.45 (2H), 0.65 (1H), 1.85 (1H), 4.60 (1H), 4.70 (1H), 4.60 (1H), 5.45 (1H), 7.25 (1H), 7.30 (1H), 7.40 (1H), 7.75-7.80 (4H), 7.85 (1H), 8.05 (1H).

TABLE of intermediates VI

| Compound No. | | Melting Point [° C.] |
|---|---|---|
| VI-1 | (structure) | 100.5 |
| VI-2 | (structure) | 118.3 |
| VI-3 | (structure) | 92.6 |
| VI-4 | (structure) | 126.1 |
| VI-5 | (structure) | 148.9 |

TABLE-continued of intermediates VI

| Compound No. | | Melting Point [° C.] |
|---|---|---|
| VI-6 | (structure: 4-bromo-2-trifluoromethylphenyl with HO, C(CH3)2, triazolylmethyl) | 112.5 |
| VI-7 | (structure: 4-bromophenyl with HO, CH3, triazolylmethyl) | 81.5 |
| VI-8 | (structure: 4-bromophenyl with HO, C2H5, triazolylmethyl) | 104.5 |
| VI-9 | (structure: 4-bromophenyl with HO, cyclopropyl, triazolylmethyl) | 100.8 |
| VI-10 | (structure: 4-bromophenyl with HO, C(CH3)2, triazolylmethyl) | 123.8 |

With due modification of the starting compounds, the procedures shown in the synthesis examples below were used to obtain further compounds I, in particular triazole compounds I.Y, wherein D is H, Y is a direct bond, Z is heteroaryl or substituted phenyl, as defined herein. The resulting compounds, together with physical data, are listed in Table I below. Compounds I.Y are a particular embodiment of the invention, wherein the substituents are as defined and preferably defined herein. Specific compounds can be found in Table I below.

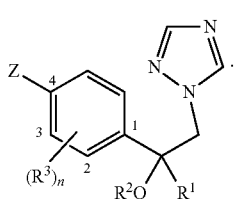

I.Y

If Z is phenyl, the position of the substituents is numbered as follows:

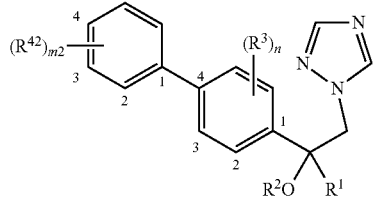

I.Aa

TABLE I

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC ** $R_t$ (min) |
|---|---|---|---|---|---|---|
| I-1  | 2-Cl | phenyl | 4-Cl      | CH$_3$       | H       | 1.138 |
| I-2  | 2-Cl | phenyl | 4-Cl      | C≡CCH$_3$    | H       | 1.153 |
| I-3  | 2-Cl | phenyl | 4-Cl      | C≡CCH$_3$    | CH$_3$  | 1.280 |
| I-4  | 2-Cl | phenyl | 4-Cl      | C$_2$H$_5$   | H       | 1.207 |
| I-5  | 2-Cl | phenyl | 4-F       | C$_2$H$_5$   | H       | 1.135 |
| I-6  | 2-Cl | phenyl | 2,4-F$_2$ | C$_2$H$_5$   | H       | 1.150 |
| I-7  | 2-Cl | phenyl | 3-F       | C$_2$H$_5$   | H       | 1.143 |
| I-8  | 2-Cl | phenyl | 2-F       | C$_2$H$_5$   | H       | 1.132 |
| I-9  | 2-Cl | phenyl | 2,4-Cl$_2$| C$_2$H$_5$   | H       | 1.262 |
| I-10 | 2-Cl | phenyl | 3,4,5-F$_3$| C$_2$H$_5$  | H       | 1.195 |
| I-11 | 2-Cl | phenyl | 4-CF$_3$  | C≡CCH$_3$    | H       | 1.177 |
| I-12 | 2-Cl | phenyl | 4-CF$_3$  | C≡CCH$_3$    | CH$_3$  | 1.294 |
| I-13 | 2-Cl | phenyl | 2-Cl      | C$_2$H$_5$   | H       | 1.173 |
| I-14 | 2-Cl | phenyl | 3-Cl      | C$_2$H$_5$   | H       | 1.200 |
| I-15 | 2-Cl | phenyl | 4-CF$_3$  | C$_2$H$_5$   | H       | 1.227 |
| I-16 | 2-Cl | phenyl | 2-CF$_3$  | C$_2$H$_5$   | H       | 1.182 |
| I-17 | 2-Cl | phenyl | 2-CF$_3$  | C≡CCH$_3$    | H       | 1.137 |
| I-18 | 2-Cl | phenyl | 2-Cl      | C≡CCH$_3$    | H       | 1.113 |
| I-19 | 2-Cl | phenyl | 3-CF$_3$  | C$_2$H$_5$   | H       | 1.213 |
| I-20 | 2-Cl | phenyl | 3,4,5-F$_3$| C≡CCH$_3$   | H       | 1.140 |
| I-21 | 2-Cl | phenyl | 3-CF$_3$  | C≡CCH$_3$    | H       | 1.162 |
| I-22 | 2-Cl | phenyl | 3-F       | C≡CCH$_3$    | H       | 1.085 |
| I-23 | 2-Cl | phenyl | 3-Cl      | C≡CCH$_3$    | H       | 1.144 |
| I-24 | 2-Cl | phenyl | 2,4-F$_2$ | C≡CCH$_3$    | H       | 1.098 |
| I-25 | 2-Cl | phenyl | 2-F       | C≡CCH$_3$    | H       | 1.090 |
| I-26 | 2-Cl | phenyl | 2,4-Cl$_2$| C≡CCH$_3$    | H       | 1.207 |
| I-27 | 2-F  | phenyl | 4-Cl      | CH$_3$       | H       | 1.087 |
| I-28 | 2-F  | phenyl | 4-Cl      | CH$_3$       | CH$_3$  | 1.195 |
| I-29 | 2-F  | phenyl | 4-F       | CH$_3$       | H       | 1.016 |
| I-30 | 2-F  | phenyl | 4-F       | CH$_3$       | CH$_3$  | 1.126 |
| I-31 | 2-F  | phenyl | 4-Cl      | C$_2$H$_5$   | H       | 1.158 |
| I-32 | 2-F  | phenyl | 4-Cl      | cyclopropyl  | H       | 1.182 |
| I-33 | 2-F  | phenyl | 4-Cl      | cyclopropyl  | CH$_3$  | 1.251 |
| I-34 | 2-F  | phenyl | 4-F       | cyclopropyl  | H       | 1.113 |
| I-35 | 2-F  | phenyl | 4-F       | cyclopropyl  | CH$_3$  | 1.187 |
| I-36 | 2-F  | phenyl | 4-Cl      | CH(CH$_3$)$_2$ | H     | 1.225 |
| I-37 | 2-F  | phenyl | 4-Cl      | CH(CH$_3$)$_2$ | CH$_3$| 1.305 |
| I-38 | 2-F  | phenyl | 4-F       | CH(CH$_3$)$_2$ | H     | 1.161 |
| I-39 | 2-F  | phenyl | 4-F       | CH(CH$_3$)$_2$ | CH$_3$| 1.236 |
| I-40 | 2-F  | phenyl | 4-Cl      | C≡CCH$_3$    | H       | 1.106 |
| I-41 | 2-F  | phenyl | 4-Cl      | C≡CCH$_3$    | CH$_3$  | 1.228 |
| I-42 | 2-F  | phenyl | 4-F       | C≡CCH$_3$    | H       | 1.037 |
| I-43 | 2-F  | phenyl | 4-F       | C≡CCH$_3$    | CH$_3$  | 1.161 |
| I-44 | 2-F  | phenyl | 4-Cl      | C(CH$_3$)$_3$ | H      | 1.327 |
| I-45 | 2-F  | phenyl | 4-Cl      | C(CH$_3$)$_3$ | CH$_3$ | 1.377 |
| I-46 | 2-F  | phenyl | 4-F       | C(CH$_3$)$_3$ | H      | 1.261 |
| I-47 | 2-F  | phenyl | 4-F       | C(CH$_3$)$_3$ | CH$_3$ | 1.309 |
| I-48 | 2-Cl | phenyl | 4-Cl      | CF$_3$       | H       | 1.217 |
| I-49 | 2-Cl | phenyl | 4-F       | CF$_3$       | H       | 1.155 |
| I-50 | 2-Cl | phenyl | 2,4-F$_2$ | CF$_3$       | H       | 1.164 |
| I-51 | 2-Cl | phenyl | 4-CF$_3$  | CF$_3$       | H       | 1.234 |
| I-52 | 2-Cl | phenyl | 3-Cl      | CF$_3$       | H       | 1.210 |
| I-53 | 2-Cl | phenyl | 2-Cl      | CF$_3$       | H       | 1.180 |
| I-54 | 2-Cl | phenyl | 3,5-F$_2$ | CF$_3$       | H       | 1.177 |
| I-55 | 2-Cl | phenyl | 3,4,5-F$_3$| CF$_3$      | H       | 1.202 |

TABLE I-continued

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC** $R_t$ (min) |
|---|---|---|---|---|---|---|
| I-56 | 2-Cl | 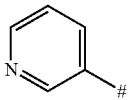 | | $CF_3$ | H | 0.717 |
| I-57 | 2-Cl | phenyl | 4-Cl | $CF_3$ | $CH_3$ | 1.291 |
| I-58 | 2-Cl | phenyl | 2,4-$Cl_2$ | cyclopropyl | H | 1.292 |
| I-59 | 2-Cl | 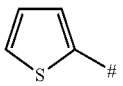 | | $CF_3$ | H | 1.126 |
| I-60 | 2-F | phenyl | 4-Cl | $CF_3$ | H | 1.178 |
| I-61 | 2-F | phenyl | 4-Cl | $CF_3$ | $CH_3$ | 1.253 |
| I-62 | 2-F | phenyl | 4-F | $CF_3$ | H | 1.113 |
| I-63 | 2-F | phenyl | 4-F | $CF_3$ | $CH_3$ | 1.190 |
| I-64 | 2-F | phenyl | 4-Cl | $C_2H_5$ | $CH_3$ | 1.247 |
| I-65 | 2-F | phenyl | 4-F | $C_2H_5$ | H | 1.085 |
| I-66 | 2-F | phenyl | 4-F | $C_2H_5$ | $CH_3$ | 1.180 |
| I-67 | 2-Cl | phenyl | 4-$CF_3$ | cyclopropyl | H | 1.253 |
| I-68 | 2-Cl | phenyl | 4-F | cyclopropyl | H | 1.168 |
| I-69 | 2-Cl | phenyl | 2,4-$F_2$ | cyclopropyl | H | 1.180 |
| I-70 | 2-Cl | phenyl | 3,4,5-$F_3$ | cyclopropyl | H | 1.222 |
| I-71 | 2-Cl | phenyl | 4-Cl | cyclopropyl | H | 1.238 |
| I-72 | 2-Cl | phenyl | 3-$CF_3$ | cyclopropyl | H | 1.246 |
| I-73 | 2-Cl | phenyl | 2-$CF_3$ | cyclopropyl | H | 1.208 |
| I-74 | 2-Cl | phenyl | 3-Cl | cyclopropyl | H | 1.235 |
| I-75 | 2-Cl | phenyl | 2-Cl | cyclopropyl | H | 1.198 |
| I-76 | 2-Cl | phenyl | 3-F | cyclopropyl | H | 1.172 |
| I-77 | 2-Cl | phenyl | 2-F | cyclopropyl | H | 1.160 |
| I-78 | 2-Cl | phenyl | 4-$CF_3$ | $CH_3$ | H | 1.162 |
| I-79 | 2-Cl | phenyl | 4-F | $CH_3$ | H | 1.067 |
| I-80 | 2-Cl | phenyl | 2,4-$F_2$ | $CH_3$ | H | 1.080 |
| I-81 | 2-Cl | phenyl | 2,4-$Cl_2$ | $CH_3$ | H | 1.195 |
| I-82 | 2-Cl | phenyl | 3,4,5-$F_3$ | $CH_3$ | H | 1.125 |
| I-83 | 2-Cl | phenyl | 3-$CF_3$ | $CH_3$ | H | 1.153 |
| I-84 | 2-Cl | phenyl | 2-$CF_3$ | $CH_3$ | H | 1.116 |
| I-85 | 2-Cl | phenyl | 3-Cl | $CH_3$ | H | 1.132 |
| I-86 | 2-Cl | phenyl | 3-F | $CH_3$ | H | 1.070 |
| I-87 | 2-Cl | phenyl | 2-F | $CH_3$ | H | 1.060 |
| I-88 | 2-Cl | phenyl | 4-Cl | $CH_3$ | $CH_3$ | 1.240 |
| I-89 | 2-$CF_3$ | phenyl | 4-Cl | $CH_3$ | H | 1.156 |
| I-90 | 2-$CF_3$ | phenyl | 4-$CF_3$ | $CH_3$ | H | 1.177 |
| I-91 | 2-$CF_3$ | phenyl | 4-F | $CH_3$ | H | 1.090 |
| I-92 | 2-$CF_3$ | phenyl | 2,4-$F_2$ | $CH_3$ | H | 1.101 |
| I-93 | 2-$CF_3$ | phenyl | 2,4-$Cl_2$ | $CH_3$ | H | 1.208 |
| I-94 | 2-$CF_3$ | phenyl | 3,4,5-$F_3$ | $CH_3$ | H | 1.145 |
| I-95 | 2-$CF_3$ | phenyl | 3-$CF_3$ | $CH_3$ | H | 1.166 |
| I-96 | 2-$CF_3$ | phenyl | 2-$CF_3$ | $CH_3$ | H | 1.132 |
| I-97 | 2-$CF_3$ | phenyl | 3-Cl | $CH_3$ | H | 1.150 |
| I-98 | 2-$CF_3$ | phenyl | 2-Cl | $CH_3$ | H | 1.118 |
| I-99 | 2-$CF_3$ | phenyl | 3-F | $CH_3$ | H | 1.090 |
| I-100 | 2-$CF_3$ | phenyl | 2-F | $CH_3$ | H | 1.081 |
| I-101 | 2-Cl | phenyl | 4-F | $CH_3$ | $CH_3$ | 1.167 |
| I-102 | 2-Cl | phenyl | 2-Cl | $CH_3$ | H | 1.098 |
| I-103 | 2-Cl | phenyl | 4-$CF_3$ | $C(CH_3)_3$ | H | 1.380 |
| I-104 | 2-Cl | phenyl | 4-F | $C(CH_3)_3$ | H | 1.305 |
| I-105 | 2-Cl | phenyl | 4-$CF_3$ | $CH_3$ | $CH_3$ | 1.280 |
| I-106 | —* | phenyl | 4-Cl | cyclopropyl | H | 1.135 |
| I-107 | —* | phenyl | 4-$CF_3$ | cyclopropyl | H | 1.166 |
| I-108 | —* | phenyl | 4-F | cyclopropyl | H | 1.064 |
| I-109 | —* | phenyl | 2,4-$F_2$ | cyclopropyl | H | 1.081 |
| I-110 | —* | phenyl | 2,4-$Cl_2$ | cyclopropyl | H | 1.197 |
| I-111 | —* | phenyl | 3,4,5-$F_3$ | cyclopropyl | H | 1.131 |
| I-112 | —* | phenyl | 3-$CF_3$ | cyclopropyl | H | 1.158 |
| I-113 | —* | phenyl | 2-$CF_3$ | cyclopropyl | H | 1.123 |
| I-114 | —* | phenyl | 3-Cl | cyclopropyl | H | 1.132 |
| I-115 | —* | phenyl | 2-Cl | cyclopropyl | H | 1.098 |
| I-116 | —* | phenyl | 3-F | cyclopropyl | H | 1.068 |
| I-117 | —* | phenyl | 2-F | cyclopropyl | H | 1.058 |
| I-118 | 2-$CF_3$ | phenyl | 4-Cl | $CH(CH_3)_2$ | H | 1.289 |
| I-119 | 2-$CF_3$ | phenyl | 4-$CF_3$ | $CH(CH_3)_2$ | H | 1.304 |
| I-120 | 2-$CF_3$ | phenyl | 4-F | $CH(CH_3)_2$ | H | 1.224 |
| I-121 | 2-$CF_3$ | phenyl | 2,4-$F_2$ | $CH(CH_3)_2$ | H | 1.230 |
| I-122 | 2-$CF_3$ | phenyl | 2,4-$Cl_2$ | $CH(CH_3)_2$ | H | 1.326 |
| I-123 | 2-$CF_3$ | phenyl | 3,4,5-$F_3$ | $CH(CH_3)_2$ | H | 1.274 |
| I-124 | 2-$CF_3$ | phenyl | 3-$CF_3$ | $CH(CH_3)_2$ | H | 1.304 |
| I-125 | 2-$CF_3$ | phenyl | 2-$CF_3$ | $CH(CH_3)_2$ | H | 1.262 |
| I-126 | 2-$CF_3$ | phenyl | 3-Cl | $CH(CH_3)_2$ | H | 1.287 |
| I-127 | 2-$CF_3$ | phenyl | 2-Cl | $CH(CH_3)_2$ | H | 1.249 |
| I-128 | 2-$CF_3$ | phenyl | 3-F | $CH(CH_3)_2$ | H | 1.226 |
| I-129 | 2-$CF_3$ | phenyl | 2-F | $CH(CH_3)_2$ | H | 1.216 |
| I-130 | 2-Cl | phenyl | 4-$CF_3$ | $C_2H_5$ | H | 1.150 |
| I-131 | 2-Cl | phenyl | 3-$CF_3$ | $C_2H_5$ | H | 1.143 |
| I-132 | 2-Cl | phenyl | 3,4-$Cl_2$ | $C_2H_5$ | H | 1.299 |
| I-133 | 2-Cl | phenyl | 3,4-$F_2$ | $C_2H_5$ | H | 1.175 |
| I-134 | 2-Cl | phenyl | 3-CN | $C_2H_5$ | H | 1.047 |
| I-135 | 2-Cl | phenyl | 3,4-$Cl_2$ | cyclopropyl | H | 1.312 |
| I-136 | 2-Cl | phenyl | 3,4-$F_2$ | cyclopropyl | H | 1.190 |
| I-137 | 2-Cl | phenyl | 3-CN | cyclopropyl | H | 1.086 |
| I-138 | 2-Cl | phenyl | 3,4-$Cl_2$ | C≡$CCH_3$ | H | 1.216 |
| I-139 | 2-Cl | phenyl | 3,4-$F_2$ | C≡$CCH_3$ | H | 1.124 |
| I-140 | 2-Cl | phenyl | 3-CN | C≡$CCH_3$ | H | 1.029 |
| I-141 | 2-Cl | phenyl | 3,4-$Cl_2$ | $CH_3$ | H | 1.227 |
| I-142 | 2-Cl | phenyl | 3,4-$F_2$ | $CH_3$ | H | 1.106 |
| I-143 | 2-Cl | phenyl | 3-CN | $CH_3$ | H | 1.001 |
| I-144 | 2-Cl | phenyl | 4-Cl | $CH_2CH(CH_3)_2$ | H | 1.342 |
| I-145 | 2-Cl | phenyl | 4-F | $CH_2CH(CH_3)_2$ | H | 1.271 |
| I-146 | 2-Cl | phenyl | 4-$CF_3$ | $CH_2CH(CH_3)_2$ | H | 1.350 |
| I-147 | 2-Cl | phenyl | 3-Cl | $CH_2CH(CH_3)_2$ | H | 1.339 |
| I-148 | 2-Cl | phenyl | 3-F | $CH_2CH(CH_3)_2$ | H | 1.272 |
| I-149 | 2-Cl | phenyl | 3-$CF_3$ | $CH_2CH(CH_3)_2$ | H | 1.344 |
| I-150 | 2-Cl | phenyl | 4-Cl | $CH_2C(CH_3)_3$ | H | 1.400 |
| I-151 | 2-Cl | phenyl | 4-F | $CH_2C(CH_3)_3$ | H | 1.331 |
| I-152 | 2-Cl | phenyl | 4-$CF_3$ | $CH_2C(CH_3)_3$ | H | 1.405 |
| I-153 | 2-Cl | phenyl | 3-Cl | $CH_2C(CH_3)_3$ | H | 1.499 |
| I-154 | 2-Cl | phenyl | 3-F | $CH_2C(CH_3)_3$ | H | 1.330 |
| I-155 | 2-Cl | phenyl | 3-$CF_3$ | $CH_2C(CH_3)_3$ | H | 1.400 |
| I-156 | —* | phenyl | 3,4-$Cl_2$ | $CF_3$ | H | 1.206 |
| I-157 | —* | phenyl | 3,4-$F_2$ | $CF_3$ | H | 1.096 |
| I-158 | 2-Cl | phenyl | 3,4-$Cl_2$ | $CF_3$ | H | 1.287 |
| I-159 | 2-Cl | phenyl | 3,4-$F_2$ | $CF_3$ | H | 1.171 |
| I-160 | 2-Cl | phenyl | 3-CN | $CF_3$ | H | 1.073 |
| I-161 | 2-Cl | phenyl | 4-CN | $CF_3$ | H | 1.090 |
| I-162 | 2-Cl | phenyl | 3,4-$(OCH_3)_2$ | $CF_3$ | H | 1.074 |
| I-163 | 2-Cl | phenyl | 3-$CF_3$ | $CF_3$ | H | 1.229 |
| I-164 | —* | phenyl | 3,4-$Cl_2$ | $CH_2CH(CH_3)_2$ | H | 1.326 |
| I-165 | —* | phenyl | 3,4-$F_2$ | $CH_2CH(CH_3)_2$ | H | 1.176 |
| I-166 | —* | phenyl | 4-Cl | $CH_2CH(CH_3)_2$ | H | 1.225 |
| I-167 | —* | phenyl | 4-$CF_3$ | $CH_2CH(CH_3)_2$ | H | 1.248 |
| I-168 | —* | phenyl | 3-Cl | $CH_2CH(CH_3)_2$ | H | 1.215 |
| I-169 | —* | phenyl | 3-$CF_3$ | $CH_2CH(CH_3)_2$ | H | 1.242 |
| I-170 | —* | phenyl | 3,4-$Cl_2$ | $CH_2C(CH_3)_3$ | H | 1.362 |
| I-171 | —* | phenyl | 3,4-$F_2$ | $CH_2C(CH_3)_3$ | H | 1.244 |
| I-172 | —* | phenyl | 4-Cl | $CH_2C(CH_3)_3$ | H | 1.292 |
| I-173 | —* | phenyl | 4-$CF_3$ | $CH_2C(CH_3)_3$ | H | 1.310 |
| I-174 | —* | phenyl | 3-Cl | $CH_2C(CH_3)_3$ | H | 1.293 |
| I-175 | —* | phenyl | 3-$CF_3$ | $CH_2C(CH_3)_3$ | H | 1.305 |
| I-176 | 2-Cl | phenyl | 3,4-$Cl_2$ | $CH(CH_3)_2$ | H | 1.392 |
| I-177 | 2-Cl | phenyl | 3,4-$F_2$ | $CH(CH_3)_2$ | H | 1.272 |
| I-178 | 2-Cl | phenyl | 4-Cl | $CH(CH_3)_2$ | H | 1.313 |
| I-179 | 2-Cl | phenyl | 4-F | $CH(CH_3)_2$ | H | 1.242 |
| I-180 | 2-Cl | phenyl | 4-$CF_3$ | $CH(CH_3)_2$ | H | 1.328 |
| I-181 | 2-Cl | phenyl | 3-Cl | $CH(CH_3)_2$ | H | 1.307 |
| I-182 | 2-Cl | phenyl | 3-F | $CH(CH_3)_2$ | H | 1.238 |
| I-183 | 2-Cl | phenyl | 3-$CF_3$ | $CH(CH_3)_2$ | H | 1.321 |
| I-184 | 2-Cl | phenyl | 3,4-$Cl_2$ | $C(CH_3)_3$ | H | 1.454 |
| I-185 | 2-Cl | phenyl | 3,4-$F_2$ | $C(CH_3)_3$ | H | 1.327 |
| I-186 | —* | phenyl | 4-Cl | $C(CH_3)_3$ | H | 1.385 |
| I-187 | —* | phenyl | 4-F | $C(CH_3)_3$ | H | 1.310 |
| I-188 | —* | phenyl | 4-$CF_3$ | $C(CH_3)_3$ | H | 1.393 |
| I-189 | —* | phenyl | 3-Cl | $C(CH_3)_3$ | H | 1.383 |
| I-190 | —* | phenyl | 3-F | $C(CH_3)_3$ | H | 1.311 |
| I-191 | —* | phenyl | 3-$CF_3$ | $C(CH_3)_3$ | H | 1.388 |

TABLE I-continued

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC** $R_t$ (min) |
|---|---|---|---|---|---|---|
| I-192 | 2-Cl | phenyl | 3,4-Cl$_2$ | CH$_2$C(CH$_3$)$_3$ | H | 1.483 |
| I-193 | 2-Cl | phenyl | 3,4-F$_2$ | CH$_2$C(CH$_3$)$_3$ | H | 1.361 |
| I-194 | 2-Cl | phenyl | 3-CN | CH$_2$C(CH$_3$)$_3$ | H | 1.261 |
| I-195 | 2-Cl | phenyl | 4-CN | CH$_2$C(CH$_3$)$_3$ | H | 1.26 |
| I-196 | 2-Cl | phenyl | 3,4-Cl$_2$ | CH$_2$CH(CH$_3$)$_2$ | H | 1.425 |
| I-197 | 2-Cl | phenyl | 3,4-F$_2$ | CH$_2$CH(CH$_3$)$_2$ | H | 1.302 |
| I-198 | 2-Cl | phenyl | 3-CN | CH$_2$CH(CH$_3$)$_2$ | H | 1.201 |
| I-199 | 2-Cl | phenyl | 4-CN | CH$_2$CH(CH$_3$)$_2$ | H | 1.2 |
| I-200 | —* | phenyl | 3,4-Cl$_2$ | C$_2$H$_5$ | H | 1.2 |
| I-201 | —* | phenyl | 3,4-F$_2$ | C$_2$H$_5$ | H | 1.079 |
| I-202 | —* | phenyl | 3,4-Cl$_2$ | CH$_3$ | H | 1.131 |
| I-203 | —* | phenyl | 3,4-F$_2$ | CH$_3$ | H | 0.983 |
| I-204 | —* | phenyl | 3,4-Cl$_2$ | CH(CH$_3$)$_2$ | H | 1.223 |
| I-205 | —* | phenyl | 3,4-Cl$_2$ | cyclopropyl | H | 1.272 |
| I-206 | —* | phenyl | 3,4-Cl$_2$ | C(CH$_3$)$_3$ | H | 1.34 |
| I-207 | —* | phenyl | 3,4-Cl$_2$ | C≡CCH$_3$ | H | 1.172 |
| I-208 | —* | phenyl | 4-Cl | CH(CH$_3$)$_2$ | H | 1.162 |
| I-209 | —* | phenyl | 4-F | CH(CH$_3$)$_2$ | H | 1.09 |
| I-210 | —* | phenyl | 4-CF$_3$ | CH(CH$_3$)$_2$ | H | 1.191 |
| I-211 | —* | phenyl | 3-Cl | CH(CH$_3$)$_2$ | H | 1.159 |
| I-212 | —* | phenyl | 3-F | CH(CH$_3$)$_2$ | H | 1.092 |
| I-213 | —* | phenyl | 3-CF$_3$ | CH(CH$_3$)$_2$ | H | 1.183 |
| I-214 | —* | phenyl | 3,4-F$_2$ | CH(CH$_3$)$_2$ | H | 1.115 |
| I-215 | —* | phenyl | 3,4-F$_2$ | cyclopropyl | H | 1.069 |
| I-216 | —* | phenyl | 3,4-F$_2$ | C(CH$_3$)$_3$ | H | 1.219 |
| I-217 | —* | phenyl | 3,4-F$_2$ | C≡CCH$_3$ | H | 1.024 |
| I-218 | —* | phenyl | 3-Cl | C≡CCH$_3$ | H | 1.098 |
| I-219 | —* | phenyl | 3-F | C≡CCH$_3$ | H | 1.033 |
| I-220 | —* | phenyl | 3-CF$_3$ | C≡CCH$_3$ | H | 1.129 |
| I-221 | —* | phenyl | 4-Cl | C≡CCH$_3$ | H | 1.103 |
| I-222 | —* | phenyl | 4-CF$_3$ | C≡CCH$_3$ | H | 1.129 |
| I-223 | —* | phenyl | 4-F | C≡CCH$_3$ | H | 1.026 |
| I-224 | —* | phenyl | 2,4-F$_2$ | C≡CCH$_3$ | H | 1.044 |
| I-225 | —* | phenyl | 2,4-Cl$_2$ | C≡CCH$_3$ | H | 1.160 |
| I-226 | —* | phenyl | 3,4,5-F$_3$ | C≡CCH$_3$ | H | 1.093 |
| I-227 | —* | phenyl | 3-CF$_3$ | C≡CCH$_3$ | H | 1.120 |
| I-228 | —* | phenyl | 2-CF$_3$ | C≡CCH$_3$ | H | 1.089 |
| I-229 | —* | phenyl | 3-Cl | C≡CCH$_3$ | H | 1.091 |
| I-230 | —* | phenyl | 2-Cl | C≡CCH$_3$ | H | 1.062 |
| I-231 | —* | phenyl | 3-F | C≡CCH$_3$ | H | 1.028 |
| I-232 | —* | phenyl | 2-F | C≡CCH$_3$ | H | 1.015 |
| I-233 | —* | 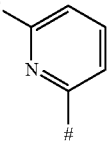 | | cyclopropyl | H | 1.194 |
| I-234 | 2-Cl | 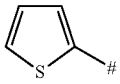 | | cyclopropyl | H | 1.162 |
| I-235 | 2-Cl | 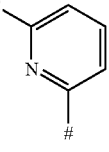 | | cyclopropyl | H | 1.194 |
| I-236 | 2-Cl | 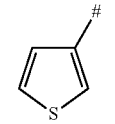 | | cyclopropyl | H | 1.131 |
| I-237 | 2-Cl | 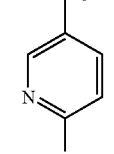 | | cyclopropyl | H | 1.195 |
| I-238 | 2-Cl | 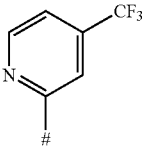 | | cyclopropyl | H | 1.165 |
| I-239 | 2-Cl | 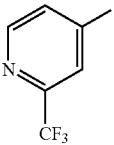 | | cyclopropyl | H | 1.108 |
| I-240 | 2-Cl | 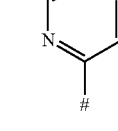 | | cyclopropyl | H | 1.129 |
| I-241 | 2-Cl | 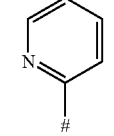 | | cyclopropyl | H | 1.130 |
| I-242 | 2-Cl | 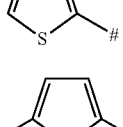 | | C$_2$H$_5$ | H | 1.093 |
| I-243 | 2-Cl | 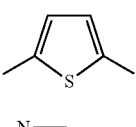 | | cyclopropyl | H | 1.258 |
| I-244 | 2-Cl | 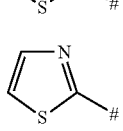 | | cyclopropyl | H | 0.931 |
| I-245 | 2-Cl | 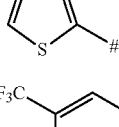 | | cyclopropyl | H | 1.129 |
| I-246 | 2-Cl |  | | C$_2$H$_5$ | H | 1.146 |

TABLE I-continued

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC** $R_t$ (min) |
|---|---|---|---|---|---|---|
| I-247 | 2-Cl | pyridine | 4-#, 2-CF3 | C2H5 | H | 1.008 |
| I-248 | 2-Cl | thiophene | 5-Cl, 2-# | C2H5 | H | 1.239 |
| I-249 | 2-Cl | thiazole | 5-# | C2H5 | H | 0.893 |
| I-250 | 2-Cl | thiadiazole | 5-CF3, 2-# | C2H5 | H | 0.904 |
| I-251 | 2-Cl | thiophene | 5-CF3, 2-# | cyclopropyl | H | 1.298 |
| I-252 | 2-Cl | pyridine | 5-CF3, 2-# | C2H5 | H | 1.163 |
| I-253 | 2-Cl | pyridine | 4-CF3, 2-# | C2H5 | H | 1.154 |
| I-254 | 2-Cl | thiophene | 5-CF3, 2-# | C2H5 | H | 1.261 |
| I-255 | 2-Cl | thiophene | 2-# | C2H5 | H | 1.103 |
| I-256 | 2-Cl | thiazole | 2-# | C2H5 | H | 0.970 |
| I-257 | 2-Cl | pyridine | 6-CF3, 2-# | C(CH3)3 | H | 1.352 |
| I-258 | 2-Cl | thiophene | 2-# | C(CH3)3 | H | 1.320 |
| I-259 | 2-Cl | pyridine | 6-CF3, 2-# | CH3 | H | 1.066 |
| I-260 | 2-Cl | thiophene | 2-# | CH3 | H | 1.016 |
| I-261 | 2-Cl | thiophene | 3-# | CH3 | H | 1.000 |
| I-262 | 2-Cl | thiophene | 5-Cl, 2-# | CH3 | H | 1.133 |
| I-263 | 2-Cl | pyridine | 6-CF3, 2-# | CH(CH3)2 | H | 1.221 |
| I-264 | 2-Cl | thiophene | 2-# | CH(CH3)2 | H | 1.181 |
| I-265 | 2-Cl | thiophene | 3-# | CH(CH3)2 | H | 1.158 |
| I-266 | 2-Cl | thiophene | 5-Cl, 2-# | CH(CH3)2 | H | 1.296 |
| I-267 | 2-Cl | pyridine | 6-CF3, 2-# | C≡CCH3 | H | 1.083 |
| I-268 | 2-Cl | thiophene | 2-# | C≡CCH3 | H | 1.067 |
| I-269 | 2-Cl | thiophene | 3-# | C≡CCH3 | H | 0.982 |
| I-270 | 2-Cl | thiophene | 5-Cl, 2-# | C≡CCH3 | H | 1.198 |

TABLE I-continued

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC** $R_t$ (min) |
|---|---|---|---|---|---|---|
| I-271 | 2-Cl | 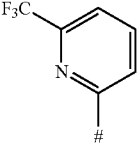 | | $CF_3$ | H | 1.206 |
| I-272 | 2-Cl | 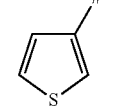 | | $CF_3$ | H | 1.148 |
| I-273 | 2-Cl | 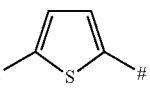 | | $CF_3$ | H | 1.256 |
| I-274 | 2-Cl | 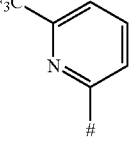 | | $CH_2CH(CH_3)_2$ | H | 1.292 |
| I-275 | 2-Cl | 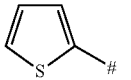 | | $CH_2CH(CH_3)_2$ | H | 1.258 |
| I-276 | 2-Cl | 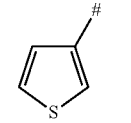 | | $CH_2CH(CH_3)_2$ | H | 1.238 |
| I-277 | 2-Cl | 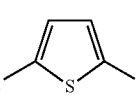 | | $CH_2CH(CH_3)_2$ | H | 1.375 |
| I-278 | 2-Cl | 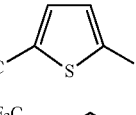 | | $CH_2CH(CH_3)_2$ | H | 1.383 |
| I-279 | 2-Cl | 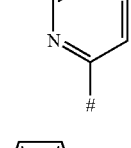 | | $CH_2C(CH_3)_3$ | H | 1.356 |
| I-280 | 2-Cl | 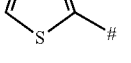 | | $CH_2C(CH_3)_3$ | H | 1.32 |
| I-281 | 2-Cl | 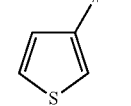 | | $CH_2C(CH_3)_3$ | H | 1.302 |
| I-282 | 2-Cl | 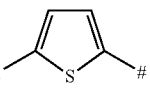 | | $CH_2C(CH_3)_3$ | H | 1.248 |
| I-283 | 2-Cl | 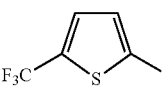 | | $CH_2C(CH_3)_3$ | H | 1.442 |
| I-284 | 2-Cl | 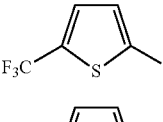 | | $CH_3$ | H | 1.191 |
| I-285 | 2-Cl | 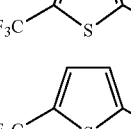 | | $CH(CH_3)_2$ | H | 1.301 |
| I-286 | 2-Cl | 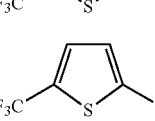 | | $C\equiv CCH_3$ | H | 1.165 |
| I-287 | 2-Cl | 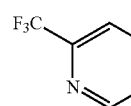 | | $CF_3$ | H | 1.235 |
| I-288 | —* | 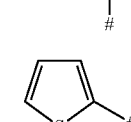 | | $C_2H_5$ | H | 1.035 |
| I-289 | —* | 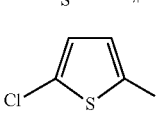 | | $C_2H_5$ | H | 0.974 |
| I-290 | —* | 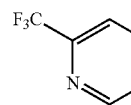 | | $C_2H_5$ | H | 1.095 |
| I-291 | —* | 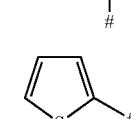 | | $CH(CH_3)_2$ | H | 1.092 |
| I-292 | —* | 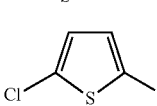 | | $CH(CH_3)_2$ | H | 1.051 |
| I-293 | —* | 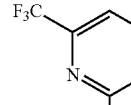 | | $CH(CH_3)_2$ | H | 1.169 |
| I-294 | —* | 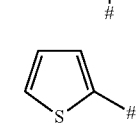 | | $C(CH_3)_3$ | H | 1.207 |
| I-295 | —* |  | | $C(CH_3)_3$ | H | 1.159 |

TABLE I-continued

Compounds of formula I; $(R^4)_m$ stands for $(R^{42})_{m2}$ if Z is a phenyl and for $(R^{41})_{m1}$ is Z is a heteroaryl

| compound No. | $(R^3)_n$ | Z | $(R^4)_m$ | $R^1$ | $R^2$ | HPLC** $R_t$ (min) |
|---|---|---|---|---|---|---|
| I-296 | —* | | Cl—[thiophene]—# | $C(CH_3)_3$ | H | 1.279 |
| I-297 | —* | | $F_3C$—[pyridine]—# | cyclopropyl | H | 1.057 |
| I-298 | —* | | [thiophene]—# | cyclopropyl | H | 1.000 |
| I-299 | —* | | Cl—[thiophene]—# | cyclopropyl | H | 1.119 |

*— stands for n = 0

** :HPLC method Data: Mobile Phase: A: Wasser + 0.1% TFA; B: acetonitrile; Gradient: 5% B to 100% B in 1.5 min; Temperature: 60° C.; MS-Method: ESI positive; mass area (m/z): 100-700; Flow: 0.8 ml/min to 1.0 ml/min in 1.5 min; Column: Kinetex XB C18 1.7 μ 50 × 2.1 mm; Aparatus: Shimadzu Nexera LC-30 LCMS-2020.

II. EXAMPLES OF THE ACTION AGAINST HARMFUL FUNGI

The fungicidal action of the compounds of the formula I was demonstrated by the following experiments:

Microtest

The active compounds were formulated separately as a stock solution having a concentration of 10000 ppm in dimethyl sulfoxide.

M1 Activity Against the Grey Mold *Botrytis cinerea* in the Microtiterplate Test (*Botrci*)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation. Compounds I-1, I-3, I-4, I-7, I-8, I-9, I-10, I-11, I-14, I-15, I-16, I-21, I-23, I-27, I-28, I-32, I-33, I-34, I-40, I-41, I-45, I-46, I-51, I-52, I-54, I-58, I-60, I-74, I-79, I-85, I-88, I-91, I-95, I-99, I-104, I-105, I-118, I-119, I-120, I-121, I-123, I-124, I-126, I-127, I-128, I-129, I-221, I-106, I-107, I-108, I-109, I-110, I-111, I-112, I-114, I-115, I-116, I-117, I-225, I-227 and 1-230, respectively, showed a growth of 17% or less at 31 ppm.

M2 Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. Compounds I-1, I-3, I-11, I-14, I-15, I-16, I-21, I-23, I-27, I-28, I-32, I-33, I-34, I-40, I-41, I-45, I-46, I-51, I-52, I-58, I-60, I-74, I-79, I-85, I-88, I-91, I-95, I-99, I-104, I-105, I-118, I-119, I-120, I-121, I-122, I-123, I-124, I-125, I-126, I-127, I-128, I-129, I-221, I-106, I-107, I-108, I-109, I-110, I-111, I-112, I-113, I-114, I-115, I-116, I-117, I-225, I-226, I-227, I-228, I-229, I-230 and 1-232, respectively, showed a growth of 15% or less at 31 ppm.

M3 Activity Against Leaf Blotch on Wheat Caused by *Septonia tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-1, I-3, I-4, I-7, I-8, I-9, I-10, I-11, I-14, I-15, I-21, I-23, I-27, I-28, I-32, I-33, I-34, I-40, I-41, I-46, I-51, I-52, I-60, I-74, I-79, I-85, I-88, I-91, I-95, I-99, I-104, I-105, I-118, I-119, I-120, I-121, I-123, I-124, I-126, I-127, I-128, I-129, I-221, I-106, I-107, I-108, I-109, I-110, I-111, I-112, I-114, I-115, I-116, I-117, I-223, I-224, I-225, I-227, I-230 and 1-232, respectively, showed a growth of 17% or less at 31 ppm.

The measured parameters were compared to the growth of the active compound-free control variant (100%) and the fungus-free and active compound-free blank value to determine the relative growth in % of the pathogens in the respective active compounds.

The invention claimed is:

1. A compound of the formula I

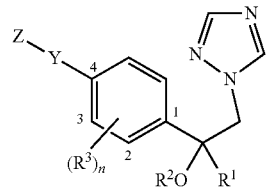

wherein $R^1$ is $C_1$-$C_6$-alkyl, $C_3$-$C_8$-cycloalkyl, or $C_3$-$C_8$-cycloalkyl-$C_1$-$C_6$-alkyl;

wherein the aliphatic moieties of $R^1$ are not further substituted or carry one, two, three or up to the maximum possible number of identical or different groups $R^{1a}$ which independently of one another are selected from:

$R^{1a}$ halogen, OH, nitro, $C_1$-$C_4$-alkoxy, $C_3$-$C_8$-cycloalkyl, $C_3$-$C_8$-halocycloalkyl and $C_1$-$C_4$-halogenalkoxy;

wherein the cycloalkyl and/or phenyl moieties of $R^1$ are not further substituted or carry one, two, three, four, five or up to the maximum number of identical or different groups $R^{1b}$ which independently of one another are selected from:

$R^{1b}$ halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy;

$R^2$ is H or $C_1$-$C_6$-alkyl;

wherein the aliphatic moieties of $R^2$ are not further substituted or carry one, two, three or up to the maximum possible number of identical or different groups $R^{2a}$ which independently of one another are selected from:

$R^{2a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;

n is 1;

$R^3$ is independently selected from halogen, CN, and $C_1$-$C_6$-alkyl; wherein each of $C_1$-$C_6$-alkyl is unsubstituted or further substituted by one, two, three or four $R^{3a}$; wherein $R^{3a}$ is independently selected from halogen;

Y is a direct bond;

Z is five or six-membered heteroaryl, wherein the heteroaryl contains 1, 2, 3 or 4 heteroatoms selected from the group consisting of O, N and S, wherein the heteroaryl is unsubstituted (m1=0) or substituted by $(R^{41})_{m1}$; or is phenyl, that is substituted by $(R^{42})_{m2}$; wherein m1 is 0, 1, 2, 3 or 4;

m2 is 1, 2, 3, 4 or 5; and $R^{41}$, $R^{42}$ is in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2)$, $C(=O)(NH(C_3$-$C_6$-cycloalkyl))$ and $C(=O)-(N(C_3$-$C_6$-cycloalkyl)$_2)$; wherein each of $R^{41}$ or $R^{42}$ is unsubstituted or further substituted by one, two, three or four $R^{41a}$ or $R^{42a}$ wherein $R^{41a}$, $R^{42a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy;

p is 0, 1 or 2;

with the proviso, that if Z is phenyl and m2 is 1, $R^1$ is not $(C_3$-$C_8)$-cycloalkyl-$(C_1$-$C_3)$-alkyl, $(C_3$-$C_8)$-(chloro)cycloalkyl-$(C_1$-$C_3)$-alkyl or $(C_3$-$C_8)$-(methyl)cycloalkyl-$(C_1$-$C_3)$-alkyl; and and the N-oxides and the agriculturally acceptable salts thereof.

2. The compound of claim 1, wherein $R^1$ is $C_1$-$C_6$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

3. The compound of claim 1, wherein $R^1$ is $C_1$-$C_3$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

4. The compound of claim 1, wherein Z is phenyl and m2 is 2, 3, 4 or 5.

5. A process for the preparation of compounds I as defined in claim 1, comprising the steps:

a1) reacting a compound VI

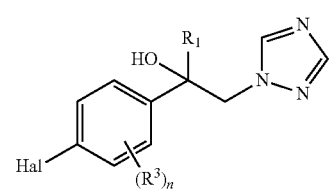

VI wherein Hal stands for halogen,

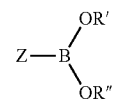

with wherein R' and R'' are independently hydrogen or $(C_1$-$C_4)$-alkyl and a catalyst; or a2) reacting a compound VI with

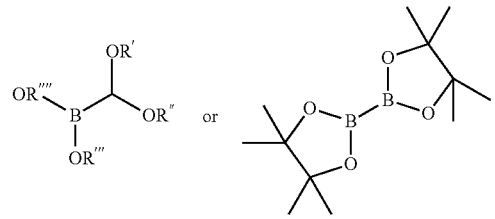

wherein R', R'', R''' and R'''' are independently hydrogen or $(C_1$-$C_4)$-alkyl, to result in compounds VII

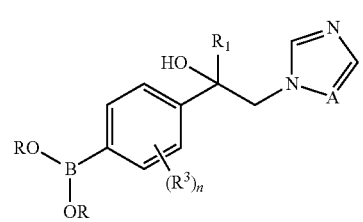

VII and further reacting with Z-Hal and a catalyst.

6. A composition, comprising one compound of formula I, as defined in claim 1, an N-oxide or an agriculturally acceptable salt thereof.

7. The composition according to claim 6, comprising, in addition to the compound of formula (I) as a first active substance, a further active substance.

8. A method for combating phytopathogenic or harmful fungi, comprising treating the fungi or the materials, plants, the soil or seeds to be protected against fungal attack with an effective amount of at least one compound of formula I, as defined in claim 1.

9. The method of claim 8, wherein, in the compound of formula (I), $R^1$ is $C_1$-$C_6$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

10. The method of claim 8, wherein, in the compound of formula (I), $R^1$ is $C_1$-$C_3$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

11. The method of claim 8, wherein, in the compound of formula (I), Z is phenyl and m2 is 2, 3, 4 or 5.

12. Seed, coated with at least one compound of the formula I, as defined in claim 1, and/or an agriculturally acceptable salt thereof, in an amount of from 0.1 to 10 kg per 100 kg of seed.

13. The seed of claim 12, wherein, in the compound of formula (I), $R^1$ is $C_1$-$C_6$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

14. The seed of claim 12, wherein, in the compound of formula (I), $R^1$ is $C_1$-$C_3$-alkyl or $C_3$-$C_8$-cycloalkyl, wherein the aliphatic moieties of $R^1$ are not further substituted or carry one, two, three or up to the maximum possible number of identical or different groups $R^{1a}$ which independently of one another are selected from halogen, OH, nitro, $C_1$-$C_4$-alkoxy and $C_1$-$C_4$-halogenalkoxy; and wherein the cycloalkyl and/or phenyl moieties of $R^1$ are not further substituted or carry one, two, three, four, five or up to the maximum number of identical or different groups $R^{1b}$ which independently of one another are selected from halogen, OH, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

15. The seed of claim 12, wherein, in the compound of formula (I), Z is phenyl and m2 is 2, 3, 4 or 5.

* * * * *